US007897609B2

(12) United States Patent
Niwas et al.

(10) Patent No.: US 7,897,609 B2
(45) Date of Patent: Mar. 1, 2011

(54) ARYL SUBSTITUTED IMIDAZONAPHTHYRIDINES

(75) Inventors: Shri Niwas, Maple Grove, MN (US); Bryon A. Merrill, River Falls, WI (US); Philip D. Heppner, Forest Lake, MN (US); Tushar A. Kshirsagar, Woodbury, MN (US); Gregory D. Lundquist, Jr., Eagan, MN (US); David T. Amos, St. Paul, MN (US); Kyle J. Lindstrom, Houlton, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 726 days.

(21) Appl. No.: 11/570,703

(22) PCT Filed: Jun. 17, 2005

(86) PCT No.: PCT/US2005/021436
§ 371 (c)(1),
(2), (4) Date: Dec. 15, 2006

(87) PCT Pub. No.: WO2006/038923
PCT Pub. Date: Apr. 13, 2006

(65) Prior Publication Data
US 2007/0219228 A1 Sep. 20, 2007

Related U.S. Application Data

(60) Provisional application No. 60/581,317, filed on Jun. 18, 2004.

(51) Int. Cl.
*C07D 215/38* (2006.01)
*A61K 31/02* (2006.01)
(52) U.S. Cl. .......................................... 514/293; 546/82
(58) Field of Classification Search ................... 546/82; 514/293
See application file for complete search history.

(56) References Cited

U.S. PATENT DOCUMENTS

| | | |
|---|---|---|
| 3,314,941 A | 4/1967 | Littell et al. |
| 3,450,693 A | 6/1969 | Suzuki et al. |
| 3,670,086 A | 6/1972 | Pryor et al. |
| 3,692,907 A | 9/1972 | Fleming et al. |
| 3,891,660 A | 6/1975 | Denzel et al. |
| 3,899,508 A | 8/1975 | Wikel |
| 3,917,624 A | 11/1975 | Abu El-Haj et al. |
| 4,006,237 A | 2/1977 | Buckle et al. |
| 4,053,588 A | 10/1977 | Konig et al. |
| 4,381,344 A | 4/1983 | Rideout et al. |
| 4,552,874 A | 11/1985 | Mardin et al. |
| 4,563,525 A | 1/1986 | Campbell, Jr. |
| 4,593,821 A | 6/1986 | Brule |
| 4,668,686 A | 5/1987 | Meanwell et al. |
| 4,689,338 A | 8/1987 | Gerster |
| 4,690,930 A | 9/1987 | Takada et al. |
| 4,698,346 A | 10/1987 | Musser et al. |
| 4,698,348 A | 10/1987 | Gerster |
| 4,753,951 A | 6/1988 | Takada et al. |
| 4,758,574 A | 7/1988 | Robertson et al. |
| 4,774,339 A | 9/1988 | Haugland et al. |
| 4,775,674 A | 10/1988 | Meanwell et al. |
| 4,800,206 A | 1/1989 | Alig et al. |
| 4,826,830 A | 5/1989 | Han et al. |
| 4,837,378 A | 6/1989 | Borgman |
| 4,880,779 A | 11/1989 | Gallaher |
| 4,904,669 A | 2/1990 | Knoll et al. |
| 4,929,624 A | 5/1990 | Gerster et al. |
| 4,988,714 A | 1/1991 | Alig et al. |
| 4,988,815 A | 1/1991 | Andre et al. |
| 5,037,986 A | 8/1991 | Gerster |
| 5,175,296 A | 12/1992 | Gerster |
| 5,187,288 A | 2/1993 | Kang et al. |
| 5,225,183 A | 7/1993 | Purewal et al. |
| 5,238,944 A | 8/1993 | Wick et al. |
| 5,248,782 A | 9/1993 | Haugland et al. |
| 5,266,575 A | 11/1993 | Gerster |
| 5,268,376 A | 12/1993 | Gester |
| 5,274,113 A | 12/1993 | Kang et al. |
| 5,346,905 A | 9/1994 | Gerster |
| 5,352,680 A | 10/1994 | Portoghese et al. |
| 5,352,784 A | 10/1994 | Nikolaides et al. |
| 5,367,076 A | 11/1994 | Gerster |
| 5,376,501 A | 12/1994 | Marien et al. |
| 5,378,848 A | 1/1995 | Takada et al. |
| 5,389,640 A | 2/1995 | Gerster et al. |
| 5,395,937 A | 3/1995 | Nikolaides et al. |

(Continued)

FOREIGN PATENT DOCUMENTS

AU     2004220534 A1    9/2004

(Continued)

OTHER PUBLICATIONS

Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983. Brennan et al., "Automated Bioassay of Interferons in Micro-test Plates.", *Biotechniques*, Jun./Jul., 78, 1983.
Testerman et al., "Cytokine Induction by the Immunomodulators Imiquimod and S-27609.", *Journal of Leukocyte Biology*, vol. 58, pp. 365-372, Sep. 1995.
Bachman et al., "Synthesis of Substituted Quinolylamines. Derivatives of 4-Amino-7-Chloroquinoline.", *J. Org. Chem*, 15, pp. 1278-1284 (1950).
Jain et al., "Chemical and Pharmacological Investigations of Some ω-Substituted Alkylamino-3-aminopyridines.", *J. Med. Chem.*, 11, pp. 87-92 (1968).

(Continued)

*Primary Examiner* — D. Margaret Seaman
(74) *Attorney, Agent, or Firm* — Wolf, Greenfield & Sacks, P.C.; C. Hunter Baker

(57) ABSTRACT

Imidazonaphthyridine ring systems substituted with an aryl substituent, pharmaceutical compositions containing the compounds, and methods of use of these compounds as immunomodulators, for inducing cytokine biosynthesis in animals and in the treatment of diseases including viral and neoplastic diseases are disclosed.

20 Claims, No Drawings

U.S. PATENT DOCUMENTS

| | | |
|---|---|---|
| 5,444,065 A | 8/1995 | Nikolaides et al. |
| 5,446,153 A | 8/1995 | Llindstrom et al. |
| 5,446,160 A | 8/1995 | Stucky et al. |
| 5,482,936 A | 1/1996 | Lindstrom |
| 5,494,916 A | 2/1996 | Lindstrom et al. |
| 5,500,228 A | 3/1996 | Lawter et al. |
| 5,525,612 A | 6/1996 | Gerster |
| 5,530,114 A | 6/1996 | Bennett et al. |
| 5,569,450 A | 10/1996 | Duan et al. |
| 5,571,819 A | 11/1996 | Sabb et al. |
| 5,578,727 A | 11/1996 | Andre et al. |
| 5,585,612 A | 12/1996 | Harp, Jr. |
| 5,602,256 A | 2/1997 | Andr e et al. |
| 5,605,899 A | 2/1997 | Gerster et al. |
| 5,612,377 A | 3/1997 | Crooks et al. |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,731,193 A | 3/1998 | Mori et al. |
| 5,736,553 A | 4/1998 | Wick et al. |
| 5,741,908 A | 4/1998 | Gerster et al. |
| 5,741,909 A | 4/1998 | Gerster et al. |
| 5,750,134 A | 5/1998 | Scholz et al. |
| 5,756,747 A | 5/1998 | Gerster et al. |
| 5,776,432 A | 7/1998 | Schultz et al. |
| 5,780,045 A | 7/1998 | McQuinn et al. |
| 5,837,809 A | 11/1998 | Grandy et al. |
| 5,840,744 A | 11/1998 | Borgman |
| 5,854,257 A | 12/1998 | Armitage et al. |
| 5,861,268 A | 1/1999 | Tang et al. |
| 5,886,006 A | 3/1999 | Nikolaides et al. |
| 5,939,047 A | 8/1999 | Jernberg |
| 5,939,090 A | 8/1999 | Beaurline et al. |
| 5,962,479 A | 10/1999 | Chen |
| 5,962,636 A | 10/1999 | Bachmaier et al. |
| 5,977,366 A | 11/1999 | Gerster et al. |
| 6,028,076 A | 2/2000 | Hirota et al. |
| 6,039,969 A | 3/2000 | Tomai et al. |
| 6,057,371 A | 5/2000 | Glennon |
| 6,069,140 A | 5/2000 | Sessler et al. |
| 6,069,149 A | 5/2000 | Nanba et al. |
| 6,071,949 A | 6/2000 | Mulshine et al. |
| 6,077,349 A | 6/2000 | Kikuchi |
| 6,083,505 A | 7/2000 | Miller et al. |
| 6,110,929 A | 8/2000 | Gerster et al. |
| 6,113,918 A | 9/2000 | Johnson et al. |
| 6,121,323 A | 9/2000 | Merrill |
| 6,123,957 A | 9/2000 | Jernberg |
| 6,126,938 A | 10/2000 | Guy et al. |
| 6,194,388 B1 | 2/2001 | Krieg et al. |
| 6,194,425 B1 | 2/2001 | Gerster et al. |
| 6,200,592 B1 | 3/2001 | Tomai et al. |
| 6,207,646 B1 | 3/2001 | Krieg et al. |
| 6,239,116 B1 | 5/2001 | Krieg et al. |
| 6,245,776 B1 | 6/2001 | Skwierczynski et al. |
| 6,294,271 B1 | 9/2001 | Sumita et al. |
| 6,303,347 B1 | 10/2001 | Johnson et al. |
| 6,309,623 B1 | 10/2001 | Weers et al. |
| 6,315,985 B1 | 11/2001 | Wu et al. |
| 6,323,200 B1 | 11/2001 | Gerster et al. |
| 6,329,381 B1 | 12/2001 | Kurimoto et al. |
| 6,331,539 B1 | 12/2001 | Crooks et al. |
| 6,339,068 B1 | 1/2002 | Krieg et al. |
| 6,348,462 B1 | 2/2002 | Gerster et al. |
| 6,365,166 B2 | 4/2002 | Beaurline et al. |
| 6,376,501 B1 | 4/2002 | Isobe et al. |
| 6,376,669 B1 | 4/2002 | Rice et al. |
| 6,387,383 B1 | 5/2002 | Dow et al. |
| 6,387,938 B1 | 5/2002 | Mizuguchi et al. |
| 6,406,705 B1 | 6/2002 | Davis et al. |
| 6,426,334 B1 | 7/2002 | Agrawal et al. |
| 6,440,992 B1 | 8/2002 | Gerster et al. |
| 6,451,485 B1 | 9/2002 | James et al. |
| 6,451,810 B1 | 9/2002 | Coleman et al. |
| 6,465,654 B2 | 10/2002 | Gerster et al. |
| 6,476,000 B1 | 11/2002 | Agrawal |
| 6,486,168 B1 | 11/2002 | Skwierczynski et al. |
| 6,486,186 B2 | 11/2002 | Fowler et al. |
| 6,511,485 B2 | 1/2003 | Hirt et al. |
| 6,514,985 B1 | 2/2003 | Gerster et al. |
| 6,518,239 B1 | 2/2003 | Kuo et al. |
| 6,518,265 B1 | 2/2003 | Kato et al. |
| 6,518,280 B2 | 2/2003 | Gerster et al. |
| 6,525,028 B1 | 2/2003 | Johnson et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,582,957 B1 | 6/2003 | Turner, Jr. et al. |
| 6,610,319 B2 | 8/2003 | Tomai et al. |
| 6,627,638 B2 | 9/2003 | Gerster et al. |
| 6,627,639 B2 | 9/2003 | Stack et al. |
| 6,627,640 B2 | 9/2003 | Gerster et al. |
| 6,630,588 B2 | 10/2003 | Rice et al. |
| 6,638,944 B2 | 10/2003 | Mickelson |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,334 B2 | 1/2004 | Gerster et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,780,873 B2 | 8/2004 | Crooks et al. |
| 6,784,188 B2 | 8/2004 | Crooks et al. |
| 6,790,961 B2 | 9/2004 | Gerster et al. |
| 6,797,718 B2 | 9/2004 | Dellaria et al. |
| 6,800,624 B2 | 10/2004 | Crooks et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,855,217 B2 | 2/2005 | Suzuki |
| 6,855,350 B2 | 2/2005 | Lu |
| 6,878,719 B2 | 4/2005 | Lindstrom et al. |
| 6,888,000 B2 | 5/2005 | Crooks et al. |
| 6,894,060 B2 | 5/2005 | Slade |
| 6,894,165 B2 | 5/2005 | Gerster et al. |
| 6,897,221 B2 | 5/2005 | Crooks et al. |
| 6,900,016 B1 | 5/2005 | Venter et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,240 B2 | 9/2005 | Bauer et al. |
| 6,943,255 B2 | 9/2005 | Lindstrom et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,253 B2 | 7/2006 | Brunner et al. |
| 7,078,523 B2 | 7/2006 | Crooks et al. |
| 7,091,214 B2 | 8/2006 | Hays et al. |

| | | | | | |
|---|---|---|---|---|---|
| 7,098,221 B2 | 8/2006 | Heppner et al. | 2004/0192585 A1 | 9/2004 | Fox et al. |
| 7,112,677 B2 | 9/2006 | Griesgraber | 2004/0197865 A1 | 10/2004 | Gupta et al. |
| 7,115,622 B2 | 10/2006 | Crooks et al. | 2004/0202720 A1 | 10/2004 | Wightman et al. |
| 7,125,890 B2 | 10/2006 | Dellaria et al. | 2004/0204436 A1 | 10/2004 | Gerster et al. |
| 7,132,429 B2 | 11/2006 | Griesgraber et al. | 2004/0214851 A1 | 10/2004 | Birmachu et al. |
| 7,163,947 B2 | 1/2007 | Griesgraber et al. | 2004/0258698 A1 | 12/2004 | Wightman et al. |
| 7,179,253 B2 | 2/2007 | Graham et al. | 2004/0265351 A1 | 12/2004 | Miller et al. |
| 7,199,131 B2 | 4/2007 | Lindstrom | 2005/0009858 A1 | 1/2005 | Martinez-Colon et al. |
| 7,214,675 B2 | 5/2007 | Griesgraber | 2005/0032829 A1 | 2/2005 | Lindstrom et al. |
| 7,220,758 B2 | 5/2007 | Dellaria et al. | 2005/0048072 A1 | 3/2005 | Kedl et al. |
| 7,226,928 B2 | 6/2007 | Mitra et al. | 2005/0054590 A1 | 3/2005 | Averett |
| 7,276,515 B2 | 10/2007 | Dellaria et al. | 2005/0054640 A1 | 3/2005 | Griesgraber et al. |
| 7,288,550 B2 | 10/2007 | Dellaria et al. | 2005/0054665 A1 | 3/2005 | Miller et al. |
| 7,375,180 B2 | 5/2008 | Gorden et al. | 2005/0059072 A1 | 3/2005 | Birmachu et al. |
| 7,387,271 B2 | 6/2008 | Noelle et al. | 2005/0070460 A1 | 3/2005 | Hammerbeck et al. |
| 7,393,859 B2 | 7/2008 | Coleman et al. | 2005/0085500 A1 | 4/2005 | Gutman et al. |
| 7,427,629 B2 | 9/2008 | Kedl et al. | 2005/0096259 A1 | 5/2005 | Tomai et al. |
| 7,544,697 B2 | 6/2009 | Hays et al. | 2005/0119273 A1 | 6/2005 | Lipford et al. |
| 7,598,382 B2 | 10/2009 | Hays et al. | 2005/0136065 A1 | 6/2005 | Valiante |
| 7,612,083 B2 | 11/2009 | Griesgraber | 2005/0148620 A1 | 7/2005 | Crooks et al. |
| 7,648,997 B2 | 1/2010 | Kshirsagar et al. | 2005/0158325 A1 | 7/2005 | Hammerbeck et al. |
| 2001/0046968 A1 | 11/2001 | Zagon et al. | 2005/0165236 A1 | 7/2005 | Colombo et al. |
| 2002/0016332 A1 | 2/2002 | Slade | 2005/0171072 A1 | 8/2005 | Tomai et al. |
| 2002/0055517 A1 | 5/2002 | Smith | 2005/0226878 A1 | 10/2005 | Tomai et al. |
| 2002/0058674 A1 | 5/2002 | Hedenstrom et al. | 2005/0234088 A1 | 10/2005 | Griesgraber |
| 2002/0107262 A1 | 8/2002 | Lindstrom | 2005/0239733 A1 | 10/2005 | Jurk et al. |
| 2002/0110840 A1 | 8/2002 | Tomai et al. | 2005/0239735 A1 | 10/2005 | Miller et al. |
| 2002/0137101 A1 | 9/2002 | Meyers | 2005/0245562 A1 | 11/2005 | Garcia-Echeverria et al. |
| 2002/0173655 A1 | 11/2002 | Dellaria et al. | 2005/0267145 A1 | 12/2005 | Merrill et al. |
| 2002/0193729 A1 | 12/2002 | Cormier et al. | 2005/0281813 A1 | 12/2005 | Dedera et al. |
| 2003/0022302 A1 | 1/2003 | Lewis et al. | 2006/0009482 A1 | 1/2006 | Tomai et al. |
| 2003/0044429 A1 | 3/2003 | Aderem et al. | 2006/0100229 A1 | 5/2006 | Hays et al. |
| 2003/0082108 A1 | 5/2003 | Mulshine et al. | 2006/0106052 A1 | 5/2006 | Crooks et al. |
| 2003/0088102 A1 | 5/2003 | Matsubara et al. | 2006/0188913 A1 | 8/2006 | Krieg et al. |
| 2003/0096835 A1 | 5/2003 | Crooks et al. | 2007/0060754 A1 | 3/2007 | Lindstrom et al. |
| 2003/0096998 A1 | 5/2003 | Gerster et al. | 2007/0066639 A1* | 3/2007 | Kshirsagar et al. ........... 514/291 |
| 2003/0130299 A1 | 7/2003 | Crooks et al. | 2007/0072893 A1 | 3/2007 | Krepski et al. |
| 2003/0133733 A1 | 7/2003 | Korhonen | 2007/0099901 A1 | 5/2007 | Krepski et al. |
| 2003/0133913 A1 | 7/2003 | Tomai et al. | 2007/0155767 A1 | 7/2007 | Radmer et al. |
| 2003/0139364 A1 | 7/2003 | Krieg et al. | 2007/0166384 A1 | 7/2007 | Zarraga |
| 2003/0144283 A1 | 7/2003 | Coleman et al. | 2007/0167476 A1 | 7/2007 | Kshirsagar et al. |
| 2003/0144286 A1 | 7/2003 | Frenkel et al. | 2007/0208052 A1 | 9/2007 | Prince et al. |
| 2003/0158192 A1 | 8/2003 | Crooks et al. | 2007/0213356 A1* | 9/2007 | Merrill et al. ................. 514/293 |
| 2003/0161797 A1 | 8/2003 | Miller et al. | 2007/0219196 A1 | 9/2007 | Krepski et al. |
| 2003/0172391 A1 | 9/2003 | Turner et al. | 2007/0259881 A1 | 11/2007 | Dellaria et al. |
| 2003/0185835 A1 | 10/2003 | Braun | 2007/0259907 A1 | 11/2007 | Prince |
| 2003/0187016 A1 | 10/2003 | Crooks et al. | 2007/0287725 A1 | 12/2007 | Miser et al. |
| 2003/0199461 A1 | 10/2003 | Averett et al. | 2007/0292456 A1 | 12/2007 | Hammerbeck et al. |
| 2003/0199538 A1 | 10/2003 | Skwierczynski et al. | 2008/0015184 A1 | 1/2008 | Kshirsagar et al. |
| 2003/0212092 A1 | 11/2003 | Heppner et al. | 2008/0070907 A1 | 3/2008 | Griesgraber et al. |
| 2003/0216481 A1 | 11/2003 | Jia | 2008/0085895 A1 | 4/2008 | Griesgraber et al. |
| 2003/0232074 A1 | 12/2003 | Lipford et al. | 2008/0114019 A1* | 5/2008 | Kshirsagar et al. ........... 514/293 |
| 2003/0232763 A1 | 12/2003 | Jia | 2008/0119508 A1 | 5/2008 | Slade et al. |
| 2003/0232852 A1 | 12/2003 | Lindstrom et al. | 2008/0207674 A1 | 8/2008 | Stoesz et al. |
| 2004/0010007 A1 | 1/2004 | Dellaria et al. | 2008/0269192 A1 | 10/2008 | Griesgraber et al. |
| 2004/0014779 A1 | 1/2004 | Gorden et al. | 2008/0306252 A1 | 12/2008 | Crooks et al. |
| 2004/0023870 A1 | 2/2004 | Dedera et al. | 2008/0312434 A1 | 12/2008 | Lindstrom et al. |
| 2004/0067975 A1 | 4/2004 | Crooks et al. | 2008/0318998 A1 | 12/2008 | Prince et al. |
| 2004/0072858 A1 | 4/2004 | Charles et al. | 2009/0005371 A1 | 1/2009 | Rice et al. |
| 2004/0076633 A1 | 4/2004 | Thomsen et al. | 2009/0017076 A1 | 1/2009 | Miller et al. |
| 2004/0091491 A1 | 5/2004 | Kedl et al. | 2009/0018122 A1 | 1/2009 | Lindstrom et al. |
| 2004/0092545 A1 | 5/2004 | Crooks et al. | 2009/0023722 A1 | 1/2009 | Coleman et al. |
| 2004/0097542 A1 | 5/2004 | Crooks et al. | 2009/0029988 A1 | 1/2009 | Kshirsagar et al. |
| 2004/0106638 A1 | 6/2004 | Lindstrom | 2009/0030030 A1 | 1/2009 | Bonk et al. |
| 2004/0132079 A1 | 7/2004 | Gupta et al. | 2009/0030031 A1 | 1/2009 | Kshirsagar et al. |
| 2004/0132748 A1 | 7/2004 | Isobe et al. | 2009/0042925 A1* | 2/2009 | Kshirsagar et al. ........... 514/293 |
| 2004/0132766 A1 | 7/2004 | Griesgraber | 2009/0062272 A1 | 3/2009 | Bonk et al. |
| 2004/0141950 A1 | 7/2004 | Noelle et al. | 2009/0062328 A1* | 3/2009 | Kshirsagar et al. ........... 514/293 |
| 2004/0147543 A1 | 7/2004 | Hays et al. | 2009/0069299 A1 | 3/2009 | Merrill et al. |
| 2004/0157874 A1 | 8/2004 | Crooks et al. | 2009/0069314 A1 | 3/2009 | Kshirsagar et al. |
| 2004/0162309 A1 | 8/2004 | Gorden et al. | 2009/0075980 A1 | 3/2009 | Hays et al. |
| 2004/0167157 A1 | 8/2004 | Masui et al. | 2009/0099161 A1 | 4/2009 | Rice et al. |
| 2004/0171086 A1 | 9/2004 | Fink et al. | 2009/0105295 A1 | 4/2009 | Kshirsagar et al. |
| 2004/0175336 A1 | 9/2004 | Egging et al. | 2009/0124611 A1 | 5/2009 | Hays et al. |
| 2004/0176367 A1 | 9/2004 | Griesgraber et al. | 2009/0163532 A1 | 6/2009 | Perman et al. |
| 2004/0180919 A1 | 9/2004 | Lee et al. | 2009/0163533 A1 | 6/2009 | Hays et al. |
| 2004/0181130 A1 | 9/2004 | Fox et al. | 2009/0176821 A1 | 7/2009 | Kshirsagar et al. |
| 2004/0181211 A1 | 9/2004 | Elliott et al. | 2009/0240055 A1 | 9/2009 | Krepski et al. |
| 2004/0191833 A1 | 9/2004 | Fink et al. | 2009/0253695 A1 | 10/2009 | Kshirsagar et al. |

| | | | |
|---|---|---|---|
| 2009/0270443 A1 | 10/2009 | Stoermer et al. | |
| 2009/0318435 A1 | 12/2009 | Hays et al. | |
| 2010/0113565 A1 | 5/2010 | Gorden et al. | |

FOREIGN PATENT DOCUMENTS

| | | | |
|---|---|---|---|
| AU | 2004229478 A1 | 10/2004 | |
| AU | 2004264336 A1 | 2/2005 | |
| AU | 2004268625 A1 | 3/2005 | |
| AU | 2002239547 B2 | 11/2006 | |
| CA | 2044087 A1 | 12/1991 | |
| CA | 2158996 A1 | 10/1994 | |
| CN | 1354663 A | 6/2002 | |
| EP | 0 145 340 A2 | 6/1985 | |
| EP | 0 223 420 A1 | 5/1987 | |
| EP | 0 310 950 A1 | 4/1989 | |
| EP | 0 385 630 A2 | 9/1990 | |
| EP | 0 389 302 A1 | 9/1990 | |
| EP | 0 394 026 | 10/1990 | |
| EP | 0 425 306 A2 | 5/1991 | |
| EP | 0 510 260 A2 | 10/1992 | |
| EP | 0 556 008 A1 | 8/1993 | |
| EP | 0 645 389 A1 | 3/1995 | |
| EP | 0 778 277 A1 | 6/1997 | |
| EP | 0 894 797 A1 | 2/1999 | |
| EP | 1 082 96 A2 | 3/2001 | |
| EP | 1 097 709 A2 | 5/2001 | |
| EP | 1 104 764 | 6/2001 | |
| EP | 1 145 340 A2 | 10/2001 | |
| EP | 1 256 582 A1 | 11/2002 | |
| EP | 1 341 791 A2 | 9/2003 | |
| EP | 1 495 758 A2 | 1/2005 | |
| HU | 34479 A2 | 3/1985 | |
| HU | 210051 A2 | 6/1991 | |
| HU | 218950 A2 | 9/1995 | |
| IL | 73534 A | 12/1990 | |
| JP | 53050197 A | 5/1978 | |
| JP | 63010787 A | 1/1988 | |
| JP | 406657 A | 3/1992 | |
| JP | 4327587 A | 11/1992 | |
| JP | 5286973 A | 11/1993 | |
| JP | 9-208584 | 8/1997 | |
| JP | 11-080156 A | 3/1999 | |
| JP | 11-222432 | 8/1999 | |
| JP | 2000-247884 | 9/2000 | |
| NZ | 545412 A | 12/2008 | |
| RU | 2076105 C1 | 3/1997 | |
| RU | 2127273 C1 | 3/1999 | |
| RU | 2221798 C2 | 1/2004 | |
| WO | WO-91/06682 A1 | 5/1991 | |
| WO | WO-92/06093 A1 | 4/1992 | |
| WO | WO-92/1558 A1 | 9/1992 | |
| WO | WO-92/15582 A1 | 9/1992 | |
| WO | WO-93/05042 A1 | 3/1993 | |
| WO | WO-93/09119 A1 | 5/1993 | |
| WO | WO-93/20847 A1 | 10/1993 | |
| WO | WO-94/10171 A1 | 5/1994 | |
| WO | WO-95/02597 A1 | 1/1995 | |
| WO | WO-95/02598 A1 | 1/1995 | |
| WO | WO-96/11199 A1 | 4/1996 | |
| WO | WO-96/21663 A1 | 7/1996 | |
| WO | WO-97/48703 A1 | 12/1997 | |
| WO | WO-97/48704 A1 | 12/1997 | |
| WO | WO-98/17279 A1 | 4/1998 | |
| WO | WO-98/30562 A1 | 7/1998 | |
| WO | WO-98/48805 A1 | 11/1998 | |
| WO | WO-98/50547 A2 | 11/1998 | |
| WO | WO-98/54226 A1 | 12/1998 | |
| WO | WO-99/18105 A1 | 4/1999 | |
| WO | WO-99/29693 A1 | 6/1999 | |
| WO | WO-00/06577 A1 | 2/2000 | |
| WO | WO-00/09506 A1 | 2/2000 | |
| WO | WO-00/19987 A1 | 4/2000 | |
| WO | WO-00/40228 A2 | 7/2000 | |
| WO | WO-00/47719 A2 | 8/2000 | |
| WO | WO-00/76505 A1 | 12/2000 | |
| WO | WO-00/76518 A1 | 12/2000 | |
| WO | WO-00/76519 A1 | 12/2000 | |
| WO | WO-00175304 A1 | 12/2000 | |
| WO | WO-01/34709 A1 | 5/2001 | |
| WO | WO-01/51486 A2 | 7/2001 | |
| WO | WO-01/55439 A1 | 8/2001 | |
| WO | WO-01/58900 A1 | 8/2001 | |
| WO | WO-01/74343 A2 | 10/2001 | |
| WO | WO-01/74821 A1 | 10/2001 | |
| WO | WO-02/07725 A1 | 1/2002 | |
| WO | WO-02/22809 A2 | 3/2002 | |
| WO | WO-02/24225 A1 | 3/2002 | |
| WO | WO 02/36592 | 5/2002 | |
| WO | WO-02/46188 A2 | 6/2002 | |
| WO | WO-02/46189 A2 | 6/2002 | |
| WO | WO-02/46190 A2 | 6/2002 | |
| WO | WO-02/46191 A2 | 6/2002 | |
| WO | WO-02/46192 A2 | 6/2002 | |
| WO | WO-02/46193 A2 | 6/2002 | |
| WO | WO-02/46194 A2 | 6/2002 | |
| WO | WO-02/46749 A2 | 6/2002 | |
| WO | WO-02/85905 A1 | 10/2002 | |
| WO | WO-02/102377 A1 | 12/2002 | |
| WO | WO-03/008421 A1 | 1/2003 | |
| WO | WO-03/09852 A1 | 2/2003 | |
| WO | WO-03/20889 A2 | 3/2003 | |
| WO | WO-03/43572 A2 | 5/2003 | |
| WO | WO-03/45391 A1 | 6/2003 | |
| WO | WO-03/45494 A2 | 6/2003 | |
| WO | WO-03/45929 A1 | 6/2003 | |
| WO | WO-03/50117 A1 | 6/2003 | |
| WO | WO-03/50118 A1 | 6/2003 | |
| WO | WO-03/50119 A2 | 6/2003 | |
| WO | WO-03/50121 A1 | 6/2003 | |
| WO | 03/077944 A1 | 9/2003 | |
| WO | WO-03/80114 A2 | 10/2003 | |
| WO | WO-03/86280 A2 | 10/2003 | |
| WO | WO-03/86350 A1 | 10/2003 | |
| WO | WO-03/89602 A2 | 10/2003 | |
| WO | WO-03/97641 A2 | 11/2003 | |
| WO | WO-03/101949 A2 | 12/2003 | |
| WO | WO-03/103584 A2 | 12/2003 | |
| WO | WO-2004/009593 A1 | 1/2004 | |
| WO | WO-2004/028539 A1 | 4/2004 | |
| WO | WO-2004/041285 A1 | 5/2004 | |
| WO | WO-2004/043913 A2 | 5/2004 | |
| WO | WO-2004/053057 A2 | 6/2004 | |
| WO | WO-2004/053452 A2 | 6/2004 | |
| WO | WO-2004/058759 A1 | 7/2004 | |
| WO | WO-2004/071459 A2 | 8/2004 | |
| WO | WO-2004/075865 A2 | 9/2004 | |
| WO | WO-2004/080398 A2 | 9/2004 | |
| WO | WO-2004/091500 A2 | 10/2004 | |
| WO | WO-2004/096144 A2 | 11/2004 | |
| WO | WO-2004/110991 A2 | 12/2004 | |
| WO | WO-2004/110992 A2 | 12/2004 | |
| WO | WO-2005/003064 A2 | 1/2005 | |
| WO | WO-2005/003065 A2 | 1/2005 | |
| WO | WO-2005/016273 A2 | 2/2005 | |
| WO | WO-2005/016275 A2 | 2/2005 | |
| WO | WO 2005/018551 | 3/2005 | |
| WO | WO 2005/018555 | 3/2005 | |
| WO | WO 2005/018556 | 3/2005 | |
| WO | WO 2005/020999 | 3/2005 | |
| WO | WO-2005/023190 A2 | 3/2005 | |
| WO | WO-2005/025614 A2 | 3/2005 | |
| WO | WO-2005/029037 A2 | 3/2005 | |
| WO | WO 2005/032484 | 4/2005 | |
| WO | WO-2005/041891 A2 | 5/2005 | |
| WO | WO 2005/048933 | 6/2005 | |
| WO | WO 2005/048945 | 6/2005 | |
| WO | WO-2005/049076 A1 | 6/2005 | |
| WO | WO 2005/051317 | 6/2005 | |
| WO | WO 2005/051324 | 6/2005 | |
| WO | WO 2005/054237 | 6/2005 | |
| WO | WO 2005/054238 | 6/2005 | |
| WO | WO-2005/065678 A1 | 7/2005 | |
| WO | WO 2005/066169 | 7/2005 | |
| WO | WO 2005/066170 | 7/2005 | |
| WO | WO 2005/066172 | 7/2005 | |
| WO | WO-2005/067500 A2 | 7/2005 | |
| WO | WO 2005/076783 | 8/2005 | |
| WO | WO 2005/079195 | 9/2005 | |

| | | |
|---|---|---|
| WO | WO 2005/094531 | 10/2005 |
| WO | WO-2005/110013 A2 | 11/2005 |
| WO | WO 2005/123079 | 12/2005 |
| WO | WO 2005/123080 | 12/2005 |
| WO | WO 2006/009826 | 1/2006 |
| WO | WO 2006/009832 | 1/2006 |
| WO | WO 2006/026760 | 3/2006 |
| WO | WO 2006/028451 | 3/2006 |
| WO | WO 2006/028545 | 3/2006 |
| WO | WO 2006/028962 | 3/2006 |
| WO | WO 2006/029115 | 3/2006 |
| WO | WO 2006/031878 | 3/2006 |
| WO | WO 2006/038923 | 4/2006 |
| WO | WO-2006/063072 A2 | 6/2006 |
| WO | WO-2006/063152 A2 | 6/2006 |
| WO | WO 2006/065280 | 6/2006 |
| WO | WO-2006/073940 A2 | 7/2006 |
| WO | WO 2006/074003 | 7/2006 |
| WO | WO-2006/074045 A2 | 7/2006 |
| WO | WO 2006/004737 | 8/2006 |
| WO | WO 2006/083400 | 8/2006 |
| WO | WO 2006/083440 | 8/2006 |
| WO | WO-2006/084251 A2 | 8/2006 |
| WO | WO 2006/086449 | 8/2006 |
| WO | WO 2006/086633 | 8/2006 |
| WO | WO-2006/086634 A2 | 8/2006 |
| WO | WO 2006/091394 | 8/2006 |
| WO | WO 2006/091567 | 8/2006 |
| WO | WO 2006/091568 | 8/2006 |
| WO | WO 2006/091647 | 8/2006 |
| WO | WO-2006/093514 A2 | 9/2006 |
| WO | WO 2006/098852 | 9/2006 |
| WO | WO-2006/107753 A2 | 10/2006 |
| WO | WO 2006/107771 | 10/2006 |
| WO | WO 2006/107851 | 10/2006 |
| WO | WO 2006/107853 | 10/2006 |
| WO | WO 2006/121528 | 11/2006 |
| WO | WO-2006/122806 A2 | 11/2006 |
| WO | WO 2007/028129 | 3/2007 |
| WO | WO 2007/030775 | 3/2007 |
| WO | WO 2007/030777 | 3/2007 |
| WO | WO-2007/035935 A1 | 3/2007 |
| WO | WO-2007/056112 A2 | 5/2007 |
| WO | WO-2007/062043 A1 | 5/2007 |
| WO | WO-2007/075468 A1 | 7/2007 |
| WO | WO-2007/079086 A1 | 7/2007 |
| WO | WO-2007/079146 A1 | 7/2007 |
| WO | WO-2007/079169 A2 | 7/2007 |
| WO | WO-2007/079171 A2 | 7/2007 |
| WO | WO-2007/079202 A2 | 7/2007 |
| WO | WO-2007/079203 A2 | 7/2007 |
| WO | WO-2007/092641 A2 | 8/2007 |
| WO | WO-2007/106852 A2 | 9/2007 |
| WO | WO-2007/106854 A2 | 9/2007 |
| WO | WO-2007/120121 A2 | 10/2007 |
| WO | WO-2007/143526 A2 | 12/2007 |
| WO | WO-2008/008432 A2 | 1/2008 |
| WO | WO-2008/030511 A2 | 3/2008 |
| WO | WO-2008/036312 A1 | 3/2008 |
| WO | WO-2008/045543 A1 | 4/2008 |

OTHER PUBLICATIONS

Baranov et al., "Pyrazoles, Imidazoles, and Other 5-Membered Rings.", *Chem. Abs.* 85, 94362, (1976).
Berényi et al., "Ring Transformation of Condensed Dihydro-as-triazines.", *J. Heterocyclic Chem.*, 18, pp. 1537-1540 (1981).
Chollet et al., "Development of a Topically Active Imiquimod Formulation.", *Pharmaceutical Development and Technology*, 4(1), pp. 35-43 (1999).
Izumi et al., "1H-Imidazo[4,5-c]quinoline Derivatives as Novel Potent TNF-α Suppressors: Synthesis and Structure-Activity Relationship of 1-, 2- and 4-Substituted 1H-imidazo[4,5-c]pyridines.", *Bioorganic & Medicinal Chemistry*, 11, pp. 2541-2550 (2003).
International Search Report and Written Opinion for PCT/US2005/021436 mailed Apr. 4, 2006.
International Preliminary Report on Patentability for PCT/US2005/021436 mailed Dec. 20, 2006.
Park et al., Sodium Dithionite Reduction of Nitroarenes Using Viologen as an Electron Phase-Transfer Catalyst. Tetrahedron Lett. 1993;34(46):7445-7446.
Li et al., An improved protocol for the preparation of 3-pyridyl- and some arylboronic acids. J Org Chem. Jul. 26, 2002;67(15):5394-5397.
Zhang et al., Structural features of azidopyridinyl neonicotinoid probes conferring high affinity and selectivity for mammalian alpha4beta2 and Drosophila nicotinic receptors. J Med Chem. Jun. 20, 2002;45(13):2832-2840.
[No Author Listed] "Comparative Tests." Filed Apr. 8, 2005 during prosecution for EP 00938205.2, EP 00950215.4 and EP 00938211.0 in the name of 3M Innovative Properties Co.
[No Author Listed] Chemical Abstracts. 1964;61(1):6060g.
[No Author Listed] Encyclopedia of Pharmaceutical Technology. 2nd Ed. Marcel Dekker, Inc. 2002:856-860.
Agrawal et al., Synthetic agonists of Toll-like receptors 7, 8 and 9. Biochem Soc Trans. Dec. 2007;35(Pt 6):1461-1467.
Ahmed et al., A new rapid and simple non-radioactive assay to monitor and determine the proliferation of lymphocytes: an alternative to [3H]thymidine incorporation assay. J Immunol Methods. Apr. 15, 1994;170(2):211-224.
Akira et al., Recognition of pathogen-associated molecular patterns by TLR family. Immunol Lett. 2003;85:85-95.
Akira et al., Toll-like receptors: critical proteins linking innate and acquired immunity. Nature Immunol. 2001;2(8):675-680.
Alexopoulou et al., Recognition of double-stranded RNA and activation of NF-kappaB by Toll-like receptor 3. Nature. Oct. 18, 2001;413(6857):732-738.
Assuma et al., IL-1 and TNF Antagonists Inhibit the Inflammatory Response and Bone Loss in Experimental Periodontitis. J Immunol. 2000;160:403-409.
Au et al., Virus-mediated induction of interferon A gene requires cooperation between multiple binding factors in the interferon alpha promoter region. J Biol Chem. Nov. 15, 1993;268(32):24032-24040.
Auerbach et al., Erythema nodosum following a jellyfish sting. J Emerg Med. 1987 Nov-Dec;5(6):487-491.
Auwers, [Uber die Isomerie-Verhaltnisse in der Pyrazol-Reihe. Berichte. VI.] 1926;601-607. German.
Baffis et al., Use of interferon for prevention of hepatocellular carcinoma in cirrhotic patients with hepatitis B or hepatitis C virus infection. Ann Intern Med. Nov. 2, 1999;131(9):696-701.
Baker et al., Oral infection with Porphyromonas gingivalis and induced alveolar bone loss in immunocompetent and severe combined immunodeficient mice. Arch Oral Biol. Dec. 1994;39(12):1035-1040.
Baldwin et al., Amino Acid Synthesis viaRing Opening of N-Sulphonyl Aziridine-2-Carboxylate Esters with Organometallic Reagents. Tetrahedron. 1993;49:6309-6330.
Bártováet al., Th1 and Th2 cytokine profile in patients with early onset periodontitis and their healthy siblings. Mediators Inflamm. 2000;9(2):115-120.
Beck et al., Dental Infections and Atherosclerosis. Am Heart J. 1999;13:528-533.
Beckett et al., Configurational Studies in Synthetic Analgesics: the Synthesis of (-)- Methadone from D-(-)- Alanine. J Chem Soc. 1957;1:858-861.
Beilman et al., Experimental brown spider bite in the guinea pig: Results of treatment with dapsone or hyperbaric oxygen. J Wilderness Medicine. 1994;5:287-294.
Belikov, Abbreviated Guide to Synthetic and Natural Medications. Pharmaceutical Chemistry. Higher School. 1993;1:43-47. Russian.
Beltrami et al., Some Methylhydrazonium Salts; An Improved Synthesis of Tetramethylhydrazine. J Am Chem Soc. 1956;78:2467-2468.
Bernstein et al., Daily or weekly therapy with resiquimod (R-848) reduces genital recurrences in herpes simplex virus-infected guinea pigs during and after treatment. J Infect Dis. Mar. 15, 2001;183(6):844-849. Epub Feb. 13, 2001.
Bertino et al., Principles of Cancer Therapy. Cecil Textbook of Medicine. Goldman et al., eds. 21th Ed. W.B. Saunders Company. 2000:1:1060-1074.
Beutler et al., Tumor necrosis factor in the pathogenesis of infectious diseases. Crit Care Med. Oct. 1993;21(10 Suppl):S423-S435.

Beutner et al., Therapeutic response of basal cell carcinoma to the immune response modifier imiquimod 5% cream. J Am Acad Dermatol. Dec. 1999;41(6):1002-1007.

Beutner et al., Treatment of genital warts with an immune-response modifier (imiquimod). J Am Acad Dermatol. Feb. 1998;38(2 Pt 1):230-239.

Binder, Acute arthropod envenomation. Incidence, clinical features and management. Med Toxicol Adverse Drug Exp. May-Jun. 1989;4(3):163-173.

Bishop et al., Molecular mechanisms of B lymphocyte activation by the immune response modifier R-848. J Immunol. Nov. 15, 2000;165(10):5552-5557.

Bitterman-Deutsch et al., [Brown spider bite]. Harefuah. Sep. 1990:119(5-6):137-139. Hebrew.

Booth et al., Dapsone suppresses integrin-mediated neutrophil adherence function. J Invest Dermatol. Feb. 1992;98(2):135-140.

Borkan et al., An outbreak of venomous spider bites in a citrus grove. Am J Trop Med Hyg. Mar. 1995;52(3):228-230.

Bourke et al., The toll-like receptor repertoire of human B lymphocytes: inducible and selective expression of TLR9 and TLR10 in normal and transformed cells. Blood. Aug. 1, 2003;102(3):956-963. Epub Apr. 10, 2003.

Brants, The Distribution of Tobacco Mosaic Virus (TMV) in Excised Tomato Roots Cultivated in Vitro. Tijdschr Plantenziekten, 1962;68:198-207.

Brassard et al., Interferon-$\alpha$as an immunotherapeutic protein. J Leukoc Biol. Apr. 2002;71(4):565-581.

Breathnach, Azelaic acid: potential as a general antitumoural agent. Med Hypotheses. Mar. 1999;52(3):221-226.

Broughton, Management of the brown recluse spider bite to the glans penis. Mil Med. Oct. 1996;161(10):627-629.

Buckle et at., 4-hydroxy-3-nitro-2-quinolones and related compounds as inhibitors of allergic reactions. J Med Chem. Jul. 1975;18(7):726-732.

Buisson et al., Preparation and use of (S)-O-acetyllactyl chloride (Mosandl's reagent) as a chiral derivatizing agent. Tetrahedron Assym. 1999;10:2997-3002.

Bulut et al., Cooperation of Toll-like receptor 2 and 6 for cellular activation by soluble tuberculosis factor and Borrelia burgdorferi outer surface protein A lipoprotein: role of Toll-interacting protein and IL-1 receptor signaling molecules in Toll-like receptor 2 signaling. J Immunol. Jul. 15, 2001;167(2):987-994.

Burleson, Chapter 14. Influenza Virus Host Resistance Model for Assessment of Immunostimulation, and Antiviral Compounds. Methods in Immunology. 1995;2:181-202.

Buschle et al., Interferon $\gamma$ inhibits apoptotic cell death in B cell chronic lymphocytic leukemia. J Exp Med. Jan. 1993 1;177(1):213-218.

Cai et al., Evaluation of trifluoroacetic acid as an ion-pair reagent in the separation of small ionizable molecules by reversed-phase liquid chromatography. Analytica Chmica Acta. 1999;399:249-258.

Cantell et al., IFN-$\gamma$ Enhances Production of IFN-$\alpha$ in Human Macrophages but Not in Monocytes. J Interferon and Cytokine Res. 1996;16:461-463.

Carceller et al., Design, synthesis, and structure-activity relationship studies of novel 1- [(1-acyl-4-piperidyl)methyl]-1H-2-methylimidazo[4,5-c]pyridine derivatives as potent, orally active platelet-activating factor antagonists. J Med Chem. Jan. 19, 1996;39(2):487-493.

Carrigan et al., Synthesis and in vitro pharmacology of substituted quinoline-2,4-dicarboxylic acids as inhibitors of vesicular glutamate transport. J Med Chem. May 23, 2002;45(11):2260-2276.

Catarzi et al., Tricyclic heteroaromatic systems. Pyrazolo[3,4-c]quinolin-4-ones and pyrazolo[3,4-c]quinoline-1,4-diones: synthesis and benzodiazepine receptor activity. Arch Pharm (Weinheim). Dec. 1997;330(12):383-386.

Cheson et al., National Cancer Institute-sponsored Working Group guidelines for chronic lymphocytic leukemia: revised guidelines for diagnosis and treatment. Blood. Jun. 15, 1996;87(12):4990-4997.

Chuang et al., Toll-like receptor 9 mediates CpG-DNA signaling. J Leukoc Biol. Mar. 2002;71(3): 538-544.

Claisen, [Uber $\alpha$-Methyl-isoxazol.] Berichte. 1909;42:59-69. German.

Cohen et al., Cytokine function: a study in biologic diversity. Am J Clin Pathol. May 1996;105(5):589-598,.

Cole et al., Brown recluse spider envenomation of the eyelid: an animal model. Ophthal Plast Reconstr Surg. Sep. 1995;11(3):153-164.

Colotta at al., Synthesis and structure-activity relationships of a new set of 2-arylpyrazolo[3,4-c]quinoline derivatives as adenosine receptor antagonists. J Med Chem. Aug. 10, 2000;43(16):3118-3124.

Cristalli at al., Adenosine deaminase inhibitors: synthesis and structure-activity relationships of imidazole analogues of erythro-9-(2-hydroxy-3-nonyl)adenine. J Med Chem. Mar. 1991;34(3):1187-1192.

Dai et al., Synthesis of a novel C2-symmetric thiourea and its application in the Pd-catalyzed cross-coupling reactions with arenediazonium salts under aerobic conditions. Org Lett. Jan. 22, 2004;6(2):221-224.

Davis, Current therapy for chronic hepatitis C. Gastroenterology. Feb. 2000;118(2 Suppl 1):S104-S114.

Davis et al., Heterocyclic Syntheses with Malonyl Chloride. Part VI. 3-Substituted Pyridine Derivatives from $\alpha$-Methylene-nitriles. J Chem Soc. 1962:3638-3644.

Davis at al., Self-administered topical imiquimod treatment of vulvar intraepithelial neoplasia. A report of four cases. J Reprod Med. Aug. 2000;45(8):619-623.

De et al., Structure-activity relationships for antiplasmodial activity among 7-substituted 4-aminoquinolines. J Med Chem. Dec. 3, 1998;41(25):4918-4926.

Debol et al., Anti-inflammatory action of dapsone: inhibition of neutrophil adherence is associated with inhibition of chemoattractant-induced signal transduction. J Leukoc Biol. Dec. 1997;62(6):827-836.

De Clerq, Synthetic interferon inducers. Top Curr Chem. 1974;52:173-208.

Decker et al., Immunostimulatory CpG-oligonucleotides cause proliferation, cytokine production, and an immunogenic phenotype in chronic lymphocytic leukemia B cells. Blood. Feb. 1, 2000;95(3):999-1006.

Decker et al., Immunostimulatory CpG-oligonucleotides induce functional high affinity IL-2 receptors on B-CLL cells: costimulation with IL-2 results in a highly immunogenic phenotype. Exp Hematol. May 2000;28(5):558-568.

Delgado, Textbook of Organic Medicinal and Pharmaceutical Chemistry, Ninth Edition, Remers, ed., 1991:30-31.

Denzel et al. Imidazo [4,5-c]- and [4,5-b]pyridines. J. Heterocyclic Chem. 1977;14:813-821.

Diaz-Arrastia et al., Clinical and molecular responses in high-grade intraepithelial neoplasia treated with topical imiquimod 5%. Clin Cancer Res. Oct. 2001;7(10):3031-3033.

Di Carlo et al., Neutrophils in anti-cancer immunological strategies: old players in new games. J Hematother Stem Cell Res. Dec. 2001;10(6):739-748.

Dicken et al., Reactions at High Pressures. [3 + 2 ]Dipolar Cycloaddition of Nitrones with Vinyl Ethers. J Org Chem. 1982;47:2047-2051.

Dockrell et al., Imiquimod and resiquimod as novel immunomodulators. J Antimicrob Chemother. Dec. 2001;48(6):751-755.

Dorwald, "Preface." Side Reactions in Organic Synthesis. A Guide to Successful Synthesis Design. Wiley-VCH. 2005: IX.

Douglas, Introduction to Viral Diseases. In: Cecil Textbook of Medicine. Bennet et al., eds. 20th Ed. W.B. Saunders Company. 1996:2:1739-1747.

Doyle et al., Toll-like receptor 3 mediates a more potent antiviral response than Toll-like receptor 4. J Immunol. Apr. 1, 2003;170(7):3565-3571.

Drexler et al., Bryostatin 1 induces differentiation of B-chronic lymphocytic leukemia cells. Blood. Oct. 1989;74(5):1747-1757.

Dzionek et al. BDCA-2, BDCA-3, and BDCA-4: three markers for distinct subsets of dendritic cells in human peripheral blood. J Immunol. Dec. 1, 2000;165(11):6037-6046.

Edwards et al., Toll-like receptor expression in murine DC subsets: lack of TLR7 expression by CD8 alpha+ DC correlates with unresponsiveness to imidazoquinolines. Eur J Immunol. Apr. 2003;33(4):827-833.

Eriks et al., Histamine H2-receptor agonists. Synthesis, in vitro pharmacology, and qualitative structure-activity relationships of substituted 4- and 5-(2-aminoethyl)thiazoles. J Med Chem. Aug. 21, 1992;35(17):3239-3246.

Fecci et al., The history, evolution, and clinical use of dendritic cell-based immunization strategies in the therapy of brain tumors. J Neurooncol. Aug-Sep. 2003,64(1-2):161-176.

Fitzgerald-Bocarsly et al., Virally-Responsive IFN-α Producing Cells in Human Blood and Tonsil Are CD11C/CD123+Cells Identical to Precursors of Type Two Dendritic Cells (pDC2). J Interferon Cytokine Res. 1999;19(1):S117. Abstract P81.

Flo et al., Involvement of toll-like receptor (TLR) 2 and TLR4 in cell activation by mannuronic acid polymers. J Biol Chem. Sep. 20, 2002;277(38):35489-35495. Epub Jun. 27, 2002.

Fonteneau et al., Human Immunodeficiency Virus Type 1 Activates Plasmacytoid Dendritic Cells and Concomitantly Induces the Bystander Maturation of Myeloid Dendritic Cells. J Virol. 2004;78(10):5223-5232.

Frankel et al., The Preparation of N-Disubstituted Formamides. Tetrahedron Lett. 1959;7:5-7.

Frantz et al., Toll4 (TLR4) expression in cardiac myocytes in normal and failing myocardium. J Clin Invest. Aug. 1999;104(3):271-280.

Fu et al., Regioselective Catalytic Hydrogenation of Polycyclic Aromatic Hydocarbons under Mild conditions. J Org Chem. 1980;45:2979-803.

Fuchsberger et al., Priming Interferon-a 1 or Interferon-a 2 Enhances the Production of Both Subtypes Simultaneously. J Interferon and Cytokine Res. 1995;15:637-639.

Galose, Dapsone (diaminodiphenylsulphone DDS). Clinical Toxicology Review. 1999:21(9). 3 pages.

Gendron, Loxosceles ignali Envenomation. Am J Emerg Med. Jan. 1990;8(1):51-54.

Genevois-Borella et al., Synthesis of 1-(3-R-Amino-4-Hydroxy Butyl)thymine Acyclonucleoside. Analogs as Potential Anti-AIDS Drugs. Tetrahedron Lett. 1990;31:4879-4882.

Giannini et al., Influence of the Mucosal Epithelium Microenvironment on Langerhans Cells: Implications for the Development of Squamous Intraepithelial Lesions of the Cervix. Int J Cancer. 2002;97:654-659.

Gibson et al., Cellular requirements for cytokine production in response to the immunomodulators imiquimod and S-27609. J Interferon Cytokine Res. Jun. 1995:15(6):537-545.

Gibson et al., Plasmacytoid dendritic cells produce cytokines and mature in response to the TLR7 agonists, imiquimod and resiquimod. Cell Immunol. Jul-Aug. 2002;218(1-2):74-86.

Gitelson of al., Chronic lymphocytic leukemia-reactive T cells during disease progression and after autologous tumor cell vaccines. Clin Cancer Res May 2003;9(5):1656-1665.

Gomez et al., Intradermal anti-Loxosceles Fab fragments attenuate dermonecrotic arachnidism. Acad Emerg Med. 1999;6:1195-1202.

Gorden et al., Synthetic TLR agonists reveal functional differences between human TLR7 and TLR8. J Immunol. Feb. 1, 2005;174(3):1259-1268.

Gordon, Pattern recognition receptors: doubling up for the innate immune response. Cell. Dec. 27, 2002;111(7):927-930.

Gunning et al., Chemoprevention by lipoxygenase and leukotriene pathway inhibitors of vinyl carbamate-induced lung tumors in mice. Cancer Res. Aug. 1, 2002;62(15):4199-4201.

Gürsel et al., Differential and competitive activation of human immune cells by distinct classes of CpG oligodeoxynucleotide. J Leukoc Biol. May 2002;71(5):813-820.

Hart, Napthyridines Hydroxynaphthyridies, Journal of Chemical Society, 1956 Part III:212-214.

Hartmann et al., Rational design of new CpG oligonucleotides that combine B cell activation with high IFN-alpha induction in plasmacytoid dendritic cells. Eur J Immunol. Jun. 2003;33(6):1633-1641.

Hayashi Toll-like receptors stimulate human neutrophil function. Blood. Oct 1, 2003;102(7):2660-2669. Epub Jun. 26, 2003.

Hayes et al., Regulation of Interferon Production by Human Monocytes: Requirements for Priming for Lipopolysaccharide-Induced Production. J Leukocyte Biol. 1991;50:176-781.

Heil et al., Species-specific recognition of single-stranded RNA via toll-like receptor 7 and 8. Science. Mar. 5, 2004;303(5663):1526-1529. Epub Feb. 19, 2004.

Heil et al., Synthetic immunostimulatory compounds activate immune cells via TLR7 and TLR8. 33th Annual Meeting of the Deutsche Gessellschaft Mr Immunologie, Marburg 2002. Abstract C.6.

Hemmi et al., Small anti-viral compounds activate immune cells via the TLR7 MyD88-dependent signaling pathway. Nat Immunol. Feb. 2002;3(2):196-200. Epub Jan. 22, 2002.

Hobbs et al., Comparison of hyperbaric oxygen and dapsone therapy for loxosceles envenomation. Acad Emerg Med. Aug. 1996;3(8):758-761.

Hoffman et al., Conformational requirements for histamine H2-receptor inhibitors: a structure-activity study of phenylene analogues related to cimetidine and tiotidine. J Med Chem. Feb. 1983;26(2):140-144.

Hofmanováet al., Lipoxygenase inhibitors induce arrest of tumor cells in S-phase of the cell cycle. Neoplasma. 2002;49(6):362-367.

Holladay et al., Structure-activity studies related to ABT-594, a potent nonopioid analgesic agent: effect of pyridine and azetidine ring substitutions on nicotinic acetylcholine receptor binding affinity and analgesic activity in mice. Bioorg Med Chem Lett. Oct. 6, 1998;8(19):2797-2802.

Horng et al., the adaptor molecule TIRAP provides signaling specificity for Toll-like receptors. Nature. Nov. 21, 2002;420(6913):329-333.

Hornung et al., Quantitative Expression of Toll-Like Receptor 1-10 mRNA in Cellular Subsets of Human Peripheral Blood Mononuclear Cells and Sensitivity to CpG Oligodeoxynucleotides. Journal of Immunol. 2002;168:4531-4537.

Houben-Weyl, Quinoline and Isoquinoline. Methoden der Organischen Chemie. 1980:271-279. German.

Houston et al., Potential inhibitors of S-adenosylmethionine-dependent methyltransferases. 8. Molecular dissections of carbocyclic 3-deazaadenosine as inhibitors of S-adenosylhomocysteine hydrolase. J Med Chem. Apr. 1985;28(4):467-471.

Huppatz, Systemic fungicides. The synthesis of certain pyrazole analogues of carboxin. Aust J Chem. 1983;36:135-147.

Iino et al., Treatment of Chronic Hepatitis C With High-Dose Interferon α-2b. Multicenter Study. Dig Dis Sci. 1993;38(4):612-618.

Ito et al., Interferon-alpha and interleukin-12 are induced differentially by Toll-like receptor 7 ligands in human blood dendritic cell subsets. J Exp Med. Jun. 3, 2002;195(11):1507-1512.

Iwashita et al., Syntheses of Isoretronecanol and Lupinine. J Org Chem. 1982;47:230-233.

Jacobs, Chapter 1. The Synthesis of Acetylenes. In: Organic Reactions. New York: Wiley & Sons, Inc., 1949. vol. 5. 1-78.

Jahnsen et al., Extensive recruitment of IL-3Rahigh dendritic-cell precursors to allergic nasal mucosa during allergen challenge. Immunology Lett. 1999;69(1):123. Abstract #32.2.

Jurk et al. Human TLR7 and TLR8 independently confer responsiveness to the antiviral compound R-848. Nat Immunol. Jun. 2002;3(6):499.

Juweid, Radioimmunotherapy of B-Cell Non-Hodgkin's Lymphoma: From Clinical Trials to Clinical Practice. J Nuclear Med. 2002;43(11):1507-1529.

Katritsky et al., Comprehensive Heterocyclic Chemistry: The Structure, Reactions, Synthesis and Uses of Heterocyclic Compounds. 1984;2:586-587.

Keating et al., Long-term follow-up of patients with chronic lymphocytic leukemia treated with fludarabine as a single agent. Blood. Jun. 1, 1993;81(11):2878-2884.

Kerkmann et al., Activation with CpG-A and CpG-B oligonucleotides reveals two distinct regulatory pathways of type I IFN synthesis in human plasmacytoid dendritic cells. J Immunol. May 1, 2003;170(9):4465-4474.

Klausen et al., Two complementary methods of assessing periodontal bone level in rats. Scand J Dent Res. Dec. 1989;97 6 :494-499.

Klinman, Immunotherapeutic uses of CpG oligodeoxynucleotides. Nat Rev Immunol. Apr. 2004;4(4) :249-258.

Kloek et al., An improved method for the synthesis of stabilized primary enamines and imines. J Org Chem. 1978;43:1460-1462.

Kloetzel, Reactions of nitroparaffins. I. Synthesis and reduction of some ó-nitrokenes. J Am Chem Soc. 1947;69:2271-2275.

Kornman, Host modulation as a therapeutic strategy in the treatment of periodontal disease. Clin Infect Dis. Mar. 1999;28(3):520-526.

Kourafalos et al., Synthesis of 7-aminopyrazolo[3,4-c]pyridine as a probe for the preparation of compounds of pharmacological interest. Heterocycles. 2002;57(12):2335-2343.

Krause et al., Autoimmune aspects of cytokine and anticytokine therapies. Am J Med. Oct. 1, 2003;115(5):390-397.

Krenitsky et al., Imidazo[4,5-c]pyridines (3-deazapurines) and their nucleosides as immunosuppressive and anti-inflammatory agents. J Med Chem. Jan. 1986;29(1):138-143.

Kurt-Jones et al., Role of toll-like receptor 2 (TLR2) in neutrophil activation: GM-CSF enhances TLR2 expression and TLR2-mediated interleukin 8 responses in neutrophils. Blood. Sep. 1, 2002;100(5):1860-1868.

Lall et al., Serine and threonine beta-lactones: a new class of hepatitis A virus 3C cysteine proteinase inhibitors. J Org Chem. Mar. 8, 2002;67(5):1536-1547.

Lee et al., p38 mitogen-activated protein kinase inhibitors - mechanisms and therapeutic potentials. Pharmacol Ther. 1999; 82:389-397.

Lee et al., Saturated fatty acid activates but polyunsaturated fatty acid inhibits Toll-like receptor 2 dimerized with Toll-like receptor 6 or 1. J Biol Chem. Apr. 23, 2004;279(17):16971-16979. Epub Feb. 13, 2004.

Lehner et al., The role of γσ cells and β-chemokines in mucosal protection against SIV infection. Immunology Lett. 1999;69:25-192. Abstract 2.1.

Levy et al., Unique efficacy of Toll-like receptor 8 agonists in activating human neonatal antigen-presenting cells. Blood. Aug. 15, 2006;108(4):1284-1290. Epub Apr. 25, 2006.

Leynadier et al., Allergic reactions to North African scorpion venom evaluated.by skin test and specific IgE. J Allergy Clin Immunol. Jun. 1997;99(6 Pt 1):851-853. 4 pages.

Li et al., Solubility behavior of imiquimod in alkanoic acids. Pharmaceutical Research, 1997 American Association of Pharmaceutical Scientists Annual Meeting. Poster Presentation. Boston, MA, Nov. 2-6, 1997;S475:Abstract 3029.

Li of al., Synthesis, CoMFA analysis, and receptor docking of 3,5-diacyl-2, 4-dialkylpyridine derivatives as selective A3 adenosine receptor antagonists. J Med Chem. Feb. 25, 1999;42(4):706-721.

Litt et al., Mucosal delivery of vaccine antigens displayed on the surface of Lactococcus lactis. Immunology Lett. 1999;69(1):61. Abstract #11.26.

Liu et al., Synthesis of halogen-substituted 3-deazaadenosine and 3-deazaguanosine analogues as potential antitumor/antiviral agents. Nucleosides Nucleotides Nucleic Acids. Dec. 2001;20(12):1975-2000.

Loesche et al., Treatment paradigms in periodontal disease. Compend Contin Educ Dent. Mar. 1997;18(3):221-226, 228-230, 232 passim; quiz 234. Review.

Luger et al., Evidence for an epidermal cytokine network. J Invest Dermatol. Dec. 1990:95(6 Suppl):100S-104S.

Luskin et at., Olefinic Derivatives of 2,4-Diamino-s-triazines. J Org Chem. 1958;23:1032-1037.

Macchia et at., Synthesis and antiviral properties of 9-(2-methyleneaminoxyethoxy)methyl) guanine derivatives as novel Acyclovir analogues. Farmaco. Feb. 2000;55(2):104-108.

Majeski et al., Action of venom from the brown recluse spider (Loxosceles reclusa) on human neutrophils. Toxicon. 1977;15(5):423-427.

Makarenkova et al., Identification of delta- and mu- type opioid receptors on human and murine dendritic cells. J Neuroimmunol. 2001;117:68-77.

Male et al., Introduction to the Immune System. In: Immunology. Elsevier. 2006:6-7.

Masihi, Progress on novel immunomodulatory agents for HIV-1 infection and other infectious diseases. Expert Opin Ther Patents. 2003;13(6):867-882.

Masiukiewicz et at., Scalable Syntheses of $N^\alpha$-Benzyloxycarbonyl-$_L$-Ornithine and of $N^\alpha$-(9- Fluorenylmethoxy)Carbonyl-$_L$-Ornithine. Org Prep Proced Int. 2002;34:531-537.

Mataka et al., Condensation reaction of 3,4-Dibenzoyl-1-methyl-2,5-diphenylpyrrole and -1-phenylpyrazole with methylamine derivatives affording pyrrolo [3,4-c] pyridine and 2H-pyrazolo[3,4-c]- and [4,3-c]pyridines. Journal of Heterocyclic Chemistry. 1981;18(6):1073-1075.

Mathur et al., Cell-mediated immune system regulation in periodontal diseases. Crit Rev Oral Biol Med. 1997;8(1):76-89.

Maynor et al., Brown recluse spider envenomation: a prospective trial of hyperbaric oxygen therapy. Acad Emerg Med. Mar. 1997;4(3):184-192.

Mbow et al., Small molecule and biologic modulators of the immune response to hepatitis C virus. Mini Rev Med Chem. May 2006;6(5):527-531.

Mccarthy et al., Opioids, opioid receptors, and the immune response. Drug & Alcohol Dependence. 2001;62:111-123.

Mckennon et al., A Convenient Reduction of Amino Acids and Their Derivatives. J Org Chem. 1993;58:3568-3571.

Mclaughlin et al., Opioid growth factor (OGF) inhibits the progression of human squamous cell carcinoma of the head and neck transplanted into nude mice. Cancer Lett. 2003;199:209-217.

Medzhitov, Toll-Like Receptors and Innate Immunity. Nature Rev Immunol. 2001;1:135-145.

Mee et al., Stille coupling made easier - the synergic effect of copper(I) salts and the fluoride ion. Angew Chem. 2004;116:1152-1156.

Merigian et al., Envenomation From the Brown Recluse Spider: Review of Mechanism and Treatment Options. Am J Ther. Oct. 1996;3(10):724-734.

Miller et al., Imiquimod applied topically: a novel immune response modifier and new class of drug. Int J Immunopharmacol. Jan. 1999;21(1):1-14.

Minakawa et al., Nucleosides and Nucleotides. 184. Synthesis and Conformational Investigation of Anti-Fixed 3-Deaza-3-halopurine Ribonucleosides. J Org Chem. 1999;64:7158-7172.

Moebius et al., The mysteries of sigma receptors: new family members reveal a role in cholesterol synthesis. Trends Pharmacol Sci. Mar. 1997;18(3):67-70.

Moldoveanu et al., Poly-L-lysine as a potential mucosa adjuvant. Immunology Lett. 1999;69(1):62. Abstract #11.28.

Mollick et al., MUC1-like tandem repeat proteins are broadly immunogenic in cancer patients. Cancer Immun. Mar. 17, 2003;3:3. 17 pages.

Moody et al., Lipoxygenase inhibitors prevent lung carcinogenesis and inhibit non-small cell lung cancer growth. Exp Lung Res. Jul-Aug. 1998;24(4):617-628.

Moraczewski et al., Using Hydrogen Bonding to Control Carbamate C-N Rotamer Equilibria. Org Chem. Oct. 16, 1998;63(21):7258-7262.

Mosbech et al., [Allergy to insect stings] Ugeskr Laeger. Oct. 28, 1999;153(44):3067-3071. Danish.

Muche et al., Imiquimod treatment of cutaneous T cell lymphoma. Journal of Investigative Dermatology. Jul. 2003;121(1):0975. Joint Meeting of the European Society for Dermatologi; Miami Beach, Florida, USA. Apr. 30-May 04, 2003. Abstract 0975.

Muller et al., An improved one-pot procedure for the synthesis of alkynes from aldehydes. Synlett. 1996;6:521-522.

Mutschler et al., 9.2 Anti-infectives. In: Drug Actions: Basic Principles and Therapeutic Aspects. 1995:515-580.

Muzio et al., Differential expression and regulation of toll-like receptors (TLR) in human leukocytes: selective expression of TLR3 in dendritic cells. J Immunol. Jun. 1, 2000;164(11):5998-6004.

Nagarajan et al., Condensed heterotricycles: synthesis of pyrazolo[3,4-c]quinoline derivatives. Indian Journal of Chemistry. 1992;31B:316-321.

Nagase et al., Expression and function of Toll-like receptors in eosinophils: activation by Toll-like receptor 7 ligand. J Immunol. Oct. 15, 2003;171(8):3977-3982.

Nanjappan et al., An efficient synthesis of some 6-substituted 4,8-diaza-3,3,9,9- tetramethylundeca-2,10-dione dioximes (propylene amine oximes, PnAOs): Ligands for 99mTc complexes used in structure distribution relationship (SDR) studies. Tetrahedron. 1994;50(29):8617-8632.

Ohana et al., Differential effect of adenosine on tumor and normal cell growth: focus on the A3 adenosine receptor. Journal of Cellular Physiology. Jan. 2001;186(1):19-23. Review.

O'Mahony et al., New patient-applied therapy for anogenital warts is rated favourably by patients. Intl J STD & AIDS. 2001;12:565-570.

Osol et al., Chapter 27: Structure-Activtiy Relationship and Drug Design. In: Remington's Pharmaceutical Sciences. 16th Ed. Mach Publishing. 1980:420-435.

Ottonello et al., Sulphonamides as anti-inflammatory agents: old drugs for new therapeutic strategies in neutrophilic inflammation? Clin Sci (Lond). Mar. 1995;88(3):331-336.

Ozinsky et al., The repertoire for pattern recognition of pathogens by the innate immune system is defined by cooperation between Toll-like receptors. Proc. Nat. Acad. Sci. 2000; 97(25):13766-13771.

Page et al., Advances in the pathogenesis of periodontitis: summary of developments, clinical implications and future directions. Periodontol 2000. Jun. 1997;14:216-248.

Park et al., Immunotherapy Cancer Treatment. Reprinted from Supportive Cancer Care, Rosenbaum et al. 2001. Available at http://www.cancersupportivecare.com/immunotherapy.html. Last accessed Jul. 13, 2010. 3 pages.

Patel et al., The necrotic venom of the brown recluse spider induces dysregulated endothelial cell-dependent neutrophil activation. Differential induction of GM-CSF, IL-8, and E-selectin expression. J Clin Invest. Aug. 1994;94(2):631-642.

Patrick et al., Paragraph 10.3: Drug optimization: strategies in drug design. In: An Introduction to Medicinal Chemistry. Oxford: Oxford University Press. Jan. 2005. 200-218.

Pavletic et al., Outcome of allogeneic stem cell transplantation for B cell chronic lymphocytic leukemia. Bone Marrow Transplant. Apr. 2000;25(7):717-722.

Pawlas et al., Novel anionic annelation tactics for construction of fused heteroaromatic frameworks. 1. Synthesis of 4-substituted pyrazolo[3,4-c]quinolines, 9-substituted pyrazolo[3,4-c]quinolines, and 1,4-dihydrochromeno[4,3-c]pyrazoles. Org Chem. Jun. 15, 2001;66(12):4214-4219.

Payvandi et al., Exogenous and Endogenous IL-10 Regulate IFN-αProduction by Peripheral Blood Mononuclear Cells in Response to Viral Stimulation. J Immunol. 1998;160:5861-5868.

Peschke et al., Synthesis and in vitro characterization of new growth hormone secretagogues derived from ipamorelin with dipeptidomimetic N-terminals. Eur J Med Chem. 1999;34:363-380.

Peterson et al., The opioid-cytokine connection. J Neuroimmunol. 1998;83:63-69.

Phillips et al., Therapy of brown spider envenomation: a controlled trial of hyperbaric oxygen, dapsone, and cyproheptadine. Ann Emerg Med. Mar. 1995;25(3):363-368.

Pickersgill et al., Preparation of functionalized, conformationally constrained DTPA analogues from L- or D-serine and trans-4-hydroxy-L-proline. Hydroxymethyl substituents on the central acetic acid and on the backbone. J Org Chem. Jun. 30, 2000;65(13):4048-4057.

Poljakovic et al., iNOS and COX-2 immunoreactivity in the mice bladder and kidney after bacterial instillation. Immunology Lett. 1999;69(1):122. Abstract #31.5.

Powell et al., Compendium of excipients for parenteral formulations. PDA J Pharm Sci Technol. Sep-Oct. 1998;52(5):238-311.

Prelog et al., Cycloalkeno-pyridine. Helv Chem Acta. 1945;28:1684-1693. German.

Rees et al., Brown recluse spider bites. A comparison of early surgical excision versus dapsone and delayed surgical excision. Ann Surg. Nov. 1985;202(5):659-663.

Regan et at., Activation of p38 MAPK by feline infectious peritonitis virus regulates pro-inflammatory cytokine production in primary blood-derived feline mononuclear cells. Virology. Feb. 5, 2009;384(1):135-143. Epub Dec. 5, 2008.

Rhodes, Discovery of immunopotentiatory drugs: current and future strategies. Clin Exp Immunol. Dec. 2002;130(3):363-369.

Ribera et al., "Spontaneous" complete remissions in chronic lymphocytic leukemia: report of three cases and review of the literature. Blood Cells. 1987;12(2):471-479.

Ritter et al., A new reaction of nitriles; amides from alkenes and mononitriles. J Am Chem Soc. Dec. 1948;70(12):4045-4048.

Rocca et al., Carbolines. Part VII. Ansidines, Convenient tools to synthesize fficien-β- carbolines. J Heterocyclic Chem. 1995;32:1171-1175.

Rocca et al., Connection between metalation and cross-coupling strategies. Anew convergent route to azacarbazoles. Tetrahedron. 1993;49(1):49-64.

Rollins, Chemokines. Blood. Aug. 1, 1997;90(3):909-928. Review.

Rosenberg et al., Treatment of 283 consecutive patients with metastatic melanoma or renal cell cancer using high-dose bolus interleukin 2. JAMA. Mar 23-30, 1994;271(12):907-913.

Rothel et al., The use of recombinant ovine IL-1beta and TNF-alpha as natural adjuvants and their physiological effects in vivo. Immunol Cell Biol. Apr. 1998;76(2):167-172.

Roy et al., QSAR of adenosine receptor antagonists II: exploring physicochemical requirements for selective binding of 2-arlypyrazolo[3,4-c] quinoline derivatives with adenosine A1 and A3 receptor subtypes. QSAR & Comb Sci. 2003;22:614-621.

Royals et al., Studies in mixed ester condensations. IV. Acylations with methyl dimethoxyacetate. J Am Chem Soc. 1956;78:4161-4164.

Rozman et al., Chronic lymphocytic leukemia. N Engl J Med. Oct. 19, 1995;333(16):1052-1057.

Sakthivel et al. Direct SnAr amination of fluorinated imizazo[4,5-c]pyridine nucleosides: efficient synthesis of 3-fluoro-3-3-deazaadenosine analogs. Tetrahedron Letters. May 2005;46(22):3883-3887.

Salaun et al., TLR3 Can Directly Trigger Apoptosis in Human Cancer Cells. J of Immunology. 2006;176:4894-4901.

Salemink, Uber 2-Propyl-1- Und 2-Propyl-Desaza-Adenin. Recueil. 1961;80:545-555. German.

Sambhi et al., Local production of tumor necrosis factor encoded by recombinant vaccinia virus is effective in controlling viral replication in vivo. Proc Natl Acad Sci U S A. May 1, 1991;88(9):4025-4029.

Sams et al., Necrotic arachnidism. J Am Acad Dermatol. Apr. 2001;44(4):561-573; quiz 573-6.

Sauder et al., Randomized, Single-Blind, Placebo-Controlled Study of Topical Application of the Immune Response Modulator Resiquimod in Healthy Adults. Antimicrobial Agents Chemo. 2003;47(12):3846-3852.

Scheerlinck, Genetic adjuvants for DNA vaccines. Vaccine. Mar. 21, 2001;19(17-19):2647- 2656.

Scheuer et al., Application of the Ritter reaction to mesityl oxide and chalcone. J Am Chem Soc. 1957;22:674-676.

Schofield et al., Reply. Low-Dose Interferon-alpha in Chronic Myeloid Leukemia. Ann Internal Med. 1995;122(9):728-729. 1 page.

Schwandner et al., Peptidoglycan- and lipoteichoic acid-induced cell activation is mediated by toll-like receptor 2. J Biol Chem. Jun. 18, 1999;274(25):17406-17409.

Seeman et al., Steric and Conformational Effects in Nicotine Chemistry. J Org Chem. 1981;46:3040-3048.

Serrat et al., A highly efficient and straightforward stereoselective synthesis of novel chiral β-acetylenic ketones. Tetrahedron: Assymmetry. 1999;10:3417-3430.

Severa et al., Sensitization to TLR7 agonist in IFN-beta-preactivated dendritic cells. J Immunol. May 15, 2007 15;178(10):6208-6216.

Seymour et al., Cellular immunity and hypersensitivity as components of periodontal destruction. Oral Dis. Mar. 1996;2(1):96-101. Review.

Shelburne et at., Quantitation of Bacteroids forsythus in subgingival plaque comparison on immunoassay and quantitative polymerase chain reaction. J Microbiol Methods. 2000;39:97-107.

Sidky et al., Inhibition of murine tumor growth by an interferon-inducing imidazoquinolinamine. Cancer Res. Jul. 1, 1992;52(13):3528-3533.

Siegal et al., The nature of the principal type 1 interferon-producing cells in human blood. Science. Jun. 11, 1999;284(5421):1835-1837.

Sletzinger et al., The Synthesis of Isomethadone. J Am Chem Soc. 1952;74:5619-5620.

Smith et al., The role of polymorphonuclear leukocytes in the lesion caused by the venom of the brown spider, Loxosceles reclusa. Lab Invest. Jan. 1970;22(1):90-93.

Sofina et al., C: Possibility of Predicting the Spectrum of Antitumor Effect of Drugs on the Basis of Experimental Data. Experimental evaluation of antitumor drugs in the USA and USSR and clinical correlations. NCI Monograph 55. NIH Publication No. 80-1933. 1980:76-78.

Sommer et al., Recent Findings on How Proinflammatory Cytokines Cause Pain: Peripheral Mechanisms in inflammatory and Neuropathic Hyperalgesia. Neurosci Letts. 2004:361:184-187.

Sonogashira et al., A convenient synthesis of acetylenes: catalytic substitutions of acetylenic hydrogen with bromoalkenes, Iodoarenes, and bromopyridines. Tetrahedron Letts. 1975;50:4467-4470.

Soria et al., Effect of food on the pharmacokinetics and bioavailability of oral imiquimod relative to a subcutaneous dose. Int J Clin Pharmacol Ther. Oct. 2000;38(10):476-481.

Spaner et al., A phase I/II trial of TLR -7 agonist immunotherapy in chronic lymphocytic leukemia. Leukemia. 2010; 24:222-226.

Spaner et al., Immunomodulatory effects of Toll-like receptor-7 activation on chronic lymphocytic leukemia cells. Leukemia. Feb. 2006;20(2):286-295.

Spaner et al., Toll-like receptor agonists in the treatment of chronic lymphocytic leukemia. Leukemia. Jan. 2007;21(1):53-60. Epub Oct. 26, 2006.

Spivey et al., Configurationally stable biaryl analogues of 4-(dimethylamino)pyridine: A novel class of chiral nucleophilic catalysts. J Org Chem. 1999;64:9430-9443.

Spruance et al., Application of a topical immune response modifier, resiquimod gel, to modify the recurrence rate of recurrent genital herpes: a pilot study. J Infect Dis. Jul. 15, 2001;184(2):196-200. Epub Jun. 8, 2001.

Stack, Images in clinical medicine. Latrodectus mactans. N Engl J Med. Jun. 5, 1997;336(23):1649.

Stanley, Imiquimod and the imidazoquinolones: mechanism of action and therapeutic potential. Clin Exp Dermatol. Oct. 2002;27(7):571-577. Review.

Stashenko et al., Periapical inflammatory responses and their modulation. Crit Rev Oral Biol Med. 1998;9(4):498-521.

Steele et al., Lipoxygenase inhibitors as potential cancer chemopreventives. Cancer Epidemiol Biomarkers Prev. May 1999;8(5):467-483.

Steele et al., Potential use of lipoxygenase inhibitors for cancer chemoprevention. Expert Opin Investig Drugs. Sep. 2000;9(9):2121-2138.

Steinmann etal., Topical imiquimod treatment of a cutaneous melanoma metastasis. J Am Acad Dermatol. Sep. 2000;43(3):555-556.

Stewart et al., Synthesis of a Carba-analog of S-Acetyl Coenzyme A,Acetonyl-dethio Coenzyme A; an Effective Inhibitor of Citrate Synthase. Liebigs Ann Chem. 1978:57-65.

Stillings et at., Substituted 1,3,4-thiadiazoles with anticonvulsant activity. 2. Aminoalkyl derivatives. J Med Chem. Nov. 1986;29(11):2280-2284.

Strandtmann et al., Reaction of cyclic β-diketones with 3,4-dihydroisoquinolines and related compounds. Preparation and anticancer activity of 2-substituted 1,3- cyclohexanediones. J Med Chem. Nov. 1967;10(6):1063-1065.

Stringfellow, Induction of interferon with low molecular weight compounds: fluorenone esters, ethers (tilorone), and pyrimidinones. Methods Enzymol. 1981;78(Pt A):262-284.

Ströher et al., Progress towards the treatment of Ebola haemorrhagic fever. Expert Opin Investig Drugs. Dec. 2006;15(12):1523-1535.

Sugisaka et al., The Physicochemical properties of imiquimod, the first imidazoquinoline immune response modifier. Pharmaceutical Research. 1997 American Association of Pharmaceutical Scientists Annual Meeting. Poster Presentation, Boston, MA, Nov. 2-6, 1997;S475. Abstract 3030.

Surrey et al., The Synthesis of Some 3-Nitro- and 3-Amino-4-dialkylaminoalkylaminoquinoline Derivatives. J Am Chem Soc. 1951;73:2413-2416.

Takeichi et al., Cytokine profiles of T-lymphocytes from gingival tissues with pathological pocketing. J Dent Res. Aug. 2000;79(8):1548-1555.

Takeshita et al., Signal transduction pathways mediated by the interaction of CpG DNA with Toll-like receptor 9. Semin Immunol. Feb. 2004;16(1):17-22.

Takeuchi et al., Discrimination of bacterial lipoproteins by Toll-like receptor 6. Int Immunol. Jul. 2001;13(7):933-940.

Temple, Antimitotic agents: synthesis of imidazo[4,5-c]pyridin-6-ylcarbamates and imidazo[4,5-b]pyridin-5-ylcarbamates. J Med Chem. Feb. 1990;33(2):656-661.

Temple et al., Potential anticancer agents: 5-(N-substituted-aminocarbonyl)- and 5-(N-substituted-aminothiocarbonyl)-5,6,7,8-tetrahydrofolic acids. J Med Chem. Mar. 1988;31(3):697-700.

Thesing et al., [Darstellung and Eigenschaften des $\Delta^1$ Al-Pyrrolin-N-oxyds.]. Chem Ber. 1959;92:1748-1755. German.

Thiruvikraman et al., Synthesis and reactions of pyrazolo-[3,4-c]quinoline derivatives. Indian Journal of Chemistry. 1987;26B:695-696.

Tomai et al., Imiquimod: in vivo and in vitro characteristics and toxicology. In: Cutaneous Infection and Therapy. Aly et al., eds. Marcel Dekkar, Inc., New York. 1997:405-415.

Tomic et al., Sensitization of IL-2 Signaling through TLR-7 Enhances B Lymphoma Cell Immunogenicity. J Immunol. 2006;176:3830-3839.

Tomioka et al., Asymmetric Alkylation of a-Alkyl β-Keto Esters. J Am Chem Soc. 1984;106:2718-19.

Totterman et al., Phorbol ester-induced differentiation of chronic lymphocytic leukaemia cells. Nature. Nov. 13, 1980;288(5787):176-178.

Tracy et al., Studies in the Pyridine Series. II. Synthesis of 2-Methyl-3-(β-3Hydroxyethyl)pyridine and of the Pyridine Analog of Thiamine (Vitamin B2). J Org Chem. 1941;6:54-62.

Uno et al., TNF-related apoptosis-inducing ligand (TRAIL) frequently induces apoptosis in Philadelphia chromosome-positive leukemia cells. Blood. May 1, 2003;101(9):3658-3667. Epub Dec 27, 2002.

Urosevic et al., Imiquimod treatment induces expression of opioid growth factor receptor: a novel tumor antigen induced by interferon-alpha? Clin Cancer Res. Aug 1, 2004;10(15):4959-4970.

Van De Kerhof, New Immunomodulatory Drugs. In: Skin and Environment: Perception and Protection. Ring et al., eds., 10th EADV Congress, Oct. 10-14, Munich, Germany. 2001:1:343-348.

Vasilakos et al., Adjuvant Activities of Immune Response Modifier R-848: Comparison with CoG ODN. Cell Immunol. 2000;204:64-74.

Vieweg et al., Tumor vaccines: from gene therapy to dendritic cells-the emerging frontier. Urol Clin North Am. Aug. 2003;30(3):633-643.

Vilcek, The cytokines: An overview. In: The Cytokine Handbook, Fourth Ed. M. Lotze and A.W. Thompson (eds.), 2003;1:3-14.

Volhardt, 18-5. Amides: The Least-Reactive Carboxylic Acid Derivatives. Organic Chemistry. 1987:813.

Vollmer et al., Highly immunostimulatory CpG-free oligodeoxynucleotides for activation of human leukocytes. Antisense Nucleic Acid Drug Dev. Jun. 2002;12(3):165-175.

Wagner et al., Induction of cytokines in cynomolgus monkeys by the immune response modifiers, imiquimod, S-27609 and S-28463. Cytokine. Nov. 1997;9(11):837-845.

Wagner et al., Modulation of TH1 and TH2 Cytokine Production with the Immune Response Modifiers, R-848 and Imiguimod. Cellular Immunology. 1999;191:10-19.

Wang, Structure and Chemistry of 4-Hydroxy-6-methyl-2-pyridone. J Heterocyclic Chem. 1970;7:389-392.

Warren et al., Macrophage Growth Factor CSF-1 Stimulates Human Monocyte Production of Interferon, Tumor Necrosis Factor, and Colony Stimulating Activity. J Immunol. 1986;137(7):2281-2285.

Wasserman et al., Loxoscelism and necrotic arachnidism. J Toxicol Clin Toxicol. 1983- 984;21(4-5):451-472.

Wedlock et al., Physiological effects and adjuvanticity of recombinant brushtail possum TNF-alpha. Immunol Cell Biol. Feb. 1999;77(1):28-33.

Wells, Additivity of Mutational Effects in Proteins. Biochemistry. 1990;29(37):8509-8517.

Wermuth, Molecular Variations Based on Isosteric Replacements. Practice of Medicinal Chemistry.1996:203-237.

Wexler et al., Accurate identification of experimental pulmonary metastases. J Natl Cancer Inst. Apr. 1966;36(4):641-645.

Wibaut et al., Syntheses of 3,4-Dimethylpyridine, 2,3-Dimethylpridine and 2-Methyl-3- Ethylpyridine. Rec Tray Chim. 1944;63:231-238.

Wierda et al., CD40-ligand (CD154) gene therapy for chronic lymphocytic leukemia. Blood. Nov. 2000 1;96(9):2917-24.

Wieseler-Frank et al., Central proinflammatory cytokines and pain enhancement. Neurosignals. 2005;14(4):166-174.

Williams et al., Grignard Reactions to Chiral Oxazolidine Aldehydes. Tetrahedron. 1996;52:11673-11694.

Wilson et al., Spiders and spider bites. Dermatol Clin. Apr. 1990;8(2):277-286.

Wright of al., Clinical presentation and outcome of brown recluse spider bite. Ann Emerg Med. Jul. 1997;30(1):28-32.

Wu et al., Murine B16 melanoma vaccination-induced tumor immunity: identification of specific immune cells and functions involved. J Interferon Cytokine Res. Dec. 2001;21(12):1117-1127.

Yamamoto et al., Essential role for TIRAP in activation of the signalling cascade shared by TLR2 and TLR4. Nature. Nov. 21, 2002;420(6913):324-329.

Yeung-Yue et al., The management of herpes simplex virus infections. Curr Opin Infect Dis. Apr. 2002;15(2):115-122.

Yutilov et al., Synthesis and some reactions of 4-nitroimidazo[4-5-c]pyridin-2-ones. CAPLUS English Abstract DN 91:175261. VINITI.1978:1193-1178. Abstract Only.

Zagon et al., Immunoelectron microscopic localization of the opioid growth factor receptor (OGFr) and OGF in the cornea. Brain Res. 2003;967:37-47.

Zagon et al., Opioids and the apoptotic pathway in human cancer cells. Neuropeptides. 2003;37:79-88.

Zagon et al., The biology of the opioid growth factor receptor (OGFr). Brain Res Rev. 2002 Feb;38(3):351-376. Review.

Zagon et al., the expression and function of the OGF-OGFr axis - a tonically active negative regulator of growth - in COS cells. Neuropeptides. Oct. 2003;37(5):290-297.

Zambon, Periodontal diseases: microbial factors. Ann Periodontol. Nov. 1, 1996(1):879-925.

Zarubin et al., Theoretical Study of Antagonists and Inhibitors of Mammalian Adenosine Deaminase: I. Adenosine and Its Aza- and Deazaanalogues. Russ J Bioorg Chem. 2002;28(4):284-292.

Zhu et al., Inhibition of murine dendritic cell activation by synthetic phosphorothioate oligodeoxynucleotides. J Leukoc Biol. Dec. 2002;72(6):1154-1163.

Zhu et al., Inhibition of murine macrophage nitric oxide production by synthetic oligonucleotides. J Leukoc Biol. Apr. 2002;71(4):686-694.

Ziegler-Heitbrock et al., Favorable response of early stage B CLL patients to treatment with IFN-alpha 2. Blood. May 1, 1989;73(6):1426-1430.

Zyryanov et al., Heterocydization of 1-(2'-Carbethoxyphenyl)-5-Methyltetrazole. Chemistry of Heterocylic Compounds. English Edition. 1981;16(12):1286-1288.

U.S. Appl. No. 11/720,862, filed on Jun. 5, 2007, Gordon et al.

U.S. Appl. No. 11/884,060, filed on May 18, 2010, Lundquist, Jr., et al.

U.S. Appl. No. 11/887,525 filed on Sep. 28, 2007, Hays et al.

U.S. Appl. No. 11/991,663, filed on Mar. 7, 2008, Kshirsagar et al.

* cited by examiner

ARYL SUBSTITUTED IMIDAZONAPHTHYRIDINES

CROSS-REFERENCE TO RELATED APPLICATIONS

This application is National Stage of international Application No. PCT/US2005/021436, filed Jun. 17, 2005, which claims priority to U.S. Provisional Application Ser. No. 60/581,317, filed on Jun. 18, 2004, which is incorporated herein by reference in its entirety.

BACKGROUND

In the 1950's the 1H-imidazo[4,5-c]quinoline ring system was developed and 1-(6-methoxy-8-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo[4,5-c]quinoline was synthesized as a possible anticonvulsant and cardiovascular agent. Also, several 2-oxoimidazo[4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo[4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifiers, rendering them useful in the treatment of a variety of disorders.

There continues to be interest in the imidazoquinoline ring system, as well as other imidazo ring systems, and there is a continuing need for compounds that have the ability to modulate the immune response, by induction of cytokine biosynthesis or other mechanisms.

SUMMARY

The present invention provides a new class of compounds that are useful in inducing cytokine biosynthesis in animals. Such compounds are of the following Formula (I):

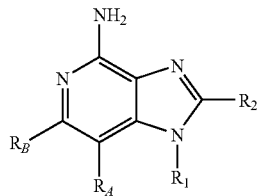

wherein $R_A$, $R_B$, $R_1$, and $R_2$, are as defined below.

The compounds of Formula I include various isomers of aryl substituted imidazonaphthyridines, in particular 1,5-naphthyridines, which are preferably substituted at the 7 position.

The compounds of Formula I are useful as immune response modifiers due to their ability to induce cytokine biosynthesis (e.g., induce the synthesis of at least one cytokine) and otherwise modulate the immune response when administered to animals (e.g., by inhibiting the induction of TNF-alpha). This makes the compounds useful in the treatment of a variety of conditions such as viral diseases and tumors that are responsive to such changes in the immune response.

The invention further provides pharmaceutical compositions containing an effective amount of a compound of Formula I, and methods of inducing cytokine biosynthesis in an animal, treating a viral infection and/or treating a neoplastic disease in an animal by administering an effective amount of a compound of Formula I to the animal.

In addition, methods of synthesizing compounds of Formula I and intermediates useful in the synthesis of these compounds are provided.

As used herein, "a," "an," "the," "at least one," and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formula (I):

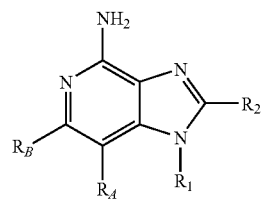

as well as more specific compounds of the following Formulas (II, III, IV, V, VI, and VII):

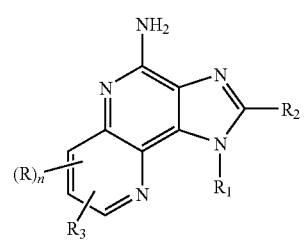

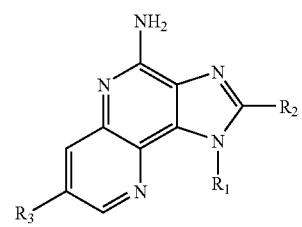

-continued

IV (structure with NH2, R2, R1, R3, (R)n on fused ring system)

V (structure with NH2, R2, R1, R3, (R)n on fused ring system)

VI (structure with NH2, R2, R1, R3, (R)n on fused ring system)

VII (structure with HN-G, R2, R1, R3 on fused ring system)

wherein $R_A$, $R_B$, R, $R_1$, $R_2$, $R_3$, G, and n are as defined below, and pharmaceutically acceptable salts thereof.

In one embodiment, there is provided a compound of the Formula (I):

I (structure with NH2, R2, R1, $R_A$, $R_B$)

wherein:

$R_A$ and $R_B$ join to form a fused pyridine ring which is substituted by one $R_3$ group or substituted by one $R_3$ group and one R group;

$R_1$ is selected from the group consisting of:
—$R_4$,
—X—$R_4$,
—X—Y—$R_4$,
—X—Y—X—Y—$R_4$, and
—X—$R_5$;

$R_2$ is selected from the group consisting of:
—$R_4$,
—X—$R_4$,
—X—Y—$R_4$, and
—X—$R_5$;

$R_3$ is selected from the group consisting of:
—Z—Ar,
—Z—Ar'—Y—$R_4$,
—Z—Ar'—X—Y—$R_4$,
—Z—Ar'—$R_5$, and
—Z—Ar'—X—$R_5$;

R is selected from the group consisting of alkyl, alkoxy, chloro, fluoro, hydroxy, and trifluoromethyl;

Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, alkoxyalkylenyl, α-aminocarboxyalkylenyl, amino, aminoalkyl, alkylamino, and dialkylamino;

Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

—S(O)$_{0-2}$—, —S(O)$_2$—N($R_8$)—, —C($R_6$)—,
—C($R_6$)—O—, —O—C($R_6$)—,
—O—C(O)—O—, —N($R_8$)—Q—,
—C($R_6$)—N($R_8$)—, —O—C($R_6$)—N($R_8$)—,
—C($R_6$)—N(O$R_9$)—, (cyclic N—Q with $R_{10}$),
(structure with $R_{11}$, (CH$_2$)$_{0-2}$, N—Q), —N—C($R_6$)—N—W—, (with $R_7$)
—N—$R_7$—N—Q—, (with $R_7$), —V—N— (with $R_{10}$), and
(cyclic N—C($R_6$)—N with $R_{10}$);

Z is selected from the group consisting of a bond, alkylene, alkenylene, and alkynylene;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, carboxy, alkylamino, dialkylamino, (dialkylamino)alkyleneoxy, and in the case of alkyl, alkenyl, alkynyl, and heterocyclyl, oxo;

$R_5$ is selected from the group consisting of:

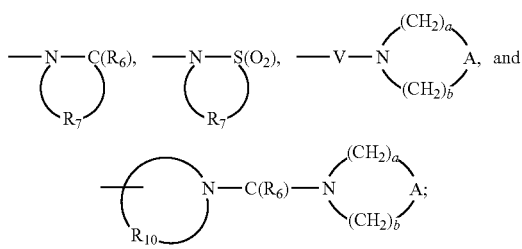

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
$R_{11}$ is selected from the group consisting of fluoro, hydroxy, and alkoxy;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$), —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7;
or a pharmaceutically acceptable salt thereof.

In one embodiment, there is provided a compound of the Formula (I):

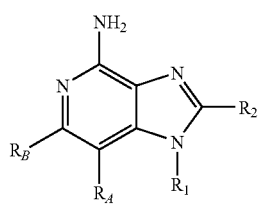

wherein:
$R_A$ and $R_B$ join to form a fused pyridine ring which is substituted by one $R_3$ group or substituted by one $R_3$ group and one R group;

$R_1$ is selected from the group consisting of:
—$R_4$,
—X—$R_4$,
—X—Y—$R_4$,
—X—Y—X—Y—$R_4$, and
—X—$R_5$;
$R_2$ is selected from the group consisting of:
—$R_4$,
—X—$R_4$,
—X—Y—$R_4$, and
—X—$R_5$;
$R_3$ is selected from the group consisting of:
—Z—Ar,
—Z—Ar'—Y—$R_4$,
—Z—Ar'—X—Y—$R_4$,
—Z—Ar'—$R_5$, and
—Z—Ar'—X—$R_5$;
R is selected from the group consisting of alkyl, alkoxy, chloro, fluoro, hydroxy, and trifluoromethyl;
Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, aminoalkyl, alkylamino, and dialkylamino;
Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;
X is selected from the group consisting of alkylene, alkenylene, alkynylene, arylene, heteroarylene, and heterocyclene wherein the alkylene, alkenylene, and alkynylene groups can be optionally interrupted or terminated with arylene, heteroarylene, or heterocyclylene, and optionally interrupted by one or more —O— groups;
Y is selected from the group consisting of:

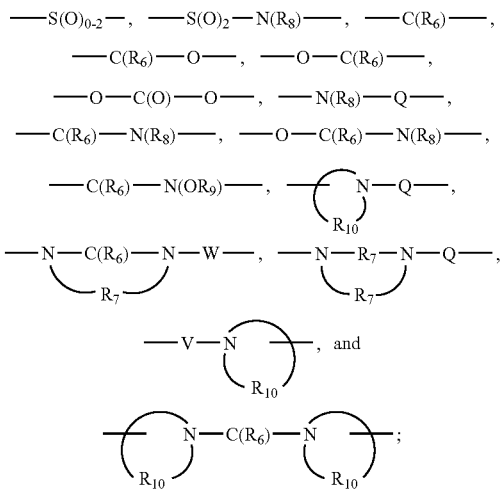

Z is selected from the group consisting of a bond, alkylene, alkenylene, and alkynylene;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

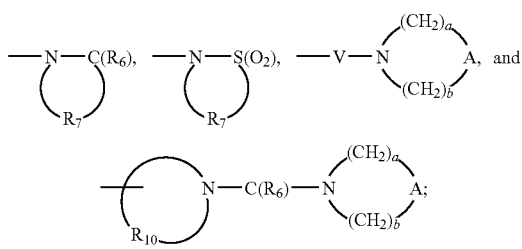

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$), —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7;
or a pharmaceutically acceptable salt thereof.

In another embodiment, there is provided a compound of the Formula (II):

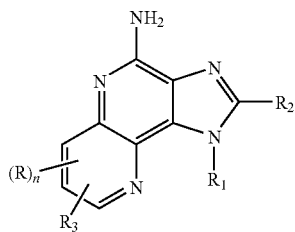

wherein:
n is 0 or 1;
$R_1$ is selected from the group consisting of:
—$R_4$,
—X—$R_4$,
—X—Y—$R_4$,
—X—Y—X—Y—$R_4$, and
—X—$R_5$;
$R_2$ is selected from the group consisting of:
—$R_4$,
—X—$R_4$,
—X—Y—$R_4$, and
—X—$R_5$;
$R_3$ is selected from the group consisting of:
—Z—Ar,
—Z—Ar'—Y—$R_4$,
—Z—Ar'—X—Y—$R_4$,
—Z—Ar'—$R_5$, and
—Z—Ar'—X—$R_5$;
R is selected from the group consisting of alkyl, alkoxy, chloro, fluoro, hydroxy, and trifluoromethyl;
Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, aminoalkyl, alkylamino, and dialkylamino;
Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y is selected from the group consisting of:

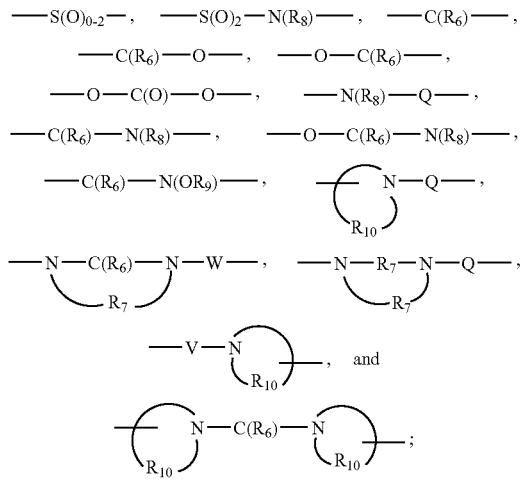

Z is selected from the group consisting of a bond, alkylene, alkenylene, and alkynylene;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

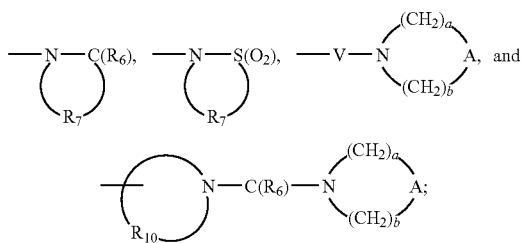

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$), —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_9$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7;
or a pharmaceutically acceptable salt thereof.

In another embodiment, there is provided a compound of the Formula (III):

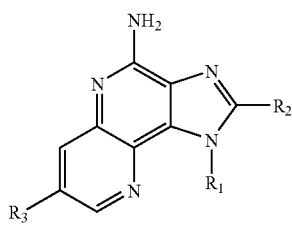

III wherein:
$R_1$ is selected from the group consisting of:
—$R_4$,
—X—$R_4$,
—X—Y—$R_4$,
—X—Y—X—Y—$R_4$, and
—X—$R_5$;
$R_2$ is selected from the group consisting of:
—$R_4$,
—X—$R_4$,
—X—Y—$R_4$, and
—X—$R_5$;
$R_3$ is selected from the group consisting of:
—Z—Ar,
—Z—Ar'—Y—$R_4$,
—Z—Ar'—X—Y—$R_4$,
—Z—Ar'—$R_5$, and
—Z—Ar'—X—$R_5$;
Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, aminoalkyl, alkylamino, and dialkylamino;
Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y is selected from the group consisting of:

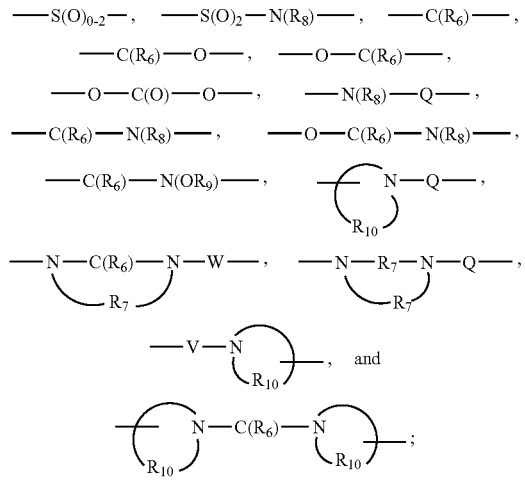

Z is selected from the group consisting of a bond, alkylene, alkenylene, and alkynylene;
$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

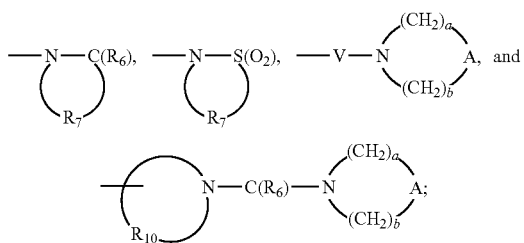

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$), —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7;
or a pharmaceutically acceptable salt thereof.

In another embodiment, the present invention provides a compound of the Formula (IV):

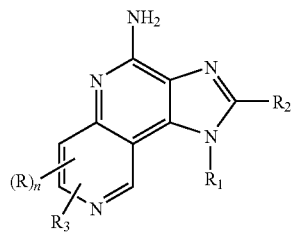

IV wherein:
n is 0 or 1;
$R_1$ is selected from the group consisting of:
—R$_4$,
—X—R$_4$,
—X—Y—R$_4$,
—X—Y—X—Y—R$_4$, and
—X—R$_5$;
$R_2$ is selected from the group consisting of:
—R$_4$,
—X—R$_4$,
—X—Y—R$_4$, and
—X—R$_5$;
$R_3$ is selected from the group consisting of:
—Z—Ar,
—Z—Ar'—Y—R$_4$,
—Z—Ar'—X—Y—R$_4$,
—Z—Ar'—R$_5$, and
—Z—Ar'—X—R$_5$;
R is selected from the group consisting of alkyl, alkoxy, chloro, fluoro, hydroxy, and trifluoromethyl;
Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, aminoalkyl, alkylamino, and dialkylamino;
Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y is selected from the group consisting of:

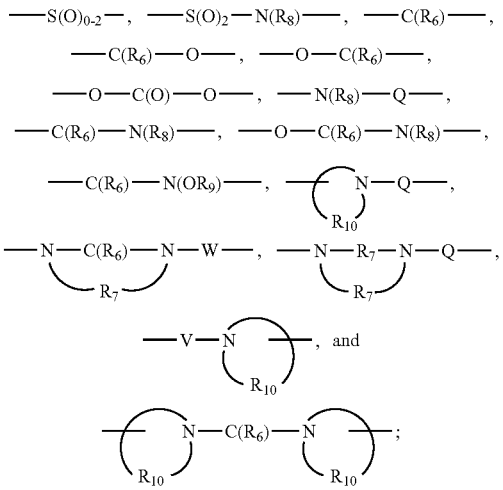

Z is selected from the group consisting of a bond, alkylene, alkenylene, and alkynylene;
$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

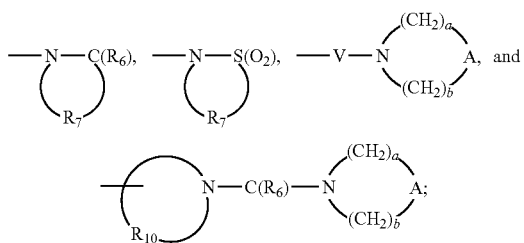

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$), —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;
or a pharmaceutically acceptable salt thereof.

In another embodiment, there is provided a compound of the Formula (V):

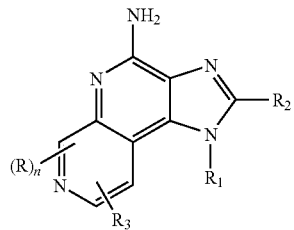

wherein:
n is 0 or 1;
$R_1$ is selected from the group consisting of:
—$R_4$,
—X—$R_4$,
—X—Y—$R_4$,
—X—Y—X—Y—$R_4$, and
—X—$R_5$;
$R_2$ is selected from the group consisting of:
—$R_4$,
—X—$R_4$,
—X—Y—$R_4$, and
—X—$R_5$;
$R_3$ is selected from the group consisting of:
—Z—Ar,
—Z—Ar'—Y—$R_4$,
—Z—Ar'—X—Y—$R_4$,
—Z—Ar'—$R_5$, and
—Z—Ar'—X—$R_5$;
R is selected from the group consisting of alkyl, alkoxy, chloro, fluoro, hydroxy, and trifluoromethyl;
Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, aminoalkyl, alkylamino, and dialkylamino;
Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y is selected from the group consisting of:

—S(O)$_{0-2}$—, —S(O)$_2$—N(R$_8$)—, —C(R$_6$)—,
—C(R$_6$)—O—, —O—C(R$_6$)—,
—O—C(O)—O—, —N(R$_8$)—Q—,
—C(R$_6$)—N(R$_8$)—, —O—C(R$_6$)—N(R$_8$)—,

—C(R$_6$)—N(OR$_9$)—, —N(-Q-)(R$_{10}$ ring)—,

—N(R$_7$ ring)—C(R$_6$)—N—W—, —N(R$_7$ ring)—R$_7$—N—Q—,

—V—N(R$_{10}$ ring)—, and

—N(R$_{10}$ ring)—C(R$_6$)—N(R$_{10}$ ring)—;

Z is selected from the group consisting of a bond, alkylene, alkenylene, and alkynylene;
$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxy-alkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

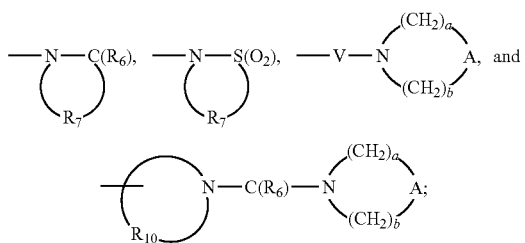

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$), —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7;
or a pharmaceutically acceptable salt thereof.

In another embodiment, there is provided a compound of the Formula (VI):

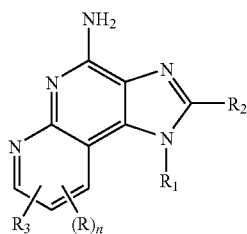

VI wherein:
n is 0 or 1;
$R_1$ is selected from the group consisting of:
—$R_4$,
—X—$R_4$,
—X—Y—$R_4$,
—X—Y—X—Y—$R_4$, and
—X—$R_5$;
$R_2$ is selected from the group consisting of:
—$R_4$,
—X—$R_4$,
—X—Y—$R_4$, and
—X—$R_5$;
$R_3$ is selected from the group consisting of:
—Z—Ar,
—Z—Ar'—Y—$R_4$,
—Z—Ar'—X—Y—$R_4$,
—Z—Ar'—$R_5$, and
—Z—Ar'—X—$R_5$;

R is selected from the group consisting of alkyl, alkoxy, chloro, fluoro, hydroxy, and trifluoromethyl;

Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, aminoalkyl, alkylamino, and dialkylamino;

Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

$$—S(O)_{0-2}—, —S(O)_2—N(R_8)—, —C(R_6)—,$$
$$—C(R_6)—O—, —O—C(R_6)—,$$
$$—O—C(O)—O—, —N(R_8)—Q—,$$
$$—C(R_6)—N(R_8)—, —O—C(R_6)—N(R_8)—,$$

—C(R$_6$)—N(OR$_9$)—, 
$$\begin{array}{c}\diagup\!\!\!\diagdown\\ —N\!\!\quad\!\!\! N—Q—,\\ R_{10}\end{array}$$

$$\begin{array}{c} —N—C(R_6)—N—W—,\quad —N—R_7—N—Q—,\\ \diagdown R_7\diagup \qquad\qquad \diagdown R_7\diagup \end{array}$$

$$—V—N\!\!\!\diagup\!\!\!\diagdown\!\!\quad, \text{ and}\\ \quad\ R_{10}$$

$$\diagup\!\!\!\diagdown\quad\diagup\!\!\!\diagdown\\ —N\!\!\quad\!\! C(R_6)—N\!\!\quad\!\!—;\\ R_{10}\qquad R_{10}$$

Z is selected from the group consisting of a bond, alkylene, alkenylene, and alkynylene;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

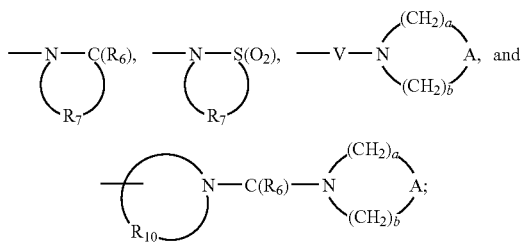

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$), —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7;
or a pharmaceutically acceptable salt thereof.

For certain embodiments, the present invention provides a compound (which is a prodrug) of the Formula (VII):

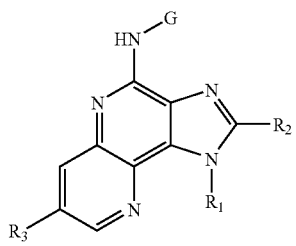

VII wherein:
G is selected from the group consisting of:
—C(O)—R',
α-aminoacyl,
α-aminoacyl-α-aminoacyl,
—C(O)—O—R',
—C(O)—N(R")R',
—C(=NY')—R',
—CH(OH)—C(O)—OY',
—CH(OC$_{1-4}$alkyl)Y$_0$,
—CH$_2$Y$_1$, and
—CH(CH$_3$)Y$_1$;

R' and R" are independently selected from the group consisting of $C_{1-10}$ alkyl, $C_{3-7}$ cycloalkyl, and benzyl, each of which may be unsubstituted or substituted by one or more substitutents selected from the group consisting of halogen, hydroxy, nitro, cyano, carboxy, $C_{1-6}$ alkyl, $C_{1-4}$ alkoxy, aryl, heteroaryl, aryl$C_{1-4}$ alkylenyl, heteroaryl$C_{1-4}$ alkylenyl, haloC$_{1-4}$ alkylenyl, haloC$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen;

α-aminoacyl is an acyl group derived from an amino acid selected from the group consisting of racemic, D-, and L-amino acids;

Y' is selected from the group consisting of hydrogen, $C_{1-6}$ alkyl, and benzyl;

$Y_0$ is selected from the group consisting of $C_{1-6}$ alkyl, carboxyC$_{1-6}$ alkylenyl, aminoC$_{1-4}$ alkylenyl, mono-N—C$_{1-6}$ alkylaminoC$_{1-4}$ alkylenyl, and di-N,N—C$_{1-6}$ alkylaminoC$_{1-4}$ alkylenyl;

$Y_1$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl;

$R_1$ is selected from the group consisting of:
—R$_4$,
—X—R$_4$,
—X—Y—R$_4$,
—X—Y—X—Y—R$_4$, and
—X—R$_5$;

$R_2$ is selected from the group consisting of:
—R$_4$,
—X—R$_4$,
—X—Y—R$_4$, and
—X—R$_5$;

$R_3$ is selected from the group consisting of:
—Z—Ar,
—Z—Ar'—Y—R$_4$,
—Z—Ar'—X—Y—R$_4$,
—Z—Ar'—R$_5$, and
—Z—Ar'—X—R$_5$;

Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, aminoalkyl, alkylamino, and dialkylamino;

Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

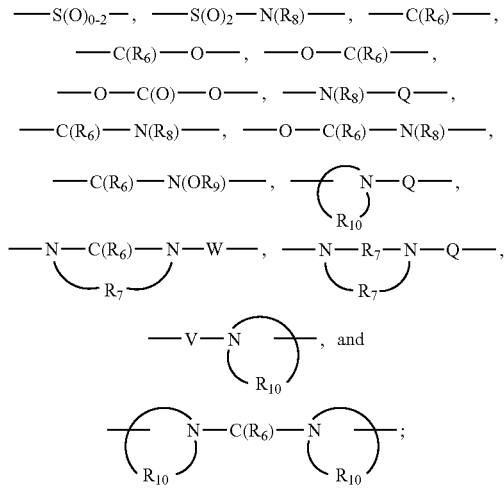

Z is selected from the group consisting of a bond, alkylene, alkenylene, and alkynylene;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

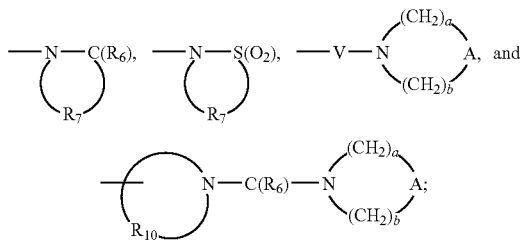

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$), —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is $\leq 7$;

or a pharmaceutically acceptable salt thereof.

For any of the compounds presented herein, each one of the following variables (e.g., Z, X, Y, R$_4$, R$_B$, R$_1$, R$_2$, R$_3$, Q, n, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments of Formulas II, IV, V, and VI, n is 0 or 1. For certain embodiments of Formulas II, IV, V, and VI, n is 0.

For certain embodiments, R is selected from the group consisting of alkyl, alkoxy, chloro, fluoro, hydroxy, and trifluoromethyl.

For certain embodiments, $R_1$ is selected from the group consisting of —R$_4$, —X—R$_4$, —X—Y—R$_4$, —X—Y—X—Y—R$_4$, and —X—R$_5$.

For certain embodiments, $R_1$ is selected from the group consisting of alkyl, arylalkylenyl, aryloxyalkylenyl, hydroxyalkyl, fluoroalkyl, heterocyclylalkylenyl which is unsubstituted or substituted by hydroxy, —X—Y—R$_4$, and —X—R$_5$. For certain alternative embodiments, $R_1$ is selected from the group consisting of alkyl, arylalkylenyl, aryloxyalkylenyl, hydroxyalky, —X—Y—R$_4$, and —X—R$_5$. Preferably, X is alkylene. Preferably, Y is selected from the group consisting of —N(R$_8$)—C(O)—, —N(R$_8$)—S(O)$_2$—, —N(R$_8$)—C(O)—N(R$_8$)—, —S(O)$_2$—, and

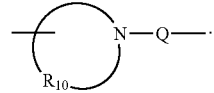

Preferably, $R_4$ is selected from the group consisting of alkyl, aryl, and heteroaryl.

Preferably, $R_5$ is selected from the group consisting of

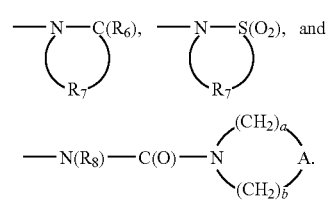

For certain embodiments, $R_1$ is selected from the group consisting of alkyl and hydroxyalkyl.

For certain embodiments, $R_1$ is selected from the group consisting of propyl, 2-methylpropyl, 2-hydroxy-2-methylpropyl, 2,3-dihydroxypropyl, 2-methyl-2-[(methylsulfonyl)amino]propyl, 4-[(methylsulfonyl)amino]butyl, 4-[(morpholin-4-ylcarbonyl)amino]butyl, (1-hydroxycyclopentyl)methyl, (1-hydroxycyclobutyl)methyl, 2-fluoro-2- methylpropyl, tetrahydro-2H-pyran-4-ylmethyl, and 4-hydroxytetrahydro-2H-pyran-4-ylmethyl.

For certain embodiments, $R_1$ is selected from the group consisting of propyl, 2-methylpropyl, 2-hydroxy-2-methylpropyl, 2,3-dihydroxypropyl, 2-methyl-2-[(methylsulfonyl)amino]propyl, 4-[(methylsulfonyl)amino]butyl, and 2-fluoro-2-methylpropyl.

For certain embodiments, $R_1$ is selected from the group consisting of 2-hydroxy-2-methylpropyl, 2-methylpropyl, propyl, 2,3-dihydroxypropyl, 2-methyl-2-[(methylsulfonyl)amino]propyl (i.e., 2-methanesulfonylamino-2-methylpropyl), and 4-[(methylsulfonyl)amino]butyl (i.e., 4-methanesulfonylaminobutyl).

For certain embodiments, $R_2$ is selected from the group consisting of —$R_4$, —X—$R_4$, —X—Y—$R_4$, and —X—$R_5$.

For certain embodiments, $R_2$ is selected from the group consisting of hydrogen, alkyl, alkoxyalkylenyl, and hydroxyalkylenyl.

For certain embodiments, $R_2$ is selected from the group consisting of hydrogen, alkyl, and alkoxyalkylenyl.

For certain embodiments, $R_2$ is selected from the group consisting of hydrogen, methyl, ethyl, propyl, butyl, methoxymethyl, ethoxymethyl, 2-methoxyethyl, hydroxymethyl, and 2-hydroxyethyl.

For certain embodiments, $R_2$ is selected from the group consisting of hydrogen, methyl, ethyl, propyl, butyl, methoxymethyl, ethoxymethyl, and 2-methoxyethyl. For certain embodiments, $R_2$ is selected from the group consisting of methyl, ethyl, propyl, methoxymethyl, ethoxymethyl, and 2-methoxyethyl.

For certain embodiments, $R_2$ is selected from the group consisting of methyl, ethyl, propyl, methoxymethyl, ethoxymethyl, 2-methoxyethyl, hydroxymethyl, and 2-hydroxyethyl.

For certain embodiments, $R_3$ is selected from the group consisting of —Z—Ar, —Z—Ar'—Y—$R_4$, —Z—Ar'—X—Y—$R_4$, —Z—Ar'—$R_5$, and —Z—Ar'—X—$R_5$.

For certain embodiments, $R_3$ is —Z—Ar.

For certain embodiments, $R_3$ is selected from the group consisting of phenyl, pyridyl, pyrrolyl, pyrazolyl, imidazolyl, thienyl, pyrimidinyl, furyl, and quinolinyl; each of which can be unsubstituted or can be substituted by one or more substituents selected from the group consisting of halogen, alkyl, alkenyl, hydroxy, hydroxyalkyl, alkoxy, amino, aminoalkyl, cyano, methylenedioxy, arylalkyleneoxy, carboxy, haloalkyl, and dialkylamino.

For certain other embodiments, $R_3$ is selected from the group consisting of phenyl, pyridyl, pyrrolyl, pyrazolyl, imidazolyl, thienyl, pyrimidinyl, and furyl; each of which can be unsubstituted or can be substituted by one or more substituents selected from the group consisting of halogen, alkyl, alkenyl, hydroxy, hydroxyalkyl, alkoxy, amino, aminoalkyl, and cyano.

For certain embodiments, $R_3$ is selected from the group consisting of pyridin-3-yl, pyridin-4-yl, 5-(hydroxymethyl)pyridin-3-yl, 2-ethoxyphenyl, 3-(morpholin-4-ylcarbonyl)phenyl, 3-[(isopropylamino)carbonyl]phenyl, 3-[(propylamino)carbonyl]phenyl, phenyl, 3-(hydroxymethyl)phenyl, 6-fluoropyridin-3-yl, 4-chlorophenyl, 2-hydroxyphenyl, 2-isopropoxyphenyl, 3,4-difluorophenyl, 3-[(methylsulfonyl)amino]phenyl, 4-[(methylsulfonyl)amino]phenyl, and 3-(aminocarbonyl)phenyl.

For certain embodiments, $R_3$ is selected from the group consisting of pyridin-3-yl (i.e., 3-pyridyl), pyridin-4-yl (i.e., 4-pyridyl), 5-(hydroxymethyl)pyridin-3-yl (i.e., 5-hydroxymethyl-3-pyridyl), 2-ethoxyphenyl, and 3-(morpholin-4-ylcarbonyl)phenyl (i.e., 3-(morpholine-4-carbonyl)phenyl). For certain embodiments, $R_3$ is selected from the group consisting of pyridin-3-yl, 3-[(isopropylamino)carbonyl]phenyl, 3-[(propylamino)carbonyl]phenyl, 3-(morpholin-4-ylcarbonyl)phenyl, 3-[(methylsulfonyl)amino]phenyl, 5-(hydroxymethyl)pyridin-3-yl, and 6-fluoropyridin-3-yl.

For certain other embodiments, $R_3$ is —Z—Ar'—Y—$R_4$, —Z—Ar'—X—Y—$R_4$, —Z—Ar'—$R_5$, or —Z—Ar'—X—$R_5$. For certain embodiments, $R_3$ is —Z—Ar'—Y—$R_4$, —Z—Ar'—X—Y—$R_4$, or —Z—Ar'—$R_5$.

Preferably, for certain embodiments, Ar' (of —Z—Ar'—Y—$R_4$, —Z—Ar'—X—Y—$R_4$, —Z—Ar'—$R_5$, or —Z—Ar'—X—$R_5$ and more particularly of —Z—Ar'—Y—$R_4$, —Z—Ar'—X—Y—$R_4$, or —Z—Ar'—$R_5$) is phenylene or pyridylene. Preferably, for certain embodiments, Y in —Z—Ar'—Y—$R_4$ or —Z—Ar'—X—Y—$R_4$ is selected from the group consisting of: —$S(O)_{0-2}$—, —$S(O)_2$—N($R_8$)—, —C(O)—, —N($R_8$)-Q-, —C($R_6$)—N($R_8$)—, —C(O)—O—, and —C(O)—N($OCH_3$)—. Preferably, for certain embodiments, Y in —Z—Ar'—Y—$R_4$ or —Z—Ar'—X—Y—$R_4$ is selected from the group consisting of —$S(O)_{0-2}$—, —C(O)—, —N($R_8$)-Q-, and —C($R_6$)—N($R_8$)—. Preferably, in such embodiments, Q is selected from the group consisting of bond, —C(O)—, —C(O)—O—, —C(O)—N(H)—, and —$S(O)_2$—. More preferably, in such embodiments, Q is selected from the group consisting of a bond, —C(O)—, —C(O)—O—, and —$S(O)_2$—. Preferably, in such embodiments, $R_8$ is selected from the group consisting of hydrogen, $C_{1-4}$ alkyl, and alkoxyalkylenyl. Preferably, for certain embodiments, X in —Z—Ar'—X—Y—$R_4$ or —Z—Ar'—X—$R_5$ (more particularly in —Z—Ar'—X—Y—$R_4$) is $C_{1-4}$ alkylene. Preferably, for certain embodiments, $R_4$ in —Z—Ar'—Y—$R_4$ or —Z—Ar'—X—Y—$R_4$ is selected from the group consisting of alkyl, aryl, arylalkylenyl, heteroarylalkylenyl, heteroaryl, and heterocyclyl. Preferably, for certain other embodiments, $R_4$ in —Z—Ar'—Y—$R_4$ or —Z—Ar'—X—Y—$R_4$ is selected from the group consisting of alkyl, haloalkyl, aryl, arylalkylenyl, heteroarylalkylenyl, heteroaryl, alkylheteroarylenyl, and heterocyclyl, preferably, with the proviso that $R_4$ may also be hydrogen when Y is —C(O)—O—, —C(O)—N($OCH_3$)—, or —N($R_8$)—. Preferably, for certain embodiments, $R_5$ in —Z—Ar'—$R_5$ or —Z—Ar'—X—$R_5$ (more particularly in —Z—Ar'—$R_5$) is

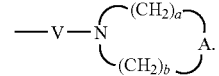

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, carboxy, alkylamino, dialkylamino, (dialkylamino)alkyleneoxy, and in the case of alkyl, alkenyl, alkynyl, and heterocyclyl, oxo.

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo.

For certain embodiments, $R_4$ is selected from the group consisting of alkyl, aryl, and heteroaryl. For certain embodiments, particularly in —Z—Ar'—Y—$R_4$ or —Z—Ar'—X—Y—$R_4$, $R_4$ is selected from the group consisting of alkyl, haloalkyl, aryl, arylalkylenyl, heteroarylalkylenyl, heteroaryl, alkylheteroarylenyl, and heterocyclyl, preferably with the proviso that $R_4$ may also be hydrogen when Y is —C(O)—O—, —C(O)—N(OCH$_3$)—, or —N($R_8$)—. For certain embodiments, particularly in —Z—Ar'—Y—$R_4$ or —Z—Ar'—X—Y—$R_4$, $R_4$ is selected from the group consisting of alkyl, aryl, arylalkylenyl, heteroarylalkylenyl, heteroaryl, and heterocyclyl.

For certain embodiments, $R_5$ is selected from the group consisting of:

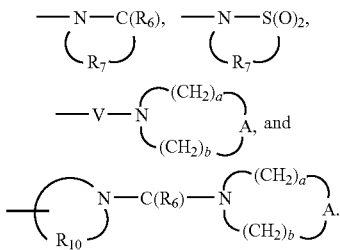

For certain embodiments, $R_5$ is selected from the group consisting of

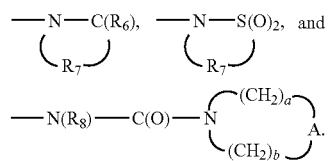

For certain embodiments, particularly in —Z—Ar'—$R_5$ or —Z—Ar'—X—$R_5$, $R_5$ is

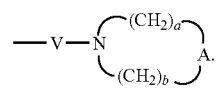

For certain embodiments, X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O- groups.

For certain embodiments, X is alkylene.

For certain embodiments, particularly in —Z—Ar'—X—Y—$R_4$ or —Z—Ar'—X—$R_5$, X is $C_{1-4}$ alkylene.

For certain embodiments, Y is selected from the group consisting of

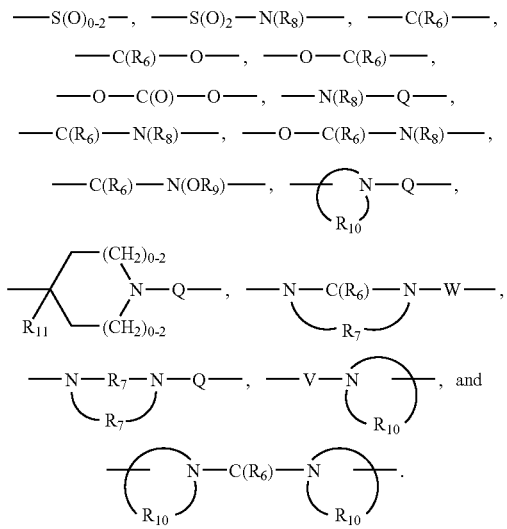

For certain embodiments, Y is selected from the group consisting of

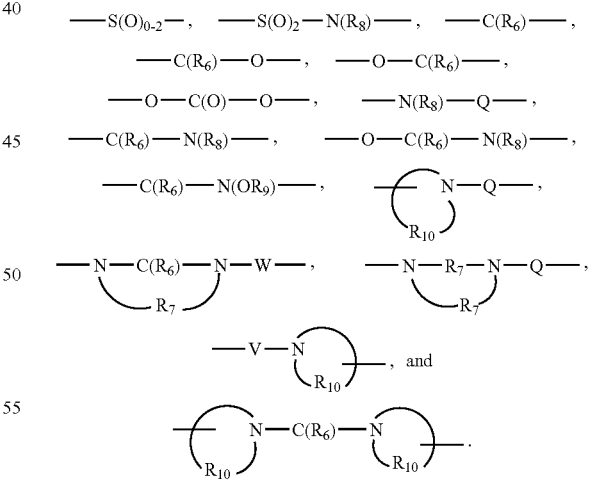

For certain embodiments, Y is selected from the group consisting of $S(O)_{0-2}$—, —C(O)—, —N($R_8$)-Q-, and —C($R_6$)—N($R_8$)—.

For certain embodiments, particularly in —Z—Ar'—Y—$R_4$ or —Z—Ar'—X—Y—$R_4$, Y is selected from the group consisting of —S(O)O$_{0-2}$—, —S(O)$_2$—N($R_8$)—, —C(O)—, —N($R_8$)-Q-, —C($R_6$)—N($R_8$)—, —C(O)—O—, and —C(O)—N(OCH$_3$)—.

For certain embodiments, particularly in —Z—Ar'—Y—R$_4$ or —Z—Ar'—X—Y—R$_4$, Y is selected from the group consisting of —S(O)$_{0-2}$—, —C(O)—, —N(R$_8$)-Q-, and —C(R$_6$)—N(R$_8$)—.

For certain embodiments, Y is selected from the group consisting of —N(R$_8$)—C(O)—, —N(R$_8$)—S(O)$_2$—, —N(R$_8$)—C(O)—N(R$_8$)—, —S(O)$_2$—, and

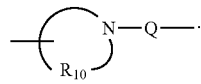

For certain embodiments, Z is selected from the group consisting of a bond, alkylene, alkenylene, and alkynylene. For certain embodiments, Z is selected from the group consisting of a bond, methylene, and ethylene. For certain embodiments, Z is a bond.

For certain embodiments, Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, alkoxyalkylenyl, α-aminocarboxyalkylenyl, amino, aminoalkyl, alkylamino, and dialkylamino.

For certain embodiments, Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, aminoalkyl, alkylamino, and dialkylamino.

For certain embodiments of Formulas I, II, and III, Ar may also be aryl or heteroaryl substituted by alkoxyalkylenyl.

For certain embodiments, Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino.

For certain embodiments, particularly in —Z—Ar'—Y—R$_4$, —Z—Ar'—X—Y—R$_4$, or —Z—Ar'—R$_5$, Ar' is phenylene or pyridylene.

For certain embodiments, Q is selected from the group consisting of a bond, —C(R$_6$)—, —C(R$_6$)—C(R$_6$), —S(O)$_2$—, —C(R$_6$)—N(R$_8$)—W—, —S(O)$_2$—N(R$_8$)—, —C(R$_6$)—O—, and —C(R$_6$)—N(OR$_9$)—. For certain embodiments, particularly embodiments of —N(R$_8$)-Q-, Q is selected from the group consisting of a bond, —C(O)—, —C(O)—O—, —C(O)—N(H)—, and —S(O)$_2$—. For certain embodiments, particularly embodiments of —N(R$_8$)-Q-, Q is selected from the group consisting of a bond, —C(O)—, —C(O)—O—, and —S(O)$_2$—. For certain embodiments, Q is selected from the group consisting of —C(O)—, —C(O)—N(R$_8$)—, and —S(O)$_2$—.

For certain embodiments, R$_6$ is =O or =S. For certain embodiments, R$_6$ is =O.

For certain embodiments, R$_7$ is C$_{2-7}$ alkylene. For certain embodiments, R$_7$ is C$_{2-3}$ alkylene.

For certain embodiments, R$_8$ is selected from the group consisting of hydrogen, alkyl, alkoxyalkylenyl, and arylalkylenyl. For certain embodiments, particularly in —N(R$_8$)-Q- and —C(R$_6$)—N(R$_8$)—, R$_8$ is selected from the group consisting of hydrogen, C$_{1-4}$ alkyl, and alkoxyalkylenyl. For certain embodiments, R$_8$ is hydrogen.

For certain embodiments, R$_9$ is hydrogen or alkyl. For certain embodiments, R$_9$ is hydrogen or methyl.

For certain embodiments, R$_{10}$ is C$_{3-8}$ alkylene. For certain embodiments, R$_{10}$ is C$_5$ alkylene.

For certain embodiments, R$_{11}$ is selected from the group consisting of fluoro, hydroxy, and alkoxy.

For certain embodiments, A is selected from the group consisting of —O—, —C(O)—, —S(O)$_{0-2}$—, —CH$_2$—, and —N(R$_4$)—. For certain embodiments, A is —O—, —CH$_2$—, or —C(O)—.

For certain embodiments, V is selected from the group consisting of —C(R$_6$)—, —O—C(R$_6$)—, —N(R$_8$)—C(R$_6$)—, and —S(O)$_2$—. For certain embodiments, V is —C(O)—. For certain embodiments, V is —N(R$_8$)—C(R$_6$)—. For certain embodiments, V is —S(O)$_2$—.

For certain embodiments, W is selected from the group consisting of a bond, —C(O)—, and —S(O)$_2$—. For certain embodiments, W is a bond.

For certain embodiments, a and b are independently integers from 1 to 6 with the proviso that a+b is ≦7.

For certain embodiments, a is 2.

For certain embodiments, b is 2.

For certain embodiments of the compounds of Formulas (I) through (VI), the —NH$_2$ group can be replaced by an —NH-G group, as shown in the compound of Formula (VII), to form prodrugs. In such embodiments, G is selected from the group consisting of: —C(O)—R', α-aminoacyl, α-aminoacyl-α-aminoacyl, —C(O)—O—R', —C(O)—N(R")R', —C(=NY')—R', —CH(OH)—C(O)—OY', —CH(OC$_{1-4}$ alkyl)Y$_0$, —CH$_2$Y$_1$, and —CH(CH$_3$)Y$_1$. For certain embodiments, G is selected from the group consisting of —C(O)—R', α-aminoacyl, α-aminoacyl-α-aminoacyl, and —C(O)—O—R'. Preferably, R' and R" are independently selected from the group consisting of C$_{1-10}$ alkyl, C$_{3-7}$ cycloalkyl, and benzyl, each of which may be unsubstituted or substituted by one or more substitutents selected from the group consisting of halogen, hydroxy, nitro, cyano, carboxy, C$_{1-6}$ alkyl, C$_{1-4}$ alkoxy, aryl, heteroaryl, arylC$_{1-4}$ alkylenyl, heteroarylC$_{1-4}$ alkylenyl, haloC$_{1-4}$ alkylenyl, haloC$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen. Preferably, α-aminoacyl is an acyl group derived from an amino acid selected from the group consisting of racemic, D-, and L-amino acids. Preferably, Y' is selected from the group consisting of hydrogen, C$_{1-6}$ alkyl, and benzyl. Preferably, Y$_0$ is selected from the group consisting of C$_{1-6}$ alkyl, carboxyC$_{1-6}$ alkylenyl, aminoC$_{1-4}$ alkylenyl, mono-N—C$_{1-6}$ alkylaminoC$_{1-4}$ alkylenyl, and di-N,N—C$_{1-6}$ alkylaminoC$_{1-4}$ alkylenyl. Preferably, Y$_1$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl.

In one embodiment, there is provided a pharmaceutical composition containing an effective amount of a compound of Formula VII. In one embodiment, there is provided a method of inducing cytokine biosynthesis in an animal by administering an effective amount of a compound of Formula VII to the animal. In one embodiment, there is provided a method of treating a viral infection in an animal by administering an effective amount of a compound of Formula VII to the animal. In one embodiment, there is provided a method of treating a neoplastic disease in an animal by administering an effective amount of a compound of Formula VII to the animal.

As used herein, the terms "alkyl," "alkenyl," "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, up to 5 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "alkenylene," and "alkynylene" are the divalent forms of the "alkyl," "alkenyl," and "alkynyl" groups defined above. Likewise, "alkylenyl," "alkenylenyl," and "alkynylenyl" are the divalent forms of the "alkyl," "alkenyl," and "alkynyl" groups defined above. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

The term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2 to 12 carbon atoms, 1 to 3 rings, 1 to 4 heteroatoms, and O, S, and N as the heteroatoms. Exemplary heterocyclic groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicyclic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one Spiro atom and three rings joined by two Spiro atoms.

When "heterocyclyl" contains a nitrogen atom, the point of attachment of the heterocyclyl group may be the nitrogen atom.

The terms "arylene," "heteroarylene," and "heterocyclylene" are the divalent forms of the "aryl," "heteroaryl," and "heterocyclyl" groups defined above. Likewise, "arylenyl," "heteroarylenyl," and "heterocyclylenyl" are the divalent forms of the "aryl," "heteroaryl," and "heterocyclyl" groups defined above. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula —N($R_8$)—C(O)—N($R_8$)— each $R_8$ group is independently selected. In another example, when an $R_2$ and an $R_3$ group both contain an $R_4$ group, each $R_4$ group is independently selected. In a further example, when more than one Y group is present (i.e., $R_2$ and $R_3$ both contain a Y group) and each Y group contains one or more $R_7$ groups, then each Y group is independently selected, and each $R_7$ group is independently selected.

The invention is inclusive of the compounds described herein in any of their pharmaceutically acceptable forms, including isomers (e.g., diastereomers and enantiomers), salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

The term "prodrug" means a compound that can be transformed in vivo to yield an immune response modifying compound in any of the salt, solvated, polymorphic, or isomeric forms described above. The prodrug, itself, may be an immune response modifying compound in any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v. 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organzischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of compounds of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic synthesis*, John Wiley & Sons, New York, USA, 1991.

Conventional methods and techniques of separation and purification can be used to isolate compounds of the invention or pharmaceutically acceptable salts thereof, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

Compounds of the invention can be prepared according to Reaction Scheme I where $R_{3a}$ is —$Z_a$—Ar, —$Z_a$—Ar'—Y—$R_4$, —$Z_a$—Ar'—C—Y—$R_4$, or —$Z_a$—Ar'—$R_5$; $Z_a$ is a bond, alkenylene, or alkynylene; Hal is bromo or iodo; and R, n, Ar, Ar', X, Y, $R_4$, and $R_5$ are as defined above. $R_{1a}$ and $R_{2b}$ are subsets of $R_1$ and $R_2$ as defined above that do not include those substituents that one skilled in the art would recognize as being susceptible to oxidation in step (8). These substituents include —S— and heteroaryl groups.

In step (1) of Reaction Scheme I, an aminopyridine of Formula X is treated with the condensation product generated from 2,2-dimethyl-1,3-dioxane-4,6-dione (Meldrum's acid) and triethyl orthoformate to provide an imine of Formula XI. The reaction is conveniently carried out by adding a solution of an aminopyridine of Formula X to a heated mixture of Meldrum's acid and triethyl orthoformate and heating the reaction at an elevated temperature, such as 70° C. Aminopyridines of Formula X are commercially available, or they can be prepared by known methods.

In step (2) of Reaction Scheme I, an imine of Formula XI undergoes thermolysis and cyclization to provide a [1,5]naphthyridin-4-ol of Formula XII. The reaction is conveniently carried out in a medium such as DOWTHERM A heat transfer fluid at a temperature not lower than about 200° C. and not higher than about 250° C.

In step (3) of Reaction Scheme I, the [1,5]naphthyridin-4-ol of Formula XII is nitrated under conventional nitration conditions to provide a 3-nitro[1,5]naphthyridin-4-ol of Formula XIII. The reaction is conveniently carried out by heating the [1,5]naphthyridin-4-ol of Formula XII in nitric acid at an elevated temperature, such as 90° C.

In step (4) of Reaction Scheme I, a 3-nitro[1,5]naphthyridin-4-ol of Formula XIII is chlorinated using conventional chlorination chemistry to provide a 4-chloro-3-nitro[1,5]naphthyridine of Formula XIV. The reaction is conveniently carried out by treating the 3-nitro[1,5]naphthyridin-4-ol of Formula XIII with phosphorous oxychloride in a suitable solvent, such as N,N-dimethylformamide (DMF). The reaction can be carried out at ambient temperature or at an elevated temperature, such as 100° C.

In step (5) of Reaction Scheme I, a 4-chloro-3-nitro[1,5]naphthyridine of Formula XIV is treated with an amine of Formula $R_{1a}$—$NH_2$ to provide a 3-nitro[1,5]naphthyridin-4-amine of Formula XV. Several amines of Formula $R_{1a}$—$NH_2$ axe commercially available; others can be prepared by known synthetic methods. The reaction is conveniently carried out by adding the amine of Formula $R_{1a}$—$NH_2$ to a solution of the 4-chloro-3-nitro[1,5]naphthyridine of Formula XIV in a suitable solvent, such as dichloromethane or methanol, in the presence of a tertiary amine, such as triethylamine. The reaction can be carried out at ambient temperature or at a subambient temperature such as, for example, 0° C.

In step (6) of Reaction Scheme I, a 3-nitro[1,5]naphthyridin-4-amine of Formula XV is reduced to provide a [1,5]naphthyridine-3,4-diamine of Formula XVI. The reaction can be carried out by hydrogenation using a heterogeneous hydrogenation catalyst such as platinum on carbon. The hydrogenation is conveniently carried out in a Parr apparatus in a suitable solvent, such as toluene, methanol, or acetonitrile, or a suitable solvent mixture, such as acetonitrile:methanol or acetonitrile:isopropyl alcohol. The reaction can be carried out at ambient temperature.

Alternatively, the reduction in step (6) can be carried out using a one- or two-phase sodium dithionite reduction. The reaction is conveniently carried out using the conditions described by Park, K. K.; Oh, C. H.; and Joung, W. K.; *Tetrahedron Lett.*, 34, pp. 7445-7446 (1993) by adding sodium dithionite to a compound of Formula XV in a mixture of dichloromethane and water at ambient temperature in the presence of potassium carbonate and ethyl viologen dibromide, ethyl viologen diiodide, or 1,1'-di-n-octyl-4,4'-bipyridinium dibromide.

In step (7) of Reaction Scheme I, a [1,5]naphthyridine-3,4-diamine of Formula XVI is treated with a carboxylic acid equivalent to provide a 1H-imidazo[4,5-c][1,5]naphthyridine of Formula XVII. Suitable carboxylic acid equivalents include orthoesters of Formula $R_{2a}C(O-alkyl)_3$, 1,1-dialkoxyalkyl alkanoates of Formula $R_{2a}C(O-alkyl)_2(O—C(O)-alkyl)$, and acid chlorides of Formula $R_{2a}C(O)Cl$. The selection of the carboxylic acid equivalent is determined by the desired substituent at $R_{2a}$. For example, triethyl orthoformate will provide a compound where $R_{2a}$ is hydrogen, and trimethyl orthovalerate will provide a compound where $R_{2a}$ is a butyl group. The reaction is conveniently carried out by adding the carboxylic acid equivalent to a [1,5]naphthyridine-3,4-diamine of Formula XVI in a suitable solvent, such as toluene or xylenes. Optionally, catalytic pyridine hydrochloride can be added. The reaction is carried out at a temperature high enough to drive off alcohol or water formed during the reaction. Conveniently, a Dean-Stark trap can be used to collect the volatiles.

Alternatively, step (7) can be carried out in two steps when an acid chloride of Formula $R_{2a}C(O)Cl$ is used as the carboxylic acid equivalent. Part (i) of step (7) is conveniently carried out by adding the acid chloride to a solution of a

[1,5]naphthyridine-3,4-diamine of Formula XVI in a suitable solvent, such as dichloromethane, chloroform, or acetonitrile, or mixtures thereof, to afford an amide. Optionally, a tertiary amine, such as triethylamine, pyridine, or 4-dimethylaminopyridine, can be added. The reaction can be carried out at ambient temperature. The amide product can be isolated and optionally purified using conventional techniques. Part (ii) of step (7) can be carried out by heating, for example, at reflux, the amide prepared in part (i) to provide a 1H-imidazo[4,5-c][1,5]naphthyridine of Formula XVII. The reaction is conveniently carried out in a suitable solvent, such as toluene, at a temperature sufficient to drive off water formed during the reaction. The reaction can also be carried out in a solvent, such as ethanol or methanol, in the presence of a base, such as triethylamine or aqueous potassium carbonate.

In step (8) of Reaction Scheme I, a 1H-imidazo[4,5-c][1,5]naphthyridine of Formula XVII is oxidized to provide a 1H-imidazo[4,5-c][1,5]naphthyridine-5N-oxide of Formula XVIII using a conventional oxidizing agent capable of forming N-oxides. The reaction is conveniently carried out by adding 3-chloroperoxybenzoic acid to a solution of a compound of Formula XVII in a solvent, such as dichloromethane or chloroform. The reaction can be carried out at ambient temperature.

In step (9) of Reaction Scheme I, a 1H-imidazo[4,5-c][1,5]naphthyridine-5N-oxide of Formula XVIII is aminated to provide a 1H-imidazo[4,5-c][1,5]naphthyridin-4-amine of Formula XIX. Step (9) can be carried out by the activation of an N-oxide of Formula XVIII by conversion to an ester and then reacting the ester with an aminating agent. Suitable activating agents include alkyl- or arylsulfonyl chlorides, such as benzenesulfonyl chloride, methanesulfonyl chloride, or p-toluenesulfonyl chloride. Suitable aminating agents include ammonia, in the form of ammonium hydroxide, for example, and ammonium salts, such as ammonium carbonate, ammonium bicarbonate, and ammonium phosphate. The reaction is conveniently carried out by adding ammonium hydroxide to a solution of the N-oxide of Formula XVIII in a suitable solvent, such as dichloromethane or chloroform, and then adding p-toluenesulfonyl chloride. The reaction can be carried out at ambient temperature.

Steps (8) and (9) can alternatively be combined and carried out as a one-pot procedure by adding 3-chloroperoxybenzoic acid to a solution of a compound of Formula XVII in a solvent, such as dichloromethane or chloroform, and then adding ammonium hydroxide and p-toluenesulfonyl chloride without isolating the N-oxide of Formula XVIII.

Step (10) of Reaction Scheme I can be carried out using known palladium-catalyzed coupling reactions, such as the Suzuki coupling, the Stille coupling, the Sonogashira coupling, and the Heck reaction. For example, a 1H-imidazo[4,5-c][1,5]naphthyridin-4-amine of Formula XIX undergoes Suzuki coupling with a boronic acid of Formula $R_{3a}$—B(OH)$_2$, an anhydride thereof, or a boronic acid ester of Formula $R_{3a}$—B(O-alkyl)$_2$ to provide an 1H-imidazo[4,5-c][1,5]naphthyridin-4-amine of Formula IIa, a subgenus of Formulas I and II, wherein $R_{3a}$ is as defined above and $Z_a$ is a bond or alkenylene. The coupling is carried out by combining a 1H-imidazo[4,5-c][1,5]naphthyridin-4-amine of Formula XIX with a boronic acid or an ester or anhydride thereof in the presence of palladium (II) acetate, triphenylphosphine, and a base, such as sodium carbonate or sodium bicarbonate, in a suitable solvent or solvent mixture, such as n-propanol:water.

The coupling reaction may also conveniently carried out by heating a mixture of a compound of Formula XIX, a boronic acid or an ester or anhydride thereof, potassium carbonate and catalytic dichlorobis(triphenylphosphine)palladium(II) in a suitable solvent or solvent mixture, such as dimethoxyethane (DME) and water. Suzuki coupling reactions may be carried out under an inert atmosphere, such as nitrogen or argon. The reactions can be carried out at an elevated temperature, for example, at the reflux temperature of the solvent, typically at a temperature not lower than 80° C. and not higher than 120° C. Numerous boronic acids of Formula $R_{3a}$—B(OH)$_2$, anhydrides thereof, and boronic acid esters of Formula $R_{3a}$—B(O-alkyl)$_2$ are commercially available; others can be readily prepared using known synthetic methods. See, for example, Li, W. et al, *J. Org. Chem.*, 67, 5394-5397 (2002).

The Heck reaction can also be used in step (10) of Reaction Scheme I to provide compounds of Formula IIa, wherein $R_{3a}$ is as defined above and —$Z_a$ is alkenylene. The Heck reaction is carried out by coupling a 1H-imidazo[4,5-c][1,5]naphthyridin-4-amine of Formula XIX with a compound of the Formula H$_2$C=C(H)—Ar$_a$, wherein Ar$_a$ is —Ar, —Ar'—Y—R$_4$, —Ar'—X—Y—R$_4$, or —Ar'—R$_5$. Several of these vinyl-substituted compounds, for example, compounds of the Formulas H$_2$C=C(H)—Ar, H$_2$C=C(H)—Ar'—Y—R$_4$, and H$_2$C=C(H)—Ar'—X—Y—R$_4$ are commercially available; others can be prepared by known methods. The reaction is conveniently carried out by combining the 1H-imidazo[4,5-c][1,5]naphthyridin-4-amine of Formula XIX and the vinyl-substituted compound in the presence of palladium (II) acetate, triphenylphosphine or tri-ortho-tolylphosphine, and a base, such as triethylamine, in a suitable solvent, such as acetonitrile or toluene. The reaction can be carried out at an elevated temperature not lower than 80° C. and not higher than about 120° C. under an inert atmosphere.

Compounds of Formula IIa, wherein $R_{3a}$ is defined as above $Z_a$ is alkynylene, can also be prepared by palladium catalyzed coupling reactions, such as the Stille coupling or Sonogashira coupling. These reactions are carried out by coupling a 1H-imidazo[4,5-c][1,5]naphthyridin-4-amine of Formula XIX with a compound of the Formula H—C≡C—Ar, (alkyl)$_3$Sn—C≡C—Ar, or (alkyl)$_3$Si—C≡C—Ar, wherein Ar is as defined above.

Isomers of the compound of Formula X or Formula XII are also available or can be synthesized and can be used to prepare compounds of Formulas IV, V, and VI according to the methods shown in Reaction Scheme I.

For some embodiments, compounds in Reaction Scheme I can be further elaborated using conventional synthetic methods. For example, an amine of Formula $R_{1a}$—NH$_2$ may be substituted by a hydroxy or second amino group, which may be further functionalized before step (7) of Reaction Scheme I or later in the synthetic route. Several examples of synthetic elaborations of an $R_{1a}$ group on a 1H-imidazo[4,5-c]quinoline or a 1H-imidazo[4,5-c]naphthyridine are known and can be used to provide a compound of Formula II wherein R$_1$ is as defined above. See, for example, U.S. Pat. No. 4,689,338 (Gerster), U.S. Pat. No. 4,929,624 (Gerster et al.), U.S. Pat. No. 5,268,376 (Gerster), U.S. Pat. No. 5,389,640 (Gerster et al.), U.S. Pat. No. 6,194,425 (Gerster et al.), U.S. Pat. No. 6,331,539 (Crooks et al.), U.S. Pat. No. 6,451,810 (Coleman et al.), U.S. Pat. No. 6,541,485 (Crooks et al.), U.S. Pat. No. 6,660,747 (Crooks et al.), U.S. Pat. No. 6,670,372 (Charles et al.), U.S. Pat. No. 6,683,088 (Crooks et al.), U.S. Pat. No. 6,656,938 (Crooks et al.), U.S. Pat. No. 6,664,264 (Dellaria et al.), U.S. Pat. No. 6,677,349 (Griesgraber), and 6,664,260 (Charles et al.), and U.S. Patent Publication Application No. US 2004/0147543 (Hays et al.).

Similar synthetic transformations can be made at $R_{2a}$ if, for example, the acid chloride used in step (7) of Reaction Scheme I contains a protected hydroxy or amino group, and these synthetic transformations can be used to provide compounds of Formula II, wherein $R_2$ is as defined above. Some acid chlorides of this type are commercially available; others can be prepared by known synthetic methods. A protected hydroxy or amino group thus installed at the $R_{2a}$ position can then be deprotected by a variety of methods well known to one of skill in the art. For example, a hydroxyalkylenyl group is conveniently introduced at the $R_{2a}$ position by the dealkylation of a methoxy- or ethoxyalkylenyl group, which can be installed by using a methoxy- or ethoxy-substituted carboxylic acid equivalent, for example, methoxyacetyl chloride, 2-methoxypropionyl chloride, or ethoxyacetyl chloride, in step (7) of Reaction Scheme I or step (3) in Reaction Scheme II below. The dealkylation can be carried out by treating a compound wherein $R_{2a}$ is an alkoxyalkylenyl group with boron tribromide in a suitable solvent such as dichloromethane at a sub-ambient temperature such as 0° C. Alternatively, acetoxyacetyl chloride can be used in step (7) of Reaction Scheme I, and hydrolysis of the ester group to reveal a hydroxy group can be carried out by conventional methods. The resulting hydroxy group may then be oxidized to an aldehyde or carboxylic acid or converted to a leaving group such as, for example, a chloro group using thionyl chloride or a trifluoromethanesulfonate group using trifluoromethanesulfonic anhydride. The resulting leaving group can then be displaced by a variety of nucleophiles. Sodium azide can be used as the nucleophile to install an azide group, which can then be reduced to an amino group using heterogeneous hydrogenation conditions. An amino group at the $R_2$ position can be converted to an amide, sulfonamide, sulfamide, or urea using conventional methods, such as those described in step (5) of Reaction Scheme II below. A leaving group at $R_2$, such as a chloro or trifluoromethanesulfonate group, can also be displaced with a secondary amine, a substituted phenol, or a mercaptan in the presence of a base such as potassium carbonate. For examples of these and other methods used to install a variety of groups at the $R_2$ position, see U.S. Pat. No. 5,389,640 (Gerster et al.). These synthetic transformations may conveniently be carried out as the last steps in the synthesis.

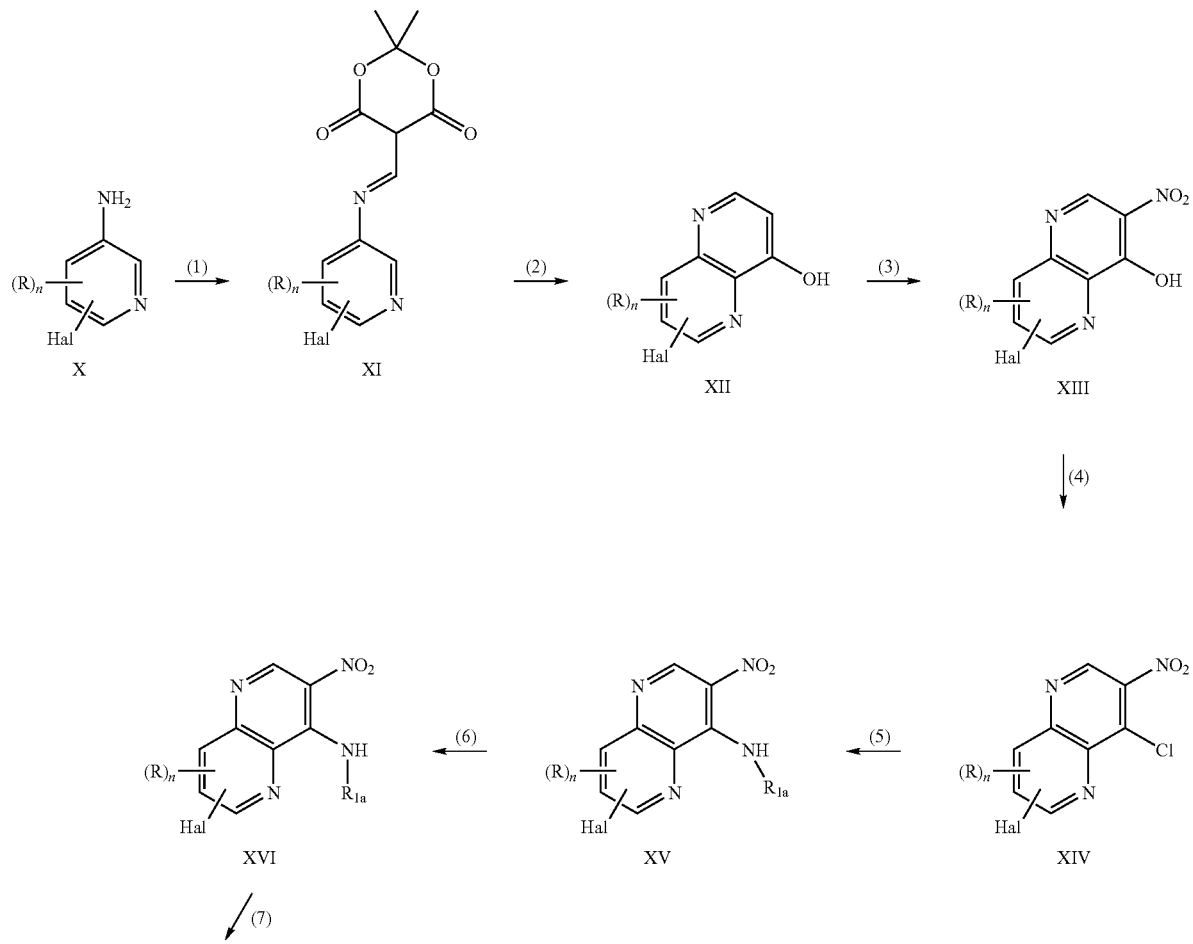

Reaction Scheme I

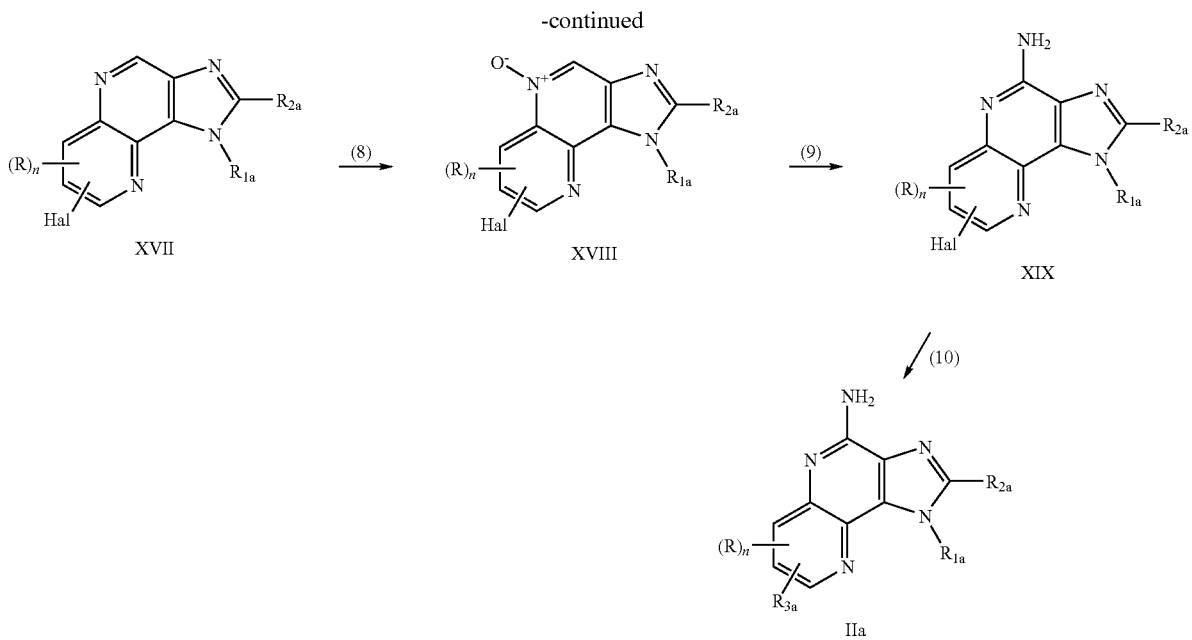

Compounds of the invention, where $R_{1b}$ is —X—N($R_8$)-Q-$R_4$ or —X—$R_5$, wherein $R_5$ is

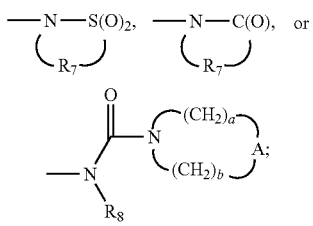

and A, X, Q, R, $R_{2a}$, $R_{3a}$, $R_7$, $R_8$, Hal, a, b, and n are as defined above, can be prepared according to Reaction Scheme II.

In step (1) of Reaction Scheme II, a 4-chloro-3-nitro[1,5] naphthyridine of Formula XIV is treated with a Boc-protected diamine of Formula $(CH_3)_3CO$—C(O)—NH—X—$NH_2$ to provide a 3-nitro[1,5]naphthyridin-4-amine of Formula XX. Several Boc-protected diamines of Formula $(CH_3)_3CO$—C(O)—NH—X—$NH_2$ are commercially available; others can be prepared by known synthetic methods. The reaction is conveniently carried out by adding a solution of the Boc-protected diamine of Formula $(CH_3)_3CO$—C(O)—NH—X—$NH_2$ to a cooled solution of the 4-chloro-3-nitro[1,5]naphthyridine of Formula XIV in a suitable solvent, such as dichloromethane, in the presence of a tertiary amine, such as triethylamine. The reaction can be carried out at ambient temperature. Alternatively, a 4-chloro-3-nitro[1,5] naphthyridine of Formula XIV can be combined with a diamine of Formula $NH_2$—X—$NH_2$ under the conditions described above, and the product can be protected with a Boc group using conventional methods.

In steps (2) and (3) of Reaction Scheme II, a 3-nitro[1,5] naphthyridin-4-amine of Formula XX is first reduced to provide a [1,5]naphthyridine-3,4-diamine of Formula XXI, which is converted to 1H-imidazo[4,5-c][1,5]naphthyridine of Formula XXII by reaction with a carboxylic acid equivalent. Steps (2) and (3) of Reaction Scheme II can be carried out as described for steps (6) and (7) of Reaction Scheme I.

In step (4) of Reaction Scheme II, the Boc-protecting group of a 1H-imidazo[4,5-c][1,5]naphthyridine of Formula XXII is removed to provide a 1-aminoalkyl-1H-imidazo[4,5-c][1,5]naphthyridine of Formula XXIII. The reaction is conveniently carried out by adding hydrochloric acid or a solution of hydrochloric acid in ethanol to a solution of a 1H-imidazo[4,5-c][1,5]naphthyridine of Formula XXII in a suitable solvent, such as ethanol. The reaction can be carried out at an elevated temperature, for example, the reflux temperature of the solvent, or at ambient temperature.

In step (5) of Reaction Scheme II, a 1H-imidazo[4,5-c][1,5]naphthyridine of Formula XXIII is converted to a 1H-imidazo[4,5-c][1,5]naphthyridine of Formula XXIV, where $R_{1b}$ is as defined above, using conventional methods. For example, a 1H-imidazo[4,5-c][1,5]naphthyridine of Formula XXIII can react with an acid chloride of Formula $R_4$C(O)Cl to provide a compound of Formula XXIV in which $R_{1b}$ is —X—N($R_8$)-Q-$R_4$, and Q is —C(O)—. In addition, a 1H-imidazo[4,5-c][1,5]naphthyridine of Formula XXIII can react with sulfonyl chloride of Formula $R_4$S(O)$_2$Cl or a sulfonic anhydride of Formula $(R_4S(O)_2)_2O$ to provide a compound of Formula XXIV in which $R_{1b}$ is —X—N($R_8$)-Q-$R_4$, and Q is —S(O)$_2$—. Numerous acid chlorides of Formula $R_4$C(O)Cl, sulfonyl chlorides of Formula $R_4$S(O)$_2$Cl, and sulfonic anhydrides of Formula $(R_4S(O)_2)_2O$ are commercially available; others can be readily prepared using known synthetic methods. The reaction is conveniently carried out by adding the acid chloride of Formula $R_4$C(O)Cl, sulfonyl chloride of Formula $R_4$S(O)$_2$Cl, or sulfonic anhydride of Formula $(R_4S(O)_2)_2O$ to a solution of the 1H-imidazo[4,5-c][1,5]naphthyridine of Formula XXIII in a suitable solvents such as chloroform, dichloromethane, or DMF. Optionally a base, such as triethylamine or N,N-diisopropylethylamine, can be added. The reaction can be carried out at ambient temperature or a sub-ambient temperature such as 0° C.

Ureas of Formula XXIV can be prepared by reacting a 1H-imidazo[4,5-c][1,5]naphthyridine of Formula XXIII with isocyanates of Formula $R_4N$=C=O or Formula $R_4$(CO)N=C=O, isothiocyanates of Formula $R_4N$=C=S, sulfonyl isocyanates of Formula R$_4$S(O)$_2$N=C=O, or carbamoyl chlorides of Formula R$_4$N—(R$_8$)—C(O)Cl or

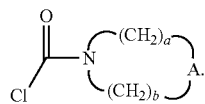

Numerous compounds of these types are commercially available; others can be readily prepared using known synthetic methods. The reaction can be carried out as described above for the reaction of a compound of Formula XXIII with acid chlorides or sulfonyl chlorides to provide a compound of Formula XXIV wherein R$_{1b}$ is —X—N(R$_8$)-Q-R$_4$ or

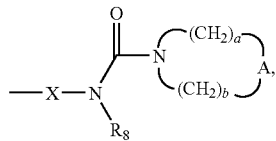

in which Q is —C(R$_6$)—N(R$_8$)—W—, and R$_6$, R$_8$, W, A, a, and b are as defined above.

Compounds of Formula XXIV where R$_{1b}$ is —X—R$_5$ and R$_5$ is

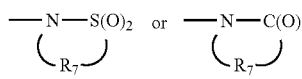

can be prepared by treating an amino-substituted 1H-imidazo [4,5-c][1,5]naphthyridine of Formula XXIII with a chloroalkanesulfonyl chloride of Formula Cl—R$_7$S(O)$_2$Cl or a chloroalkanoyl chloride of Formula Cl—R$_7$C(O)Cl. The reaction is conveniently carried out by adding the chloroalkanesulfonyl chloride or chloroalkanoyl chloride to a solution of the amino-substituted 1H-imidazo[4,5-c][1,5]naphthyridine of Formula XXIII in a suitable solvent, such as chloroform, at ambient temperature. The isolable intermediate chloroalkanesulfonamide or chloroalkanamide can then be treated with a base, such as 1,8-diazabicyclo[5.4.0]undec-7-ene, at ambient temperature in a suitable solvent, such as DMF, to effect the cyclization.

Sulfamides of Formula XXIV, where R$_{1b}$ is —X—N(R$_8$)-Q-R$_4$, and Q is —S(O)$_2$—N(R$_8$)—, can be prepared by reacting a compound or salt of Formula XXIII with sulfuryl chloride to generate a sulfamoyl chloride in situ, and then reacting the sulfamoyl chloride with an amine of formula HN(R$_8$)R$_4$. Alternatively, sulfamides of Formula XXIV can be prepared by reacting a compound of Formula XXIII with a sulfamoyl chloride of formula R$_4$(R$_8$)N—S(O)$_2$Cl. Many amines of Formula HN(R$_8$)R$_4$, and some sulfamoyl chlorides of Formula R$_4$(R$_8$)N—S(O)$_2$Cl are commercially available; others can be prepared using known synthetic methods.

In steps (6) and (7) of Reaction Scheme II, a 1H-imidazo [4,5-c][1,5]naphthyridine of Formula XXIV is oxidized to afford a 1H-imidazo[4,5-c][1,5]naphthyridine-5N-oxide of Formula XXV, which is aminated to provide a 1H-imidazo [4,5-c][1,5]naphthyridin-4-amine of Formula XIXa. Steps (6) and (7) of Reaction Scheme II can be carried out as described for steps (8) and (9), respectively, of Reaction Scheme I.

In step (8) of Reaction Scheme II, a 1H-imidazo[4,5-c][1, 5]naphthyridin-4-amine of Formula XIXa undergoes a palladium-catalyzed coupling reaction to provide a 1H-imidazo[4, 5-c][1,5]naphthyridin-4-amine of Formula IIb, which is a subgenus of Formulas I and II. The Suzuki coupling or Heck reaction can be carried out as described in step (10) of Reaction Scheme I.

Reaction Scheme II

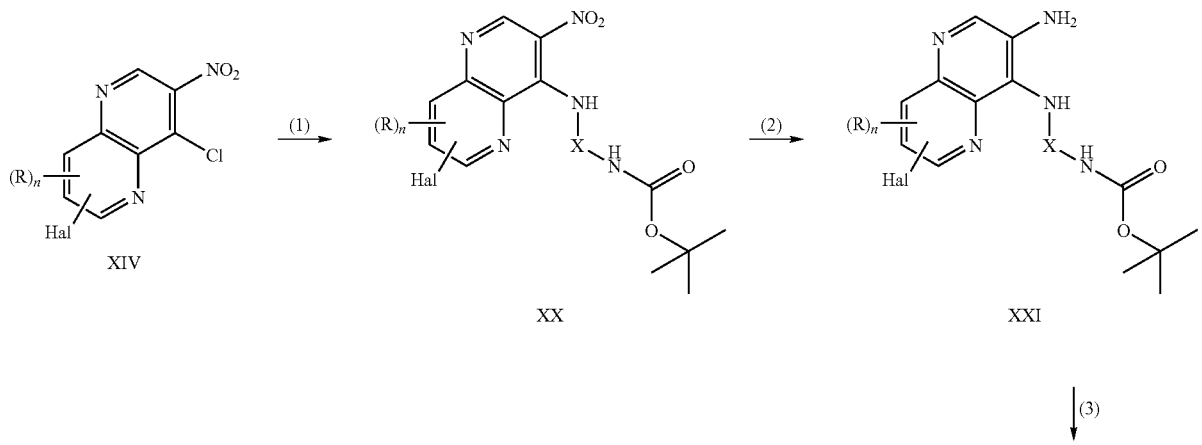

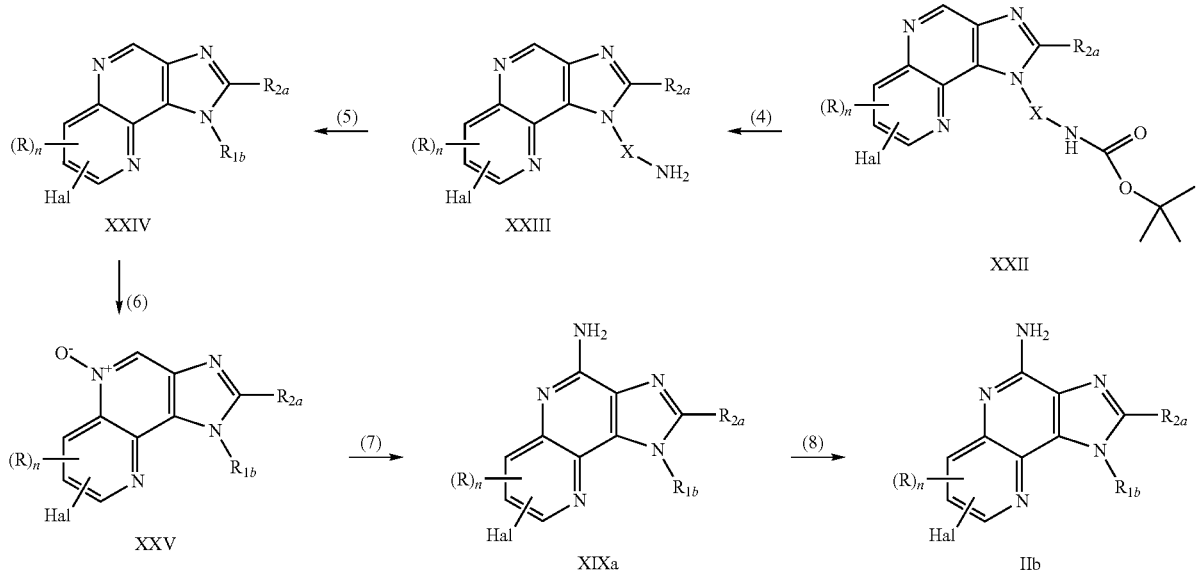

Compounds of the invention, wherein —Z— is ethylene, can be prepared as shown in Reaction Scheme III, wherein $Ar_a$, R, and n are as defined above; and $R_{2c}$ and $R_{1c}$ include $R_{2a}$, $R_{1a}$, and $R_{1b}$ groups as defined above that are not subject to reduction under the conditions described in Reaction Scheme III. These groups include, for example, alkenyl and alkynyl groups.

In Reaction Scheme III, the vinyl group of a 1H-imidazo [4,5-c][1,5]naphthyridin-4-amine of Formula XXVII is reduced to provide an 1H-imidazo[4,5-c][1,5]naphthyridin-4-amine of Formula XXVIII, which is a subgenus of Formulas I and II. Compounds of Formula XXVII can be prepared by the Suzuki coupling or the Heck reaction described in step (10) of Reaction Scheme I. The reduction can be carried out by hydrogenation using a conventional heterogeneous hydrogenation catalyst, such as palladium on carbon. The reaction can conveniently be carried out on a Parr apparatus in a suitable solvent, such as ethanol, methanol, or mixtures thereof.

Reaction Scheme III

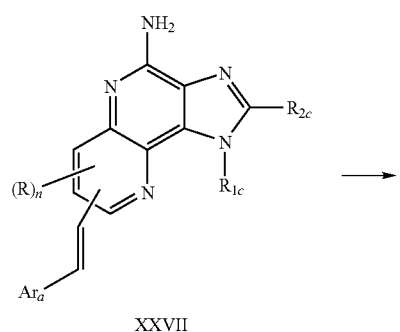

XXVII

-continued

Palladium-catalyzed coupling reactions can also be used to prepare compounds of the invention according to Reaction Scheme IV, wherein $R_{1c}$, $R_{2c}$, $R_9$, R, Hal, $Ar_a$, and n are as defined above. In step (1) of Reaction Scheme IV, a halogen-substituted 1H-imidazo[4,5-c][1,5]naphthyridin-4-amine of Formula XIXb undergoes a Suzuki-type coupling with a potassium alkenyltrifluoroborate of Formula XXIX to provide a vinyl-substituted 1H-imidazo[4,5-c][1,5]naphthyridin-4-amine of Formula XXX. The reaction is conveniently carried out by combining the compound of Formula XIXb and a compound of Formula XXIX, such as potassium vinyltrifluoroborate, in the presence of dichloro[1,1'-bis(diphenylphosphino)ferrocene]palladium (II) dichloromethane adduct and a base, such as triethylamine, in a suitable solvent, such as n-propanol. The reaction can be carried out at an elevated temperature such as the reflux temperature of the solvent under an inert atmosphere.

In step (2) of Reaction Scheme IV, the Heck reaction is used to couple a vinylated 1H-imidazo[4,5-c][1,5]naphthyridin-4-amine of Formula XXX with an aryl or heteroaryl halide of Formula $Ar_a$-Hal or a trifluoromethanesulfonate of Formula $Ar_a$—$OSO_2CF_3$. Numerous compounds of Formula $Ar_a$-Hal are commercially available; others can be prepared using known synthetic methods. The reaction is conveniently carried out under the Heck reaction conditions described in step (10) of Reaction Scheme I to provide a 1H-imidazo[4,5- c][1,5]naphthyridin-4-amine of Formula XXXI, which is a subgenus of Formulas I and II.

In step (3) of Reaction Scheme IV, the vinyl group of a 1H-imidazo[4,5-c][1,5]naphthyridin-4-amine of Formula XXXI is reduced to provide a 1H-imidazo[4,5-c][1,5]naphthyridin-4-amine of Formula XXXII. The reaction is conveniently carried out by hydrogenation under the conditions described in Reaction Scheme III.

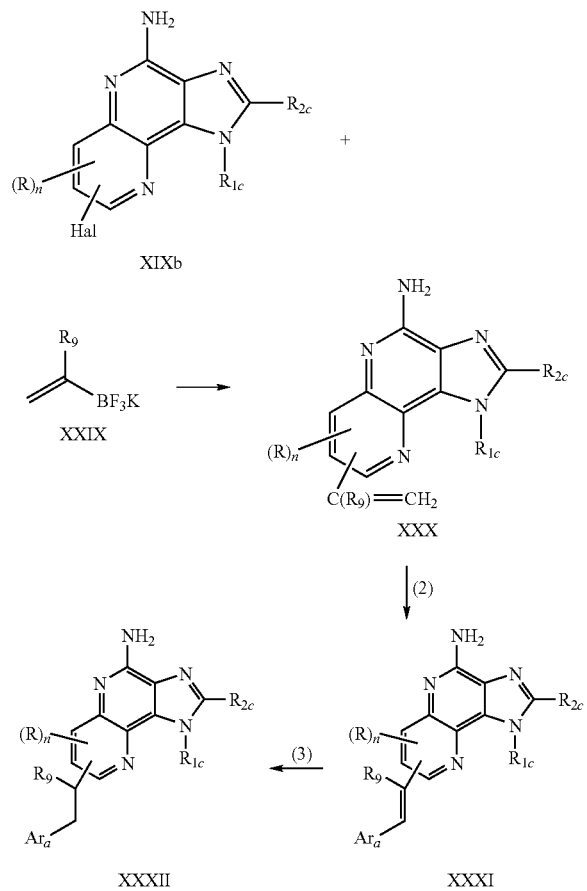

Compounds of the invention can also be prepared according to Reaction Scheme V, wherein R, $R_{2a}$, Hal, and n are as defined above; $R_{1d}$ includes groups defined by $R_{1a}$ and $R_{1b}$ described above; and HA is a heteroaryl group attached to the ring at a nitrogen atom. In Reaction Scheme V, a halogen-substituted 1H-imidazo[4,5-c][1,5]naphthyridin-4-amine of Formula XIXc undergoes a copper-catalyzed amination with a nitrogen-containing heteroaryl compound to provide a 1H-imidazo[4,5-c][1,5]naphthyridin-4-amine of Formula XXXIII, which is a subgenus of Formulas I and II. Several nitrogen-containing heteroaryl compounds, such as imidazole, pyrazole, and pyrrole, are commercially available; others can be prepared by known methods. The reaction is conveniently carried out by combining the 1H-imidazo[4,5-c][1,5]naphthyridin-4-amine of Formula XIXc and the nitrogen-containing heteroaryl compound in the presence of copper (I) iodide, potassium phosphate, and trans-1,2-diaminocyclohexane in a suitable solvent, such as 1,4-dioxane. The reaction can be carried out at an elevated temperature, such as 110° C.

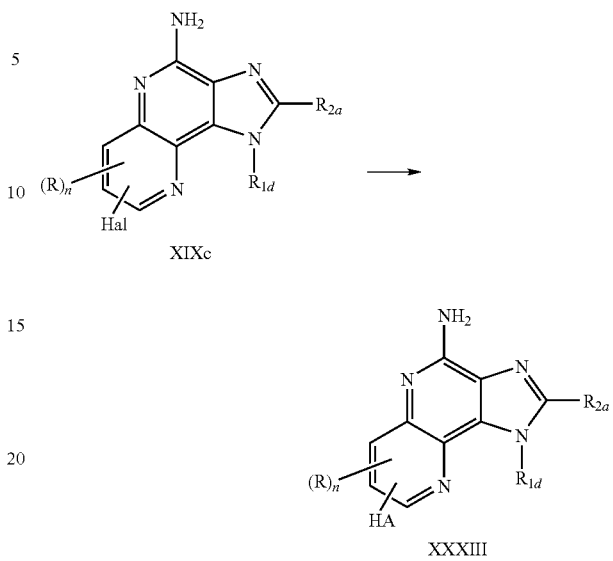

For some embodiments, compounds of the invention can be prepared according to Reaction Scheme VI, wherein R, $R_{1d}$, $R_{2a}$, Ar', X, Hal, $Z_a$, and n are as defined above; and $Ar_b$ is —Ar'—X—Y—$R_4$ or —Ar'—X—$R_5$, wherein Y, $R_4$, and $R_5$ are as defined above. In step (1) of Reaction Scheme VI, a halogen-substituted 1H-imidazo[4,5-c][1,5]naphthyridin-4-amine of Formula XIXc undergoes Suzuki coupling with a boronic acid of Formula $NH_2$—X—Ar'—$Z_a$—$B(OH)_2$, an anhydride thereof, or a boronic acid ester of Formula $NH_2$—X—Ar'—$Z_a$—$B(O-alkyl)_2$ to provide an 1H-imidazo[4,5-c][1,5]naphthyridin-4-amine of Formula XXXIV, a subgenus of Formulas I and II. The reaction can be carried out according to one of the Suzuki coupling methods described in step (10) of Reaction Scheme I. Some reagents of Formula $NH_2$—X—Ar'—$Z_a$—$B(OH)_2$, anhydrides thereof, and $NH_2$—X—Ar'—$Z_a$—$B(O-alkyl)_2$ are commercially available; others can be prepared by known methods.

In step (2) of Reaction Scheme VI, a 1H-imidazo[4,5-c][1,5]naphthyridine of Formula XXXIV is converted to a 1H-imidazo[4,5-c][1,5]naphthyridine of Formula XXXV, a subgenus of Formulas I and II, using one of the methods described in step (5) of Reaction Scheme II.

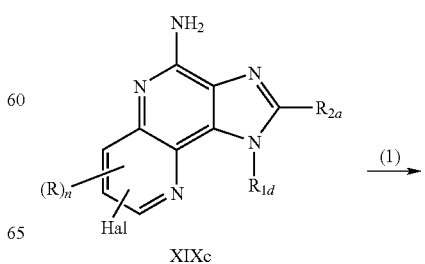

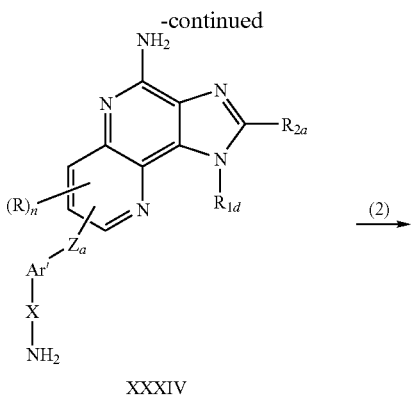

XXXIV

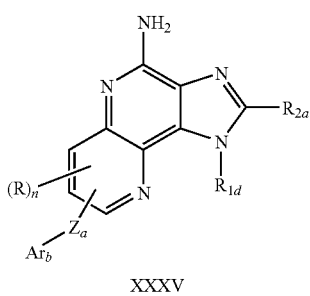

XXXV

Some amines of the Formula H₂N—R₁ₐ, which are used in step (5) of Reaction Scheme I, can be made according to the following methods. For some embodiments, R₁ₐ is a 1-hydroxycycloalkylmethyl group, a (4-hydroxytetrahydro-2H-pyran-4-yl)methyl group, or a group derived from a [1-(tert-butoxycarbonyl)-4-hydroxypiperidin-4-yl]methyl group. The corresponding amines of Formula H₂N—R₁ₐ can be prepared by combining a cyclic ketone, such as cyclopentanone, cyclobutanone, tetrahydro-4H-pyran-4-one, and tert-butyl 4-oxo-1-piperidinecarboxylate, with excess nitromethane in a suitable solvent, such as ethanol or methanol, in the presence of a catalytic amount of base, such as sodium ethoxide or sodium hydroxide, and reducing the resultant nitromethyl-substituted compound using conventional heterogeneous hydrogenation conditions. The hydrogenation is typically carried out in the presence of a catalyst, such as palladium hydroxide on carbon, palladium on carbon, or Raney nickel, in a suitable solvent, such as ethanol. Both the reaction with nitromethane and the reduction can be carried out at room temperature. A wide variety of cyclic ketones can be obtained from commercial sources; others can be synthesized using known synthetic methods.

For some embodiments, R₁ₐ is a 2-fluoro-2-methylpropyl group. The corresponding amine of Formula H₂N—R₁ₐ or a salt thereof can be prepared in three steps by (i) protecting the amino group of 1-amino-2-methylpropan-2-ol with a suitable protecting group such as a Boc group, (ii) converting the hydroxy group into a fluoro group, and (iii) deprotecting the amino group. The fluorination in step (ii) can be carried out by combining the protected amino alcohol with (diethylamino)sulfur trifluoride in a suitable solvent, such as dichloromethane. The reaction can be carried out at or below room temperature.

Compounds of the invention can also be prepared using variations of the synthetic routes shown in Reaction Schemes I through VI. For example, position isomers of Formula XIX such as [1,6]naphthyridines, [1,7]naphthyridines, and [1,8]naphthyridines can be prepared according to the methods shown in Reaction Scheme I and can be used as starting materials in Reaction Schemes III through VI. In addition, steps in Reaction Schemes I and II may be carried out in a different order. Compounds of the invention can also be prepared using the synthetic routes described in the EXAMPLES below.

Prodrugs can be prepared in a variety of ways. For example, a compound wherein R₂ or R₁ is —X—OH (e.g. hydroxyalkyl) can be converted into a prodrug wherein R₂ or R₁ is, for example, —X—O—C(R₆)—R₄, —X—O—C (R₆)—O—R₄, or —X—O—C(R₆)—N(R₈)—R₄, wherein X, R₄, R₆, and R₉ are as defined above, using methods known to one skilled in the art. In addition, a compound wherein R is hydroxy may also be converted to an ester, an ether, a carbonate, or a carbamate. For any of these compounds containing an alcohol functional group, a prodrug can be formed by the replacement of the hydrogen atom of the alcohol group with a group such as $C_{1-6}$ alkanoyloxymethyl, 1-($C_{1-6}$ alkanoyloxy)ethyl, 1-methyl-1-($C_{1-6}$ alkanoyloxy)ethyl, $C_{1-6}$ alkoxycarbonyloxymethyl, N—($C_{1-6}$ alkoxycarbonyl)aminomethyl, succinoyl, $C_{1-6}$ alkanoyl, α-amino$C_{1-4}$ alkanoyl, arylacyl, —P(O)(OH)₂, —P(O)(O—$C_{1-6}$ alkyl)₂, $C_{1-6}$ alkoxycarbonyl, $C_{1-6}$ alkylcarbamoyl, and α-aminoacyl or α-aminoacyl-α-aminoacyl, where each α-aminoacyl group is independently selected from racemic, D-, and L-amino acids. For compounds containing an alcohol functional group, particularly useful prodrugs are esters made from carboxylic acids containing one to six carbon atoms, unsubstituted or substituted benzoic acid esters, or esters made from amino acids.

Prodrugs can also be made from a compound containing an amino group by conversion of the amino group to a functional group such as an amide, carbamate, urea, amidine, or another hydroylizable group using conventional methods. A prodrug of this type can be made by the replacement of a hydrogen atom in an amino group, particularly the amino group at the 4-position, with a group such as —C(O)—R', α-aminoacyl, α-aminoacyl-α-aminoacyl, —C(O)—O—R', —C(O)—N (R'')—R', —C(=NY')—R', —CH(OH)—C(O)—OY', —CH(OC$_{1-4}$ alkyl)Y₀, —CH₂Y₁, or —CH(CH₃)Y₁; wherein R' and R'' are each independently $C_{1-10}$ alkyl, $C_{3-7}$ cycloalkyl, or benzyl, each of which may be unsubstituted or substituted by one or more substitutents selected from the group consisting of halogen, hydroxy, nitro, cyano, carboxy, $C_{1-6}$ alkyl, $C_{1-4}$ alkoxy, aryl, heteroaryl, aryl$C_{1-4}$ alkylenyl, heteroaryl$C_{1-4}$ alkylenyl, halo$C_{1-4}$ alkyl, halo$C_{1-4}$ alkoxy, —O—C(O)—CH₃, —C(O)—O—CH₃, —C(O)—NH₂, —O—CH₂—C(O)—NH₂, —NH₂, and —S(O)₂—NH₂, with the proviso that R'' can also be hydrogen; each α-aminoacyl group is independently selected from racemic, D-, and L-amino acids; Y' is hydrogen, $C_{1-6}$ alkyl, or benzyl; Y₀ is $C_{1-6}$ alkyl, carboxy$C_{1-6}$ alkylenyl, amino$C_{1-4}$ alkylenyl, mono-N—$C_{1-6}$ alkylamino$C_{1-4}$ alkylenyl, or di-N,N—$C_{1-6}$ alkylamino$C_{1-4}$ alkylenyl; and Y₁ is mono-N—$C_{1-6}$ alkylamino, di-N,N—$C_{1-6}$ alkylamino, morpholin-4-yl, piperidin-1-yl, pyrrolidin-1-yl, or 4-$C_{1-4}$ alkylpiperazin-1-yl. For compounds containing an amine functional group, particularly useful prodrugs are amides derived from carboxylic acids containing one to ten carbon atoms, amides derived from racemic, D-, or L-amino acids, and carbamates containing one to ten carbon atoms.

Pharmaceutical Compositions and Biological Activity

Pharmaceutical compositions of the invention contain a therapeutically effective amount of a compound or salt of the invention as described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. Although the exact amount of active compound or salt used in a pharmaceutical composition of the invention will vary according to factors known to those of skill in the art, such as the physical and chemical nature of the compound or salt, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (µg/kg) to about 5 mg/kg, of the compound or salt to the subject. A variety of dosage forms may be used, such as tablets, lozenges, capsules, parenteral formulations, syrups, creams, ointments, aerosol formulations, transdermal patches, transmucosal patches and the like.

The compounds or salts of the invention can be administered as the single therapeutic agent in the treatment regimen, or the compounds or salts of the invention may be administered in combination with one another or with other active agents, including additional immune response modifiers, antivirals, antibiotics, antibodies, proteins, peptides, oligonucleotides, etc.

Compounds or salts of the invention have been shown to induce, and certain compounds or salts of the invention may inhibit, the production of certain cytokines in experiments performed according to the tests set forth below. These results indicate that the compounds or salts are useful as immune response modifiers that can modulate the immune response in a number of different ways, rendering them useful in the treatment of a variety of disorders.

Cytokines whose production may be induced by the administration of compounds or salts of the invention generally include interferon-α (IFN-α) and/or tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt or composition of the invention to the animal. The animal to which the compound or salt or composition is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts of the invention can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Other cytokines whose production may be inhibited by the administration of compounds or salts of the invention include tumor necrosis factor-α (TNF-α). Among other effects, inhibition of TNF-α production can provide prophylaxis or therapeutic treatment of TNF-α mediated diseases in animals, making the compounds or salt useful in the treatment of, for example, autoimmune diseases. Accordingly, the invention provides a method of inhibiting TNF-α biosynthesis in an animal comprising administering an effective amount of a compound or salt or composition of the invention to the animal. The animal to which the compound or salt or composition is administered for inhibition of TNF-α biosynthesis may have a disease as described infra, for example an autoimmune disease, and administration of the compound or salt may provide therapeutic treatment. Alternatively, the compound or salt may be administered to the animal prior to the animal acquiring the disease so that administration of the compound or salt may provide a prophylactic treatment.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt and other component or components may be administered separately; together but independently such as in a solution; or together and associated with one another such as (a) covalently linked or (b) non-covalently associated, e.g., in a colloidal suspension.

Conditions for which compounds or salts identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picomavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella*;

(c) other infectious diseases, such chlamydia, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, a compound or salt of the present invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus influenza* b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts of the present invention may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An amount of a compound or salt effective to induce or inhibit cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) or decreased (inhibited) over a background level of such cytokines. The precise amount will vary according to factors known in the art but is expected to be a dose of about 100 ng/kg to about 50 mg/kg, preferably about 10 µg/kg to about 5 mg/kg. The invention also provides a method of treating a viral infection in an animal and a method of treating a neoplastic disease in an animal comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

EXAMPLES

Objects and advantages of this invention are further illustrated by the following examples, but the particular materials and amounts thereof recited in these examples, as well as other conditions and details, should not be construed to unduly limit this invention.

In the examples below automated flash chromatography was carried out using a HORIZON HPFC system (an automated high-performance flash purification product available from Biotage, Inc, Charlottesville, Va., USA). For some of these purifications, either a FLASH 40+M silica cartridge or a FLASH 65I silica cartridge (both available from Biotage, Inc, Charlottesville, Va., USA) was used. The eluent used for each purification is given in the example. In some chromatographic separations, the solvent mixture 80/18/2 v/v/v chloroform/methanol/concentrated ammonium hydroxide (CMA) was used as the polar component of the eluent. In these separations, CMA was mixed with chloroform in the indicated ratio.

Preparation of 5-(tert-Butyldimethylsilanyloxymethyl)pyridine-3-boronic acid

3-Bromo-5-(tert-butyldimethylsilanyloxymethyl)pyridine was prepared according to the published procedure (Zhang, N. et al, *J. Med. Chem.*, 45, 2832-2840 (2002)). Under a nitrogen atmosphere, a solution of 3-bromo-5-(tert-butyldimethylsilanyloxymethyl)pyridine (28.70 g, 94.94 mmol) and triisopropyl borate (26.3 mL, 114 mmol) in dry tetrahydrofuran was cooled to −70° C. n-Butyllithium (45.6 mL, 114 mmol) was added dropwise over a period of 1.5 hours. The reaction was stirred for an additional 30 minutes and then allowed to warm to −20° C. Dilute aqueous ammonium chloride was added, and the mixture was allowed to warm to ambient temperature. The aqueous layer was separated and extracted with diethyl ether. The combined organic fractions were concentrated under reduced pressure, and methanol was added to the resulting oil. A solid formed, which was stirred with water for two days, isolated by filtration, and dried under reduced pressure to provide 18.19 g of 5-(tert-butyldimethylsilanyloxymethyl)pyridine-3-boronic acid as a white solid.

Example 1

2-(Ethoxymethyl)-1-(2-methylpropyl)-7-(pyridin-3-yl)-1H-imidazo[4,5-c][1,5]naphthyridin-4-amine

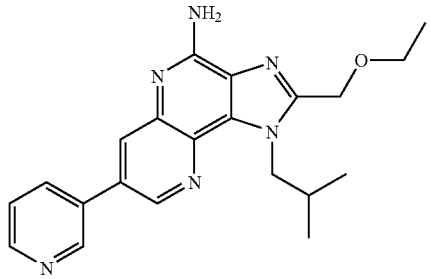

Part A

A mixture of triethyl orthoformate (10 mL, 60.1 mmol) and 2,2-dimethyl-[1,3]-dioxane-4,6-dione (40.9 g, 0.23 mol) (Meldrum's acid) was heated at 92° C. for 90 minutes and then cooled to 70° C. over one hour. 3-Amino-5-bromopyridine (40.9 g, 0.20 mol) was slowly added over 10 minutes with an ethanol rinse while maintaining the reaction temperature between 60 and 70° C. The reaction was then heated for an additional 20 minutes and allowed to cool to room temperature. The reaction mixture was filtered and washed with ethanol (150 mL) yielding a tan solid. The solid was dried under vacuum for 2 hours to yield 59.14 g of 5-{[(5-bromopyridin-3-yl)imino]methyl}-2,2-dimethyl-1,3-dioxane-4,6-dione as a light yellow crystalline solid, mp 200-202° C.

$^1$H NMR (300 MHz, CDCl$_3$) δ 11.26 (d, J=14.3 Hz, 1H), 8.80 (d, J=2.3 Hz, 1H), 8.62 (d, J=14.3 Hz, 1H), 8.56(d, J=1.9 Hz, 1H), 8.44-8.40 (m, 1H), 1.68 (s, 6H).

Part B

5-{[(5-Bromopyridin-3-yl)imino]methyl}-2,2-dimethyl-1,3-dioxane-4,6-dione (59 g, 0.18 mol) was slowly added to DOWTHERM A heat transfer fluid (2000 mL) over a period of 5 minutes at 235-238° C. Following addition, the reaction was maintained for an additional 5 minutes and then allowed to cool to 40° C. A brown precipitate formed, which was filtered and washed with hexanes (150 mL). The brown solid was suspended in an ethanol/water mixture (90:10, 1500 mL), heated to a boil for 30 minutes, isolated by filtration, and washed with ethanol (200 mL) to yield 30.8 g of 7-bromo[1,5]naphthyridin-4-ol as a dark brown powder.

$^1$H NMR (300 MHz, CDCl$_3$) δ 11.81(br s, 1H), 8.69(d, J=1.9 Hz, 1H), 8.21 (d, J=1.9 Hz, 1H), 7.95(d, J=7.7 Hz, 1H), 6.22 (d, J=7.5 Hz, 1H).

Part C

A mixture of 7-bromo[1,5]naphthyridin-4-ol (33 g, 0.147 mol) and fuming nitric acid (350 mL) was heated at reflux (90° C. internal reaction vessel temperature) for 3 hours. The reaction mixture was cooled to 50° C., poured over 1 L of ice and neutralized to pH 2-3 with a solution of 50% aqueous NaOH. The resulting precipitate was filtered, washed with water, and dried over vacuum for 3 days to yield 25.1 g of 7-bromo-3-nitro[1,5]naphthyridin-4-ol as a yellow crystalline solid.

$^1$H NMR (300 MHz, CDCl$_3$) δ 13.06(br s, 1H), 9.26(s, 1H), 8.88 (d, J=2.0 Hz, 1H), 8.37(d, J=2.0 Hz, 1H).

Part D

Phosphorous oxychloride (16.76 g, 10.19 mL, 109.3 mmol) was added slowly dropwise to a suspension of 7-bromo-3-nitro[1,5]naphthyridin-4-ol (21.09 g, 78.1 mmol) in N,N-dimethylformamide (250 mL)(DMF) at ambient temperature and maintained overnight. The reaction mixture was then added to ice water (400 mL) with stirring. A solid precipitate formed, which was isolated by vacuum filtration and washed with water. The material was dried under high vacuum at ambient temperature overnight to yield 20.79 g of 7-bromo-4-chloro-3-nitro[1,5]naphthyridine as a tan solid.

$^1$H NMR (300 MHz, CDCl$_3$) δ 9.51(s, 1H), 9.36 (d, J=2.2 Hz, 1H), 9.02(d, J=2.1 Hz, 1H).

Part E

Triethylamine (17.97 mL, 129.0 mmol) was added to a solution of 7-bromo-4-chloro-3-nitro[1,5]naphthyridine (24.8 g, 86.0 mmol) in dichloromethane (200 mL) at 0° C. Isobutylamine (9.40 mL, 94.6 mmol) was added dropwise to the mixture, and the mixture was stirred for 3 hours at ambient temperature. The reaction mixture was condensed under reduced pressure to a solid, which was triturated with water (200 mL). The precipitate was filtered, washed sequentially with water and hexanes, and dried to yield 27.5 g of 7-bromo-3-nitro[1,5]naphthyridin-4-yl-(2-methylpropyl)amine as a yellow powder, mp 114-115° C.

$^1$H NMR (300 MHz, CDCl$_3$) δ 9.98(br s, 1H), 9.37(br s, 1H), 8.81 (d, J=2.2 Hz, 1H), 8.39(d, J=2.2 Hz, 1H), 4.36-4.01(br m, 2H), 2.06(heptet, J=6.7 Hz, 1H), 1.09(d, J=6.7, 6H). MS (APCI) m/z 325.2 and 327.2 (M+H)$^+$;

Anal. calcd for $C_{12}H_{13}BrN_4O_2$: C, 44.33; H, 4.03; N, 17.23. Found: C, 44.32; H, 3.81; N, 17.33.

Part F

A solution of sodium dithionite (77.95 g, 380.6 mmol) and potassium carbonate (58.35 g, 422.2 mmol) in water (250 mL) was added dropwise to a mechanically stirred solution of 7-bromo-3-nitro[1,5]naphthyridin-4-yl-(2-methylpropyl)amine (27.6 g, 84.6 mmol) and ethyl viologen dibromide (0.63 g, 1.7 mmol) in dichloromethane (300 mL) and water (50 mL). The reaction mixture was stirred overnight at ambient temperature. Water (500 mL) was added, and the reaction mixture was stirred for 10 minutes. The organic layer was separated and the aqueous layer was filtered through WHATMAN paper to remove insoluble material. The emulsion-free filtrate was extracted with dichloromethane, washed sequentially with water and brine, dried over sodium sulfate, filtered, and concentrated under reduced pressure to yield 22.3 g of 7-bromo-N$^4$-(2-methylpropyl)[1,5]naphthyridine-3,4-diamine as an orange solid.

$^1$H NMR (300 MHz, CDCl$_3$) δ 8.70 (d, J=2.2 Hz, 1H), 8.36(s, 1H), 8.33(d, J=2.2 Hz, 1H), 6.03-5.89(br m, 1H), 3.66(br s, 2H), 3.27(t, J=6.8, 2H), 1.83(heptet, J=6.7 Hz, 1H), 1.00(d, J=6.7 Hz, 6H).

Part G

A solution of 7-bromo-N$^4$-(2-methylpropyl)[1,5]naphthyridine-3,4-diamine (22.29 g, 75.51 mmol) in dichloromethane (300 mL) was cooled to 0° C., and triethylamine (13.15 mL, 94.39 mmol) was added to the reaction mixture. Ethoxyacetyl chloride (11.56 g, 94.39 mmol) was added dropwise to the reaction mixture, and the reaction was maintained at ambient temperature for 2.5 hours. The reaction mixture was concentrated under reduced pressure, triethylamine (52.62 mL, 377.6 mmol) and ethanol (250 mL) was added, and the resulting mixture was heated at reflux for 16 hours. The solvent was removed under reduced pressure and the residue was triturated with n-heptanes. The resulting precipitate was collected by filtration, washed with water, and dried. The product was then recrystallized from acetonitrile to yield 14 g of 7-bromo-2-(ethoxymethyl)-1-(2-methylpropyl)-1H-imidazo[4,5-c][1,5]naphthyridine as an off-white solid. The mother liquor was concentrated, and the residue was recrystallized from acetonitrile to yield an additional 2.37 g of 7-bromo-2-(ethoxymethyl)-1-(2-methylpropyl)-1H-imidazo[4,5-c][1,5]naphthyridine. The n-heptanes fraction from the trituration was concentrated under reduced pressure, triturated with acetonitrile, and isolated by filtration to give an additional 0.88 g of 7-bromo-2-(ethoxymethyl)-1-(2-methylpropyl)-1H-imidazo[4,5-c][1,5]naphthyridine, for a total yield of 17.25 g of an off-white solid, mp 115-116° C.

¹H NMR (300 MHz, CDCl₃) δ 9.33(s, 1H), 8.96(d, J=2.2 Hz, 1H), 8.68(d, J=2.2 Hz, 1H), 4.90(s, 2H), 4.78(d, J=7.6 Hz, 2H), 3.64(q, J=7.0 Hz, 2H), 2.47(heptet, J=6.9 Hz, 1H), 1.26 (t, J=7.0, 3H), 0.98(d, J=7.0 Hz, 6H). ¹³C NMR (75 MHz, CDCl₃) δ 152.6, 149.7, 147.2, 140.3, 139.3, 139.1, 134.5, 133.9, 117.9, 66.5, 65.3, 53.2, 29.7, 19.8, 15.0.

MS (APCI) m/z 363.2 and 365.2 (M+H)⁺;

Anal. calcd for $C_{16}H_{19}BrN_4O$: C, 52.90; H, 5.27; N, 15.42. Found: C, 52.93; H, 5.22; N, 15.55.

Part H

3-Chloroperoxybenzoic acid (77% pure, 17.11 g, 76.36 mmol)(mCPBA) was added to a stirred solution of 7-bromo-2-(ethoxymethyl)-1-(2-methylpropyl)-1H-imidazo[4,5-c][1,5]naphthyridine (13.87 g, 38.18 mmol) in dichloromethane (275 mL), and the reaction was stirred for 2 hours with additional mCPBA (2.91 g, 13.0 mmol) added after 1 hour. Ammonium hydroxide (90 mL) was added followed by addition of p-toluenesulfonyl chloride (9.10 g, 47.73 mmol) in small portions at 0° C.; the reaction was then allowed to warm to ambient temperature for 4 hours. The reaction mixture was filtered and then diluted with dichloromethane (300 mL) and a 4% solution of sodium carbonate (200 mL). The organic layer was separated and the aqueous layer was extracted with dichloromethane (2×100 mL). The combined organic fractions were dried over sodium sulfate, filtered, and concentrated under reduced pressure to produce an orange solid. The crude product was triturated with acetonitrile to yield 8.4 g of a tan solid, which upon purification by automated flash chromatography (using a silica gel cartridge, eluting with chloroform:CMA, ranging in ratios from 100:0 to 80:20) to provide 7.03 g of 7-bromo-2-(ethoxymethyl)-1-(2-methylpropyl)-1H-imidazo[4,5-c][1,5]naphthyridin-4-amine as an off-white solid, mp 163-164° C.

¹H-NMR (300 MHz, DMSO) δ 8.57(d, J=2.2 Hz, 1H), 8.10(d, J=2.2 Hz, 1H), 7.15(br s, 2H), 4.77(s, 2H), 4.64(d, J=7.6 Hz, 2H), 3.60(q, J=7.0 Hz, 2H), 2.43-2.28(m, 1H), 1.16(t, J=7.0, 3H), 0.89(d, J=6.7 Hz, 6H). MS (APCI) m/z 378.2 and 380.2 (M+H)⁺.

Anal. calcd for $C_{16}H_{20}BrN_5O$: C, 50.80; H, 5.33; N, 18.51. Found: C, 50.62; H, 5.30; N, 18.52.

Part I

Pyridine-3-boronic acid (0.39 g, 3.2 mmol) was added to 7-bromo-2-(ethoxymethyl)-1-(2-methylpropyl)-1H-imidazo[4,5-c][1,5]naphthyridin-4-amine (1.0 g, 2.6 mmol) and 1-propanol (17 mL). The mixture was degassed and back-filled with nitrogen. Aqueous 2M sodium carbonate (1.6 mL), water (2 mL), triphenylphosphine (0.021 g, 0.079 mmol), and palladium (II) acetate (0.0058 g, 0.026 mmol) were added to the reaction mixture followed by subsequent degassing. The mixture became homogenous upon heating at reflux for 1 hour. After an additional 1 hour of heating, the reaction was cooled to ambient temperature and extracted into chloroform. The resulting solution was washed with saturated aqueous sodium chloride solution, dried over sodium sulfate, filtered and concentrated under reduced pressure. The crude product was purified by automated flash chromatography (using a silica gel cartridge, eluting with CMA:chloroform ranging in ratios from 0:100 to 30:70) and concentrated under reduced pressure. The product was recrystallized from acetonitrile, filtered, and dried at 60° C. under vacuum to provide 0.66 g of 2-(ethoxymethyl)-1-(2-methylpropyl)-7-(pyridin-3-yl)-1H-imidazo[4,5-c][1,5]naphthyridin-4-amine as a white solid, mp 177-179° C.

¹H NMR (300 MHz, DMSO) δ 9.07(m, 1H), 8.91(d, J=2.2 Hz, 1H), 8.64(dd, J=4.8, 1.6 Hz, 1H), 8.31-8.25(m, 1H), 8.22(d, J=2.2 Hz, 1H), 7.58-7.51(m, 1H). 7.03 (br s, 2H), 4.80(s, 2H), 4.72(d, J=7.6 Hz, 2H), 3.60(q, J=7.0 Hz, 2H), 2.51-2.40(m, 1H), 1.18(t, J=7.0 Hz, 3H), 0.92(d, J=6.7 Hz, 6H). ¹³C NMR (75 MHz, DMSO) δ 152.6, 150.1, 148.8, 147.8, 141.2, 140.2, 134.4, 133.2, 132.9, 132.5, 130.9, 129.9, 128.9, 123.9, 65.4, 63.9, 51.9, 29.1, 19.3, 14.8. MS (APCI) m/z 377.1 (M+H)⁺;

Anal. calcd for $C_{21}H_{24}N_6O$: C, 67.00; H, 6.43; N, 22.32. Found: C, 66.82; H, 6.20; N, 22.36.

Example 2

2-(Ethoxymethyl)-1-(2-methylpropyl)-7-[3-(morpholin-4-ylcarbonyl)phenyl]-1H-imidazo[4,5-c][1,5] naphthyridin-4-amine

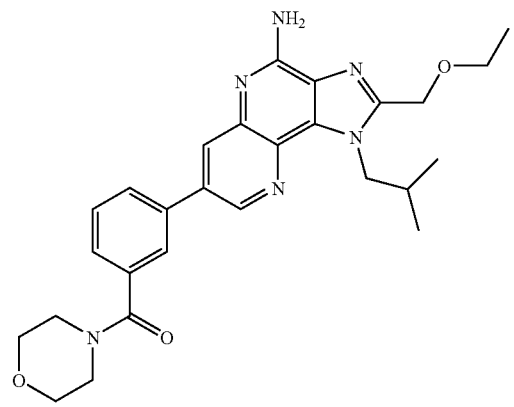

The general method of Part I of Example 1 was followed using 3-(morpholine-4-carbonyl)phenylboronic acid (0.745 g, 3.17 mmol) in lieu of pyridine-3-boronic acid. The crude reaction was purified automated flash chromatography (using a silica gel cartridge, eluting with CMA:chloroform ranging in ratios from 0:100 to 25:75). The combined clean fractions were concentrated under reduced pressure, recrystallized from acetonitrile, filtered, washed with acetonitrile and dried at 60° C. under vacuum to give 0.63 g of 2-(ethoxymethyl)-1-(2-methylpropyl)-7-[3-(morpholin-4-ylcarbonyl)phenyl]-1H-imidazo[4,5-c][1,5]naphthyridin-4-amine as a white solid, mp 185-187° C.

¹H NMR (300 MHz, DMSO) δ 8.88(d, J=2.2 Hz, 1H), 8.16(d, J=2.2 Hz, 1H), 7.97-7.91(m, 1H), 7.89-7.84(m, 1H), 7.61(t, J=7.7 Hz, 1H), 7.49-7.43(m, 1H). 6.98(br s, 2H), 4.79 (s, 2H), 4.72(d, J=7.5 Hz, 2H), 3.77-3.36(br abs, 8H), 3.60(q, J=7.0 Hz, 2H), 2.50-2.38(m, 1H), 1.17(t, J=7.0 Hz, 3H), 0.93(d, J=6.7 Hz, 6H). ¹³C NMR (75 MHz, DMSO) δ 168.6, 152.6, 150.0, 141.4, 140.3, 137.4, 136.5, 133.1, 133.0, 132.5, 129.8, 129.3, 128.8, 128.0, 126.4, 125.2, 65.9, 65.4, 63.9, 51.9, 47.7, 29.1, 19.3, 14.8. MS (APCD) m/z 489.2 (M+H)⁺;

Anal. calcd for $C_{27}H_{32}N_6O_3$: C, 66.37; H, 6.60; N, 17.20. Found: C, 66.20; H, 6.68; N, 17.40.

Example 3

2-(Ethoxymethyl)-7-(imidazol-1-yl)-1-(2-methylpropyl)-1H-imidazo[4,5-c][1,5]naphthyridin-4-amine

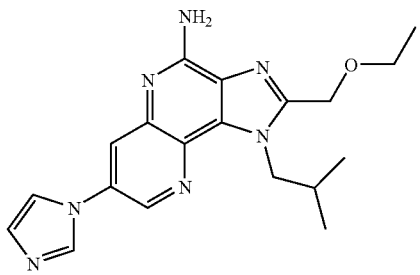

Copper (I) iodide (0.06 g, 0.53 mmol), potassium phosphate (1.18 g, 5.56 mmol), and imidazole (0.22 g, 3.17 mmol) were added to a glass tube. Sequential addition of 7-bromo-2-(ethoxymethyl)-1-(2-methylpropyl)-1H-imidazo[4,5-c][1,5]naphthyridin-4-amine (1.0 g, 2.64 mmol), trans-1,2-diaminocyclohexane (0.06 g, 0.53 mmol) and dioxane (9 mL) followed. The tube was flushed with nitrogen, sealed, and heated to 110° C., and the reaction mixture was stirred for 10 days. The reaction mixture was then diluted with a 1:1 mixture of chloroform and methanol (50 mL) and filtered through CELITE filter aid. The filtrate was concentrated under reduced pressure to give a black liquid, which was purified by automated flash chromatography (using a silica gel cartridge, eluting with CMA:chloroform ranging in ratios from 0:100 to 20:80), and concentrated under reduced pressure. The residue was recrystallized from diethyl ether to give 0.18 g of 2-(ethoxymethyl)-7-(imidazol-1-yl)-1-(2-methylpropyl)-1H-imidazo[4,5-c][1,5]naphthyridin-4-amine as a tan solid, mp 175-176° C.

$^1$H NMR (300 MHz, CDCl$_3$) δ 8.72 (d, J=2.4 Hz, 1H), 8.02 (d, J=2.4 Hz, 2H), 7.478-7.281 (m, 2H), 5.75 (br s, 2H), 4.84 (s, 2H), 4.74 (d, J=7.6 Hz, 2H), 3.65 (q, J=7.0 Hz, 2H), 2.559-2.407 (m, 1H), 1.27 (t, J=7.0 Hz, 3H), 1.00 (d, J=6.7 Hz, 6H). $^{13}$C NMR (75 MHz, CDCl$_3$) δ 153.0, 151.1, 141.5, 137.5, 134.2, 134.0, 132.7, 131.5, 124.9, 77.8, 77.4, 76.9, 66.9, 65.4, 53.4, 30.2, 20.2, 15.4. MS (ESI) m/z 366.3 (M+H)$^+$;

Anal. calcd for C$_{19}$H$_{23}$N$_7$O: C, 62.45; H, 6.34; N, 26.83. Found: C, 62.16; H, 6.20; N, 27.06.

Examples 4-58

The compounds in the table below were prepared according to the following method. A solution of 7-bromo-2-(ethoxymethyl)-1-(2-methylpropyl)-1H-imidazo[4,5-c][1,5]naphthyridin-4-amine (21.8 mg, 0.10 mmol) in 7:3 volume:volume (v:v) dichloromethane:methanol (2 mL) was added to a test tube, and the solvent was removed by vacuum centrifugation. The boronic acid (0.11 mmol) indicated in the table below and n-propanol (1.6 mL) were sequentially added, and the test tube was purged with nitrogen. The reaction mixture was sonicated until it had the consistency of milk. Palladium (II) acetate (0.292 mL of a 0.9 mol % solution in toluene, 0.0026 mmol), 2M aqueous sodium carbonate solution (600 μL), deionized water (113 μL), and a solution of 0.15 mol % triphenylphosphine in n-propanol (52 μL, 0.78 mmol) were sequentially added. The test tube was purged with nitrogen, capped, and then heated to 80° C. overnight in a sand bath. For Example 11, the solvent was removed by vacuum centrifugation, and glacial acetic acid (3 mL), tetrahydrofuran (1 mL), and deionized water (1 mL) were added to the test tube. The reaction was heated for six hours at 60° C.

The contents of each test tube were passed through a Waters Oasis Sample Extractions Cartridge MCX (6 cc) according to the following procedure. Hydrochloric acid (3 mL of 1 N in methanol) was added to adjust each example to pH 5-7, and the resulting solution was passed through the cartridge optionally using light nitrogen pressure. The cartridge was washed with methanol (5 mL) optionally using light nitrogen pressure and transferred to a clean test tube. A solution of 1% ammonia in methanol (2×5 mL) was then passed through the cartridge optionally using light nitrogen pressure, and the basic solution was collected and concentrated.

The compounds were purified by reversed phase preparative high-performance liquid chromatography (prep HPLC) using a Waters Fraction Lynx automated purification system. The prep HPLC fractions were analyzed using a Micromass LC/TOF-MS, and the appropriate fractions were centrifuge evaporated to provide the trifluoroacetate salt of the desired compound. Column: Zorbax BonusRP, 21.2×50 millimeters (mm), 5 micron particle size; non-linear gradient elution from 5-95% B where A is 0.05% trifluoroacetic acid/water and B is 0.05% trifluoroacetic acid/acetonitrile; fraction collection by mass-selective triggering. The table below shows the reagent used for each example, the structure of the resulting compound, and the observed accurate mass for the isolated trifluoroacetate salt.

Examples 4-58

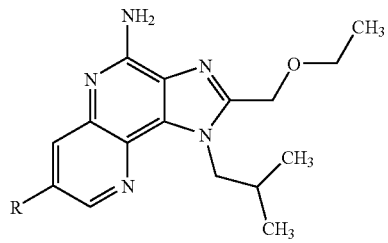

| Example | Boronic acid | R | Measured Mass (M + H) |
|---|---|---|---|
| 4 | Phenylboronic acid | phenyl | 376.2146 |
| 5 | Pyridine-3-boronic acid | pyridin-3-yl | 377.2119 |

-continued

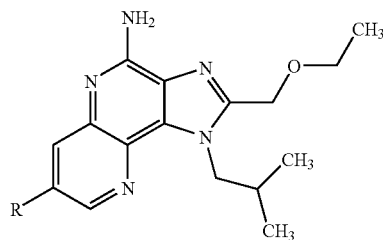

| Example | Boronic acid | R | Measured Mass (M + H) |
|---|---|---|---|
| 6 | Pyridine-4-boronic acid | 4-pyridyl | 377.2121 |
| 7 | Thiophene-2-boronic acid | thiophen-2-yl | 382.1711 |
| 8 | Thiophene-3-boronic acid | thiophen-3-yl | 382.1700 |
| 9 | 3-Methylphenylboronic acid | 3-methylphenyl | 390.2309 |
| 10 | 4-Methylphenylboronic acid | 4-methylphenyl | 390.2287 |
| 11 | 5-(tert-butyldimethylsilanyloxy-methyl)pyridine-3-boronic acid | 5-(hydroxymethyl)pyridin-3-yl | 407.2219 |
| 12 | 3-Aminophenylboronic acid monohydrate | 3-aminophenyl | 391.2284 |
| 13 | 2-Chlorophenylboronic acid | 2-chlorophenyl | 410.1754 |
| 14 | 3-(N,N-Dimethylamino-carbonyl)phenylboronic acid | 3-(N,N-dimethylaminocarbonyl)phenyl | 447.2524 |

-continued

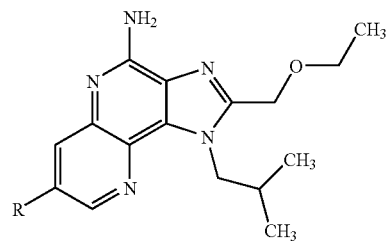

| Example | Boronic acid | R | Measured Mass (M + H) |
|---|---|---|---|
| 15 | o-Tolylboronic acid | 2-methylphenyl | 390.2317 |
| 16 | 4-Vinylphenylboronic acid | 4-vinylphenyl | 402.2272 |
| 17 | 4-Ethylphenylboronic acid | 4-ethylphenyl | 404.2445 |
| 18 | 3,5-Dimethylphenylboronic acid | 3,5-dimethylphenyl | 404.2451 |
| 19 | Phenethylboronic acid | phenethyl | 404.2451 |
| 20 | 2-Methoxyphenylboronic acid | 2-methoxyphenyl | 406.2242 |
| 21 | (4-Fluoro-2-hydroxy)phenylboronic acid | 4-fluoro-2-hydroxyphenyl | 410.1995 |
| 22 | 2,4-Difluorophenylboronic acid | 2,4-difluorophenyl | 412.1924 |
| 23 | Benzo[B]furan-2-boronic acid | benzofuran-2-yl | 416.2080 |

-continued

| Example | Boronic acid | R | Measured Mass (M + H) |
|---|---|---|---|
| 24 | 4-Acetylphenylboronic acid | 4-acetylphenyl | 418.2242 |
| 25 | 3-Acetylphenylboronic acid | 3-acetylphenyl | 418.2247 |
| 26 | 3,4-Methylenedioxyphenylboronic acid | 3,4-methylenedioxyphenyl | 420.2025 |
| 27 | 3-Ethoxyphenylboronic acid | 3-ethoxyphenyl | 420.2388 |
| 28 | 3-Aminophenylboronic acid hydrochloride | 3-aminophenyl | 391.2283 |
| 29 | (2-Acetylaminophenyl)boronic acid | 2-acetylaminophenyl | 433.2321 |
| 30 | 2-Ethoxy-5-methylphenylboronic acid | 2-ethoxy-5-methylphenyl | 434.2546 |

-continued

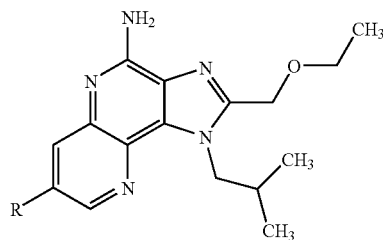

| Example | Boronic acid | R | Measured Mass (M + H) |
|---|---|---|---|
| 31 | 2-Isopropoxyphenylboronic acid | 2-isopropoxyphenyl | 434.2542 |
| 32 | 2,4-Dimethoxyphenylboronic acid | 2,4-dimethoxyphenyl | 436.2352 |
| 33 | 3,4-Dichlorophenylboronic acid | 3,4-dichlorophenyl | 444.1331 |
| 34 | 4-(2-Carboxyvinyl)phenylboronic acid | 4-(2-carboxyvinyl)phenyl | 446.2193 |
| 35 | 3-(4-Boronophenyl)propionic acid | 4-(2-carboxyethyl)phenyl | 448.2319 |
| 36 | 4-(Methoxycarbonyl-amino)phenylboronic acid | 4-(methoxycarbonylamino)phenyl | 449.2280 |
| 37 | 4-(O-Methylhydroxylaminocarbonyl)-phenylboronic acid | 4-(O-methylhydroxylaminocarbonyl)phenyl | 449.2285 |
| 38 | [4-(E-3-Methoxy-3-oxo-1-propen-1-yl)phenyl]boronic acid | 4-(E-3-methoxy-3-oxo-1-propen-1-yl)phenyl | 460.2364 |

-continued
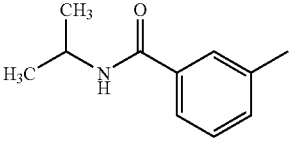
| Example | Boronic acid | R | Measured Mass (M + H) |
|---|---|---|---|
| 39 | 3-(N-Isopropylamino-carbonyl)phenylboronic acid | 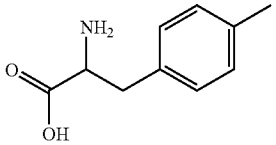 | 461.2662 |
| 40 | 4-Borono-DL-phenylalanine | 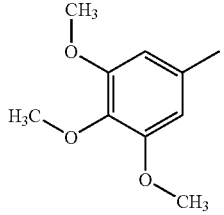 | 463.2442 |
| 41 | 3,4,5-Trimethoxyphenylboronic acid | 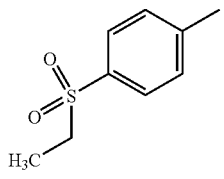 | 466.2456 |
| 42 | 4-(Ethylsulfonyl)phenylboronic acid | 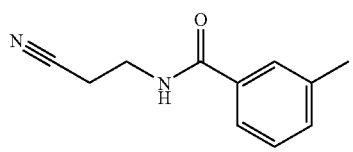 | 468.2053 |
| 43 | 3-(2-Cyanoethylamino-carbonyl)phenylboronic acid | 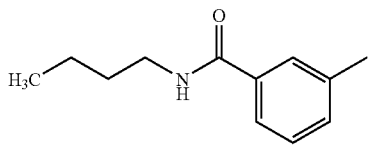 | 472.2439 |
| 44 | 3-(Butylamino-carbonyl)phenylboronic acid | 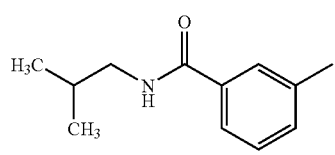 | 475.2809 |
| 45 | 3-(Isobutylamino-carbonyl)phenylboronic acid | | 475.2811 |

-continued
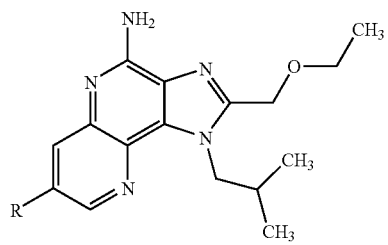
| Example | Boronic acid | R | Measured Mass (M + H) |
|---|---|---|---|
| 46 | 4-(Isobutylamino-carbonyl)phenylboronic acid | | 475.2798 |
| 47 | 3-(Piperidine-1-carbonyl)phenylboronic acid | | 487.2775 |
| 48 | 3-(Morpholine-4-carbonyl)phenylboronic acid | | 489.2620 |
| 49 | 4-(Morpholine-4-carbonyl)phenylboronic acid | | 489.2597 |
| 50 | 3-(Furfurylamino-carbonyl)phenylboronic acid | | 499.2435 |
| 51 | 4-Benzyloxy-3-fluorophenylboronic acid | | 500.2449 |
| 52 | 4-(4-Oxopiperidine-1-carbonyl)phenylboronic acid | | 501.2581 |

-continued

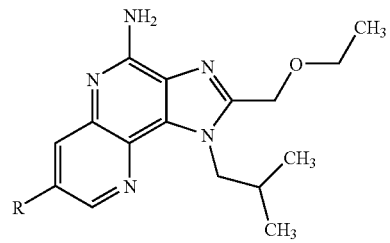

| Example | Boronic acid | R | Measured Mass (M + H) |
|---|---|---|---|
| 53 | 3-(N-Benzylamino-carbonyl)phenylboronic acid | *N-benzyl-3-methylbenzamide substituent* | 509.2629 |
| 54 | (4-Aminomethyl-phenyl)boronic acid, pinacol ester hydrochloride | *4-(aminomethyl)toluene substituent* | 405.2411 |
| 55 | 3-Cyanophenylboronic acid | *3-cyanotoluene substituent* | 401.2065 |
| 56 | 4-Methoxyphenylboronic acid | *4-methoxytoluene substituent* | 406.2264 |
| 57 | 4-Isopropoxyphenylboronic acid | *4-isopropoxytoluene substituent* | 434.2543 |
| 58 | (3-Aminomethyl-phenyl)boronic acid hydrochloride | *3-(aminomethyl)toluene substituent* | 405.2431 |

Preparation of 1-[4-Amino-7-bromo-2-(ethoxymethyl)-1H-imidazo[4,5-c][1,5]naphthyridin-1-yl]-2-methylpropan-2-ol

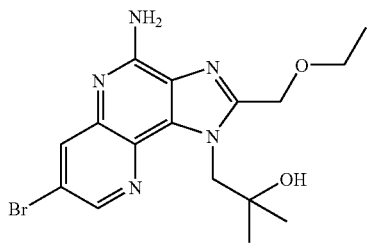

Part A

A mixture of 7-bromo-4-chloro-3-nitro[1,5]naphthyridine (92.5 g, 321 mmol) and dichloromethane (1.5 L) was cooled to 10° C. 1-Amino-2-methylpropan-2-ol (63.01 g, 707 mmol) was added dropwise over a period of 30 minutes; during the addition, the reaction temperature did not rise above 13° C. The reaction mixture was allowed to warm to room temperature slowly and stirred overnight. The solvent was removed under reduced pressure, and the solid residue was mixed with deionized water (200 mL). The solid was isolated by filtration, washed with deionized water (2×200 mL), and dried in a vacuum oven overnight at 35° C. to provide 1-[(7-bromo-3-nitro[1,5]naphthyridin-4-yl)amino]-2-methylpropan-2-ol.

Part B

The material from Part A was added to a Parr vessel followed by methanol (1.13 L) and acetonitrile (2.26 L). The vessel was purged with nitrogen, and 5% platinum on carbon (3.4 g), which had been wet with acetonitrile, was added. The reaction mixture was placed under hydrogen pressure (50 psi, 3.4×10⁵ Pa) overnight and filtered. The filtrate was concentrated under reduced pressure to provide 103 g of 1-[(3-amino-7-bromo[1,5]naphthyridin-4-yl)amino]-2-methylpropan-2-ol as a yellow solid.

Part C

A mixture of 1-[(3-amino-7-bromo[1,5]naphthyridin-4-yl)amino]-2-methylpropan-2-ol (100.0 g, 321.4 mmol) and acetonitrile (1 L) was stirred for five minutes and ethoxyacetyl chloride (43.3 g, 353.3 mmol) was added. The reaction was stirred overnight at room temperature. The solid product was isolated by filtration and washed with acetonitrile (200 mL) to provide 113 g of N-{7-bromo-4-[(2-hydroxy-2-methylpropyl)amino][1,5]naphthyridin-3-yl}-2-ethoxyacetamide hydrochloride as a yellow solid.

Part D

Potassium carbonate (113 g) and deionized water (565 mL) were sequentially added to a solution of N-{7-bromo-4-[(2-hydroxy-2-methylpropyl)amino][1,5]naphthyridin-3-yl}-2-ethoxyacetamide hydrochloride (113 g, 261 mmol) in denatured ethanol (1.695 L), and the resulting mixture was heated at reflux (77° C.) overnight and allowed to cool to room temperature. The ethanol was removed under reduced pressure, and the resulting mixture was filtered to isolate a solid. The solid was washed with deionized water (100 mL) and dried over two nights in a vacuum oven at 40° C. to provide 90 g of 1-[7-bromo-2-(ethoxymethyl)-1H-imidazo[4,5-c][1,5]naphthyridin-1-yl]-2-methylpropan-2-ol as a brown solid. Material from a separate run was used in the next step.

Part E mCPBA (35.5 g of 77% purity, 158 mmol) was added to a stirred solution of 1-[7-bromo-2-(ethoxymethyl)-1H-imidazo[4,5-c][1,5]naphthyridin-1-yl]-2-methylpropan-2-ol (15 g, 0.040 mol) in chloroform (400 mL), and the reaction was stirred at room temperature for 2.5 hours. Concentrated ammonium hydroxide (200 mL) was added, and then p-toluenesulfonyl chloride (18.9 g, 98.9 mmol) was added over a period of five minutes. The reaction mixture was stirred at room temperature for 2.5 hours, and an analysis by liquid chromatography/mass spectrometry (LC/MS) indicated the presence of starting material. Additional p-toluenesulfonyl chloride (11 g) was added, and the reaction mixture was stirred at room temperature for one hour. An analysis by LC/MS indicated the reaction was still incomplete. Additional ammonium hydroxide (100 mL) and p-toluenesulfonyl chloride (10 g) were added, and the mixture was stirred for 30 minutes at room temperature. The aqueous layer was separated and extracted with dichloromethane (2×300 mL). The combined organic fractions were dried over magnesium sulfate, filtered, and concentrated under reduced pressure. The residue (41.4 g) was purified by automated flash chromatography (FLASH 65I cartridge, eluting with ethyl acetate:methanol in a gradient from 97:3 to 85:15) to provide 5.96 g of 1-[4-amino-7-bromo-2-(ethoxymethyl)-1H-imidazo[4,5-c][1,5]naphthyridin-1-yl]-2-methylpropan-2-ol as a yellow solid.

Example 59

1-[4-Amino-7-(3,4-difluorophenyl)-2-(ethoxymethyl)-1H-imidazo[4,5-c][1,5]naphthyridin-1-yl]-2-methylpropan-2-ol

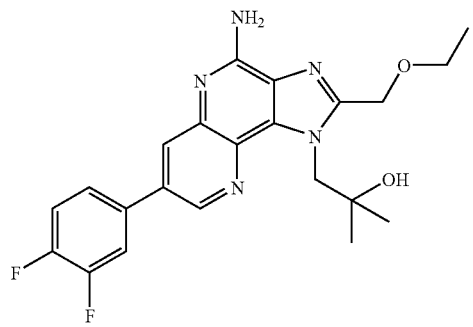

A suspension of 1-[4-amino-7-bromo-2-(ethoxymethyl)-1H-imidazo[4,5-c][1,5]naphthyridin-1-yl]-2-methylpropan-2-ol (1.4 g, 3.55 mmol), 3,4-difluorophenylboronic acid (1.12 g, 7.10 mmol), potassium carbonate (1.62 g, 11.7 mmol), 1,2-dimethyoxyethane (DME)(13 mL), and water (7 mL) was stirred under nitrogen. Dichlorobis(triphenylphosphine)palladium(II)(0.025 g, 0.036 mmol) was added, and the suspension was heated at reflux for five hours, allowed to cool to room temperature, diluted with water (20 mL), and extracted with dichloromethane (50 mL). An emulsion formed. Solid sodium chloride was added to saturate the aqueous layer. The organic layer was then removed under reduced pressure. The aqueous layer was extracted with dichloromethane (4×50 mL); the third extraction was allowed to stand overnight. The combined organic extracts were dried over magnesium sulfate, filtered, and concentrated under reduced pressure. The resulting brown solid (2.03 g) was dissolved in dichloromethane (45 mL), purified by automated flash chromatography (40+M silica cartridge, eluting with 3% to 10% methanol in ethyl acetate), and then triturated with acetonitrile. The resulting solid was isolated by filtration, washed with acetonitrile, and dried in a vacuum oven to provide 485 mg of 1-[4-amino-7-(3,4-difluorophenyl)-2-(ethoxymethyl)-1H-imidazo[4,5-c][1,5]naphthyridin-1-yl]-2-methylpropan-2-ol as an off-white solid, mp 193-195° C.

Anal. calcd for $C_{22}H_{23}F_2N_5O_2$: C, 61.82; H, 5.42; N, 16.38. Found: C, 61.95; H, 5.46; N, 16.34.

Example 60

1-[4-Amino-7-(3,4-dichlorophenyl)-2-(ethoxymethyl)-1H-imidazo[4,5-c][1,5]naphthyridin-1-yl]-2-methylpropan-2-ol

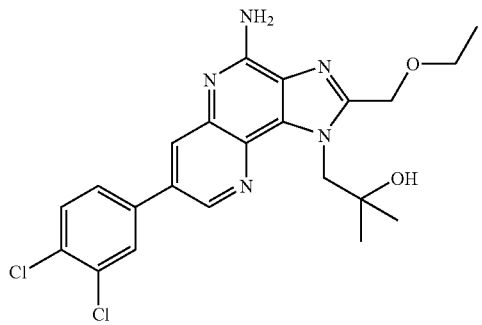

A suspension of 1-[4-amino-7-bromo-2-(ethoxymethyl)-1H-imidazo[4,5-c][1,5]naphthyridin-1-yl]-2-methylpropan-2-ol (1.4 g, 3.55 mmol), 3,4-difluorophenylboronic acid (1.36 g, 7.10 mmol), potassium carbonate (1.62 g, 11.7 mmol), DME (13 mL), and water (7 mL) was stirred under nitrogen. Dichlorobis(triphenylphosphine)palladium(II)(0.025 g, 0.036 mmol) was added, and the suspension was heated at reflux for five hours and allowed to cool to room temperature. The DME was removed under reduced pressure, and the resulting mixture was diluted with water (20 mL) and extracted with dichloromethane (3×50 mL). An emulsion formed; the second extraction was allowed to stand overnight. The combined organic extracts were dried over magnesium sulfate, filtered, and concentrated under reduced pressure. The resulting brown solid (2.2 g) was dissolved in dichloromethane (15 mL), purified as described in Example 59 to provide 264 mg of 1-[4-amino-7-(3,4-dichlorophenyl)-2-(ethoxymethyl)-1H-imidazo[4,5-c][1,5]naphthyridin-1-yl]-2-methylpropan-2-ol as an off-white solid, mp 144-147° C.

Anal. calcd for $C_{22}H_{23}Cl_2N_5O_2$: C, 57.40; H, 5.04; N, 15.21. Found: C, 57.11; H, 5.07; N, 14.99.

Example 61

1-{4-Amino-2-(ethoxymethyl)-7-[3-(morpholin-4-ylcarbonyl)phenyl]-1H-imidazo[4,5-c][1,5]naphthyridin-1-yl}-2-methylpropan-2-ol

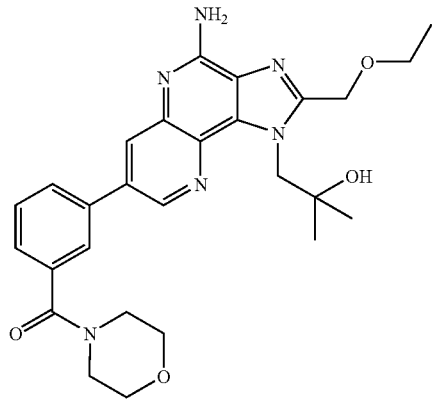

Under a nitrogen atmosphere, a suspension of 1-[4-amino-7-bromo-2-(ethoxymethyl)-1H-imidazo[4,5-c][1,5]naphthyridin-1-yl]-2-methylpropan-2-ol (1.5 g, 3.8 mmol), 3-(morpholine-4-carbonyl)phenylboronic acid (1.07 g, 4.57 mmol), potassium carbonate (1.74 g, 12.6 mmol), dichlorobis(triphenylphosphine)palladium(II)(0.027 g, 0.038 mmol), DME (13 mL), and water (7 mL) was stirred in a pressure vessel. The vessel was sealed, and the suspension was heated at 110° C. for 22 hours and allowed to cool to room temperature. The DME was removed under reduced pressure, and the resulting mixture was extracted with dichloromethane (3×25 mL) and ethyl acetate (25 mL). The combined organic extracts were dried over magnesium sulfate, filtered, and concentrated under reduced pressure. The resulting tan solid (2.11 g) was dissolved in dichloromethane (15 mL), purified by automated flash chromatography (40+M silica cartridge, eluting with 5% to 20% methanol in ethyl acetate). The resulting foamy solid was concentrated twice from methyl acetate, and the resulting solid was triturated with acetonitrile, isolated by filtration, washed with acetonitrile, and dried in a vacuum oven to provide 601 mg of 1-{4-amino-2-(ethoxymethyl)-7-[3-(morpholin-4-ylcarbonyl)phenyl]-1H-imidazo[4,5-c][1,5]naphthyridin-1-yl}-2-methylpropan-2-ol as a white solid, mp 149-152° C.

Anal. calcd for $C_{27}H_{32}N_6O_4$: C, 64.27; H, 6.39; N, 16.66. Found: C, 64.13; H, 6.62; N, 16.68.

Example 62

1-[4-Amino-2-(ethoxymethyl)-7-(6-fluoropyridin-3-yl)-1H-imidazo[4,5-c][1,5]naphthyridin-1-yl]-2-methylpropan-2-ol

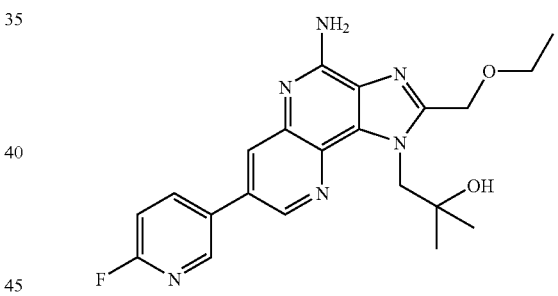

A suspension of 1-[4-amino-7-bromo-2-(ethoxymethyl)-1H-imidazo[4,5-c][1,5]naphthyridin-1-yl]-2-methylpropan-2-ol (1.4 g, 3.55 mmol), 6-fluoropyridine-3-boronic acid (0.597 g, 4.26 mmol), potassium carbonate (1.62 g, 11.7 mmol), dichlorobis(triphenylphosphine)palladium(II)(0.025 g, 0.036 mmol), DME (13 mL), and water (7 mL) was stirred under a nitrogen atmosphere and then heated at 110° C. for 17.5 hours and allowed to cool to room temperature. The volatiles were removed under reduced pressure, and the residue was partitioned between water (25 mL) and dichloromethane (25 mL). A solid was present in the organic layer, and methanol was added to dissolve the solid. The aqueous layer was extracted with dichloromethane (3×20 mL). Silica gel was added to the combined organic fractions, and the mixture was concentrated under reduced pressure. The residue was purified by automated flash chromatography (40+M silica cartridge, eluting with 5% to 15% methanol in ethyl acetate) followed by recrystallization from acetonitrile. The crystals were isolated by filtration, washed with acetonitrile, and dried in a vacuum oven to provide 530 mg of 1-[4-amino- 2-(ethoxymethyl)-7-(6-fluoropyridin-3-yl)-1H-imidazo[4,5-c][1,5]naphthyridin-1-yl]-2-methylpropan-2-ol as white crystals, mp 218-220° C.

Anal. calcd for $C_{21}H_{23}FN_6O_2$: C, 61.45; H, 5.65; N, 20.47. Found: C, 61.35; H, 5.55; N, 20.72.

Example 63

N-{3-[4-Amino-2-(ethoxymethyl)-1-(2-hydroxy-2-methylpropyl)-1H-imidazo[4,5-c][1,5]naphthyridin-1-yl]phenyl}methanesulfonamide

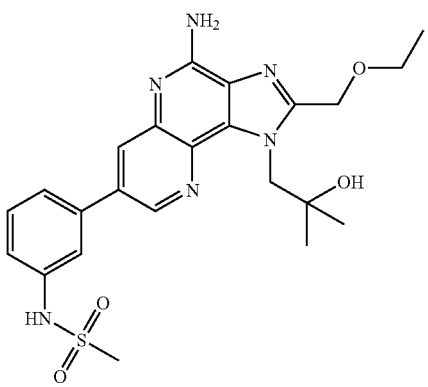

A suspension of 1-[4-amino-7-bromo-2-(ethoxymethyl)-1H-imidazo[4,5-c][1,5]naphthyridin-1-yl]-2-methylpropan-2-ol (1.4 g, 3.55 mmol), (3-methylsulfonylaminophenyl)boronic acid (0.916 g, 4.26 mmol), potassium carbonate (1.62 g, 11.7 mmol), dichlorobis(triphenylphosphine)palladium(II) (0.025 g, 0.036 mmol), DME (13 mL), and water (7 mL) was stirred under a nitrogen atmosphere and then heated at 110° C. for 18.5 hours and allowed to cool to room temperature. An analysis by LC/MS indicated the reaction was incomplete, and additional (3-methylsulfonylaminophenyl)boronic acid (1.0 g) and dichlorobis(triphenylphosphine)palladium(II) (0.15 g) were added. The reaction was heated at 110° C. for six hours and allowed to cool to room temperature. The volatiles were removed under reduced pressure. The entire reaction mixture was diluted with methanol, and silica gel was added. The mixture was concentrated under reduced pressure. The residue was purified by chromatography according to the method described in Example 62 followed by crystallization from methyl acetate (20 mL). The crystals were isolated by filtration, washed with acetonitrile, and dried in a vacuum oven to provide 679 mg of N-{3-[4-amino-2-(ethoxymethyl)-1-(2-hydroxy-2-methylpropyl)-1H-imidazo[4,5-c][1,5]naphthyridin-1-yl]phenyl}methanesulfonamide as yellow crystals, mp 206-208° C.

Anal. calcd for $C_{23}H_{28}N_6O_4S$: C, 57.01; H, 5.82; N, 17.34. Found: C, 56.96; H, 5.82; N, 16.99.

Example 64

1-[4-Amino-2-(ethoxymethyl)-7-phenyl-1H-imidazo[4,5-c][1,5]naphthyridin-1-yl]-2-methylpropan-2-ol

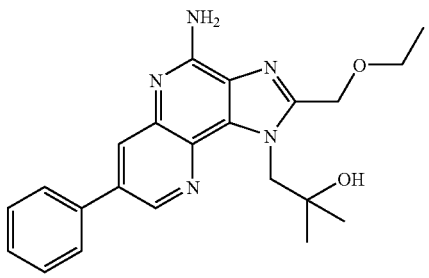

A suspension of 1-[4-amino-7-bromo-2-(ethoxymethyl)-1H-imidazo[4,5-c][1,5]naphthyridin-1-yl]-2-methylpropan-2-ol (1.55 g, 3.93 mmol), phenylboronic acid (0.575 g, 4.72 mmol), potassium carbonate (1.79 g, 13.0 mmol), dichlorobis(triphenylphosphine)palladium(II)(0.028 g, 0.039 mmol), DME (13 mL), and water (7 mL) was stirred under a nitrogen atmosphere and then heated at reflux for 61 hours and allowed to cool to room temperature. The volatiles were removed under reduced pressure. The residue was diluted with methanol, and silica gel was added. The mixture was concentrated under reduced pressure. The residue was purified by chromatography according to the method described in Example 59. The resulting foamy solid (1.55 g) was concentrated twice from acetonitrile and then triturated with acetonitrile (25 mL) to provide a solid. The solid was isolated by filtration, washed with acetonitrile, and dried in a vacuum oven at 65° C. to provide 887 mg of 1-[4-amino-2-(ethoxymethyl)-7-phenyl-1H-imidazo[4,5-c][1,5]naphthyridin-1-yl]-2-methylpropan-2-ol as an off-white solid, mp 158-159° C.

Anal. calcd for $C_{22}H_{25}N_5O_2$: C, 67.50; H, 6.44; N, 17.89. Found: C, 67.27; H, 6.66; N, 18.08.

Example 65

1-{4-Amino-2-(ethoxymethyl)-7-[3-(pyrrolidin-1-ylcarbonyl)phenyl]-1H-imidazo[4,5-c][1,5]naphthyridin-1-yl}-2-methylpropan-2-ol

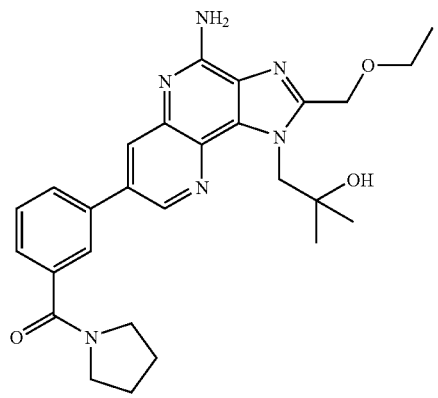

A suspension of 1-[4-amino-7-bromo-2-(ethoxymethyl)-1H-imidazo[4,5-c][1,5]naphthyridin-1-yl]-2-methylpropan- 2-ol (1.2 g, 3.0 mmol), (3-pyrrolidinylcarbonylphenyl)boronic acid (0.800 g, 3.65 mmol), potassium carbonate (1.4 g, 10.0 mmol), dichlorobis(triphenylphosphine)palladium(II) (0.021 g, 0.030 mmol), DME (13 mL), and water (7 mL) was stirred under a nitrogen atmosphere in a pressure vessel. The vessel was then sealed and heated at 110° C. for 16.5 hours and allowed to cool to room temperature. The volatiles were removed under reduced pressure. The residue was diluted with methanol, and silica gel was added. The mixture was concentrated under reduced pressure. The residue was purified by automated flash chromatography (FLASH 40+M silica cartridge, eluting with 10% to 25% methanol in ethyl acetate). The resulting material was concentrated twice from acetonitrile and then triturated with acetonitrile (100 mL) to provide a solid. The solid was isolated by filtration, washed with acetonitrile, and dried in a vacuum oven at 65° C. to provide 403 mg of 1-{4-amino-2-(ethoxymethyl)-7-[3-(pyrrolidin-1-ylcarbonyl)phenyl]-1H-imidazo[4,5-c][1,5]naphthyridin-1-yl}-2-methylpropan-2-ol as a white solid, mp 185-187° C.

Anal. calcd for $C_{27}H_{32}N_6O_3$: C, 66.37; H, 6.60; N, 17.20. Found: C, 66.26; H, 6.53; N, 17.26.

Example 66

1-{4-Amino-2-(ethoxymethyl)-7-[3-(hydroxymethyl)phenyl]-1H-imidazo[4,5-c][1,5]naphthyridin-1-yl]-2-methylpropan-2-ol

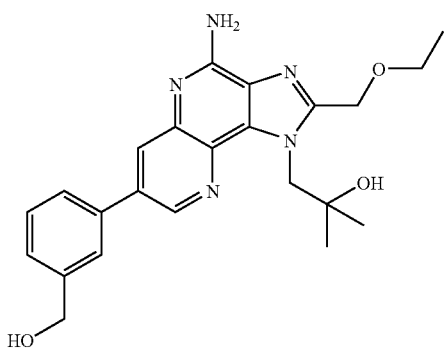

A suspension of 1-[4-amino-7-bromo-2-(ethoxymethyl)-1H-imidazo[4,5-c][1,5]naphthyridin-1-yl]-2-methylpropan-2-ol (1.2 g, 3.0 mmol), 3-(hydroxymethyl)benzeneboronic acid (0.555 g, 3.65 mmol), potassium carbonate (1.4 g, 10.0 mmol), dichlorobis(triphenylphosphine)palladium(II)(0.021 g, 0.030 mmol), DME (13 mL), and water (7 mL) was stirred under a nitrogen atmosphere in a pressure vessel. The vessel was then sealed and heated at 110° C. for 16.5 hours and allowed to cool to room temperature. The volatiles were removed under reduced pressure. The residue was diluted with methanol, and silica gel was added. The mixture was concentrated under reduced pressure. The residue was purified by automated flash chromatography (FLASH 40+M silica cartridge, eluting with 5% to 20% methanol in ethyl acetate) followed by trituration with acetonitrile. The resulting solid was isolated by filtration, washed with acetonitrile, and dried in a vacuum oven at 65° C. to provide 449 mg of 1-{4-amino-2-(ethoxymethyl)-7-[3-(hydroxymethyl)phenyl]-1H-imidazo[4,5-c][1,5]naphthyridin-1-yl]-2-methylpropan-2-ol as a white solid, mp 186-187° C.

Anal. calcd for $C_{23}H_{27}N_5O_3$: C, 65.54; H, 6.46; N, 16.62. Found: C, 65.47; H, 6.31; N, 16.67.

Example 67

3-[4-Amino-2-(ethoxymethyl)-1-(2-hydroxy-2-methylpropyl)-1H-imidazo[4,5-c][1,5]naphthyridin-7-yl] benzamide

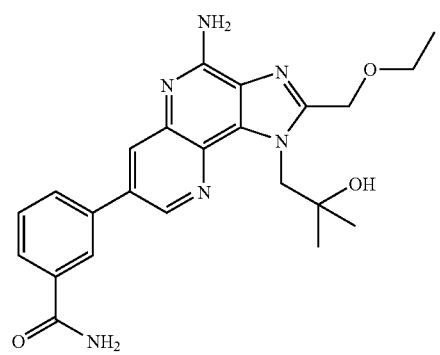

A suspension of 1-[4-amino-7-bromo-2-(ethoxymethyl)-1H-imidazo[4,5-c][1,5]naphthyridin-1-yl]-2-methylpropan-2-ol (1.2 g, 3.0 mmol), (3-aminocarbonylphenyl)boronic acid (0.603 g, 3.65 mmol), potassium carbonate (1.4 g, 10.0 mmol), dichlorobis(triphenylphosphine)palladium(II)(0.021 g, 0.030 mmol), DME (13 mL), and water (7 mL) was stirred under a nitrogen atmosphere in a pressure vessel. The vessel was then sealed and heated at 110° C. for 64 hours and allowed to cool to room temperature. A precipitate formed and was isolated by filtration, washed with water and DME, and recrystallized from methanol (100 mL/900 mg). The crystals were isolated by filtration, washed with methanol, and dried in a vacuum oven at 65° C. to provide 191 mg of 3-[4-amino-2-(ethoxymethyl)-1-(2-hydroxy-2-methylpropyl)-1H-imidazo[4,5-c][1,5]naphthyridin-7-yl]benzamide as an off-white solid, mp >250° C.

Anal. calcd for $C_{23}H_{26}N_6O_3$: C, 63.58; H, 6.03; N, 19.34. Found: C, 63.57; H, 6.16; N, 19.38.

Example 68

1-{4-Amino-2-(ethoxymethyl)-7-[5-(hydroxymethyl)pyridin-3-yl]-1H-imidazo[4,5-c][1,5]naphthyridin-1-yl}-2-methylpropan-2-ol

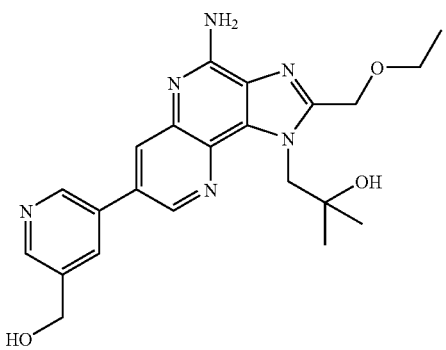

Part A

A suspension of 1-[4-amino-7-bromo-2-(ethoxymethyl)-1H-imidazo[4,5-c][1,5]naphthyridin-1-yl]-2-methylpropan-2-ol (1.5 g, 3.80 mmol), 5-(tert-butyldimethylsilanyloxymethyl)pyridine-3-boronic acid (1.22 g, 4.57 mmol), potassium carbonate (1.74 g, 12.6 mmol), dichlorobis(triphenylphosphine)palladium(II)(0.027 g, 0.038 mmol), DME (13 mL), and water (7 mL) was stirred under a nitrogen atmosphere and then heated at 110° C. in a pressure vessel for 6 hours and allowed to cool to room temperature. An analysis by LC/MS indicated the reaction was incomplete, and additional dichlorobis(triphenylphosphine)palladium(II)(0.035 g) was added. The reaction was heated at 110 C for 16 hours and allowed to cool to room temperature. The DME was removed under reduced pressure, and the resulting mixture was extracted with dichloromethane (3×25 mL). The combined organic extracts were dried over magnesium sulfate, filtered, and concentrated under reduced pressure. The resulting brown solid was dissolved in dichloromethane (15 mL) purified by chromatography according to the method described in Example 62 to provide 1.37 g of 1-{4-amino-7-[5-(tert-butyldimethylsilanyloxymethyl)pyridin-3-yl]-2-(ethoxymethyl)-1H-imidazo[4,5-c][1,5]naphthyridin-1-yl}-2-methylpropan-2-ol as a yellow solid.

Part B

A solution of 1-{4-amino-7-[5-(tert-butyldimethylsilanyloxymethyl)pyridin-3-yl]-2-(ethoxymethyl)-1H-imidazo[4,5-c][1,5]naphthyridin-1-yl]-2-methylpropan-2-ol (1.37 g, 2.55 mmol) in acetic acid (10 mL), tetrahydrofuran (10 mL), and water (10 mL) was stirred at 60° C. for 18.5 hours and allowed to cool to room temperature. The solvent was removed under reduced pressure, and the residue was diluted with saturated aqueous sodium bicarbonate (30 mL). Dichloromethane was added, but an oil was present that remained insoluble in both phases. Both phases were decanted away from the oil, which was dissolved in methanol. The aqueous phase was then separated and extracted with dichloromethane (30 mL) and ethyl acetate (2×30 mL). Silica gel was added to the combined dichloromethane, ethyl acetate, and methanol fractions, and the solvent was removed under reduced pressure. The residue was purified by automated flash chromatography (FLASH 40+M silica cartridge, eluting with 5% to 20% methanol in dichloromethane). The resulting material was concentrated from acetonitrile to form a solid, which was triturated with acetonitrile (30 mL), isolated by filtration, washed with acetonitrile, and dried overnight in a vacuum oven to provide 530 mg of 1-{4-amino-2-(ethoxymethyl)-7-[5-(hydroxymethyl)pyridin-3-yl]-1H-imidazo[4,5-c][1,5]naphthyridin-1-yl}-2-methylpropan-2-ol as a light yellow solid, mp 212-214° C.

Anal. calcd for $C_{22}H_{26}N_6O_3$: C, 62.54; H, 6.20; N, 19.89. Found: C, 62.39; H, 6.09; N, 19.91.

Example 69

1-[4-Amino-7-(3,4-difluorophenyl)-2-(hydroxymethyl)-1H-imidazo[4,5-c][1,5]naphthyridin-1-yl]-2-methylpropan-2-ol

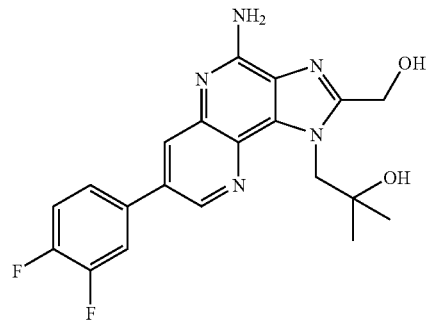

A suspension of 1-[4-amino-7-(3,4-difluorophenyl)-2-(ethoxymethyl)-1H-imidazo[4,5-c][1,5]naphthyridin-1-yl]-2-methylpropan-2-ol (0.790 g, 1.85 mmol), obtained from the filtrate from the trituration in Example 59, in dichloromethane (20 mL) was cooled to 0° C. Boron tribromide (5.54 mL of a 1 M solution in dichloromethane) was added dropwise, and the reaction was stirred at room temperature for 22.5 hours. An analysis by LC/MS indicated the reaction was incomplete, and additional boron tribromide (2.7 mL) was added. The reaction was stirred for three hours at room temperature, and then methanol (25 mL) was carefully added. The resulting solution was stirred at room temperature for one hour and concentrated under reduced pressure. A solution of ammonia in methanol (30 mL of 2 M) was added, and the mixture was stirred for 30 minutes and then diluted with methanol (50 mL) and dichloromethane (50 mL). Silica gel was added, and the mixture was concentrated under reduced pressure. The residue was purified by chromatography according to the method described in Example 62. The resulting solid was triturated with acetonitrile, isolated by filtration, washed with acetonitrile, and dried in a vacuum oven to provide 269 mg of 1-[4-amino-7-(3,4-difluorophenyl)-2-(hydroxymethyl)-1H-imidazo[4,5-c][1,5]naphthyridin-1-yl]-2-methylpropan-2-ol as a light yellow solid, mp 256-258° C.

Anal. calcd for $C_{20}H_{19}F_2N_5O_2$: C, 60.15; H, 4.80; N, 17.53. Found: C, 60.15; H, 4.74; N, 17.80.

Example 70

1-[4-Amino-7-(3,4-dichlorophenyl)-2-(hydroxymethyl)-1H-imidazo[4,5-c][1,5]naphthyridin-1-yl]-2-methylpropan-2-ol

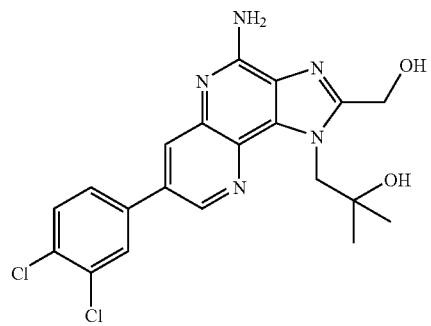

A solution of 1-[4-amino-7-(3,4-dichlorophenyl)-2-(ethoxymethyl)-1H-imidazo[4,5-c][1,5]naphthyridin-1-yl]-2-methylpropan-2-ol (0.850 g, 1.85 mmol), obtained from the filtrate from the trituration in Example 60, in dichloromethane (20 mL) was cooled to 0° C. Boron tribromide (5.5 mL of a 1 M solution in dichloromethane) was added dropwise, and the reaction was stirred at room temperature for 24 hours. An analysis by LC/MS indicated the reaction was incomplete, and additional boron tribromide (5.5 mL) was added. The reaction was stirred for three hours at room temperature, and the work-up and purification procedures described in Example 69 were followed to provide 233 mg of 1-[4-amino-7-(3,4-dichlorophenyl)-2-(hydroxymethyl)-1H-imidazo[4,5-c][1,5]naphthyridin-1-yl]-2-methylpropan-2-ol, mp 254-256° C.

Anal. calcd for $C_{20}H_{19}Cl_2N_5O_2$: C, 55.57; H, 4.43; N, 16.20. Found: C, 55.50; H, 4.58; N, 16.01.

Example 71

1-{4-Amino-2-(hydroxymethyl)-7-[3-(morpholin-4-ylcarbonyl)phenyl]-1H-imidazo[4,5-c][1,5]naphthyridin-1-yl}-2-methylpropan-2-ol

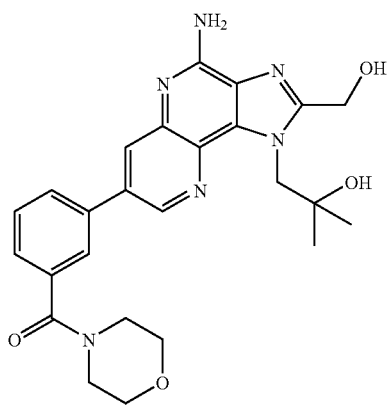

A solution of 1-{4-amino-2-(ethoxymethyl)-7-[3-(morpholin-4-ylcarbonyl)phenyl]-1H-imidazo[4,5-c][1,5]naphthyridin-1-yl}-2-methylpropan-2-ol (1.10 g, 2.18 mmol), obtained from the filtrate from the trituration in Example 61, in dichloromethane (20 mL) was cooled to −78° C. Boron tribromide (10.9 mL of a 1 M solution in dichloromethane) was added dropwise, and the reaction was allowed to warm to room temperature and stirred for 5.5 hours. Methanol (20 mL) was carefully added, and the resulting solution was stirred at room temperature for one hour and concentrated under reduced pressure. A solution of ammonia in methanol (50 mL of 1 M) was added, and the mixture was stirred for one hour. Silica gel was added, and the mixture was concentrated under reduced pressure. The resulting mixture was purified according to the methods described in Example 61 with the modification that chromatographed material was concentrated from acetonitrile instead of methyl acetate. 1-{4-Amino-2-(hydroxymethyl)-7-[3-(morpholin-4-ylcarbonyl)phenyl]-1H-imidazo[4,5-c][1,5]naphthyridin-1-yl}-2-methylpropan-2-ol (307 mg) was obtained as a light yellow solid, mp 153-155° C.

Anal. calcd for $C_{25}H_{28}N_6O_4$: C, 63.01; H, 5.92; N, 17.64. Found: C, 62.92; H, 5.67; N, 17.51.

Example 72

N-{3-[4-Amino-2-(hydroxymethyl)-1-(2-hydroxy-2-methylpropyl)-1H-imidazo[4,5-c][1,5]naphthyridin-1-yl]phenyl}methanesulfonamide

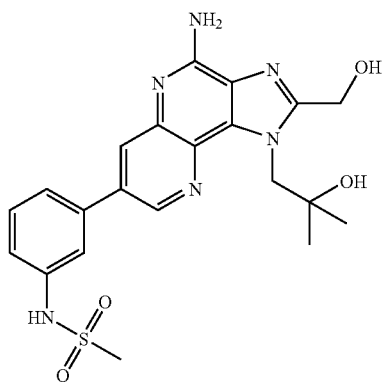

A suspension of N-{3-[4-amino-2-(ethoxymethyl)-1-(2-hydroxy-2-methylpropyl)-1H-imidazo[4,5-c][1,5]naphthyridin-1-yl]phenyl}methanesulfonamide (1.17 g, 2.41 mmol), obtained from the filtrate from the recrystallization in Example 63, in dichloromethane (20 mL) was cooled to 0° C. Boron tribromide (12.1 mL of a 1 M solution in dichloromethane) was added dropwise, and the reaction was stirred at room temperature for 22 hours. Methanol (40 mL) was carefully added, and the resulting solution was stirred at room temperature for one hour and concentrated under reduced pressure. A solution of ammonia in methanol (100 mL of 1 M) was added, and the mixture was stirred at room temperature and then concentrated under reduced pressure. The residue was triturated with methanol (50 mL), and the resulting solid was isolated by filtration and washed with methanol and acetonitrile. The solid (710 mg) was then recrystallized from acetonitrile. The crystals were isolated by filtration, washed with acetonitrile, and dried in a vacuum oven to provide 493 mg of N-{3-[4-amino-2-(hydroxymethyl)-1-(2-hydroxy-2-methylpropyl)-1H-imidazo[4,5-c][1,5]naphthyridin-1-yl]phenyl}methanesulfonamide as a yellow solid, mp>250° C.

Anal. calcd for $C_{21}H_{24}N_6O_4S$: C, 55.25; H, 5.30; N, 18.41. Found: C, 54.99; H, 5.06; N, 18.26.

Example 73

1-[4-Amino-2-(hydroxymethyl)-7-phenyl-1H-imidazo[4,5-c][1,5]naphthyridin-1-yl]-2-methylpropan-2-ol

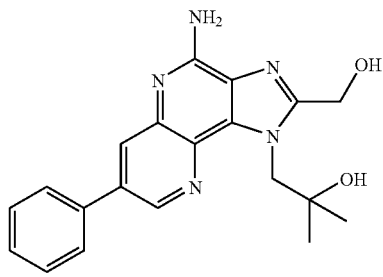

A solution of 1-[4-amino-2-(ethoxymethyl)-7-phenyl-1H-imidazo[4,5-c][1,5]naphthyridin-1-yl]-2-methylpropan-2-ol (1.0 g, 2.55 mmol), obtained from the filtrate from the trituration in Example 64, in dichloromethane (25 mL) was cooled to 0° C. Boron tribromide (12.8 mL of a 1 M solution in dichloromethane) was added dropwise, and the resulting suspension was stirred at room temperature for 14.5 hours. Methanol (50 mL) was carefully added, and the resulting solution was stirred at room temperature for one hour and concentrated under reduced pressure. A solution of ammonia in methanol (50 mL of 1 M) was added, and the suspension was stirred at room temperature for three hours. A solid was isolated by filtration, washed with methanol and acetonitrile, and dried in a vacuum oven at 65° C. to provide 403 mg of 1-[4-amino-2-(hydroxymethyl)-7-phenyl-1H-imidazo[4,5-c][1,5]naphthyridin-1-yl]-2-methylpropan-2-ol as a white solid, mp 244-245° C.

Anal. calcd for $C_{20}H_{21}N_5O_2$: C, 66.10; H, 5.82; N, 19.27. Found: C, 65.90; H, 5.77; N, 19.34.

Example 74

1-{4-Amino-2-(hydroxymethyl)-7-[3-(hydroxymethyl)phenyl]-1H-imidazo[4,5-c][1,5]naphthyridin-1-yl]-2-methylpropan-2-ol

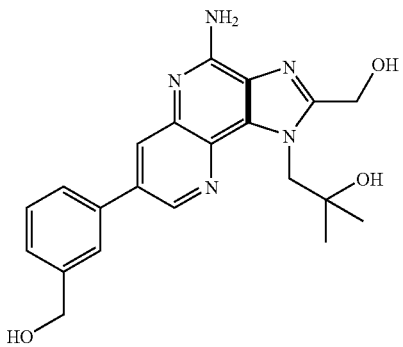

A suspension of 1-{4-amino-2-(ethoxymethyl)-7-[3-(hydroxymethyl)phenyl]-1H-imidazo[4,5-c][1,5]naphthyridin-1-yl]-2-methylpropan-2-ol (0.800 g, 1.90 mmol) obtained from the filtrate from the trituration in Example 66, in dichloromethane (20 mL) was cooled to 0° C. Boron tribromide (9.5 mL of a 1 M solution in dichloromethane) was added dropwise, and the resulting suspension was stirred at room temperature for 15 hours. Methanol was carefully added, and the resulting solution was stirred at room temperature for one hour and concentrated under reduced pressure. The residue (1.33 g) was dissolved in DMF (15 mL), and potassium acetate was added. The mixture was heated at 50° C. for 18 hours and then concentrated under reduced pressure. The residue was dissolved in methanol (20 mL) and water (10 mL), and lithium hydroxide monohydrate (1.5 g) was added. The reaction was stirred at room temperature for 64 hours and concentrated under reduced pressure. Methanol and silica gel were added, and the mixture was concentrated under reduced pressure. The residue was purified by automated flash chromatography (FLASH 40+M cartridge, eluting with 7% to 20% 1 M methanolic ammonia in dichloromethane) followed by recrystallization from acetonitrile after a hot filtration. The crystals were washed with acetonitrile and dried in a vacuum oven at 65° C. to provide 146 mg of 1-{4-amino-2-(hydroxymethyl)-7-[3-(hydroxymethyl)phenyl]-1H-imidazo[4,5-c][1,5]naphthyridin-1-yl]-2-methylpropan-2-ol as a yellow solid, mp 227-229° C.

Anal. calcd for $C_{21}H_{23}N_5O_3 \cdot 0.1H_2O$: C, 63.82; H, 5.92; N, 17.72. Found: C, 63.62; H, 5.93; N, 17.79.

Example 75

1-{4-Amino-2-(hydroxymethyl)-7-[3-(pyrrolidin-1-ylcarbonyl)phenyl]-1H-imidazo[4,5-c][1,5]naphthyridin-1-yl}-2-methylpropan-2-ol

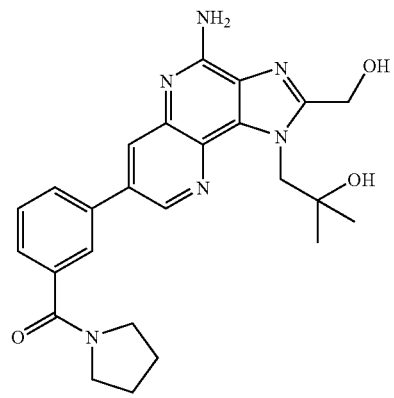

A solution of 1-{4-amino-2-(ethoxymethyl)-7-[3-(pyrrolidin-1-ylcarbonyl)phenyl]-1H-imidazo[4,5-c][1,5]naphthyridin-1-yl}-2-methylpropan-2-ol (1.0 g, 2.0 mmol), obtained from the filtrate from the trituration in Example 65, in dichloromethane (20 mL) was cooled to 0° C. Boron tribromide (10.2 mL of a 1 M solution in dichloromethane) was added dropwise, and the reaction was allowed to warm to room temperature and stirred for 15 hours. Methanol (50 mL) was carefully added, and the resulting solution was stirred at room temperature for one hour and concentrated under reduced pressure. A solution of ammonia in methanol (50 mL of 1 M) was added, and the mixture was stirred for one hour. Silica gel was added, and the mixture was concentrated under reduced pressure. The resulting mixture was purified by automated flash chromatography (FLASH 40+M cartridge, eluting with 5% to 20% methanolic ammonia in dichloromethane), triturated with acetonitrile, isolated by filtration, washed with acetonitrile, and dried in a vacuum oven at 65° C. to provide 169 mg of 1-{4-amino-2-(hydroxymethyl)-7-[3-(pyrrolidin-1-ylcarbonyl)phenyl]-1H-imidazo[4,5-c][1,5]naphthyridin-1-yl}-2-methylpropan-2-ol as an off-white solid, mp 157-160° C.

Anal. calcd for $C_{25}H_{28}N_6O_3 \cdot 0.5H_2O$: C, 63.95; H, 6.23; N, 17.90. Found: C, 63.59; H, 5.87; N, 17.97.

Example 76

1-{4-Amino-2-(hydroxymethyl)-7-[5-(hydroxymethyl)pyridin-3-yl]-1H-imidazo[4,5-c][1,5]naphthyridin-1-yl}-2-methylpropan-2-ol

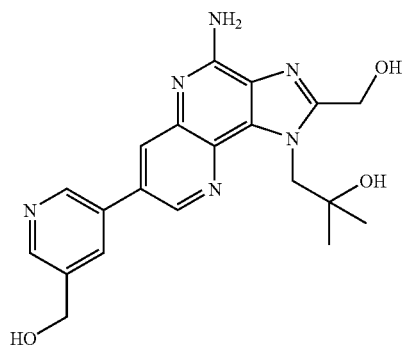

A suspension of 1-{4-amino-2-(ethoxymethyl)-7-[5-(hydroxymethyl)pyridin-3-yl]-1H-imidazo[4,5-c][1,5]naphthyridin-1-yl}-2-methylpropan-2-ol (627 mg, 1.48 mmol), obtained from the filtrate from the trituration in Example 68, in dichloromethane (25 mL) was cooled to −78° C. Boron tribromide (15 mL of a 1 M solution in dichloromethane) was added dropwise, and the reaction was allowed to warm to room temperature and stirred for 3.5 hours. Methanol (50 mL) was carefully added, and the resulting solution was stirred at room temperature for 30 minutes and concentrated under reduced pressure. A solution of ammonia in methanol (50 mL of 1 M) was added, and the mixture was stirred for 30 minutes. Silica gel was added, and the mixture was concentrated under reduced pressure. The resulting mixture was purified by automated flash chromatography (FLASH 40+M cartridge, eluting with 15% to 30% methanolic ammonia in dichloromethane). All fractions containing product were combined and concentrated, and the residue was dissolved in methanol (50 mL) and treated with 6 M hydrochloric acid. The solution was heated at 50° C. for two hours, concentrated under reduced pressure, and diluted with 2 N ammonia in methanol. Silica gel was added, and the mixture was concentrated under reduced pressure. Chromatographic purification was carried out again as described above with the modification that the elution gradient began with 5% methanolic ammonia in dichloromethane. The resulting product was dissolved in methanol (20 mL), divided in ten equal portions, and loaded onto ten Waters Oasis Sample Extractions Cartridge MCX columns (500 mg) according to the following procedure. Each column was washed with methanol (2 volumes) and 1 N ammonia in methanol (3 volumes), and the ammonia washes were combined and concentrated under reduced pressure. The resulting solid (200 mg) was triturated with acetonitrile, isolated by filtration, washed with acetonitrile, and dried in a vacuum oven to provide 175 mg of 1-{4-amino-2-(hydroxymethyl)-7-[5-(hydroxymethyl)pyridin-3-yl]-1H-imidazo[4,5-c][1,5]naphthyridin-1-yl}-2-methylpropan-2-ol as a light yellow solid, mp 149-151° C.

Anal. calcd for $C_{20}H_{22}N_6O_3$: C, 60.90; H, 5.62; N, 21.31. Found: C, 60.75; H, 5.69; N, 21.40.

Examples 77-127

A solution of 1-[4-amino-7-bromo-2-(ethoxymethyl)-1H-imidazo[4,5-c][1,5]naphthyridin-1-yl]-2-methylpropan-2-ol (42.0 mg, 0.11 mmol) in 7:3 volume:volume (v:v) chloroform:methanol (2 mL) was added to a test tube, and the solvent was removed by vacuum centrifugation. The boronic acid (0.12 mmol) indicated in the table below and n-propanol (1.6 mL) were sequentially added. Palladium (II) acetate (0.150 mL of a 4 mg/mL solution in toluene, 0.0027 mmol), 2 M aqueous sodium carbonate solution (600 μL), deionized water (113 μL), and a solution of 0.15 mol % triphenylphosphine in n-propanol (53 μL, 0.0078 mmol) were sequentially added. The test tube was purged with nitrogen, capped, and then heated at 80° C. overnight in a sand bath.

The contents of each test tube were passed through a Waters Oasis Sample Extractions Cartridge MCX (6 cc) according to the procedure described in Examples 4-58. The resulting basic solutions were concentrated by vacuum centrifugation. The compounds were purified by reversed phase prep HPLC using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. The table below shows the reagent added to each test tube, the structure of the resulting compound, and the observed accurate mass for the isolated trifluoroacetate salt.

Examples 77-127

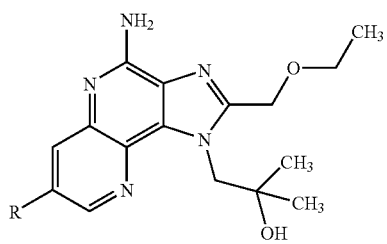

| Example | Reagent | R | Measured Mass (M + H) |
|---|---|---|---|
|  | None | Br— | 394.0867 |
| 77 | Furan-3-boronic acid | (furan-3-yl) | 382.1894 |
| 78 | Pyridine-3-boronic acid | (pyridin-3-yl) | 393.2059 |

-continued

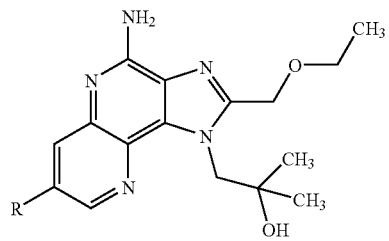

| Example | Reagent | R | Measured Mass (M + H) |
|---|---|---|---|
| 79 | Pyridine-4-boronic acid | 4-pyridyl | 393.2078 |
| 80 | 3-Methylphenylboronic acid | 3-methylphenyl | 406.2238 |
| 81 | 4-Methylphenylboronic acid | 4-methylphenyl | 406.2264 |
| 82 | o-Tolylboronic acid | 2-methylphenyl | 406.2216 |
| 83 | 2-Hydroxyphenylboronic acid | 2-hydroxyphenyl | 408.2068 |
| 84 | 3-Hydroxyphenylboronic acid | 3-hydroxyphenyl | 408.2061 |
| 85 | 4-Cyanophenylboronic acid | 4-cyanophenyl | 417.2075 |
| 86 | 4-Vinylphenylboronic acid | 4-vinylphenyl | 418.2259 |
| 87 | 3,5-Dimethylphenylboronic acid | 3,5-dimethylphenyl | 420.2406 |

-continued

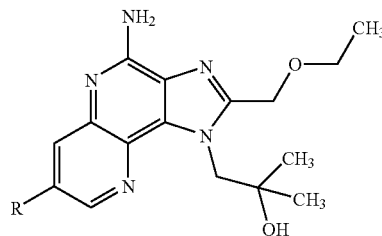

| Example | Reagent | R | Measured Mass (M + H) |
|---|---|---|---|
| 88 | 4-Ethylphenylboronic acid | 4-ethylphenyl | 420.2379 |
| 89 | 2-Methoxyphenylboronic acid | 2-methoxyphenyl | 422.2213 |
| 90 | 4-(Hydroxymethyl)phenylboronic acid | 4-(hydroxymethyl)phenyl | 422.2196 |
| 91 | 4-Methoxyphenylboronic acid | 4-methoxyphenyl | 422.2149 |
| 92 | 3-Aminophenylboronic acid monohydrate | 3-aminophenyl | 407.2189 |
| 93 | (4-Fluoro-2-hydroxy)phenylboronic acid | 4-fluoro-2-hydroxyphenyl | 426.1971 |
| 94 | 3-Chlorophenylboronic acid | 3-chlorophenyl | 426.1695 |
| 95 | 2-Chlorophenylboronic acid | 2-chlorophenyl | 426.1694 |
| 96 | 4-Chlorophenylboronic acid | 4-chlorophenyl | 426.1713 |

-continued

| Example | Reagent | R | Measured Mass (M + H) |
|---|---|---|---|
| 97 | 2,4-Difluorophenylboronic acid | 2,4-difluorophenyl | 428.1916 |
| 98 | Benzo[b]furan-2-boronic acid | benzo[b]furan-2-yl | 432.2041 |
| 99 | 3-Acetylphenylboronic acid | 3-acetylphenyl | 434.2236 |
| 100 | 4-Acetylphenylboronic acid | 4-acetylphenyl | 434.2192 |
| 101 | 3,4-Methylenedioxyphenylboronic acid | 3,4-methylenedioxyphenyl | 436.1993 |
| 102 | 3-Carboxyphenylboronic acid | 3-carboxyphenyl | 436.2005 |
| 103 | 4-Carboxyphenylboronic acid | 4-carboxyphenyl | 436.1992 |
| 104 | 2-Ethoxyphenylboronic acid | 2-ethoxyphenyl | 436.2338 |

-continued
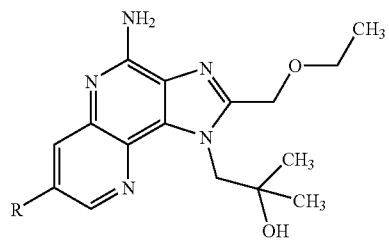
| Example | Reagent | R | Measured Mass (M + H) |
|---|---|---|---|
| 105 | 3-Ethoxyphenylboronic acid | 3-(ethoxy)phenyl | 436.2353 |
| 106 | 4-(Methylthio)phenylboronic acid | 4-(methylthio)phenyl | 438.1939 |
| 107 | 2-Ethoxy-5-methylphenylboronic acid | 2-ethoxy-5-methylphenyl | 450.2491 |
| 108 | 2-Isopropoxyphenylboronic acid | 2-(isopropoxy)phenyl | 450.2470 |
| 109 | 4-Isopropoxyphenylboronic acid | 4-(isopropoxy)phenyl | 450.2492 |
| 110 | [3-(Hydroxypropyl)phenyl]boronic acid | 3-(3-hydroxypropyl)phenyl | 450.2535 |

-continued

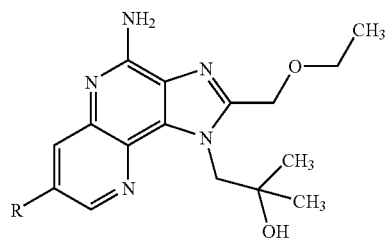

| Example | Reagent | R | Measured Mass (M + H) |
|---|---|---|---|
| 111 | 3,4-Dimethoxyphenylboronic acid | 3,4-dimethoxyphenyl | 452.2313 |
| 112 | 3-(4-Boronophenyl)propionic acid | 4-(2-carboxyethyl)phenyl | 464.2318 |
| 113 | 4-(Methoxycarobonylamino)phenylboronic acid | 4-(methoxycarbonylamino)phenyl | 465.2205 |
| 114 | 4-(Cyclopropylaminocarbonyl)phenylboronic acid | 4-(cyclopropylaminocarbonyl)phenyl | 475.2462 |
| 115 | 3-(N-Isopropylaminocarbonyl)phenylboronic acid | 3-(isopropylaminocarbonyl)phenyl | 477.2596 |

-continued

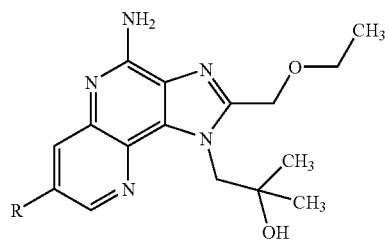

| Example | Reagent | R | Measured Mass (M + H) |
|---|---|---|---|
| 116 | 3-(N-Propylaminocarbonyl)phenyl-boronic acid | *phenyl with meta-C(O)NH-propyl* | 477.2637 |
| 117 | 4-Borono-DL-phenylalanine | *para-substituted phenyl-CH2-CH(NH2)-COOH* | 479.2398 |
| 118 | 3,4,5-Trimethoxyphenylboronic acid | *3,4,5-trimethoxyphenyl* | 482.2416 |
| 119 | 4-(Ethylsulfonyl)phenylboronic acid | *4-(ethylsulfonyl)phenyl* | 484.2023 |
| 120 | 3-(2-Cyanoethylaminocarbonyl)-phenylboronic acid | *phenyl with meta-C(O)NH-CH2CH2-CN* | 488.2415 |

-continued
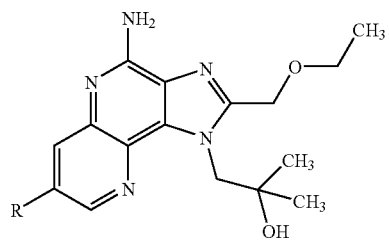
| Example | Reagent | R | Measured Mass (M + H) |
|---|---|---|---|
| 121 | 3-(Isobutylaminocarbonyl)phenyl-boronic acid | | 491.2749 |
| 122 | 4-(Isobutylaminocarbonyl)phenyl-boronic acid | | 491.2750 |
| 123 | 3-(Piperidine-1-carbonyl)phenylboronic acid | | 503.2775 |
| 124 | 4-(Cyclopentylaminocarbonyl)-phenylboronic acid | | 503.2757 |

-continued

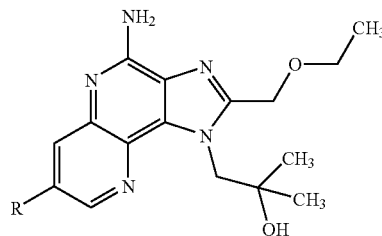

| Example | Reagent | R | Measured Mass (M + H) |
|---|---|---|---|
| 125 | 4-Benzyloxy-3-fluorophenylboronic acid | | 516.2405 |
| 126 | 3-(N-Benzylaminocarbonyl)phenyl-boronic acid | | 525.2625 |
| 127 | 1-(Phenylsulfonyl)-1H-indol-3-ylboronic acid | | 571.2138 |

Examples 128-151

A solution of 1-[4-amino-7-bromo-2-(ethoxymethyl)-1H-imidazo[4,5-c][1,5]naphthyridin-1-yl]-2-methylpropan-2-ol (53.0 mg, 0.135 mmol) in 7:3 volume:volume (v:v) chloroform:methanol (2 mL) was added to a test tube, and the solvent was removed by vacuum centrifugation. The boronic acid (0.16 mmol) indicated in the table below and n-propanol (1.6 mL) were sequentially added. Palladium (II) acetate (0.198 mL of a 4 mg/mL solution in toluene, 0.0035 mmol), 2 M aqueous sodium carbonate solution (813 µL), deionized water (113 µL), and a solution of 0.15 mol % triphenylphosphine in n-propanol (70 µL, 0.0078 mmol) were sequentially added. The test tube was purged with nitrogen, capped, and then heated at 80° C. overnight in a sand bath. Each sample was purified using Waters Oasis Sample Extractions Cartridge MCX according to the method described in Examples 4-58, and the resulting basic solution was concentrated by vacuum centrifugation. The residue from each tube was dissolved in dichloromethane (1 mL) with the aid of sonication. Each tube was placed in an ice bath for five minutes to cool to 0° C., and then boron tribromide (0.640 mL of a 1 M solution in dichloromethane) was added. The solution was vortexed, stirred at 0° C. for 30 minutes, and then stirred overnight at room temperature. Methanol (1 mL) and 6 N hydrochloric acid (0.500 mL) were added to each tube. The contents were vortexed, and the volatiles were removed by vacuum centrifugation. The compounds were purified by reversed phase prep HPLC according to the method described in Examples 77-127. The table below shows the reagent added to each test tube, the structure of the resulting compound, and the observed accurate mass for the isolated trifluoroacetate salt.

Examples 128-151

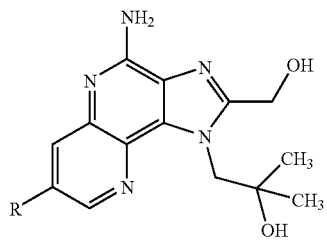

| Example | Reagent | R | Measured Mass (M + H) |
|---|---|---|---|
|  | None | Br— | 366.0562 |
| 128 | 3-Methylphenylboronic acid | 3-methylphenyl | 378.1936 |
| 129 | 4-Methylphenylboronic acid | 4-methylphenyl | 378.1937 |
| 130 | o-Tolylboronic acid | 2-methylphenyl | 378.1938 |
| 131 | 2-Hydroxyphenylboronic acid | 2-hydroxyphenyl | 380.1721 |
| 132 | 3-Hydroxyphenylboronic acid | 3-hydroxyphenyl | 380.1718 |
| 133 | 3,5-Dimethylphenylboronic acid | 3,5-dimethylphenyl | 392.2099 |
| 134 | 4-Ethylphenylboronic acid | 4-ethylphenyl | 392.2090 |
| 135 | (2-Hydroxymethylphenyl)boronic acid dehydrate | 2-(hydroxymethyl)phenyl | 394.1907 |

-continued

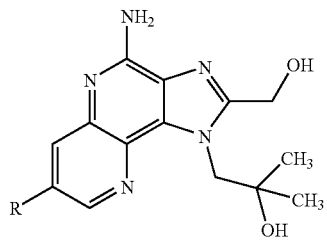

| Example | Reagent | R | Measured Mass (M + H) |
|---|---|---|---|
| 136 | 3-Chlorophenylboronic acid | 3-chlorophenyl | 398.1390 |
| 137 | 4-Chlorophenylboronic acid | 4-chlorophenyl | 398.1394 |
| 138 | 4-Acetylphenylboronic acid | 4-acetylphenyl | 406.1883 |
| 139 | 3,4-Dichlorophenylboronic acid | 3,4-dichlorophenyl | 432.1010 |
| 140 | 3-(N,N-Dimethylaminocarbonyl)phenyl-boronic acid | 3-(N,N-dimethylaminocarbonyl)phenyl | 435.2148 |
| 141 | 3-(N-Isopropylaminocarbonyl)phenyl-boronic acid | 3-(N-isopropylaminocarbonyl)phenyl | 449.2317 |

-continued
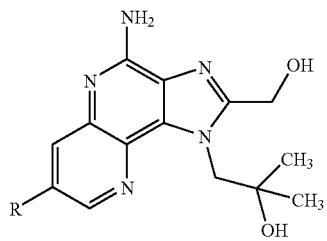
| Example | Reagent | R | Measured Mass (M + H) |
|---|---|---|---|
| 142 | 3-(N-Propylaminocarbonyl)phenylboronic acid | 3-methylphenyl-C(O)NH-CH2CH2CH3 | 449.2323 |
| 143 | 3-(Methylsulfonylamino)phenylboronic acid | 3-methylphenyl-NH-S(O)2-CH3 | 457.1663 |
| 144 | 3-(2-Cyanoethylaminocarbonyl)phenylboronic acid | 3-methylphenyl-C(O)NH-CH2CH2CN | 460.2130 |
| 145 | 4-(Pyrrolidine-1-carbonyl)phenylboronic acid | 4-methylphenyl-C(O)-pyrrolidine | 461.2330 |

-continued

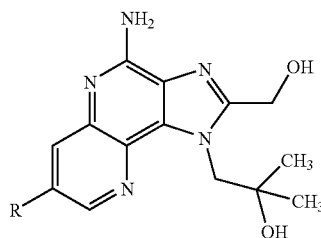

| Example | Reagent | R | Measured Mass (M + H) |
|---|---|---|---|
| 146 | 3-(Butylaminocarbonyl)phenylboronic acid | 3-C(=O)NH-butyl-phenyl | 463.2459 |
| 147 | 3-(Isobutylaminocarbonyl)phenylboronic acid | 3-C(=O)NH-isobutyl-phenyl | 463.2463 |
| 148 | 4-(Isobutylaminocarbonyl)phenylboronic acid | 4-C(=O)NH-isobutyl-phenyl | 463.2461 |
| 149 | 3-(Piperidine-1-carbonyl)phenylboronic acid | 3-(piperidine-1-carbonyl)phenyl | 475.2453 |
| 150 | 4-(Cyclopentylaminocarbonyl)phenylboronic acid | 4-C(=O)NH-cyclopentyl-phenyl | 475.2463 |

-continued

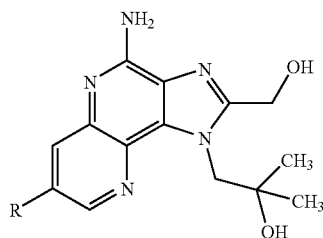

| Example | Reagent | R | Measured Mass (M + H) |
|---|---|---|---|
| 151 | (4-Aminomethylphenyl)boronic acid, pinacol ester, hydrochloride | ![structure] | 393.2034 |

Preparation of 1-(4-Amino-7-bromo-2-ethyl-1H-imidazo[4,5-c][1,5]naphthyridin-1-yl)-2-methylpropan-2-ol

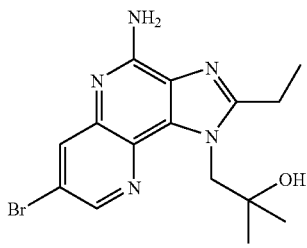

Part A

Pyridine hydrochloride (0.095 g, 0.82 mmol) and triethyl orthopropionate (6.36 g, 36.1 mmol) were sequentially added to a solution of 1-[(3-amino-7-bromo[1,5]naphthyridin-4-yl)amino]-2-methylpropan-2-ol (10.2 g, 32.8 mmol) in toluene (200 mL), and the resulting mixture was heated at reflux for three hours. Most of the solvent was removed under reduced pressure, and a solid was present. The solid was isolated by filtration and dried to provide 8.59 g of 1-(7-bromo-2-ethyl-1H-imidazo[4,5-c][1,5]naphthyridin-1-yl)-2-methylpropan-2-ol as a light yellow solid. A small portion of the solid was recrystallized from acetonitrile to provide an off-white solid, mp 207-208° C.

Anal. calcd for $C_{15}H_{17}BrN_4O$: C, 51.59; H, 4.91; N, 16.04. Found: C, 51.27; H, 4.62; N, 15.78.

Part B mCPBA (11.2 g of 75% purity, 48.7 mmol) was added to a stirred solution of 1-(7-bromo-2-ethyl-1H-imidazo[4,5-c][1,5]naphthyridin-1-yl)-2-methylpropan-2-ol (8.5 g, 24 mmol) in dichloromethane (150 mL), and the reaction was stirred at room temperature overnight. The reaction mixture was diluted with dichloromethane (100 mL), washed sequentially with 4% aqueous sodium carbonate (2×150 mL) and brine (1×150 mL), and concentrated under reduced pressure. The residue was dissolved in dichloromethane (150 mL), and concentrated ammonium hydroxide (80 mL) was added. The mixture was stirred vigorously and cooled to 4° C., and then p-toluenesulfonyl chloride (5.80 g, 30.4 mmol) was added in portions. The reaction mixture was stirred at room temperature for 16 hours and diluted with dichloromethane (200 mL). A solid was present and was isolated by filtration, washed well with water and acetonitrile, and dried to provide 2.94 of 1-(4-amino-7-bromo-2-ethyl-1H-imidazo[4,5-c][1,5]naphthyridin-1-yl)-2-methylpropan-2-ol. The organic layer was separated and washed with 4 N aqueous sodium carbonate (2×150 mL). The combined washings were extracted with dichloromethane (100 mL), and the combined organic fractions were washed with brine, dried over sodium sulfate, filtered, and concentrated under reduced pressure. The residue was triturated with acetonitrile to provide an additional 1.36 g of 1-(4-amino-7-bromo-2-ethyl-1H-imidazo[4,5-c][1,5]naphthyridin-1-yl)-2-methylpropan-2-ol as an off-white solid, mp 235-236° C.

Anal. calcd for $C_{15}H_{18}BrN_5O$: C, 49.46; H, 4.98; N, 19.23. Found: C, 49.19; H, 4.84; N, 19.21.

Example 152

1-[4-Amino-2-ethyl-7-(6-fluoropyridin-3-yl)-1H-imidazo[4,5-c][1,5]naphthyridin-1-yl)-2-methylpropan-2-ol

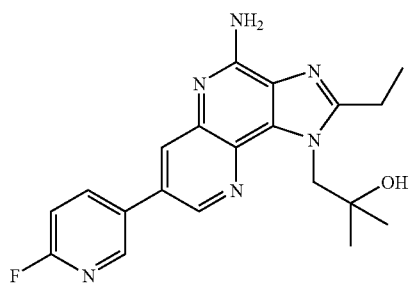

2-Fluoropyridine-5-boronic acid (0.468 g, 3.32 mmol) was added to 1-(4-amino-7-bromo-2-ethyl-1H-imidazo[4,5-c][1,5]naphthyridin-1-yl)-2-methylpropan-2-ol (1.1 g, 3.0 mmol) and 1-propanol (10 mL). The mixture was degassed and back-filled with nitrogen. Triphenylphosphine (23.8 mg, 0.0900 mmol), aqueous sodium carbonate (4.53 mL of 2 M), and water (2 mL) were added followed by palladium (II) acetate (6.8 mg, 0.030 mmol). The yellow suspension was heated at reflux for two hours. Water (20 mL) was added, and the 1-propanol was removed under reduced pressure. The remaining mixture was extracted with chloroform (2×100 mL). The combined extracts were washed with brine, dried over sodium sulfate, filtered, and concentrated under reduced pressure. The crude product was triturated with acetonitrile and isolated by filtration to provide 0.84 g of 1-[4-amino-2-ethyl-7-(6-fluoropyridin-3-yl)-1H-imidazo[4,5-c][1,5]naphthyridin-1-yl)-2-methylpropan-2-ol as a white powder, mp 250-251° C.

Anal. calcd for $C_{20}H_{21}FN_6O$: C, 63.15; H, 5.56; N, 22.09. Found: C, 63.03; H, 5.83; N, 22.13.

Example 153

1-[4-Amino-2-ethyl-7-(quinolin-3-yl)-1H-imidazo[4,5-c][1,5]naphthyridin-1-yl)-2-methylpropan-2-ol

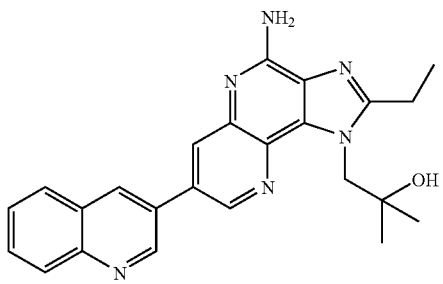

The method described in Example 152 was used to treat 1-(4-amino-7-bromo-2-ethyl-1H-imidazo[4,5-c][1,5]naphthyridin-1-yl)-2-methylpropan-2-ol (1.0 g, 2.7 mmol) and 3-quinolineboronic acid (0.52 g, 3.0 mmol) in 1-propanol (10 mL) with triphenylphosphine (21.6 mg, 0.0820 mmol), aqueous sodium carbonate (4.1 mL of 2 M), water (2 mL), and palladium (II) acetate (6.2 mg, 0.027 mmol) with the following modifications. The reaction mixture was heated at reflux for four hours. The crude product was purified by recrystallization from ethyl acetate to provide 0.58 g of 1-[4-amino-2-ethyl-7-(quinolin-3-yl)-1H-imidazo[4,5-c][1,5]naphthyridin-1-yl)-2-methylpropan-2-ol as beige needles, mp >270° C.

Anal. Calcd for $C_{24}H_{24}N_6O \cdot 0.3HCl$: C, 68.08; H, 5.78; N, 19.85. Found: C, 67.74; H, 5.63; N, 19.79.

Examples 154-194

A solution of 1-(4-amino-7-bromo-2-ethyl-1H-imidazo[4,5-c][1,5]naphthyridin-1-yl)-2-methylpropan-2-ol (36.4 mg, 0.10 mmol) in 7:3 volume:volume (v:v) chloroform:methanol (2 mL) was added to a test tube, and the solvent was removed by vacuum centrifugation. The boronic acid (0.11 mmol) indicated in the table below and n-propanol (1.6 mL) were sequentially added. The test tube was purged with nitrogen. Palladium (II) acetate (0.150 mL of a 4 mg/mL solution in toluene, 0.0027 mmol), 2 M aqueous sodium carbonate solution (600 µL), deionized water (113 µL), and a solution of 0.15 mol % triphenylphosphine in n-propanol (53 µL, 0.0078 mmol) were sequentially added. The test tube was purged with nitrogen, capped, and then heated at 80° C. overnight in a sand bath. Methanol (1 mL) was added to each reaction, which was heated at 80° C. for six hours.

The contents of each test tube were passed through a Waters Oasis Sample Extractions Cartridge MCX (6 cc) according to the procedure described in Examples 4-58. The resulting basic solutions were concentrated by vacuum centrifugation. The compounds were purified by reversed phase prep HPLC according to the method described in Examples 77-127. The table below shows the reagent added to each test tube, the structure of the resulting compound, and the observed accurate mass for the isolated trifluoroacetate salt.

Examples 154-194

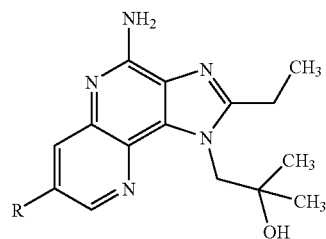

| Example | Reagent | R | Measured Mass (M + H) |
|---|---|---|---|
| | None | Br— | 364.0771 |
| 154 | Phenylboronic acid | phenyl | 362.1984 |
| 155 | Pyridine-3-boronic acid | pyridin-3-yl | 363.1940 |

-continued

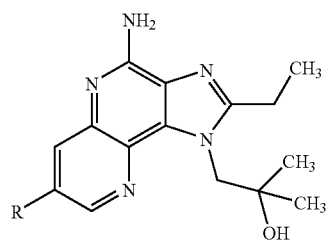

| Example | Reagent | R | Measured Mass (M + H) |
|---|---|---|---|
| 156 | 3-Methylphenylboronic acid | 3-methylphenyl | 376.2139 |
| 157 | 4-Methylphenylboronic acid | 4-methylphenyl | 376.2125 |
| 158 | o-Tolylboronic acid | 2-methylphenyl | 376.2099 |
| 159 | 2-Hydroxyphenylboronic acid | 2-hydroxyphenyl | 378.1943 |
| 160 | 3-Hydroxyphenylboronic acid | 3-hydroxyphenyl | 378.1950 |
| 161 | 3-Cyanophenylboronic acid | 3-cyanophenyl | 387.1916 |
| 162 | 4-Cyanophenylboronic acid | 4-cyanophenyl | 387.1917 |
| 163 | 2-Methoxyphenylboronic acid | 2-methoxyphenyl | 392.2068 |
| 164 | 4-(Hydroxymethyl)phenylboronic acid | 4-(hydroxymethyl)phenyl | 392.2070 |

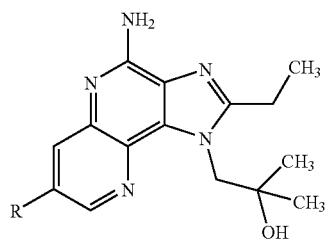

| Example | Reagent | R | Measured Mass (M + H) |
|---|---|---|---|
| 165 | 4-Methoxyphenylboronic acid | 4-methoxyphenyl | 392.2078 |
| 166 | (4-Fluoro-2-hydroxy)phenylboronic acid | 4-fluoro-2-hydroxyphenyl | 396.1834 |
| 167 | 3-Chlorophenylboronic acid | 3-chlorophenyl | 396.1577 |
| 168 | 2-Chlorophenylboronic acid | 2-chlorophenyl | 396.1611 |
| 169 | 2,4-Difluorophenylboronic acid | 2,4-difluorophenyl | 398.1794 |
| 170 | (3-Aminocarbonylphenyl)-boronic acid | 3-aminocarbonylphenyl | 405.2054 |
| 171 | [3-(Hydroxypropyl)phenyl]-boronic acid | 3-(3-hydroxypropyl)phenyl | 420.2407 |
| 172 | 2,4-Dimethoxyphenylboronic acid | 2,4-dimethoxyphenyl | 422.2228 |

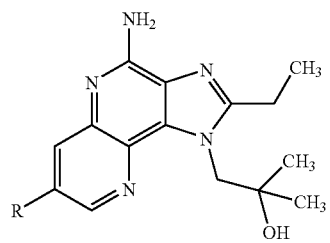

| Example | Reagent | R | Measured Mass (M + H) |
|---|---|---|---|
| 173 | 2,6-Dimethoxyphenylboronic acid | 2,6-dimethoxyphenyl | 422.2192 |
| 174 | 3,4-Dimethoxyphenylboronic acid | 3,4-dimethoxyphenyl | 422.2192 |
| 175 | 3,4-Dichlorophenylboronic acid | 3,4-dichlorophenyl | 430.1209 |
| 176 | 4-(4,4,5,5-Tetramethyl-1,3,2-dioxaborolan-2-yl-1H-pyrazole | 1H-pyrazol-4-yl | 352.1907 |
| 177 | 4-(Methoxycarobonylamino)-phenylboronic acid | 4-(methoxycarbonylamino)phenyl | 435.2133 |
| 178 | 4-(Methanesulfonyl)phenyl-boronic acid | 4-(methanesulfonyl)phenyl | 440.1761 |
| 179 | 4-(Cyclopropylaminocarbonyl)-phenylboronic acid | 4-(cyclopropylaminocarbonyl)phenyl | 445.2351 |
| 180 | 3-(N-Isopropylaminocarbonyl)-phenylboronic acid | 3-(N-isopropylaminocarbonyl)phenyl | 447.2488 |

-continued

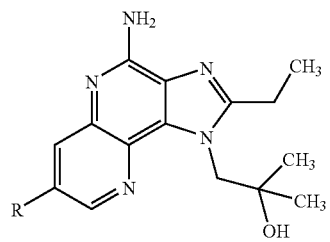

| Example | Reagent | R | Measured Mass (M + H) |
|---|---|---|---|
| 181 | 3-(N-Propylaminocarbonyl)-phenylboronic acid | 3-(N-propylaminocarbonyl)phenyl | 447.2490 |
| 182 | 3,4,5-Trimethoxyphenylboronic acid | 2,4-difluorophenyl | 452.2300 |
| 183 | 4-(Ethylsulfonyl)phenylboronic acid | 4-(ethylsulfonyl)phenyl | 454.1888 |
| 184 | 3-(Methylsulfonylamino)-phenylboronic acid | 3-(methylsulfonylamino)phenyl | 455.1872 |
| 185 | 4-(Methylsulfonylamino)-phenylboronic acid | 4-(methylsulfonylamino)phenyl | 455.1880 |
| 186 | 3-(Pyrrolidine-1-carbonyl)phenylboronic acid | 3-(pyrrolidine-1-carbonyl)phenyl | 459.2503 |
| 187 | 4-(Pyrrolidine-1-carbonyl)phenylboronic acid | 4-(pyrrolidine-1-carbonyl)phenyl | 459.2505 |
| 188 | 3-(Butylaminocarbonyl)-phenylboronic acid | 3-(butylaminocarbonyl)phenyl | 461.2662 |

-continued

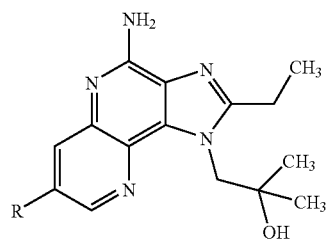

| Example | Reagent | R | Measured Mass (M + H) |
|---|---|---|---|
| 189 | 3-(Isobutylaminocarbonyl)-phenylboronic acid | 3-(isobutylaminocarbonyl)phenyl | 461.2663 |
| 190 | 4-(Isobutylaminocarbonyl)-phenylboronic acid | 4-(isobutylaminocarbonyl)phenyl | 461.2668 |
| 191 | 3-(Piperidine-1-carbonyl)phenylboronic acid | 3-(piperidine-1-carbonyl)phenyl | 473.2675 |
| 192 | 4-(Cyclopentylaminocarbonyl)-phenylboronic acid | 4-(cyclopentylaminocarbonyl)phenyl | 473.2658 |
| 193 | 3-(Morpholine-4-carbonyl)phenylboronic acid | 3-(morpholine-4-carbonyl)phenyl | 475.2444 |

-continued

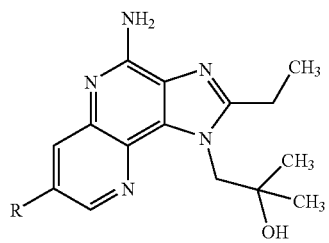

| Example | Reagent | R | Measured Mass (M + H) |
|---|---|---|---|
| 194 | 3-(N-Benzylaminocarbonyl)-phenylboronic acid | 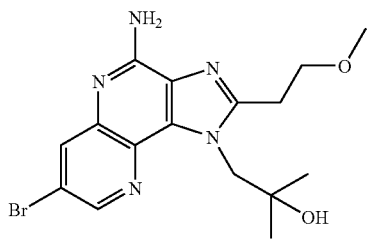 | 495.2519 |

Preparation of 1-[4-Amino-7-bromo-2-(2-methoxyethyl)-1H-imidazo[4,5-c][1,5]naphthyridin-1-yl]-2-methylpropan-2-ol Part A Triethylamine (35.95 mL, 257.9 mmol) was added to a suspension of 7-bromo-4-chloro-3-nitro[1,5]naphthyridine (49.6 g, 172 mmol) in dichloromethane (500 mL). 1-Amino-2-methylpropan-2-ol (16.86 g, 189 mmol) was added dropwise. The reaction mixture was stirred at ambient temperature for 16 hours and then concentrated under reduced pressure. The residue was triturated with water and stirred for 1 hour. The precipitated solid was isolated by filtration, washed with water, and dried. This material was suspended in diethyl ether (400 mL), sonicated, isolated by filtration, and then dried in a vacuum oven at 40° C. for 16 hours to provide 58.1 g of 1-[(7-bromo-3-nitro[1,5]naphthyridin-4-yl)amino]-2-methylpropan-2-ol as a yellow solid, mp 189-190° C.

Part B

A Parr vessel was charged with 5% platinum on carbon (5.8 g) and a suspension of 1-[(7-bromo-3-nitro[1,5]naphthyridin-4-yl)amino]-2-methylpropan-2-ol (58.00 g) in acetonitrile (800 mL) and methanol (400 mL). The vessel was placed under hydrogen pressure (30 psi, $2.1 \times 10^5$ Pa) for 8 hours. The reaction mixture was filtered through a layer of CELITE filter aid. The filtrate was concentrated under reduced pressure to provide 52.70 g of 1-[(3-amino-7-bromo[1,5]naphthyridin-4-yl)amino]-2-methylpropan-2-ol as a yellow solid.

Part C

3-Methoxypropionyl chloride (24.90 g, 203 mmol) was added over a period of five minutes to a mixture of 1-[(3-amino-7-bromo[1,5]naphthyridin-4-yl)amino]-2-methylpropan-2-ol (52.70 g, 169 mmol), chloroform (100 mL), and acetonitrile (530 mL). The reaction mixture was stirred at room temperature overnight. The precipitated solid was isolated by filtration, washed well with acetonitrile, and then dried to provide 60.10 g of N-{7-bromo-4-[(2-hydroxy-2-methylpropyl)amino][1,5]naphthyridin-3-yl}-3-methoxypropionamide hydrochloride as a brown solid, mp 206-208° C.

Part D

A mixture of N-{7-bromo-4-[(2-hydroxy-2-methylpropyl)amino][1,5]naphthyridin-3-yl}-3-methoxypropionamide hydrochloride (60.00 g, 138 mmol), potassium carbonate (60 g), water (300 mL), and ethanol (900 mL) was heated at reflux for 16 hours and then concentrated under reduced pressure. The precipitated solid was isolated by filtration, washed sequentially with water and methanol, and dried to provide a brown solid. This material was dissolved in a 3/1 mixture of chloroform/methanol and decolorized with activated charcoal to provide 38.5 g of 1-[7-bromo-2-(2-methoxyethyl)-1H-imidazo[4,5-c][1,5]naphthyridin-1-yl]-2-methylpropan-2-ol as a white solid, mp 125° C. Anal. calcd for $C_{16}H_{19}BrN_4O_2$: % C, 50.67; % H, 5.05; % N, 14.77; Found: % C, 50.86; % H 4.94; % N, 15.01.

Part E mCPBA (34.77 g of 75% pure material, 151 mmol) was added to a solution of 1-[7-bromo-2-(2-methoxyethyl)-1H-imidazo[4,5-c][1,5]naphthyridin-1-yl]-2-methylpropan-2-ol (38.2 g, 101 mmol) in dichloromethane (450 mL) and the reaction mixture was stirred for 3 hours. The reaction mixture was diluted with dichloromethane (200 mL), washed sequentially with 4% aqueous sodium carbonate (2×150 mL) and brine (1×150 mL), and concentrated under reduced pressure to provide the N-oxide derivative. The N-oxide derivative was combined with dichloromethane (450 mL) and concentrated ammonium hydroxide (200 mL) and the mixture was cooled in an ice bath. p-Toluenesulfonyl chloride (24 g) was added in portions. After the addition was complete the ice bath was removed and the reaction mixture was stirred at ambient temperature for 16 hours. The reaction mixture was diluted with dichloromethane (200 mL). Suspended solids were isolated by filtration, washed with water, and dried to provide 7.60 g of 1-[4-amino-7-bromo-2-(2-methoxyethyl)-1H-imidazo[4,5-c][1,5]naphthyridin-1-yl]-2-methylpropan-2-ol as an off white solid, mp 210-211° C.

Anal. Calcd for $C_{16}H_{20}BrN_5O_2$: C, 48.74; H, 5.11; N, 17.76. Found: C, 48.63; H, 5.10; N, 17.80.

Examples 195-239

The methods described in Examples 154-194 were followed using 1-[4-amino-7-bromo-2-(2-methoxyethyl)-1H-imidazo[4,5-c][1,5]naphthyridin-1-yl]-2-methylpropan-2-ol (39.6 mg, 0.100 mmol) instead of 1-(4-amino-7-bromo-2-ethyl-1H-imidazo[4,5-c][1,5]naphthyridin-1-yl)-2-methyl-propan-2-ol with the modification that the samples were not diluted in methanol after the initial heating at 80° C. overnight. The table below shows the reagent added to each test tube, the structure of the resulting compound, and the observed accurate mass for the isolated trifluoroacetate salt.

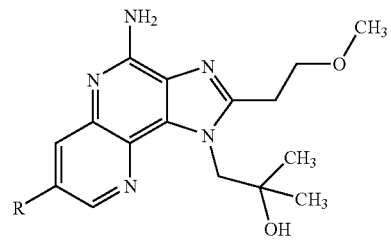

| Example | Reagent | R | Measured Mass (M + H) |
|---|---|---|---|
|  | None | Br— | 394.0905 |
| 195 | Furan-3-boronic acid | 3-furyl | 382.1880 |
| 196 | Phenylboronic acid | phenyl | 392.2085 |
| 197 | Pyridine-3-boronic acid | 3-pyridyl | 393.2048 |
| 198 | 3-Methylphenylboronic acid | 3-methylphenyl | 406.2235 |
| 199 | 4-Methylphenylboronic acid | 4-methylphenyl | 406.2226 |
| 200 | o-Tolylboronic acid | 2-methylphenyl | 406.2256 |
| 201 | 3-Hydroxyphenylboronic acid | 3-hydroxyphenyl | 408.2012 |

-continued

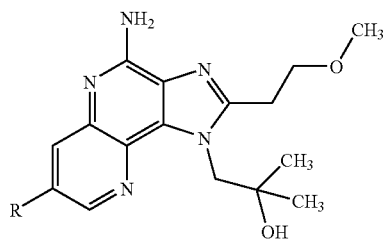

| Example | Reagent | R | Measured Mass (M + H) |
|---|---|---|---|
| 202 | 3-Cyanophenylboronic acid | 3-cyanophenyl | 417.2042 |
| 203 | 4-Cyanophenylboronic acid | 4-cyanophenyl | 417.2022 |
| 204 | 4-Vinylphenylboronic acid | 4-vinylphenyl | 418.2255 |
| 205 | E-Phenylethenylboronic acid | E-phenylethenyl | 418.2242 |
| 206 | 3,5-Dimethylphenylboronic acid | 3,5-dimethylphenyl | 420.2391 |
| 207 | 4-Ethylphenylboronic acid | 4-ethylphenyl | 420.2406 |
| 208 | 2-Methoxyphenylboronic acid | 2-methoxyphenyl | 422.2182 |
| 209 | 4-Methoxyphenylboronic acid | 4-methoxyphenyl | 422.2198 |

-continued

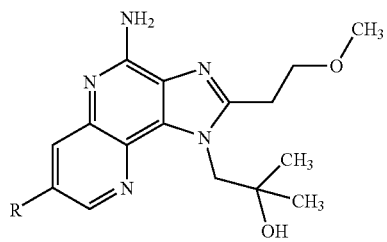

| Example | Reagent | R | Measured Mass (M + H) |
|---|---|---|---|
| 210 | 3-Aminophenylboronic acid monohydrate | 3-aminophenyl | 407.2192 |
| 211 | 3-Chlorophenylboronic acid | 3-chlorophenyl | 426.1703 |
| 212 | 4-Chlorophenylboronic acid | 4-chlorophenyl | 426.1657 |
| 213 | 2,4-Difluorophenylboronic acid | 2,4-difluorophenyl | 428.1884 |
| 214 | Benzo[b]furan-2-boronic acid | benzo[b]furan-2-yl | 432.2018 |
| 215 | 3-Acetylphenylboronic acid | 3-acetylphenyl | 434.2191 |
| 216 | 4-Acetylphenylboronic acid | 4-acetylphenyl | 434.2188 |
| 217 | (3-Aminocarbonylphenyl)-boronic acid | 3-aminocarbonylphenyl | 435.2119 |

-continued

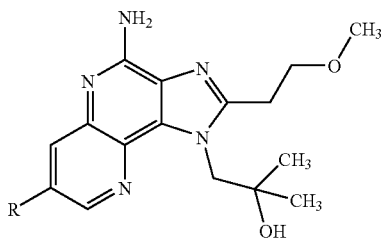

| Example | Reagent | R | Measured Mass (M + H) |
|---|---|---|---|
| 218 | 3,4-Methylenedioxyphenylboronic acid | benzo[1,3]dioxol-5-yl | 436.1964 |
| 219 | 2-Ethoxyphenylboronic acid | 2-ethoxyphenyl | 436.2356 |
| 220 | 3-Ethoxyphenylboronic acid | 3-ethoxyphenyl | 436.2342 |
| 221 | 4-(Methylthio)phenylboronic acid | 4-(methylthio)phenyl | 438.1961 |
| 222 | 2-Ethoxy-5-methylphenylboronic acid | 2-ethoxy-5-methylphenyl | 450.2529 |
| 223 | 2-Isopropoxyphenylboronic acid | 2-isopropoxyphenyl | 450.2491 |
| 224 | 4-Isopropoxyphenylboronic acid | 4-isopropoxyphenyl | 450.2483 |

-continued

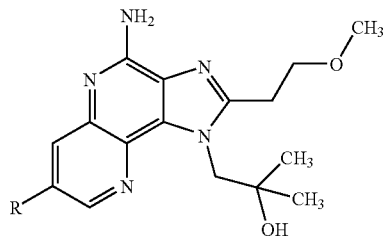

| Example | Reagent | R | Measured Mass (M + H) |
|---|---|---|---|
| 225 | 3,4-Dimethoxyphenylboronic acid | 3,4-dimethoxyphenyl | 452.2301 |
| 226 | 3-(4-Boronophenyl)propionic acid | 4-(2-carboxyethyl)phenyl | 464.2289 |
| 227 | 4-(Methoxycarobonylamino)phenyl boronic acid | 4-(methoxycarbonylamino)phenyl | 465.2238 |
| 228 | 3-(N-Isopropylaminocarbonyl)-phenylboronic acid | 3-(N-isopropylaminocarbonyl)phenyl | 477.2588 |
| 229 | 3-(N-Propylaminocarbonyl)-phenylboronic acid | 3-(N-propylaminocarbonyl)phenyl | 477.2597 |

-continued

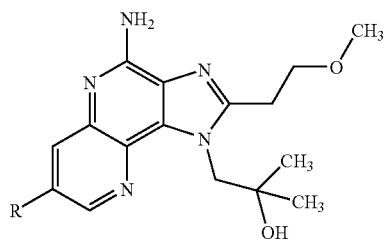

| Example | Reagent | R | Measured Mass (M + H) |
|---|---|---|---|
| 230 | 4-Borono-DL-phenylalanine | 4-(CH₂CH(NH₂)COOH)-phenyl | 479.2408 |
| 231 | 3,4,5-Trimethoxyphenylboronic acid | 3,4,5-trimethoxyphenyl | 482.2391 |
| 232 | 3-(Butylaminocarbonyl)phenylboronic acid | 3-(butylaminocarbonyl)phenyl | 491.2756 |
| 233 | 3-(Isobutylaminocarbonyl)phenylboronic acid | 3-(isobutylaminocarbonyl)phenyl | 491.2758 |
| 234 | 4-(Isobutylaminocarbonyl)phenylboronic acid | 4-(isobutylaminocarbonyl)phenyl | 491.2774 |

-continued

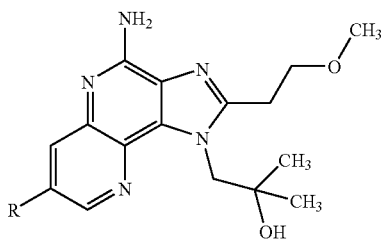

| Example | Reagent | R | Measured Mass (M + H) |
|---|---|---|---|
| 235 | 4-(Cyclopentylaminocarbonyl)-phenylboronic acid | *4-methylphenyl with para C(O)NH-cyclopentyl* | 503.2751 |
| 236 | 4-Benzyloxy-3-fluorophenylboronic acid | *4-methyl-2-fluoro-phenyl with OBn* | 516.2403 |
| 237 | 3-(N-Benzylaminocarbonyl)-phenylboronic acid | *3-methylphenyl with meta C(O)NHBn* | 525.2590 |
| 238 | (4-Aminomethylphenyl)boronic acid Pinacol Ester, hydrochloride | *4-methylphenyl with CH2NH2* | 421.2362 |
| 239 | 1-(Phenylsulfonyl)1H-indol-3-ylboronic acid | *3-methyl-1-(phenylsulfonyl)-1H-indol-yl* | 571.2127 |

Examples 240-272

The methods described in Examples 154-194 were followed using 1-[4-amino-7-bromo-2-(2-methoxyethyl)-1H-imidazo[4,5-c][1,5]naphthyridin-1-yl]-2-methylpropan-2-ol (39.5 mg, 0.100 mmol) instead of 1-(4-amino-7-bromo-2-ethyl-1H-imidazo[4,5-c][1,5]naphthyridin-1-yl)-2-methyl-propan-2-ol. After the samples were heated overnight, Example 241 was driven to completion by adding additional palladium (II) acetate (0.150 mL), heating for 30 minutes at 80° C., adding pyridine-3-boronic acid (0.11 mmol) and methanol (1 mL), and heating at 80° C. for 16 hours. After each sample was purified using Waters Oasis Sample Extractions Cartridge MCX according to the method described in Examples 4-58, and the resulting basic solution was concentrated by vacuum centrifugation, the reaction with boron tribromide described in Examples 128-151 was carried out using 0.400 mL of boron tribromide solution for each test tube. The compounds were purified by reversed phase prep HPLC according to the method described in Examples 77-127. The table below shows the reagent added to each test tube, the structure of the resulting compound, and the observed accurate mass for the isolated trifluoroacetate salt.

Examples 240-272

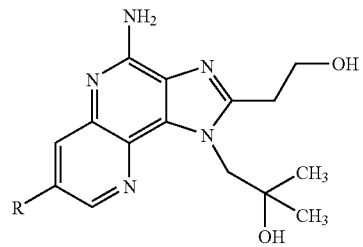

| Example | Reagent | R | Measured Mass (M + H) |
|---|---|---|---|
| 240 | Phenylboronic acid | phenyl | 378.1948 |
| 241 | Pyridine-3-boronic acid | pyridin-3-yl | 379.1908 |
| 242 | Pyridine-4-boronic acid | pyridin-4-yl | 379.1918 |
| 243 | Thiophene-3-boronic acid | thiophen-3-yl | 384.1483 |
| 244 | 4-Methylphenylboronic acid | 4-methylphenyl | 392.2052 |
| 245 | 3-Hydroxyphenylboronic acid | 3-hydroxyphenyl | 394.1910 |
| 246 | 3,5-Dimethylphenylboronic acid | 3,5-dimethylphenyl | 406.2278 |
| 247 | 4-Ethylphenylboronic acid | 4-ethylphenyl | 406.2274 |

-continued

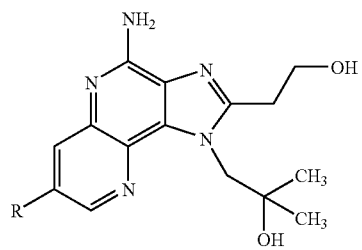

| Example | Reagent | R | Measured Mass (M + H) |
|---|---|---|---|
| 248 | 3-Chlorophenylboronic acid | 3-chlorophenyl | 412.1532 |
| 249 | 4-Chlorophenylboronic acid | 4-chlorophenyl | 412.1524 |
| 250 | Benzo[b]furan-2-boronic acid | benzofuran-2-yl | 418.1891 |
| 251 | (3-Aminocarbonylphenyl)-boronic acid | 3-(aminocarbonyl)phenyl | 421.1974 |
| 252 | 4-(N,N-Dimethylamino)phenyl-boronic acid | 4-(N,N-dimethylamino)phenyl | 421.2391 |
| 253 | 2-Ethoxy-5-methylphenylboronic acid | 2-ethoxy-5-methylphenyl | 408.2050 |
| 254 | 3,4-Dichlorophenylboronic acid | 3,4-dichlorophenyl | 446.1184 |
| 255 | 3-(4-Boronophenyl)propionic acid | 4-(2-carboxyethyl)phenyl | 450.2180 |

-continued
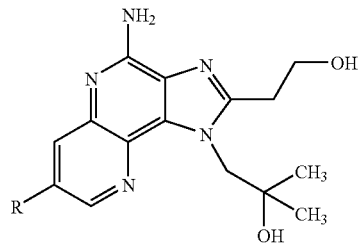
| Example | Reagent | R | Measured Mass (M + H) |
|---|---|---|---|
| 256 | 3-(N-Isopropylaminocarbonyl)phenylboronic acid | 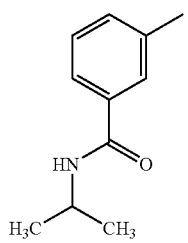 | 463.2501 |
| 257 | 3-(N-Propylaminocarbonyl)phenylboronic acid | 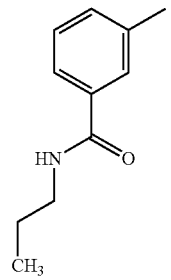 | 463.2482 |
| 258 | 4-Borono-DL-phenylalanine | 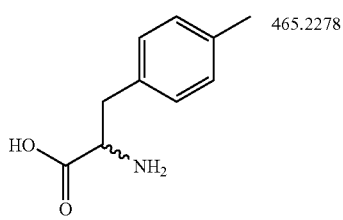 | 465.2278 |
| 259 | 4-(Ethylsulfonyl)phenylboronic acid | 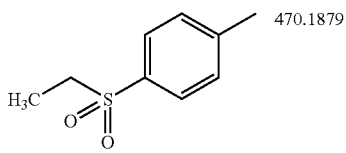 | 470.1879 |
| 260 | 3-(Methylsulfonylamino)-phenylboronic acid | 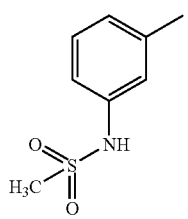 | 471.1835 |

-continued

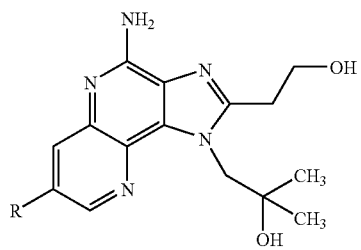

| Example | Reagent | R | Measured Mass (M + H) |
|---|---|---|---|
| 261 | 4-(Methylsulfonylamino)-phenylboronic acid | 4-(CH₃SO₂NH)-C₆H₄– | 471.1864 |
| 262 | 3-(2-Cyanoethylaminocarbonyl)phenylboronic acid | 3-(NCCH₂CH₂NHC(O))-C₆H₄– | 474.2297 |
| 263 | 3-(Pyrrolidine-1-carbonyl)phenylboronic acid | 3-(pyrrolidin-1-ylC(O))-C₆H₄– | 475.2468 |
| 264 | 4-(Pyrrolidine-1-carbonyl)phenylboronic acid | 4-(pyrrolidin-1-ylC(O))-C₆H₄– | 475.2480 |
| 265 | 3-(Butylaminocarbonyl)-phenylboronic acid | 3-(CH₃CH₂CH₂CH₂NHC(O))-C₆H₄– | 477.2648 |

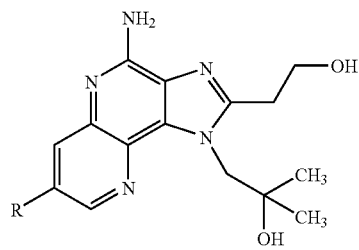

| Example | Reagent | R | Measured Mass (M + H) |
|---|---|---|---|
| 266 | 4-(Isobutylaminocarbonyl)-phenylboronic acid | 4-[(isobutylamino)carbonyl]phenyl | 477.2640 |
| 267 | 3-(Piperidine-1-carbonyl)phenylboronic acid | 3-(piperidine-1-carbonyl)phenyl | 489.2656 |
| 268 | 4-(Cyclopentylaminocarbonyl)-phenylboronic acid | 4-[(cyclopentylamino)carbonyl]phenyl | 489.2626 |
| 269 | 4-(Morpholine-4-carbonyl)phenylboronic acid | 4-(morpholine-4-carbonyl)phenyl | 491.2423 |
| 270 | 3-(N-Benzylaminocarbonyl)-phenylboronic acid | 3-[(benzylamino)carbonyl]phenyl | 511.2478 |

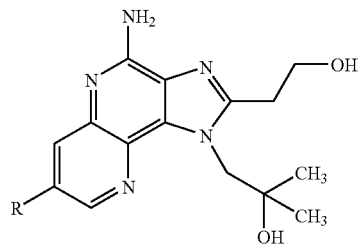

| Example | Reagent | R | Measured Mass (M + H) |
|---|---|---|---|
| 271 | (4-Aminomethylphenyl)boronic acid pinacol ester, hydrochloride | 4-(aminomethyl)phenyl | 407.2218 |
| 272 | 1-(Phenylsulfonyl)-1H-indol-3-ylboronic acid | 1-(phenylsulfonyl)-1H-indol-3-yl | 557.2020 |

Preparation of 1-{[4-Amino-7-bromo-2-(ethoxymethyl)-1H-imidazo[4,5-c][1,5]naphthyridin-1-yl]methyl}cyclopentanol

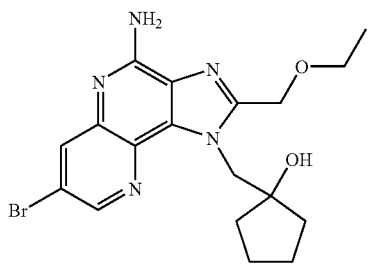

Part A

To a solution of cyclopentanone (40.0 mL, 452 mmol) in nitromethane (36 mL) and ethanol (14 mL) was added a solution of sodium ethoxide in ethanol (2.67 M, 8.5 mL, 23 mmol). The solution was stirred for five days at room temperature. Water (400 mL) was added, and the mixture was extracted with ethyl acetate (2×350 mL). The combined organic extracts were washed with water (2×200 mL) and brine (200 mL), dried over magnesium sulfate, filtered, and concentrated under reduced pressure. The starting materials and solvent were removed from the product by distillation under reduced pressure to yield 8.3 g of 1-(nitromethyl)cyclopentanol as a yellow liquid.

Part B

A mixture of 1-(nitromethyl)cyclopentanol (8.3 g, 57 mmol) and 20% palladium hydroxide on carbon (0.6 g) in ethanol (150 mL) was hydrogenated at 35 psi ($2.4 \times 10^5$ Pa) on a Parr apparatus for one day. After workup, the reaction was not complete and was subjected to the reaction conditions again for eight days using fresh catalyst. The mixture was filtered through CELITE filter agent and the filtrate was concentrated to yield an oil that contained a 13:1 ratio of the desired amine product, 1-(aminomethyl)cyclopentanol, to the corresponding hydroxylamine. The oil was concentrated from toluene. Material from a separate run was used in the next step.

Part C

A suspension of 7-bromo-4-chloro-3-nitro[1,5]naphthyridine (54.42 g, 188.6 mmol) in chloroform (820 mL) was cooled to 0° C., and triethylamine (105 mL, 755 mmol) was added. A solution of 1-(aminomethyl)cyclopentanol (28.25 g, 245.2 mmol) in chloroform (272 mL) was added slowly over a period of 15 minutes. The reaction was allowed to warm to room temperature and stirred for 30 minutes. The solution was washed sequentially with water (500 mL) and saturated aqueous sodium bicarbonate (750 mL), dried over sodium sulfate, filtered, and concentrated under reduced pressure to provide 1-{[(7-bromo-3-nitro[1,5]naphthyridin-4-yl)amino]methyl}cyclopentanol.

Part D

The material from Part C was dissolved in acetonitrile (1.66 L) and isopropyl alcohol (496 mL) and added to a Parr vessel. Catalytic 5% platinum on carbon (6.6 g) was added, and the reaction mixture was placed under hydrogen pressure for three days and filtered through a layer of CELITE filter agent. The filtrate was concentrated under reduced pressure to provide 1-{[(3-amino-7-bromo[1,5]naphthyridin-4-yl)amino]methyl}cyclopentanol.

Part E

Ethoxyacetyl chloride (25.4 g, 207 mmol) was added to a mixture of the material from Part D and acetonitrile (1.27 L). The reaction was stirred at room temperature, and over the course of two hours, additional ethoxyacetyl chloride (20.8 g, 0.170 mol) was added. The solvent was removed under reduced pressure to provide N-(7-bromo-4-{[(1-hydroxycyclopentyl)methyl]amino}[1,5]naphthyridin-3-yl)-2-ethoxyacetamide hydrochloride.

Part F

Triethylamine (38 mL, 270 mmol) was added to a suspension of the material from Part E in ethanol (380 mL), and the resulting solution was heated at reflux (85° C.) for seven hours, allowed to cool to room temperature, and stirred overnight. The volatiles were removed under reduced pressure, and the residue was partitioned between chloroform (800 mL) and water (200 mL). The organic layer was separated, washed with brine (2×300 mL), dried over sodium sulfate, and concentrated under reduced pressure to provide 1-{[7-bromo-2-(ethoxymethyl)-1H-imidazo[4,5-c][1,5]naphthyridin-1-yl]methyl}cyclopentanol as a brown solid.

Part G mCBPA (21 g of about 50% pure material, 61 mmol) was added to a solution of 1-{[7-bromo-2-(ethoxymethyl)-1H-imidazo[4,5-c][1,5]naphthyridin-1-yl]methyl}cyclopentanol (18.89 g, 46.6 mmol) in chloroform (190 mL), and the reaction was stirred for one hour at room temperature. Additional mCPBA (11 g) was added, and the reaction was stirred for an additional 30 minutes. Concentrated ammonium hydroxide (40 mL) was added slowly followed by p-toluenesulfonyl chloride (9.32 g, 48.9 mmol). The reaction was stirred for one hour at room temperature, and additional chloroform (600 mL) was added. The reaction was stirred for one additional hour, and additional p-toluenesulfonyl chloride (4.45 g, 23.3 mmol) and ammonium hydroxide (10 mL) were added. After the reaction mixture was stirred for an additional 1.5 hours, it was filtered to remove a precipitate. The filtrate layers were separated, and the organic phase was washed with saturated aqueous sodium bicarbonate (2×200 mL), dried over sodium sulfate, and concentrated under reduced pressure. The residue (25.86 g) was triturated with acetonitrile at 98° C., and a solid impurity was removed by filtration. The acetonitrile was removed under reduced pressure, and the residue was dissolved in chloroform. The resulting solution was washed with 1% aqueous sodium carbonate, dried over sodium sulfate, filtered, and concentrated under reduced pressure. The residue was purified by column chromatography on silica gel (eluting with 98.5:1.5 chloroform:methanol) and then triturated with acetonitrile at 98° C., isolated by filtration at room temperature, and dried in a vacuum oven at 110° C. over two nights to provide 4.83 g of 1-{[4-amino-7-bromo-2-(ethoxymethyl)-1H-imidazo[4,5-c][1,5]naphthyridin-1-yl]methyl}cyclopentanol as a white solid, mp 166-167.5° C.

Anal. calcd for $C_{18}H_{22}BrN_5O_2$: C, 51.44; H, 5.28; N, 16.66. Found: C, 51.32; H, 5.24; N, 16.63.

Example 273

1-{[4-Amino-2-(ethoxymethyl)-7-(4-fluorophenyl)-1H-imidazo[4,5-c][1,5]naphthyridin-1-yl]methyl}cyclopentanol

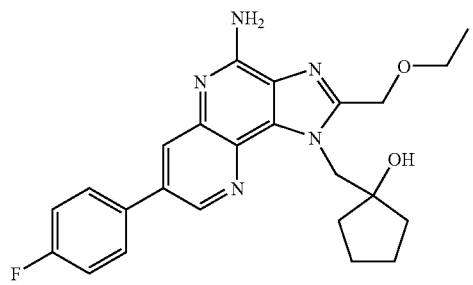

1-{[4-Amino-7-bromo-2-(ethoxymethyl)-1H-imidazo[4,5-c][1,5]naphthyridin-1-yl]methyl}cyclopentanol (1.13 g, 2.7 mmol), 4-fluorobenzeneboronic acid (0.43 g, 3.1 mmol), triphenylphosphine (6.3 mg, 0.024 mmol), and 5:1 (v/v) 1-propanol/water (6.6 mL) were combined under a nitrogen atmosphere. A 5 mg/mL solution of palladium (II) acetate (1.8 mg, 0.008 mmol) in toluene and aqueous sodium carbonate (1.8 mL of 2 M) were sequentially added. The reaction mixture was heated at reflux for two hours, allowed to cool to room temperature, and partitioned between chloroform (75 mL) and brine (20 mL). The organic fraction was separated, dried over sodium sulfate, filtered, and concentrated under reduced pressure. The residue (1.27 g) was purified by trituration with acetonitrile at 98° C. followed by recrystallization from chloroform/hexane. The crystals were dried in a vacuum oven at 110 C for two hours to provide 0.67 g of 1-{[4-amino-2-(ethoxymethyl)-7-(4-fluorophenyl)-1H-imidazo[4,5-c][1,5]naphthyridin-1-yl]methyl}cyclopentanol as a steel-gray solid, mp 212-212.5° C.

MS (APCI) m/z 436 (M+H)$^+$;

Anal. calcd for $C_{24}H_{26}FN_5O_2$: C, 66.19; H, 6.02; N, 16.08. Found: C, 66.16; H, 5.82; N, 16.09.

Examples 274-318

The methods described in Examples 154-194 were followed using 1-{[4-amino-2-(ethoxymethyl)-7-(4-fluorophenyl)-1H-imidazo[4,5-c][1,5]naphthyridin-1-yl]methyl}cyclopentanol (42 mg, 0.10 mmol) instead of 1-(4-amino-7-bromo-2-ethyl-1H-imidazo[4,5-c][1,5]naphthyridin-1-yl)-2-methylpropan-2-ol with the modification that the samples were not diluted in methanol after the initial heating at 80° C. overnight. After Example 318 was heated, it was treated with glacial acetic acid (0.500 mL) in deionized water (0.500 mL) and tetrahydrofuran (THF)(0.500 mL) and heated at 60° C. for four hours before the purification procedures. The table below shows the reagent added to each test tube, the structure of the resulting compound, and the observed accurate mass for the isolated trifluoroacetate salt.

Examples 274-318

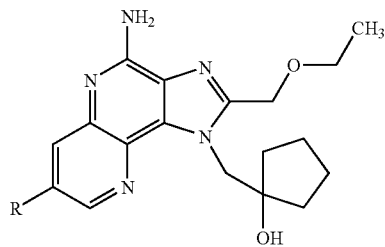

| Example | Reagent | R | Measured Mass (M + H) |
|---|---|---|---|
| | None | Br— | 420.1010 |
| 274 | Furan-3-boronic acid | 3-furyl | 408.2018 |
| 275 | Phenylboronic acid | phenyl | 418.2246 |
| 276 | Pyridine-3-boronic acid | 3-pyridyl | 419.2180 |
| 277 | 3-Methylphenylboronic acid | 3-methylphenyl | 432.2399 |
| 278 | 4-Methylphenylboronic acid | 4-methylphenyl | 432.2399 |
| 279 | o-Tolylboronic acid | 2-methylphenyl | 432.2370 |
| 280 | 2-Hydroxyphenylboronic acid | 2-hydroxyphenyl | 434.2184 |
| 281 | 3-Hydroxyphenylboronic acid | 3-hydroxyphenyl | 434.2200 |
| 282 | 4-Vinylphenylboronic acid | 4-vinylphenyl | 444.2399 |

-continued

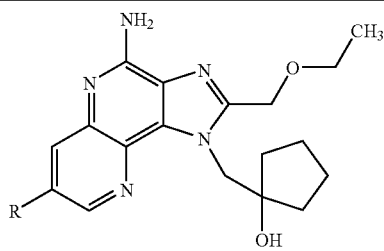

| Example | Reagent | R | Measured Mass (M + H) |
|---|---|---|---|
| 283 | 3,5-Dimethylphenylboronic acid | 3,5-dimethylphenyl | 446.2534 |
| 284 | 4-Ethylphenylboronic acid | 4-ethylphenyl | 446.2546 |
| 285 | 2-Methoxyphenylboronic acid | 2-methoxyphenyl | 448.2359 |
| 286 | 4-Methoxyphenylboronic acid | 4-methoxyphenyl | 448.2319 |
| 287 | (4-Fluoro-2-hydroxy)phenylboronic acid | 4-fluoro-2-hydroxyphenyl | 452.2119 |
| 288 | 3-Chlorophenylboronic acid | 3-chlorophenyl | 452.1844 |
| 289 | 2-Chlorophenylboronic acid | 2-chlorophenyl | 452.1846 |
| 290 | 4-Chlorophenylboronic acid | 4-chlorophenyl | 452.1821 |
| 291 | 2,4-Difluorophenylboronic acid | 2,4-difluorophenyl | 454.2068 |

-continued

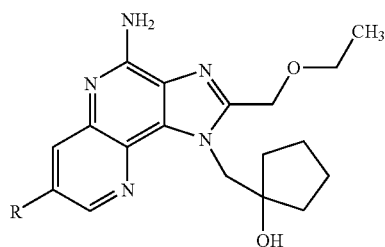

| Example | Reagent | R | Measured Mass (M + H) |
|---|---|---|---|
| 292 | Benzo[b]furan-2-boronic acid | benzofuran-2-yl | 458.2165 |
| 293 | 3-Acetylphenylboronic acid | 3-acetylphenyl | 460.2357 |
| 294 | (3-Aminocarbonylphenyl)-boronic acid | 3-aminocarbonylphenyl | 461.2298 |
| 295 | 3,4-Methylenedioxyphenyl-boronic acid | 3,4-methylenedioxyphenyl | 462.2112 |
| 296 | 4-(Methylthio)phenylboronic acid | 4-(methylthio)phenyl | 464.2138 |
| 297 | 3-Aminophenylboronic acid monohydrate | 3-aminophenyl | 433.2337 |
| 298 | 2-Isopropoxyphenylboronic acid | 2-isopropoxyphenyl | 476.2664 |

-continued

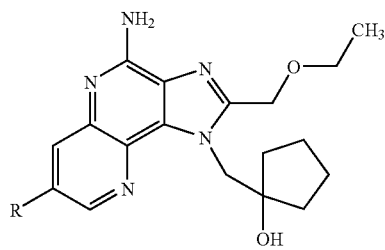

| Example | Reagent | R | Measured Mass (M + H) |
|---|---|---|---|
| 299 | 4-Isopropoxyphenylboronic acid | 4-isopropoxyphenyl | 476.2672 |
| 300 | 2,4-Dimethoxyphenylboronic acid | 2,4-dimethoxyphenyl | 478.2456 |
| 301 | 3,4-Dimethoxyphenylboronic acid | 3,4-dimethoxyphenyl | 478.2443 |
| 302 | (3-Aminomethylphenyl)-boronic acid, hydrochloride | 3-aminomethylphenyl | 447.2491 |
| 303 | 3,4-Dichlorophenylboronic acid | 3,4-dichlorophenyl | 486.1453 |
| 304 | 4-(Methoxycarbonylamino)-phenylboronic acid | 4-(methoxycarbonylamino)phenyl | 491.2386 |

-continued

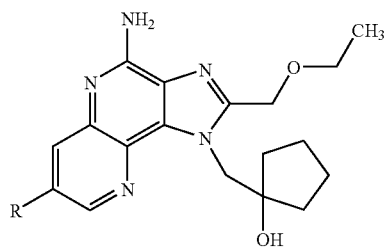

| Example | Reagent | R | Measured Mass (M + H) |
|---|---|---|---|
| 305 | 3-(N-Isopropylaminocarbonyl)-phenylboronic acid | 3-(isopropylaminocarbonyl)phenyl | 503.2766 |
| 306 | 3-(N-Propylaminocarbonyl)phenyl boronic acid | 3-(propylaminocarbonyl)phenyl | 503.2786 |
| 307 | 4-Borono-DL-phenylalanine | 4-(2-amino-2-carboxyethyl)phenyl | 505.2545 |
| 308 | 3,4,5-Trimethoxyphenylboronic acid | 3,4,5-trimethoxyphenyl | 508.2562 |
| 309 | 4-(Ethylsulfonyl)phenylboronic acid | 4-(ethylsulfonyl)phenyl | 510.2166 |

-continued
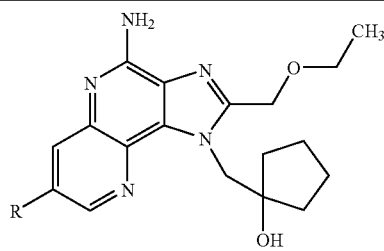
| Example | Reagent | R | Measured Mass (M + H) |
|---|---|---|---|
| 310 | (Methylsulfonylamino)phenyl boronic acid | 3-(CH₃SO₂NH)-C₆H₄- | 511.2104 |
| 311 | 3-(Butylaminocarbonyl)-phenylboronic acid | 3-(n-BuNHC(O))-C₆H₄- | 517.2953 |
| 312 | 3-(Isobutylaminocarbonyl)-phenylboronic acid | 3-(iBuNHC(O))-C₆H₄- | 517.2916 |
| 313 | 4-(Isobutylaminocarbonyl)-phenylboronic acid | 4-(iBuNHC(O))-C₆H₄- | 517.2930 |
| 314 | 3-(Piperidine-1-carbonyl)phenylboronic acid | 3-(piperidine-1-C(O))-C₆H₄- | 529.2957 |

-continued

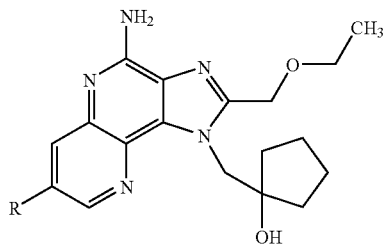

| Example | Reagent | R | Measured Mass (M + H) |
|---|---|---|---|
| 315 | 4-(Cyclopentylaminocarbonyl)-phenylboronic acid | 4-(cyclopentylaminocarbonyl)phenyl | 529.2908 |
| 316 | 3-(Furfurylaminocarbonyl)phenylboronic acid | 3-(furfurylaminocarbonyl)phenyl | 541.2592 |
| 317 | 4-Benzyloxy-3-fluorophenylboronic acid | 4-benzyloxy-3-fluorophenyl | 542.2554 |
| 318 | 5-(tert-butyldimethylsilanyloxymethyl)pyridine-3-boronic acid | 5-(hydroxymethyl)pyridin-3-yl | 449.2278 |

Examples 319-330

The methods described in Examples 154-194 were followed using 1-{[4-amino-2-(ethoxymethyl)-7-(4-fluorophenyl)-1H-imidazo[4,5-c][1,5]naphthyridin-1-yl-]methyl}cyclopentanol (42 mg, 0.10 mmol) instead of 1-(4-amino-7-bromo-2-ethyl-1H-imidazo [4,5-c][1,5]naphthyridin-1-yl)-2-methylpropan-2-ol with the modification that the samples were not diluted in methanol after the initial heating at 80° C. overnight. After each sample was purified using Waters Oasis Sample Extractions Cartridge MCX according to the method described in Examples 4-58, and the resulting basic solution was concentrated by vacuum centrifugation, the reaction with boron tribromide described in Examples 128-151 was carried out using 0.400 mL of boron tribromide solution for each test tube. The compounds were purified by reversed phase prep HPLC according to the method described in Examples 77-127. The table below shows the reagent added to each test tube, the structure of the resulting compound, and the observed accurate mass for the isolated trifluoroacetate salt.

Examples 319-330
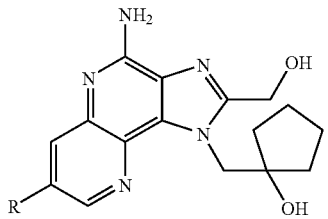
| Example | Reagent | R | Measured Mass (M + H) |
|---|---|---|---|
|  | None | Br— | 392.0712 |
| 319 | Phenylboronic acid | phenyl | 390.1926 |
| 320 | 2-Hydroxyphenylboronic acid | 2-HO-phenyl | 406.1866 |
| 321 | 3-Hydroxyphenylboronic acid | 3-HO-phenyl | 406.1866 |
| 322 | 3-Chlorophenylboronic acid | 3-Cl-phenyl | 424.1538 |
| 323 | 2-Chlorophenylboronic acid | 2-Cl-phenyl | 424.1515 |
| 324 | 4-Chlorophenylboronic acid | 4-Cl-phenyl | 424.1515 |
| 325 | 3,4-Dichlorophenylboronic acid | 3,4-diCl-phenyl | 458.1111 |

-continued

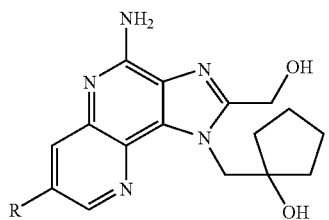

| Example | Reagent | R | Measured Mass (M + H) |
|---|---|---|---|
| 326 | 3-(N-Isopropylaminocarbonyl)-phenylboronic acid | 3-(N-isopropylcarbamoyl)phenyl | 475.2462 |
| 327 | 3-(N-Propylaminocarbonyl)-phenylboronic acid | 3-(N-propylcarbamoyl)phenyl | 475.2446 |
| 328 | 4-(Ethylsulfonyl)phenylboronic acid | 4-(ethylsulfonyl)phenyl | 482.1849 |
| 329 | 3-(Methylsulfonylamino)-phenylboronic acid | 3-(methylsulfonylamino)phenyl | 483.1805 |
| 330 | 3-(Piperidine-1-carbonyl)phenylboronic acid | 3-(piperidine-1-carbonyl)phenyl | 501.2579 |

Preparation of N-{2-[4-Amino-7-bromo-2-(ethoxymethyl)-1H-imidazo[4,5-c][1,5]naphthyridin-1-yl]-1,1-dimethylethyl}methanesulfonamide

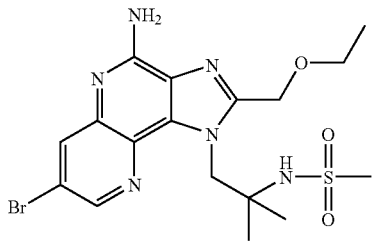

Part A

A modification of the method described in Part A of the preparation of 1-[4-amino-7-bromo-2-(ethoxymethyl)-1H-imidazo[4,5-c][1,5]naphthyridin-1-yl]-2-methylpropan-2-ol was followed using 150 g (0.42 mol) of 7-bromo-4-chloro-3-nitro[1,5]naphthyridine and 1,2-diamino-2-methylpropane (80.7 g, 0.915 mol) in lieu of 1-amino-2-methylpropan-2-ol. The reaction was at 3° C. at the start of the addition of the diamine. Following the addition, the reaction was stirred for 4.5 hours before it was concentrated under reduced pressure. N-1-(7-Bromo-3-nitro[1,5]naphthyridin-4-yl)-2-methylpropane-1,2-diamine (140 g) was obtained after drying over two nights in a vacuum oven at 35° C.

Part B

A solution of sodium hydroxide (11.8 g,) in deionized water (295 mL) was added dropwise to a solution of N-1-(7-bromo-3-nitro[1,5]naphthyridin-4-yl)-2-methylpropane-1,2-diamine (100.0 g, 294.0 mmol) in tetrahydrofuran (1.3 L). A solution of di-tert-butyl dicarbonate (72.8 g, 333 mmol) in THF (219 mL) was added slowly over a period of 25 minutes. The reaction was stirred at room temperature for three days. The THF was removed under reduced pressure, and the resulting mixture was diluted with deionized water (1 L) and extracted twice with dichloromethane (1.5 L). The combined extracts were washed sequentially with saturated aqueous sodium carbonate (2×900 mL) and brine (250 mL), dried over magnesium sulfate, filtered, and concentrated under reduced pressure to provide 141 g of tert-butyl 2-[(7-bromo-3-nitro[1,5]naphthyridin-4-yl)amino]-1,1-dimethylethylcarbamate.

Part C

A modification of the method described in Part B of the preparation of 1-[4-amino-7-bromo-2-(ethoxymethyl)-1H-imidazo[4,5-c][1,5]naphthyridin-1-yl]-2-methylpropan-2-ol was used to reduce tert-butyl 2-[(7-bromo-3-nitro[1,5]naphthyridin-4-yl)amino]-1,1-dimethylethylcarbamate (138.0 g, 313.4 mmol). The reaction was placed under hydrogen pressure for 5.5 hours. The reaction yielded 128 g of tert-butyl 2-[(3-amino-7-bromo[1,5]naphthyridin-4-yl)amino]-1,1-dimethylethylcarbamate containing some acetonitrile.

Part D

The method described in Part C of the preparation of 1-[4-amino-7-bromo-2-(ethoxymethyl)-1H-imidazo[4,5-c][1,5]naphthyridin-1-yl]-2-methylpropan-2-ol was used to treat tert-butyl 2-[(3-amino-7-bromo[1,5]naphthyridin-4-yl)amino]-1,1-dimethylethylcarbamate (64.0 g, 0.156 mol) with ethoxyacetyl chloride (21.0 g, 0.171 mol) in acetonitrile (640 mL). At the completion of the reaction, additional acetonitrile (200 mL) was added, and the solid product was isolated by filtration, washed with a small volume of acetonitrile, and dried for four hours to provide 55.6 g of tert-butyl 2-({7-bromo-3-[(ethoxyacetyl)amino][1,5]naphthyridin-4-yl}amino)-1,1-dimethylethylcarbamate hydrochloride.

Part E

A modification of the method described in Part D of the preparation of 1-[4-amino-7-bromo-2-(ethoxymethyl)-1H-imidazo[4,5-c][1,5]naphthyridin-1-yl]-2-methylpropan-2-ol was used to treat tert-butyl 2-({7-bromo-3-[(ethoxyacetyl)amino][1,5]naphthyridin-4-yl}amino)-1,1-dimethylethyl-carbamate (55.6 g, 0.104 mol) with potassium carbonate (55.6 g). After the ethanol was removed under reduced pressure, and the resulting mixture was extracted with dichloromethane (4×300 mL). The combined extracts were concentrated under reduced pressure to provide 51 g of tert-butyl {2-[7-bromo-2-(ethoxymethyl)-1H-imidazo[4,5-c][1,5]naphthyridin-1-yl]-1,1-dimethylethyl}carbamate as a yellowish brown solid.

Part F

A modification of the method described in Part B of the preparation of 1-(4-amino-7-bromo-2-ethyl-1H-imidazo[4,5-c][1,5]naphthyridin-1-yl)-2-methylpropan-2-ol was used to treat the material from Part E above with mCPBA (37.52 g of 75%, 163.1 mmol) in dichloromethane (800 mL) followed by ammonium hydroxide (200 mL) and p-toluenesulfonyl chloride (25.90 g, 135.9 mmol) in dichloromethane (450 mL). After the reaction was complete and diluted with dichloromethane (200 mL), it was washed with 4N aqueous sodium carbonate (2×200 mL). The combined aqueous fractions were washed extracted with dichloromethane (200 mL), and the combined organic fractions were washed with brine, dried over sodium sulfated, filtered, and concentrated under reduced pressure. The residue was triturated with acetonitrile to provide 18.77 g of tert-butyl {2-[4-amino-7-bromo-2-(ethoxymethyl)-1H-imidazo[4,5-c][1,5]naphthyridin-1-yl]-1,1-dimethylethyl}carbamate as an off-white solid. A portion was recrystallized from acetonitrile to provide the following analytical data, mp 176-178° C.

Anal. calcd for $C_{21}H_{29}BrN_6O_3$: C, 51.12; H, 5.92; N, 17.03. Found: C, 51.07; H, 5.92; N, 17.09.

Part G

Hydrogen chloride (56.74 g of a 2.2 M solution in ethanol, 124.8 mmol) was added to a suspension of tert-butyl {2-[4-amino-7-bromo-2-(ethoxymethyl)-1H-imidazo[4,5-c][1,5]naphthyridin-1-yl]-1,1-dimethylethyl}carbamate (15.40 g, 31.21 mmol) in anhydrous ethanol (120 mL), and the reaction mixture was heated at reflux for four hours and allowed to cool to room temperature. A precipitate had formed and was isolated by filtration, washed with a small volume of cold ethanol, and dried in a vacuum oven at 60° C. to provide 12.26 g of 1-(2-amino-2-methylpropyl)-7-bromo-2-(ethoxymethyl)-1H-imidazo[4,5-c][1,5]naphthyridin-4-amine dihydrochloride.

Part H

Triethylamine (13.02 g, 128.7 mmol) was added to a suspension of 1-(2-amino-2-methylpropyl)-7-bromo-2-(ethoxymethyl)-1H-imidazo[4,5-c][1,5]naphthyridin-4-amine dihydrochloride (6.00 g, 12.9 mmol) in dichloromethane (500 mL), and the reaction was cooled to 4° C. A solution of methanesulfonyl chloride (1.62 g, 14.2 mmol) in dichloromethane (10 mL) was then added dropwise. The reaction mixture was allowed to warm to room temperature, stirred for 24 hours, diluted with dichloromethane (200 mL), washed sequentially with water (200 mL), 4% aqueous sodium carbonate (2×200 mL), water (200 mL), and brine (200 mL), and concentrated under reduced pressure. The crude product was purified by automated flash chromatography (FLASH 40+M silica cartridge, eluting with 0 to 25% CMA in chloroform) followed by recrystallization from acetonitrile to provide 5.21 g of N-{2-[4-amino-7-bromo-2-(ethoxymethyl)-1H-imidazo[4,5-c][1,5]naphthyridin-1-yl]-1,1-dimethylethyl}methanesulfonamide as a white solid, 211-212° C.

Anal. calcd for $C_{17}H_{23}BrN_6O_3S$: C, 43.32; H, 4.92; N, 17.83. Found: C, 43.35; H, 4.85; N, 18.07.

Example 331

N-(2-{4-Amino-2-(ethoxymethyl)-7-[3-(hydroxymethyl)phenyl]-1H-imidazo[4,5-c][1,5]naphthyridin-1-yl}-1,1-dimethylethyl)methanesulfonamide

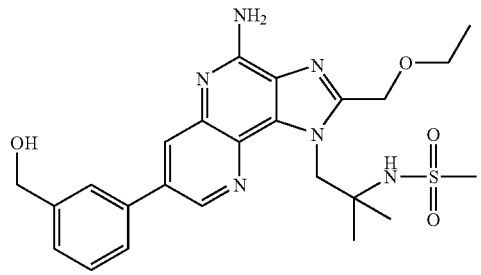

The method described in Example 152 was used to treat N-{2-[4-amino-7-bromo-2-(ethoxymethyl)-1H-imidazo[4,5-c][1,5]naphthyridin-1-yl]-1,1-dimethylethyl}methanesulfonamide (1.2 g, 2.55 mmol) and 3-(hydroxymethyl)benzeneboronic acid (0.58 g, 3.8 mmol) in 1-propanol (15 mL) with triphenylphosphine (20.0 mg, 0.0760 mmol), aqueous sodium carbonate (3.82 mL of 2 M), water (3 mL), and palladium (II) acetate (5.7 mg, 0.025 mmol) with the following modifications. The reaction mixture was heated at reflux overnight. The crude product was purified by automated flash chromatography (FLASH 40+M cartridge, eluting with 0% to 35% CMA in chloroform) followed by recrystallization from acetonitrile to provide 0.98 g of N-(2-{4-amino-2-(ethoxymethyl)-7-[3-(hydroxymethyl)phenyl]-1H-imidazo[4,5-c][1,5]naphthyridin-1-yl}-1,1-dimethylethyl)methanesulfonamide as a white solid, mp 173-174° C.

MS (APCI) m/z 499.33 $(M+H)^+$;

Anal. Calcd for $C_{24}H_{30}N_6O_4S$: C, 57.81; H, 6.06; N, 16.85. Found: C, 57.67; H, 5.80; N, 16.90.

Examples 332-336

N-{2-[4-Amino-7-bromo-2-(ethoxymethyl)-1H-imidazo[4,5-c][1,5]naphthyridin-1-yl]-1,1-dimethylethyl}methanesulfonamide (0.100 g, 0.21 mmol) was added to a test tube. The boronic acid (0.22 mmol) indicated in the table below and n-propanol (3.2 mL) were sequentially added. The test tube was purged with nitrogen. Palladium (II) acetate (0.300 mL of a 4 mg/mL solution in toluene, 0.0053 mmol), 2M aqueous sodium carbonate solution (1.2 mL), deionized water (226 µL), and a solution of 0.15 mol % triphenylphosphine in n-propanol (106 µL, 0.016 mmol) were sequentially added. The test tube was purged with nitrogen, capped, and then heated at 80° C. for four hours in a sand bath.

The contents of each test tube were passed through a Waters Oasis Sample Extractions Cartridge MCX (6 cc) according to the procedure described in Examples 4-58. The resulting basic solutions were concentrated by vacuum centrifugation. Half of the material from each tube was purified by reversed phase prep HPLC according to the method described in Examples 77-127. The other half of the material was used in Examples 337-338. The table below shows the reagent added to each test tube, the structure of the resulting compound, and the observed accurate mass for the isolated trifluoroacetate salt.

Example 332-336

| Example | Reagent | R | Measured Mass (M + H) |
|---|---|---|---|
|  | None | Br— | 471.0826 |
| 332 | Phenylboronic acid | phenyl | 469.2024 |
| 333 | Pyridine-3-boronic acid | pyridin-3-yl | 470.1975 |
| 334 | Thiophene-3-boronic acid | thiophen-3-yl | 475.1560 |
| 335 | 4-(Hydroxymethyl)-phenylboronic acid | 4-(hydroxymethyl)phenyl | 499.2130 |
| 336 | 3-Chlorophenylboronic acid | 3-chlorophenyl | 503.1670 |

Example 337-338

The reserved material from Examples 332-336 was subjected to the reaction with boron tribromide described in Examples 128-151 using 0.400 mL of boron tribromide solution for each test tube. After each reaction was stirred for four hours at room temperature, additional boron tribromide (0.200 mL of 1 M in dichloromethane) was added. The reaction was stirred for one hour at room temperature and allowed to stand for 65 hours. Methanol (1 mL) and 6 N hydrochloric acid (0.500 mL) were added to each tube. The contents were vortexed for 30 minutes, and the volatiles were removed by vacuum centrifugation. The compounds were purified by reversed phase prep HPLC according to the method described in Examples 77-127. The table below shows the reagent added to each test tube, the structure of the resulting compound, and the observed accurate mass for the isolated trifluoroacetate salt.

Examples 337-338

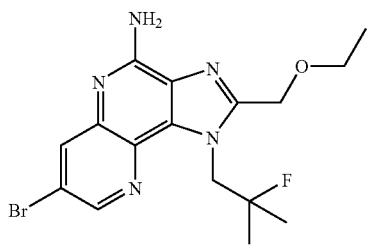

| Example | Reagent | R | Measured Mass (M + H) |
|---|---|---|---|
| 337 | Pyridine-3-boronic acid | 3-pyridyl | 442.1650 |
| 338 | 3-Chlorophenylboronic acid | 3-chlorophenyl | 475.1310 |

Preparation of 7-Bromo-2-(ethoxymethyl)-1-(2-fluoro-2-methylpropyl)-1H-imidazo[4,5-c][1,5]naphthyridin-4-amine Part A A solution of tert-butyl 2-hydroxy-2-methylpropylcarbamate (19.2 g, 101 mmol) in dichloromethane (500 mL) was stirred at −78° C. under a nitrogen atmosphere, and (diethylamino)sulfur trifluoride (DAST)(18.0 g, 112 mmol) was added dropwise. The solution was allowed to warm to room temperature and stirred overnight. Saturated aqueous sodium bicarbonate (150 mL) was added. The organic layer was then separated and washed sequentially with saturated aqueous sodium bicarbonate (150 mL), water (150 mL), and brine (150 mL); dried over magnesium sulfate; filtered; and concentrated under reduced pressure. The resulting oil was purified by automated flash chromatography (FLASH 65I cartridge, eluting with 10% ethyl acetate in hexane) to provide 13.7 g of tert-butyl 2-fluoro-2-methylpropylcarbamate as a light yellow oil that crystallized overnight.

Part B

Hydrogen chloride (50 mL of a 4 M solution in 1,4-dioxane) was added to a solution of tert-butyl 2-fluoro-2-methylpropylcarbamate (13.7 g, 71.6 mmol) in dichloromethane (300 mL), and the reaction was stirred for five hours at room temperature and concentrated under reduced pressure. The residue was three times dissolved in toluene and concentrated under reduced pressure to provide 8.08 g of 2-fluoro-2-methylpropan-1-amine hydrochloride as a white solid.

Part C

Triethylamine (17.3 g, 171 mmol) was added to a suspension of 7-bromo-4-chloro-3-nitro[1,5]naphthyridine (52.2 mmol) in DMF (50 mL), and then a solution of 2-fluoro-2-methylpropan-1-amine hydrochloride (5.46 g, 42.8 mmol) in DMF (25 mL) was added dropwise over a period of ten minutes. The reaction mixture was stirred at room temperature for 14.5 hours, and water (500 mL) was added. The resulting mixture was stirred for one hour. A solid was present and was isolated by filtration, washed with water, and dried overnight in a vacuum oven at 65° C. to provide 14.7 g of 7-bromo-N-(2-fluoro-2-methylpropyl)-3-nitro[1,5]naphthyridin-4-amine as a reddish-brown solid.

Part D

A Parr vessel was charged with 5% platinum on carbon (700 mg), 7-bromo-N-(2-fluoro-2-methylpropyl)-3-nitro[1,5]naphthyridin-4-amine (7.00 g, 20.4 mmol), and acetonitrile (50 mL) and placed under hydrogen pressure (30 psi, $2.1 \times 10^5$ Pa) for two hours. The reaction mixture was filtered through a layer of CELITE filter aid. The filter cake was washed with acetonitrile. The filtrate was concentrated under reduced pressure to provide 6.22 g of 7-bromo-N-(2-fluoro-2-methylpropyl)[1,5]naphthyridin-3,4-diamine as a dark brown oil.

Part E

Ethoxyacetyl chloride (2.7 g, 22 mmol) was added dropwise to a solution of 7-bromo-N-(2-fluoro-2-methylpropyl)[1,5]naphthyridin-3,4-diamine (6.2 g, 19.8 mmol) in acetonitrile (65 mL). The reaction was stirred for 20 minutes at room temperature and concentrated under reduced pressure. The residue was treated with potassium carbonate (4.1 g, 29.7 mmol) in ethanol (90 mL) and water (30 mL) according to the method described in Part D of the preparation of 1-[4-amino-7-bromo-2-(ethoxymethyl)-1H-imidazo[4,5-c][1,5]naphthyridin-1-yl]-2-methylpropan-2-ol with the modification that the reaction was stirred at room temperature for 19 hours and then heated at reflux for five hours. After the drying step 6.65 g of product were obtained. A portion of the isolated product (0.5 g) was purified by automated flash chromatography (40+M silica cartridge, eluting with 3% to 10% methanol in dichloromethane) followed by recrystallization from acetonitrile. The crystals were isolated by filtration, washed with cold acetonitrile, and dried in a vacuum oven at 65° C. to provide 21 mg of analytically pure 7-bromo-2-(ethoxymethyl)-1-(2-fluoro-2-methylpropyl)-1H-imidazo[4,5-c][1,5]naphthyridine as white needles, mp 127-128° C.

Anal. Calcd for $C_{16}H_{18}BrFN_4O$: C, 50.41; H, 4.76; N, 14.70. Found: C, 50.42; H, 4.73; N, 14.78.

Part F mCPBA (5.4 g of 77% purity, 24 mmol) was added to a stirred solution of 7-bromo-2-(ethoxymethyl)-1-(2-fluoro-2-methylpropyl)-1H-imidazo[4,5-c][1,5]naphthyridine (6.1 g, 16 mmol) in chloroform (160 mL), and the reaction was stirred at room temperature for 17.5 hours. Concentrated ammonium hydroxide (80 mL) was added, and then p-toluenesulfonyl chloride (3.7 g, 19.2 mmol) was added over a period of five minutes. The reaction mixture was stirred at room temperature for 1.5 hours, and an analysis by LC/MS indicated the presence of starting material. Additional p-toluenesulfonyl chloride (3.7 g) was added, and the reaction mixture was stirred at room temperature for three hours. The aqueous layer was separated and extracted with dichloromethane (3×100 mL). The combined organic fractions were dried over magnesium sulfate, filtered, and concentrated under reduced pressure. The residue (14.5 g) was triturated with dichloromethane (50 mL), isolated by filtration, and washed with dichloromethane to provide 970 mg of desired product. The filtrate was concentrated under reduced pressure, and the residue was triturated with methanol, isolated by filtration, washed with methanol, and dried in a vacuum oven at 65° C. for five hours to provide an additional 2.45 g of product. Silica gel was added to the filtrate. The mixture was concentrated under reduced pressure and purified by automated flash chromatography (FLASH 65I cartridge, eluting with 3% to 10% methanol in ethyl acetate) to provide 530 mg of product. A portion of the isolated material (220 mg) was recrystallized from acetonitrile (50 mL). The crystals were isolated by filtration, washed with acetonitrile, and dried in a vacuum oven at 80° C. to provide 92 mg of analytically pure 7-bromo-2-(ethoxymethyl)-1-(2-fluoro-2-methylpropyl)-1H-imidazo[4,5-c][1,5]naphthyridin-4-amine as a light yellow solid, mp 221-222° C.

Anal. Calcd for $C_{16}H_{19}BrFN_5O$: C, 48.50; H, 4.83; N, 17.67. Found: C, 48.60; H, 4.69; N, 17.64.

Examples 339-342

Under a nitrogen atmosphere, a suspension of 7-bromo-2-(ethoxymethyl)-1-(2-fluoro-2-methylpropyl)-1H-imidazo[4,5-c][1,5]naphthyridin-4-amine (0.600 g, 1.51 mmol), the boronic acid indicated in the following table (1.82 mmol), potassium carbonate (0.691 g, 5.00 mmol), dichlorobis(triphenylphosphine)palladium(II)(0.011 g, 0.015 mmol), DME (7 mL), and water (3 mL) was stirred in a pressure vessel. The vessel was sealed, and the suspension was heated at 110° C. for the time indicated in the following table, allowed to cool to room temperature, and concentrated under reduced pressure. The residue was dissolved in methanol and dichloromethane. Silica gel was added, and the mixture was concentrated under reduced pressure. The residue was purified by automated flash chromatography (FLASH 40+M cartridge, eluting with methanol in ethyl acetate with the percentage of methanol given in the table). Acetonitrile was added to the purified product to form a solid, which was isolated by filtration, washed with acetonitrile, and dried in a vacuum oven at 65° C. or 80° C. to provide the products with the structures indicated in the table. Analytical data is provided below the table.

Examples 339-342

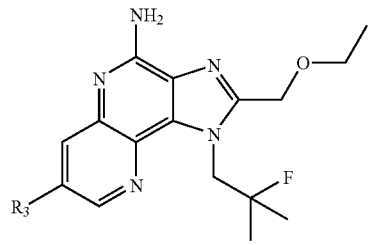

| Example | Boronic acid | Reaction Time | Methanol in eluent | R₃ |
|---|---|---|---|---|
| 339 | Phenylboronic acid | 64 hours | 3% to 10% | |
| 340 | (3-Methylsulfonylamino-phenyl)boronic acid | 14.5 hours | 3% to 12% | |
| 341 | 3-(Morpholine-4-carbonyl)-phenylboronic acid | 16 hours | 5% to 15% | |

-continued

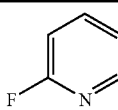

| Example | Boronic acid | Reaction Time | Methanol in eluent | R₃ |
|---|---|---|---|---|
| 342 | 6-Fluoropyridine-3-boronic acid | 16 hours | 3% to 10% | |

Example 339: 2-(Ethoxymethyl)-1-(2-fluoro-2-methylpropyl)-7-phenyl-1H-imidazo[4,5-c][1,5]naphthyridin-4-amine (150 mg) was obtained as a white solid, mp 173-174° C.

Anal. Calcd for $C_{22}H_{24}FN_5O$: C, 67.16; H, 6.15; N, 17.80. Found: C, 67.09; H, 6.31; N, 17.71.

Example 340: N-{3-[4-Amino-2-(ethoxymethyl)-1-(2-fluoro-2-methylpropyl)-1H-imidazo[4,5-c][1,5]naphthyridin-7-yl]phenyl}methanesulfonamide (126 mg) was obtained as a white solid, mp 208-209° C.

Anal. Calcd for $C_{23}H_{27}FN_6O_3S$: C, 56.78; H, 5.59; N, 17.27. Found: C, 56.67; H, 5.41; N, 17.23.

Example 341: 2-(Ethoxymethyl)-1-(2-fluoro-2-methylpropyl)-7-[3-(morpholin-4-ylcarbonyl)phenyl]-1H-imidazo[4,5-c][1,5]naphthyridin-4-amine (192 mg) was obtained as a white solid, mp 167-168° C.

Anal. Calcd for $C_{27}H_{31}FN_6O_3$: C, 64.02; H, 6.17; N, 16.59. Found: C, 63.80; H, 6.01; N, 16.67.

Example 342: 2-(Ethoxymethyl)-1-(2-fluoro-2-methylpropyl)-7-(6-fluoropyridin-3-yl)-1H-imidazo[4,5-c][1,5]naphthyridin-4-amine (177 mg) was obtained as a white solid, mp 198-199° C.

Anal. Calcd for $C_{21}H_{22}F_2N_6O$: C, 61.16; H, 5.38; N, 20.38. Found: C, 60.95; H, 5.17; N, 20.48.

Examples 343-350

The methods described in Examples 154-194 were followed using 7-bromo-2-(ethoxymethyl)-1-(2-fluoro-2-methylpropyl)-1H-imidazo[4,5-c][1,5]naphthyridin-4-amine (40.0 mg, 0.100 mmol) instead of 1-(4-amino-7-bromo-2-ethyl-1H-imidazo[4,5-c][1,5]naphthyridin-1-yl)-2-methylpropan-2-ol with the modification that the samples were not diluted in methanol after the initial heating at 80° C. overnight. The table below shows the reagent added to each test tube, the structure of the resulting compound, and the observed accurate mass for the isolated trifluoroacetate salt.

Examples 343-350

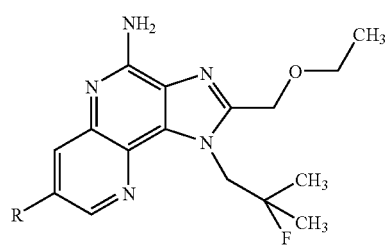

| Example | Reagent | R | Measured Mass (M + H) |
|---|---|---|---|
| | None |  | 396.0825 |
| 343 | Pyridine-3-boronic acid | 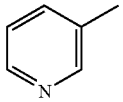 | 395.1991 |
| 344 | Thiophene-3-boronic acid | 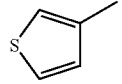 | 400.1602 |
| 345 | 3-Hydroxyphenylboronic acid | 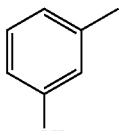 | 410.2020 |
| 346 | 4-(Hydroxymethyl)-phenylboronic acid | 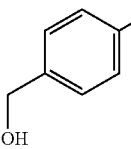 | 424.2136 |

-continued

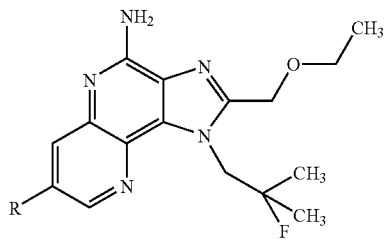

| Example | Reagent | R | Measured Mass (M + H) |
|---|---|---|---|
| 347 | 4-Methoxyphenylboronic acid | 4-methoxyphenyl | 424.2139 |
| 348 | 3-Chlorophenylboronic acid | 3-chlorophenyl | 428.1655 |
| 349 | (3-Aminocarbonylphenyl)-boronic acid | 3-(aminocarbonyl)phenyl | 437.2093 |
| 350 | 3-(N-Propylaminocarbonyl)-phenylboronic acid | 3-(N-propylaminocarbonyl)phenyl | 479.2554 |

Examples 351-365

Part A

The method described in Examples 339-342 was used to treat 1-[4-amino-7-bromo-2-(ethoxymethyl)-1H-imidazo[4,5-c][1,5]naphthyridin-1-yl]-2-methylpropan-2-ol (1.6 g, 4.06 mmol) with (3-aminomethylphenyl)boronic acid hydrochloride (1.3 g, 6.94 mmol), potassium carbonate (3.0 g, 22 mmol), and dichlorobis(triphenylphosphine)palladium(II) (0.128 g, 0.182 mmol) in DME (20 mL) aid water (10 mL). The reaction was heated for 15.5 hours. The eluent used for chromatographic purification was 5% to 25% 1 M methanolic ammonia in dichloromethane. Following chromatographic purification 1.19 g of 1-[4-amino-7-[3-(aminomethyl)phenyl]-2-(ethoxymethyl)-1H-imidazo[4,5-c][1,5]naphthyridin-1-yl]-2-methylpropan-2-ol were obtained as a yellow solid.

Part B

An acid chloride, sulfonyl chloride, or isocyanate (0.11 mmol, 1.1 equivalents) from the table below was added to a test tube containing 1-[4-amino-7-[3-(aminomethyl)phenyl]-2-(ethoxymethyl)-1H-imidazo[4,5-c][1,5]naphthyridin-1-yl]-2-methylpropan-2-ol (41.7 mg, 0.10 mmol) and N,N-diisopropylethylamine (0.034 mL, 0.20 mmol) in N,N-dimethylacetamide (DMA)(1 mL). The test tube was capped and vortexed overnight at room temperature. Water (0.100 mL) was added to each test tube, and the solvent was removed by vacuum centrifugation.

The compounds were purified according to the method described in Examples 77-127. The table below shows the reagent added to each test tube, the structure of the resulting compound, and the observed accurate mass for the isolated trifluoroacetate salt Examples 351-365

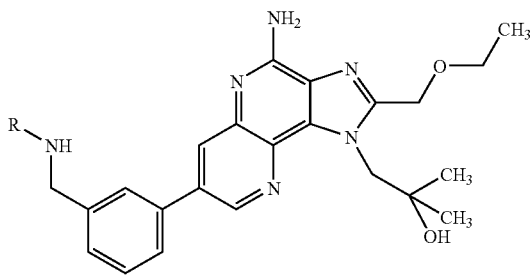

| Example | Reagent | R | Measured Mass (M + H) |
|---|---|---|---|
| 351 | None | H | 421.2331 |

-continued

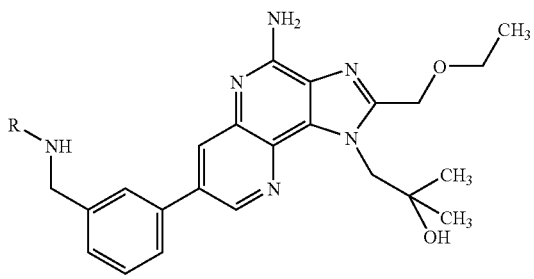

| Example | Reagent | R | Measured Mass (M + H) |
|---|---|---|---|
| 352 | Acetyl chloride | H₃C-C(=O)- | 463.2497 |
| 353 | Cyclopentanecarbonyl chloride | cyclopentyl-C(=O)- | 517.2947 |
| 354 | Benzoyl chloride | phenyl-C(=O)- | 525.2606 |
| 355 | Cyclohexanecarbonyl chloride | cyclohexyl-C(=O)- | 531.3110 |
| 356 | Nicotinoyl chloride hydrochloride | pyridin-3-yl-C(=O)- | 526.2570 |
| 357 | Ethanesulfonyl chloride | H₃C-CH₂-S(=O)₂- | 513.2332 |
| 358 | Isopropylsulfonyl chloride | (H₃C)₂CH-S(=O)₂- | 527.2480 |
| 359 | Benzenesulfonyl chloride | phenyl-S(=O)₂- | 561.2324 |

-continued
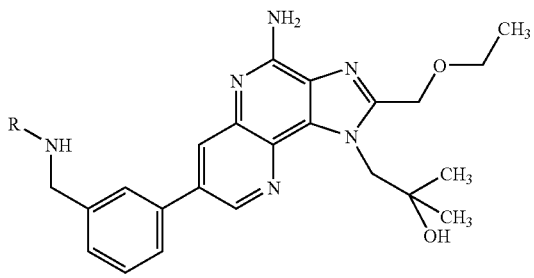
| Example | Reagent | R | Measured Mass (M + H) |
|---|---|---|---|
| 360 | 1-Methylimidazole-4-sulfonyl chloride | 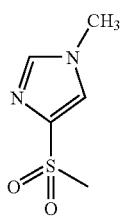 | 565.2375 |
| 361 | 2,2,2-Trifluoroethanesulfonyl chloride | 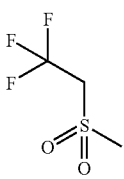 | 567.2000 |
| 362 | Methyl isocyanate | 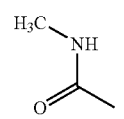 | 478.2566 |
| 363 | Cyclopentyl isocyanate | 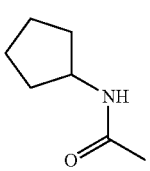 | 532.3046 |
| 364 | Phenyl isocyanate | 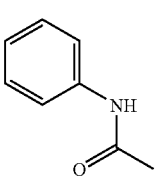 | 540.2700 |
| 365 | 4-Morpholinylcarbonyl chloride | 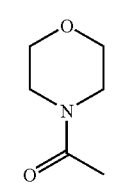 | 534.2824 |

Examples 366-369

Part A

A suspension of 1-[4-amino-7-bromo-2-(ethoxymethyl)-1H-imidazo[4,5-c][1,5]naphthyridin-1-yl]-2-methylpropan-2-ol (1.6 g, 4.06 mmol), (4-aminomethylphenyl)boronic acid hydrochloride (0.913 g, 4.87 mmol), potassium carbonate (2.5 g, 18 mmol), dichlorobis(triphenylphosphine)palladium(II)(0.028 g, 0.041 mmol), DME (15 mL), and water (7 mL) was stirred under a nitrogen atmosphere and then heated at 110° C. for 18 hours and allowed to cool to room temperature. An analysis by LC/MS indicated the reaction was incomplete, and additional dichlorobis(triphenylphosphine)palladium(II) (0.050 g) was added. Heating was continued for another six hours, but the reaction did not progress. Additional (4-aminomethylphenyl)boronic acid hydrochloride (0.400 g), potassium carbonate (0.500 g) and dichlorobis(triphenylphosphine)palladium(II)(0.050 g) were added. The reaction was heated at 110° C. for six hours, allowed to cool to room temperature, and concentrated under reduced pressure. Chromatographic purification was carried out as described in Examples 351-365 to provide 1.13 g of 1-[4-amino-7-[4-(aminomethyl)phenyl]-2-(ethoxymethyl)-1H-imidazo[4,5-c][1,5]naphthyridin-1-yl]-2-methylpropan-2-ol as a yellow solid.

Part B

The method described in Part B of Examples 351-365 was followed using 1-[4-amino-7-[4-(aminomethyl)phenyl]-2-(ethoxymethyl)-1H-imidazo[4,5-c][1,5]naphthyridin-1-yl]-2-methylpropan-2-ol instead of 1-[4-amino-7-[3-(aminomethyl)phenyl]-2-(ethoxymethyl)-1H-imidazo[4,5-c][1,5]naphthyridin-1-yl]-2-methylpropan-2-ol. The table below shows the reagent added to each test tube, the structure of the resulting compound, and the observed accurate mass for the isolated trifluoroacetate salt.

Examples 366-369

| Example | Reagent | R | Measured Mass (M + H) |
|---|---|---|---|
| 366 | None | H | 421.2330 |
| 367 | Isobutyryl chloride | (CH₃)₂CHC(O)– | 491.2799 |
| 368 | Benzoyl chloride | PhC(O)– | 525.2647 |
| 369 | Isopropylsulfonyl chloride | (CH₃)₂CHS(O)₂– | 527.2454 |

Examples 370-378

The methods described in Examples 154-194 were followed using 1-[4-amino-7-bromo-2-(ethoxymethyl)-1H-imidazo[4,5-c][1,5]naphthyridin-1-yl]-2-methylpropan-2-ol (39.2 mg, 0.100 mmol) instead of 1-(4-amino-7-bromo-2-ethyl-1H-imidazo[4,5-c][1,5]naphthyridin-1-yl)-2-methylpropan-2-ol with the modification that the samples were not diluted in methanol after the initial heating at 80° C. overnight. The table below shows the reagent added to each test tube, the structure of the resulting compound, and the observed accurate mass for the isolated trifluoroacetate salt.

Examples 370-378

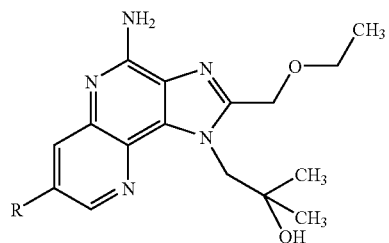

| Example | Reagent | R | Measured Mass (M + H) |
|---|---|---|---|
| 370 | (2-Methoxymethylphenyl)-boronic acid | 2-(methoxymethyl)phenyl | 436.2349 |
| 371 | (2-Acetylaminophenyl)-boronic acid | 2-(acetylamino)phenyl | 449.2288 |
| 372 | (2-Trifluoromethylphenyl)-boronic acid | 2-(trifluoromethyl)phenyl | 460.1941 |
| 373 | (2-Methylsulfonylphenyl)-boronic acid | 3-(methylsulfonyl)phenyl | 470.1868 |
| 374 | N,N-Dimethyl 4-boronobenzenesulfonamide | 4-(N,N-dimethylsulfamoyl)phenyl | 499.2109 |
| 375 | Methanesulfonylaminomethyl phenyl)boronic acid | 4-(methanesulfonylaminomethyl)phenyl | 499.2140 |
| 376 | N-Pyrrolidinyl 4 boronobenzenesulfonamide | 4-(pyrrolidin-1-ylsulfonyl)phenyl | 525.2261 |

-continued

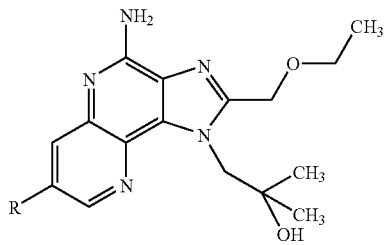

| Example | Reagent | R | Measured Mass (M + H) |
|---|---|---|---|
| 377 | N-Morpholinyl 3-borono-4-methylbenzenesulfonamide |  | 555.2371 |
| 378 | 4-(3-Butylureido)phenyl-boronic acid, pinacol ester |  | 506.2886 |

Examples 379-388

1-[4-Amino-7-bromo-2-(ethoxymethyl)-1H-imidazo[4,5-c][1,5]naphthyridin-1-yl]-2-methylpropan-2-ol (0.039 g, 0.10 mmol) was added to a test tube. The boronic acid (0.11 mmol) indicated in the table below and n-propanol (1.6 mL) were sequentially added. The test tube was purged with nitrogen. Palladium (II) acetate (0.150 mL of a 4 mg/mL solution in toluene, 0.0026 mmol), 2 M aqueous sodium carbonate solution (0.600 mL), deionized water (113 µL), and a solution of 0.15 mol % triphenylphosphine in n-propanol (53 µL, 0.0078 mmol) were sequentially added. The test tube was purged with nitrogen, capped, and then heated at 80° C. overnight.

The contents of each test tube were passed through a Waters Oasis Sample Extractions Cartridge MCX (6 cc) according to the procedure described in Examples 4-58. The resulting basic solutions were concentrated by vacuum centrifugation. Each sample was subjected to the reaction with boron tribromide described in Examples 128-151 using 0.400 mL of boron tribromide solution for each test tube. Each reaction was stirred for six hours at room temperature. After methanol and 6 N hydrochloric acid were added to each tube, the contents were vortexed for 30 minutes, and the volatiles were removed by vacuum centrifugation. The compounds were purified by reversed phase prep HPLC according to the method described in Examples 77-127. The table below shows the reagent added to each test tube, the structure of the resulting compound, and the observed accurate mass for the isolated trifluoroacetate salt.

Examples 379-388

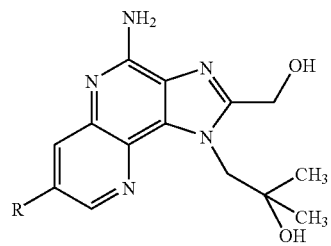

| Example | Reagent | R | Measured Mass (M + H) |
|---|---|---|---|
| 379 | (2-Methoxymethylphenyl)-boronic acid |  | 394.1862 |

-continued

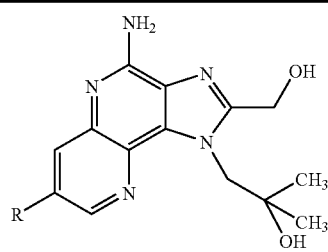

| Example | Reagent | R | Measured Mass (M + H) |
|---|---|---|---|
| 380 | (2-Acetylaminophenyl)boronic acid | 2-(NHC(O)CH₃)-phenyl | 421.1979 |
| 381 | (2-Trifluoromethylphenyl) boronic acid | 2-(CF₃)-phenyl | 432.1639 |
| 382 | (3-Methylsulfonylphenyl)- boronic acid | 3-(SO₂CH₃)-phenyl | 442.1564 |
| 383 | [4-(2-Methoxyethylaminocarbonyl)- phenyl]boronic acid | 4-(C(O)NHCH₂CH₂OH)-phenyl | 451.2094 |
| 384 | N,N-Dimethyl 4-boronobenzenesulfonamide | 4-(SO₂N(CH₃)₂)-phenyl | 471.1804 |
| 385 | (4-Methanesulfonylamino-methylphenyl)boronic acid | 4-(CH₂NHSO₂CH₃)-phenyl | 471.1806 |
| 386 | N-Pyrrolidinyl 4-boronobenzenesulfonamide | 4-(SO₂-pyrrolidinyl)-phenyl | 497.1988 |

-continued

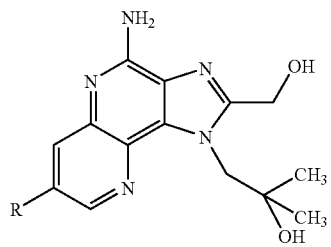

| Example | Reagent | R | Measured Mass (M + H) |
|---|---|---|---|
| 387 | N-Morpholinyl 3-borono-4-methylbenzenesulfonamide | (morpholinyl sulfonyl tolyl structure) | 527.2061 |
| 388 | 4-(3-Butylureido)phenyl-boronic acid, pinacol ester | (butyl urea phenyl structure) | 478.2562 |

Exemplary Compounds Table

Certain exemplary compounds, including some of those described above in the Examples, have the following Formula (III) wherein $R_1$, $R_2$, and $R_3$ are defined immediately below and in the table. In this table, each row represents one specific compound and a specific embodiment of the invention.

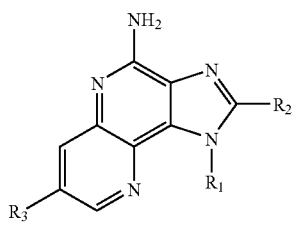

III wherein:

$R_1$ is preferably selected from the following:

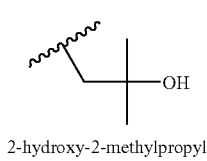 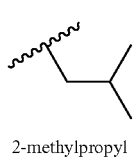 

2-hydroxy-2-methylpropyl    2-methylpropyl    propyl

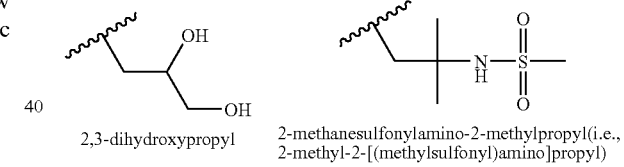

2,3-dihydroxypropyl    2-methanesulfonylamino-2-methylpropyl (i.e., 2-methyl-2-[(methylsulfonyl)amino]propyl)

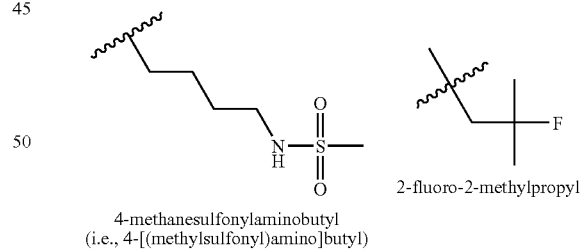

4-methanesulfonylaminobutyl (i.e., 4-[(methylsulfonyl)amino]butyl)    2-fluoro-2-methylpropyl $R_2$ is preferably selected from the following:

—$CH_3$ —$CH_2CH_3$ —$CH_2CH_2CH_3$ —$CH_2OCH_3$ methyl ethyl propyl methoxymethyl —$CH_2OCH_2CH_3$ —$CH_2CH_2OCH_3$ ethoxymethyl 2-methoxyethyl —$CH_2OH$ —$CH_2CH_2OH$ hydroxymethyl 2-hydroxyethyl R₃ is preferably selected from the following:

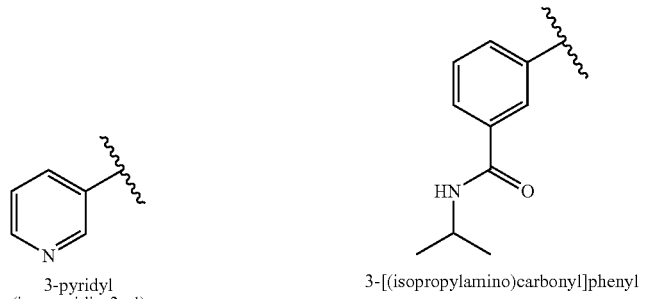

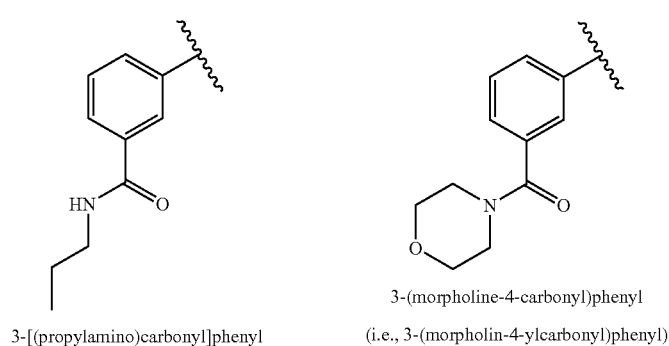

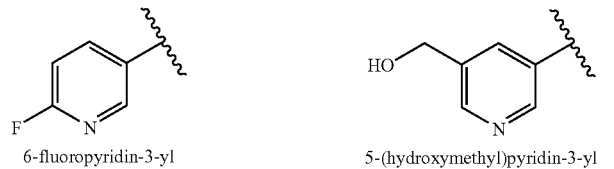

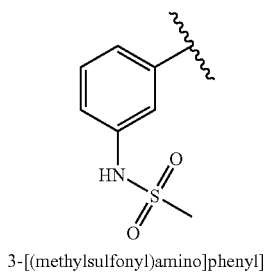

3-[(methylsulfonyl)amino]phenyl]

| R₁ | R₂ | R₃ |
|---|---|---|
| 2-hydroxy-2-methylpropyl | methyl | pyridin-3-yl |
| 2-hydroxy-2-methylpropyl | methyl | 3-[(isopropylamino)carbonyl]phenyl |
| 2-hydroxy-2-methylpropyl | methyl | 3-[(propylamino)carbonyl]phenyl |
| 2-hydroxy-2-methylpropyl | methyl | 3-(morpholin-4-ylcarbonyl)phenyl |
| 2-hydroxy-2-methylpropyl | methyl | 6-fluoropyridin-3-yl |
| 2-hydroxy-2-methylpropyl | methyl | 5-(hydroxymethyl)pyridin-3-yl |
| 2-hydroxy-2-methylpropyl | methyl | 3-[(methylsulfonyl)amino]phenyl |
| 2-hydroxy-2-methylpropyl | ethyl | pyridin-3-yl |
| 2-hydroxy-2-methylpropyl | ethyl | 3-[(isopropylamino)carbonyl]phenyl |
| 2-hydroxy-2-methylpropyl | ethyl | 3-[(propylamino)carbonyl]phenyl |
| 2-hydroxy-2-methylpropyl | ethyl | 3-(morpholin-4-ylcarbonyl)phenyl |
| 2-hydroxy-2-methylpropyl | ethyl | 6-fluoropyridin-3-yl |
| 2-hydroxy-2-methylpropyl | ethyl | 5-(hydroxymethyl)pyridin-3-yl |
| 2-hydroxy-2-methylpropyl | ethyl | 3-[(methylsulfonyl)amino]phenyl |
| 2-hydroxy-2-methylpropyl | propyl | pyridin-3-yl |
| 2-hydroxy-2-methylpropyl | propyl | 3-[(isopropylamino)carbonyl]phenyl |
| 2-hydroxy-2-methylpropyl | propyl | 3-[(propylamino)carbonyl]phenyl |
| 2-hydroxy-2-methylpropyl | propyl | 3-(morpholin-4-ylcarbonyl)phenyl |
| 2-hydroxy-2-methylpropyl | propyl | 6-fluoropyridin-3-yl |
| 2-hydroxy-2-methylpropyl | propyl | 5-(hydroxymethyl)pyridin-3-yl |
| 2-hydroxy-2-methylpropyl | propyl | 3-[(methylsulfonyl)amino]phenyl |

-continued

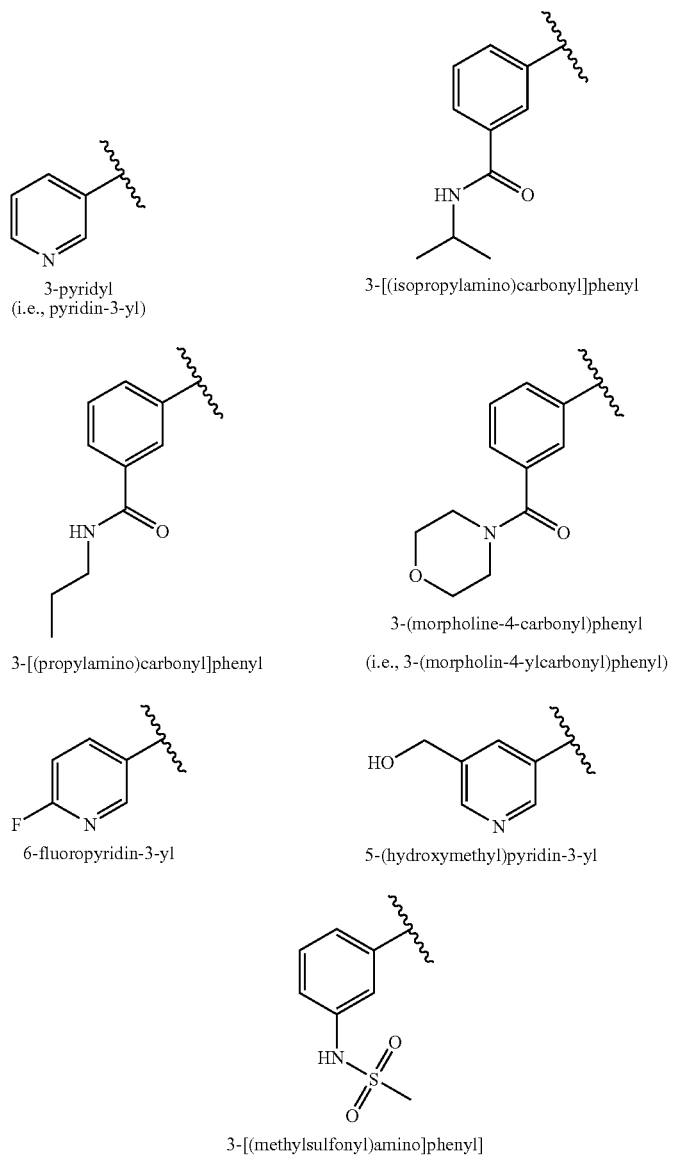

| R₁ | R₂ | R₃ |
|---|---|---|
| 2-hydroxy-2-methylpropyl | methoxymethyl | pyridin-3-yl |
| 2-hydroxy-2-methylpropyl | methoxymethyl | 3-[(isopropylamino)carbonyl]phenyl |
| 2-hydroxy-2-methylpropyl | methoxymethyl | 3-[(propylamino)carbonyl]phenyl |
| 2-hydroxy-2-methylpropyl | methoxymethyl | 3-(morpholin-4-ylcarbonyl)phenyl) |
| 2-hydroxy-2-methylpropyl | methoxymethyl | 6-fluoropyridin-3-yl |
| 2-hydroxy-2-methylpropyl | methoxymethyl | 5-(hydroxymethyl)pyridin-3-yl |
| 2-hydroxy-2-methylpropyl | methoxymethyl | 3-[(methylsulfonyl)amino]phenyl |
| 2-hydroxy-2-methylpropyl | ethoxymethyl | pyridin-3-yl |
| 2-hydroxy-2-methylpropyl | ethoxymethyl | 3-[(isopropylamino)carbonyl]phenyl |
| 2-hydroxy-2-methylpropyl | ethoxymethyl | 3-[(propylamino)carbonyl]phenyl |
| 2-hydroxy-2-methylpropyl | ethoxymethyl | 3-(morpholin-4-ylcarbonyl)phenyl) |
| 2-hydroxy-2-methylpropyl | ethoxymethyl | 6-fluoropyridin-3-yl |
| 2-hydroxy-2~methy1propy1 | ethoxymethyl | 5-(hydroxymethyl)pyridin-3-yl |
| 2-hydroxy-2-methylpropyl | ethoxymethyl | 3-[(methylsulfonyl)amino]phenyl |
| 2-hydroxy-2-methylpropyl | 2-methoxyethyl | pyridin-3-yl |
| 2-hydroxy-2-methylpropyl | 2-methoxyethyl | 3-[(isopropylamino)carbonyl]phenyl |
| 2-hydroxy-2-methylpropyl | 2-methoxyethyl | 3-[(propylamino)carbonyl]phenyl |
| 2-hydroxy-2-methylpropyl | 2-methoxyethyl | 3-(morpholin-4-ylcarbonyl)phenyl) |
| 2-hydroxy-2-methylpropyl | 2-methoxyethyl | 6-fluoropyridin-3-yl |
| 2-hydroxy-2-methylpropyl | 2-methoxyethyl | 5-(hydroxymethyl)pyridin-3-yl |
| 2-hydroxy-2-methylpropyl | 2-methoxyethyl | 3-[(methylsulfonyl)amino]phenyl |
| 2-hydroxy-2-methylpropyl | hydroxymethyl | pyridin-3-yl |
| 2-hydroxy-2-methylpropyl | hydroxymethyl | 3-[(isopropylamino)carbonyl]phenyl |

-continued

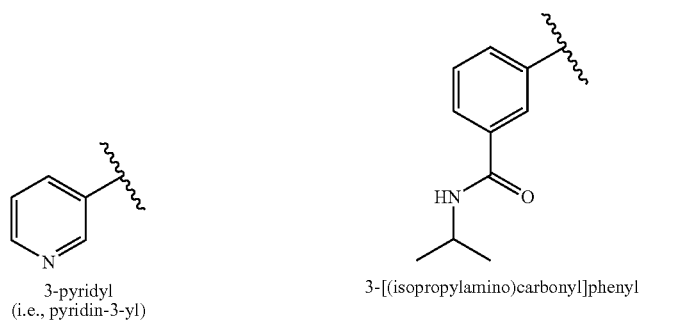

3-pyridyl
(i.e., pyridin-3-yl)

3-[(isopropylamino)carbonyl]phenyl

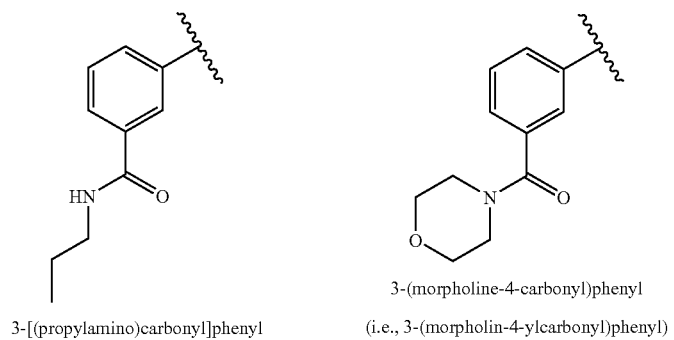

3-[(propylamino)carbonyl]phenyl 3-(morpholine-4-carbonyl)phenyl
(i.e., 3-(morpholin-4-ylcarbonyl)phenyl)

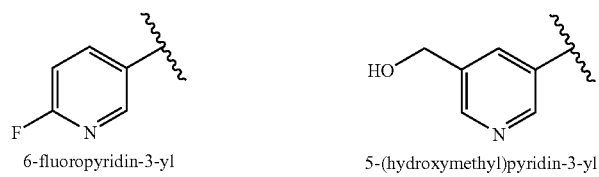

6-fluoropyridin-3-yl 5-(hydroxymethyl)pyridin-3-yl

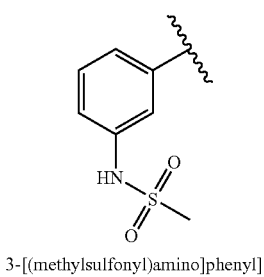

3-[(methylsulfonyl)amino]phenyl]

| $R_1$ | $R_2$ | $R_3$ |
|---|---|---|
| 2-hydroxy-2-methylpropyl | hydroxymethyl | 3-[propylamino)carbonyl]phenyl |
| 2-hydroxy-2-methylpropyl | hydroxymethyl | 3-(morpholin-4-ylcarbonyl)phenyl) |
| 2-hydroxy-2-methylpropyl | hydroxymethyl | 6-fluoropyridin-3-yl |
| 2-hydroxy-2-methylpropyl | hydroxymethyl | 5-(hydroxymethyl)pyridin-3-yl |
| 2-hydroxy-2-methylpropyl | hydroxymethyl | 3-[(methylsulfonyl)amino]phenyl |
| 2-hydroxy-2-methylpropyl | 2-hydroxyethyl | pyridin-3-yl |
| 2-hydroxy-2-methylpropyl | 2-hydroxyethyl | 3-[(isopropylamino)carbonyl]phenyl |
| 2-hydroxy-2-methylpropyl | 2-hydroxyethyl | 3-[(propylamino)carbonyl]phenyl |
| 2-hydroxy-2-methylpropyl | 2-hydroxyethyl | 3-(morpholin-4-ylcarbonyl)phenyl) |
| 2-hydroxy.-2-methylpropyl | 2-hydroxyethyl | 6-fluoropyridin-3-yl |
| 2-hydroxy-2-methylpropyl | 2-hydroxyethyl | 5-(hydroxymethyl)pyridin-3-yl |
| 2-hydroxy-2-methylpropyl | 2-hydroxyethyl | 3-[(methylsulfonyl)amino]phenyl |
| 2-methyipropyl | methyl | pyridin-3-yl |
| 2-methyipropyl | methyl | 3-[(isopropylamino)carbonyl]phenyl |
| 2-methyipropyl | methyl | 3-[(propylamino)carbonyl]phenyl |
| 2-methylpropyl | methyl | 3-(morpholin-4-ylcarbonyl)phenyl) |
| 2-methyipropyl | methyl | 6-fluoropyridin-3-yl |
| 2-methyipropyl | methyl | 5-(hydroxymethyl)pyridin-3-yl |
| 2-methyipropyl | methyl | 3-[(methylsulfonyl)amino]phenyl |
| 2-methyipropyl | ethyl | pyridin-3-yl |
| 2-methylpropyl | ethyl | 3-[(isopropylamino)carbonyl]phenyl |
| 2-methylpropyl | ethyl | 3-[(propylamino)carbonyl]phenyl |

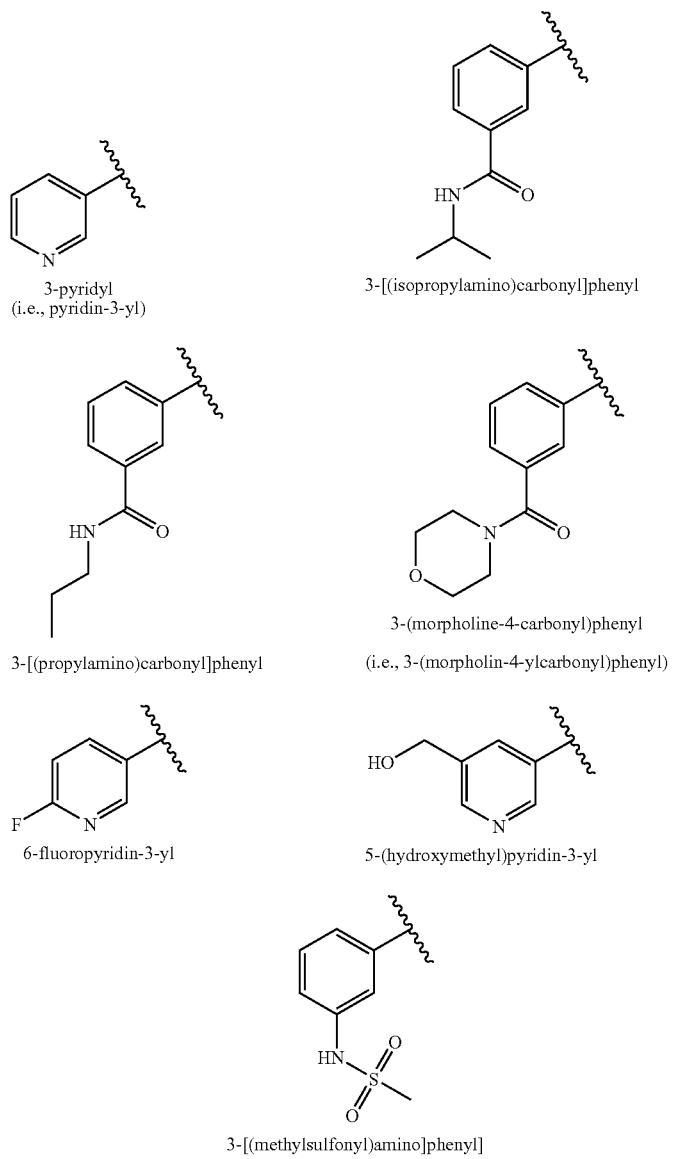

| $R_1$ | $R_2$ | $R_3$ |
|---|---|---|
| 2-methylpropyl | ethyl | 3-(morpholin-4-ylcarbonyl)phenyl |
| 2-methylpropyl | ethyl | 6-fluoropyridin-3-yl |
| 2-methylpropyl | ethyl | 5-(hydroxymethyl)pyridin-3-yl |
| 2-methylpropyl | ethyl | 3-[(methylsulfonyl)amino]phenyl |
| 2-methylpropyl | propyl | pyridin-3-yl |
| 2-methylpropyl | propyl | 3-[(isopropylamino)carbonyl]phenyl |
| 2-methylpropyl | propyl | 3-[(propylamino)carbonyl]phenyl |
| 2-methylpropyl | propyl | 3-(morpholn-4-ylcarbonyl)phenyl |
| 2-methylpropyl | propyl | 6-fluoropyridin-3-yl |
| 2-methylpropyl | propyl | 5-(hydroxymethyl)pyridin-3-yl |
| 2-methylpropyl | propyl | 3-[(methylsulfonyl)amino]phenyl |
| 2-methylpropyl | methoxymethyl | pyridin-3-yl |
| 2-methylpropyl | methoxymethyl | 3-[(isopropylamino)carbonyl]phenyl |
| 2-methylpropyl | methoxymethyl | 3-[(propylamino)carbonyl]phenyl |
| 2-methylpropyl | methoxymethyl | 3-(morpholin-4-ylcarbonyl)phenyl |
| 2-methylpropyl | methoxymethyl | 6-fluoropyridin-3-yl |
| 2-methylpropyl | methoxymethyl | 5-(hydroxymethyl)pyridin-3-yl |
| 2-methylpropyl | methoxymethyl | 3-[(methylsulfonyl)amino]phenyl |
| 2-methylpropyl | ethoxymethyl | pyridin-3-yl |
| 2-methylpropyl | ethoxymethyl | 3-[(isopropylamino)carbonyl]phenyl |
| 2-methylpropyl | ethoxymethyl | 3-[(propylamino)carbonyl]phenyl |
| 2-methylpropyl | ethoxymethyl | 3-(morpholin-4-ylcarbonyl)phenyl |

-continued

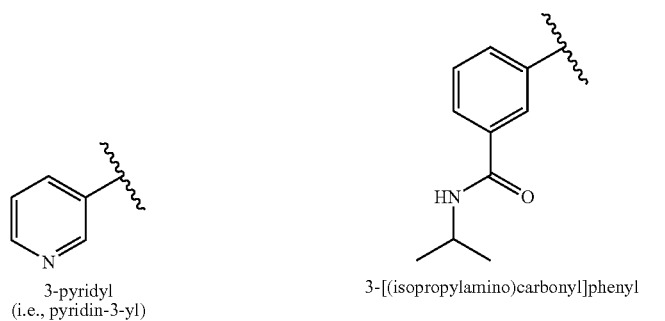

3-pyridyl
(i.e., pyridin-3-yl)

3-[(isopropylamino)carbonyl]phenyl

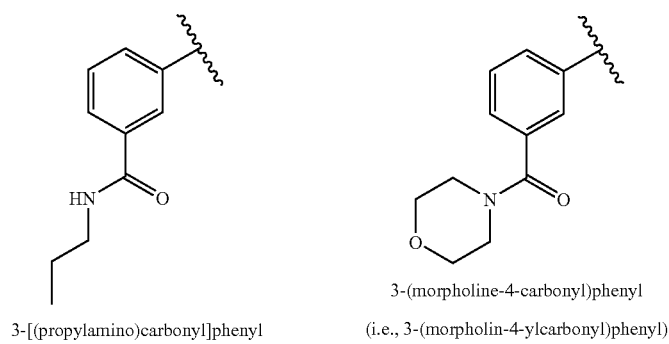

3-[(propylamino)carbonyl]phenyl 3-(morpholine-4-carbonyl)phenyl
(i.e., 3-(morpholin-4-ylcarbonyl)phenyl)

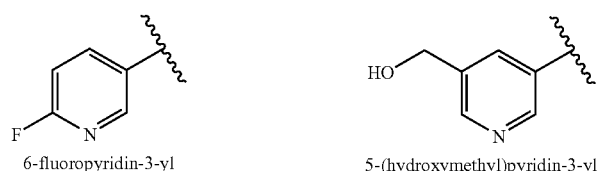

6-fluoropyridin-3-yl 5-(hydroxymethyl)pyridin-3-yl

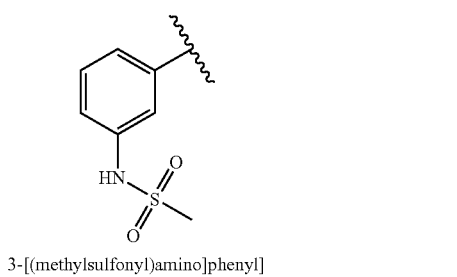

3-[(methylsulfonyl)amino]phenyl]

| R₁ | R₂ | R₃ |
|---|---|---|
| 2-methylpropyl | ethoxymethyl | 6-fluoropyridin-3-yl |
| 2-methylpropyl | ethoxymethyl | 5-(hydroxymethyl)pyridin-3-yl |
| 2-methylpropyl | ethoxymethyl | 3-[(methylsulfonyl)amino]phenyl |
| 2-methylpropyl | 2-methoxyethyl | pyridin-3-yl |
| 2-methylpropyl | 2-methoxyothyl | 3-[(isopropylamino)carbonyl]phenyl |
| 2-methylpropyl | 2-methoxyethyl | 3-[(propylamino)carbonyl]phenyl |
| 2-methylpropyl | 2-methoxyethyl | 3-(morpholin-4-ylcarbonyl)phenyl) |
| 2-methylpropyl | 2-methoxyethyl | 6-fluoropyridin-3-yl |
| 2-methylpropyl | 2-methoxyethyl | 5-(hydroxymethyl)pyridin-3-yl |
| 2-methylpropyl | 2-methoxyethyl | 3-[(methylsulfonyl)amino]phenyl |
| 2-methylpropyl | hydroxymethyl | pyridin-3-yl |
| 2-methylpropyl | hydroxymethyl | 3-[(isopropylamino)carbonyl]phenyl |
| 2-methylpropyl | hydroxymethyl | 3-[(propylamino)carbonyl]phenyl |
| 2-methylpropyl | hydroxymethyl | 3-(morpholin-4-ylcarbonyl)phenyl) |
| 2-methylpropyl | hydroxymethyl | 6-fluoropyridin-3-yl |
| 2-methylpropyl | hydroxymethyl | 5-(hydroxymethyl)pyridin-3-yl |
| 2-methylpropyl | hydroxymethyl | 3-[(methylsulfonyl)amino]phenyl |
| 2-methylpropyl | 2-hydroxyethyl | pyridin-3-yl |
| 2-methylpropyl | 2-hydroxyethyl | 3-[(isopropylamino)carbonyl]phenyl |
| 2-methylpropyl | 2-hydroxyethyl | 3-[(propylamino)carbonyl]phenyl |
| 2-methylpropyl | 2-hydroxyethyl | 3-(morpholin-4-ylcarbonyl)phenyl) |
| 2-methylpropyl | 2-hydroxyethyl | 6-fluoropyridin-3-yl |

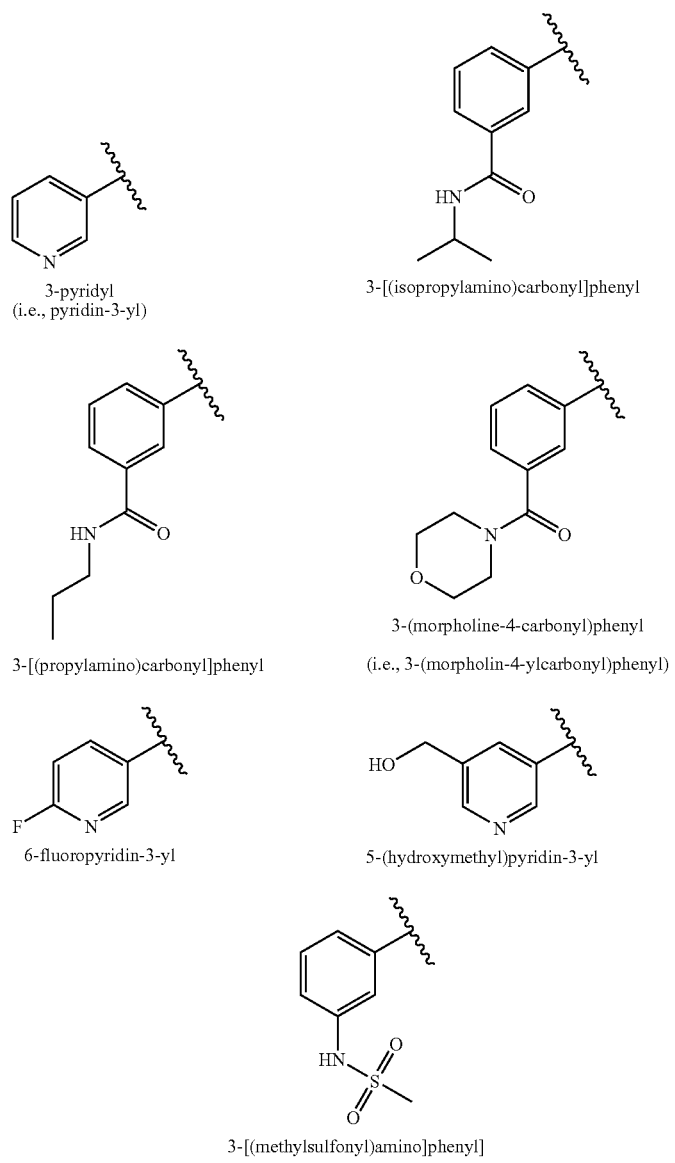

| R₁ | R₂ | R₃ |
| --- | --- | --- |
| 2-methylpropyl | 2-hydroxyethyl | 5-(hydroxymethyl)pyridin-3-yl |
| 2-methylpropyl | 2-hydroxyethyl | 3-[(methylsulfonyl)amino]phenyl |
| propyl | methyl | pyridin-3-yl |
| propyl | methyl | 3-[(isopropylamino)carbonyl]phenyl |
| propyl | methyl | 3-[(propylamino)carbonyl]phenyl |
| propyl | methyl | 3-(morpholin-4-ylcarbonyl)phenyl |
| propyl | methyl | 6-fluoropyridin-3-yl |
| propyl | methyl | 5-(hydroxymethyl)pyridin-3-yl |
| propyl | methyl | 3-[(methylsulfonyl)amino]phenyl |
| propyl | ethyl | pyridin-3-yl |
| propyl | ethyl | 3-[(isopropylamino)carbonyl]phenyl |
| propyl | ethyl | 3-[(propylamino)carbonyl]phenyl |
| propyl | ethyl | 3-(morpholin-4-ylcarbonyl)phenyl |
| propyl | ethyl | 6-fluoropyridin-3-yl |
| propyl | ethyl | 5-(hydroxymethyl)pyridin-3-yl |
| propyl | ethyl | 3-[(methylsulfonyl)amino]phenyl |
| propyl | propyl | pyridin-3-yl |
| propyl | propyl | 3-[(isopropylamino)carbonyl]phenyl |
| propyl | propyl | 3-[(propylamino)carbonyl]phenyl |
| propyl | propyl | 3-(morpholin-4-ylcarbonyl)phenyl |
| propyl | propyl | 6-fluoropyridin-3-yl |
| propyl | propyl | 5-(hydroxymethyl)pyridin-3-yl |

-continued

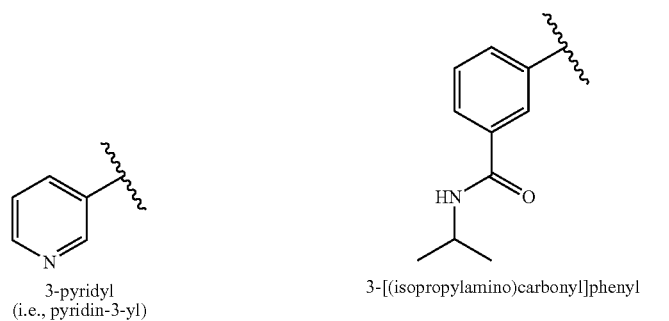

3-pyridyl
(i.e., pyridin-3-yl)

3-[(isopropylamino)carbonyl]phenyl

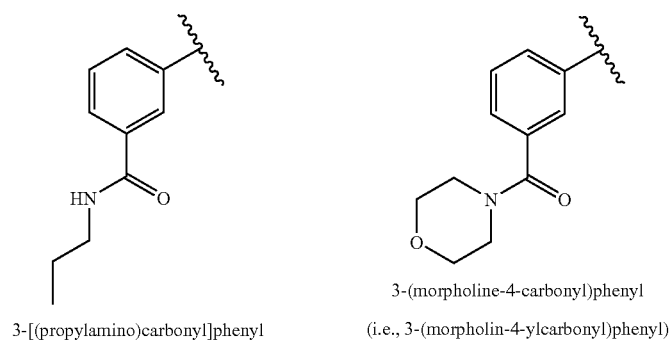

3-[(propylamino)carbonyl]phenyl 3-(morpholine-4-carbonyl)phenyl
(i.e., 3-(morpholin-4-ylcarbonyl)phenyl)

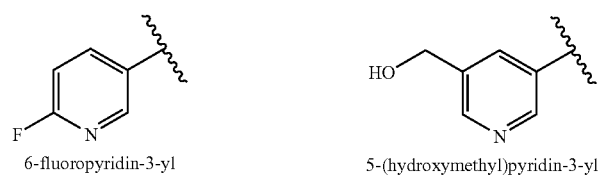

6-fluoropyridin-3-yl 5-(hydroxymethyl)pyridin-3-yl

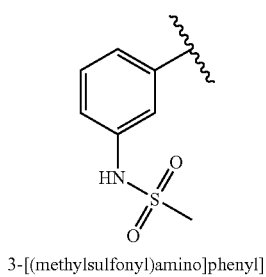

3-[(methylsulfonyl)amino]phenyl]

| $R_1$ | $R_2$ | $R_3$ |
|---|---|---|
| propyl | propyl | 3-[(methylsulfonyl)amino]phenyl |
| propyl | methoxymethyl | pyridin-3-yl |
| propyl | methoxymethyl | 3-[(isopropylamino)carbonyl]phenyl |
| propyl | methoxymethyl | 3-[(propylamino)carbonyl]phenyl |
| propyl | methoxymethyl | 3-(morpholin-4-ylcarbonyl)phenyl) |
| propyl | methoxymethyl | 6-fluoropyridin-3-yl |
| propyl | methoxymethyl | 5-(hydroxymethyl)pyridin-3-yl |
| propyl | methoxymethyl | 3-[(methylsulfonyl)amino]phenyl |
| propyl | ethoxymethyl | pyridin-3-yl |
| propyl | ethoxymethyl | 3-[(isopropylamino)carbonyl]phenyl |
| propyl | ethoxymethyl | 3-[(propylamino)carbonyl]phenyl |
| propyl | ethoxymethyl | 3-(morpholin-4-ylcarbonyl)phenyl) |
| propyl | ethoxymethyl | 6-fluoropyridin-3-yl |
| propyl | ethoxymethyl | 5-(hydroxymethyl)pyridin-3-yl |
| propyl | ethoxymethyl | 3-[(methylsulfonyl)amino]phenyl |
| propyl | 2-methoxyethyl | pyridin-3-yl |
| propyl | 2-methoxyethyl | 3-[(isopropylamino)carbonyl]phenyl |
| propyl | 2-methoxyethyl | 3-[(propylamino)carbonyl]phenyl |
| propyl | 2-methoxyethyl | 3-(morpholin-4-ylcarbonyl)phenyl) |
| propyl | 2-methoxyethyl | 6-fluoropyridin-3-yl |
| propyl | 2-methoxyethyl | 5-(hydroxymethyl)pyridin-3-yl |
| propyl | 2-methoxyethyl | 3-[(methylsulfonyl)amino]phenyl |

-continued

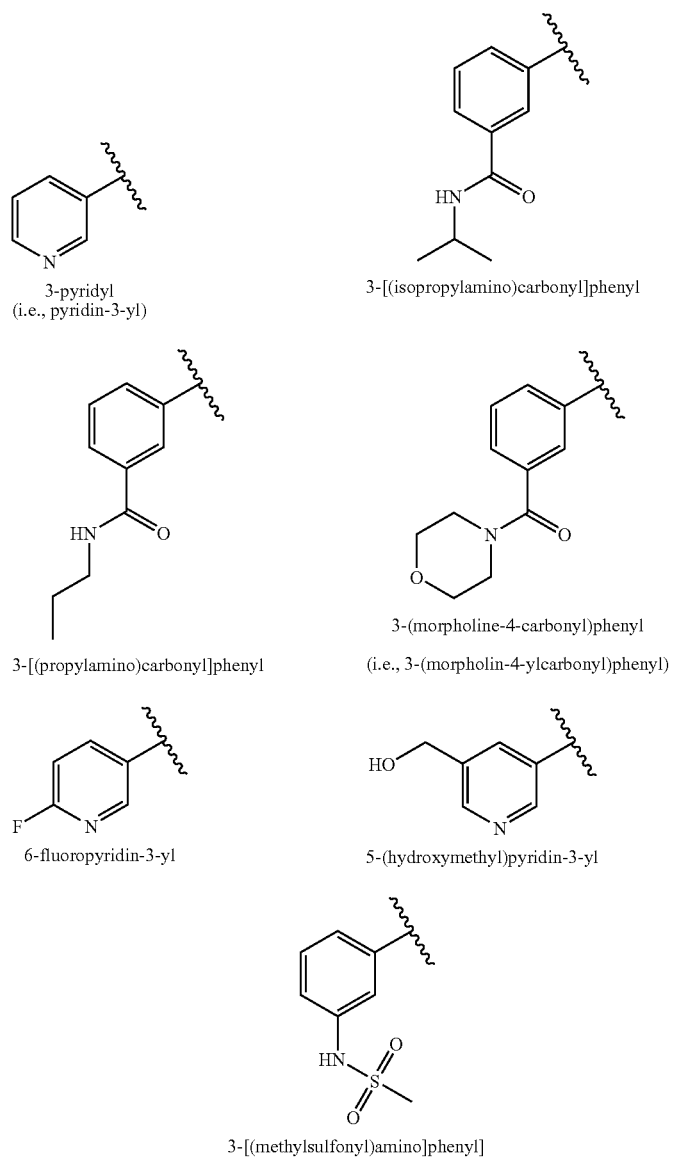

| R₁ | R₂ | R₃ |
|---|---|---|
| propyl | hydroxymethyl | pyridin-3-yl |
| propyl | hydroxymethyl | 3-[(isopropylamino)carbonyl]phenyl |
| propyl | hydroxymethyl | 3-[(propylamino)carbonyl]phenyl |
| propyl | hydroxymethyl | 3-(morpholin-4-ylcarbonyl)phenyl) |
| propyl | hydroxymethyl | 6-fluoropyridin-3-yl |
| propyl | hydroxymethyl | 5-(hydroxymethyl)pyridin-3-yl |
| propyl | hydroxymethyl | 3-[(methylsulfonyl)amino]phenyl |
| propyl | 2-hydroxyethyl | pyridin-3-yl |
| propyl | 2-hydroxyethyl | 3-[(isopropylamino)carbonyl]phenyl |
| propyl | 2-hydroxyethyl | 3-[(propylamino)carbonyl]phenyl |
| propyl | 2-hydroxyethyl | 3-(morpholin-4-ylcarbonyl)phenyl) |
| propyl | 2-hydroxyethyl | 6-fluoropyridin-3-yl |
| propyl | 2-hydroxyethyl | 5-(hydroxymethyl)pyridin-3-yl |
| propyl | 2-hydroxyethyl | 3-[(methylsulfonyl)amino]phenyl |
| 2,3-dihydroxypropyl | methyl | pyridin-3-yl |
| 2,3-dihydroxypropyl | methyl | 3-[(isopropylamino)carbonyl]phenyl |
| 2,3-dihydroxypropyl | methyl | 3-[(propylamino)carbonyl]phenyl |
| 2,3-dihydroxypropyl | methyl | 3-(morpholin-4-ylcarbonyl)phenyl) |
| 2,3-dihydroxypropyl | methyl | 6-fluoropyridin-3-yl |
| 2,3-dihydroxypropyl | methyl | 5-(hydroxymethyl)pyridin-3-yl |
| 2,3-dihydroxypropyl | methyl | 3-[(methylsulfonyl)amino]phenyl |
| 2,3-dihydroxypropyl | ethyl | pyridin-3-yl |

-continued

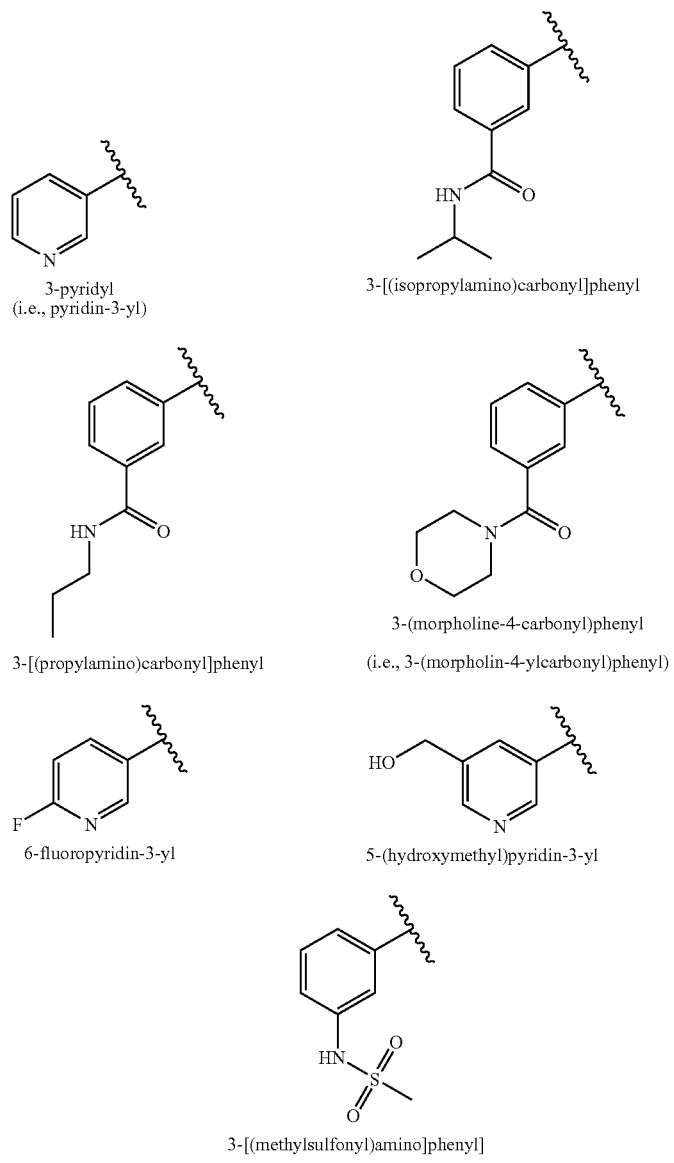

| R₁ | R₂ | R₃ |
|---|---|---|
| 2,3-dihydroxypropyl | ethyl | 3-[(isopropylamino)carbonyl]phenyl |
| 2,3-dihydroxypropyl | ethyl | 3-[(propylamino)carbonyl]phenyl |
| 2,3-dihydroxypropyl | ethyl | 3-(morpholin-4-ylcarbonyl)phenyl |
| 2,3-dihydroxypropyl | ethyl | 6-fluoropyridin-3-yl |
| 2,3-dihydroxypropyl | ethyl | 5-(hydroxymethyl)pyridin-3-yl |
| 2,3-dihydroxypropyl | ethyl | 3-[(methylsulfonyl)amino]phenyl |
| 2,3-dihydroxypropyl | propyl | pyridin-3-yl |
| 2,3-dihydroxypropyl | propyl | 3-[(isopropylamino)carbonyl]phenyl |
| 2,3-dihydroxypropyl | propyl | 3-[(propylamino)carbonyl]phenyl |
| 2,3-dihydroxypropyl | propyl | 3-(morpholin-4-ylcarbonyl)phenyl |
| 2,3-dihydroxypropyl | propyl | 6-fluoropyridin-3-yl |
| 2,3-dihydroxypropyl | propyl | 5-(hydroxymethyl)pyridin-3-yl |
| 2,3-dihydroxypropyl | propyl | 3-[(methylsulfonyl)amino]phenyl |
| 2,3-dihydroxypropyl | methoxymethyl | pyridin-3-yl |
| 2,3-dihydroxypropyl | methoxymethyl | 3-[(isopropylamino)carbonyl]phenyl |
| 2,3-dihydroxypropyl | methoxymethyl | 3-[(propylamino)carbonyl]phenyl |
| 2,3-dihydroxypropyl | methoxymethyl | 3-(morpholin-4-ylcarbonyl)phenyl |
| 2,3-dihydroxypropyl | methoxymethyl | 6-fluoropyridin-3-yl |
| 2,3-dihydroxypropyl | methoxymethyl | 5-(hydroxymethyl)pyridin-3-yl |
| 2,3-dihydroxypropyl | methoxymethyl | 3-[(methylsulfonyl)amino]phenyl |
| 2,3-dihydroxypropyl | ethoxymethyl | pyridin-3-yl |
| 2,3-dihydroxypropyl | ethoxymethyl | 3-[(isopropylamino)carbonyl]phenyl |

-continued

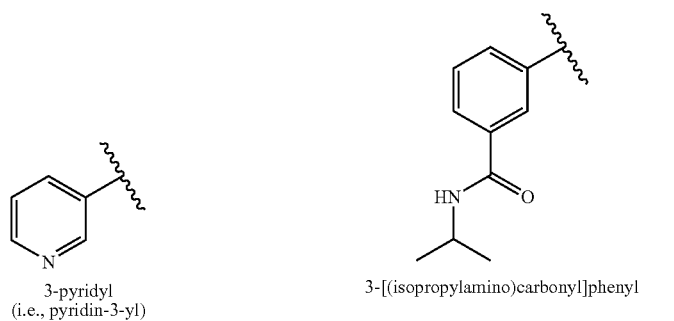

3-pyridyl
(i.e., pyridin-3-yl)

3-[(isopropylamino)carbonyl]phenyl

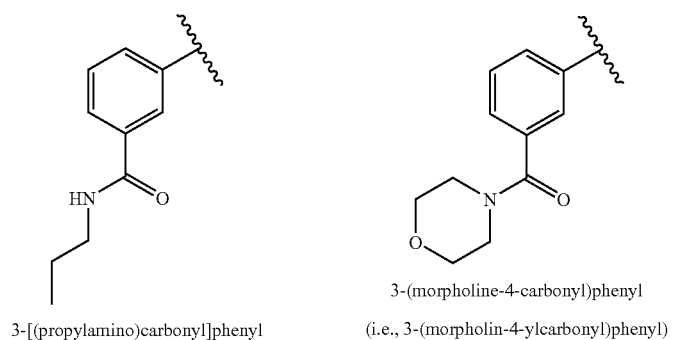

3-[(propylamino)carbonyl]phenyl 3-(morpholine-4-carbonyl)phenyl
(i.e., 3-(morpholin-4-ylcarbonyl)phenyl)

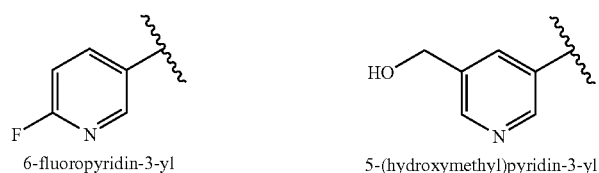

6-fluoropyridin-3-yl 5-(hydroxymethyl)pyridin-3-yl

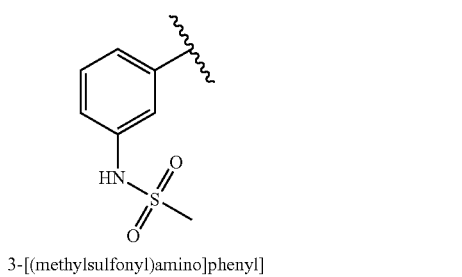

3-[(methylsulfonyl)amino]phenyl]

| $R_1$ | $R_2$ | $R_3$ |
|---|---|---|
| 2,3-dihydroxypropyl | ethoxymethyl | 3-[(propylamino)carbonyl]phenyl |
| 2,3-dihydroxypropyl | ethoxymethyl | 3-(morpholin-4-ylcarbonyl)phenyl |
| 2,3-dihydroxypropyl | ethoxymethyl | 6-fluoropyridin-3-yl |
| 2,3-dihydroxypropyl | ethoxymethyl | 5-(hydroxymethyl)pyridin-3-yl |
| 2,3-dihydroxypropyl | ethoxymethyl | 3-[(methylsulfonyl)amino]phenyl |
| 2,3-dihydroxypropyl | 2-methoxyethyl | pyridin-3-yl |
| 2,3-dihydroxypropyl | 2-methoxyethyl | 3-[(isopropylamino)carbonyl]phenyl |
| 2,3-dihydroxypropyl | 2-methoxyethyl | 3-[(propylamino)carbonyl]phenyl |
| 2,3-dihydroxypropyl | 2-methoxyethyl | 3-(morpholin-4-ylcarbonyl)phenyl |
| 2,3-dihydroxypropyl | 2-methoxyethyl | 6-fluoropyridin-3-yl |
| 2,3-dihydroxypropyl | 2-methoxyethyl | 5-(hydroxymethyl)pyridin-3-yl |
| 2,3-dihydroxypropyl | 2-methoxyethyl | 3-[(methylsulfonyl)amino]phenyl |
| 2,3-dihydroxypropyl | hydroxymethyl | pyridin-3-yl |
| 2,3-dihydroxypropyl | hydroxymethyl | 3-[(isopropylamino)carbonyl]phenyl |
| 2,3-dihydroxypropyl | hydroxymethyl | 3-[(propylamino)carbonyl]phenyl |
| 2,3-dihydroxypropyl | hydroxymethyl | 3-(morpholin-4-ylcarbonyl)phenyl |
| 2,3-dihydroxypropyl | hydroxymethyl | 6-fluoropyridin-3-yl |
| 2,3-dihydroxypropyl | hydroxymethyl | 5-(hydroxymethyl)pyridin-3-yl |
| 2,3-dihydroxypropyl | hydroxymethyl | 3-[(methylsulfonyl)amino]phenyl |
| 2,3-dihydroxypropyl | 2-hydroxyethyl | pyridin-3-yl |
| 2,3-dihydroxypropyl | 2-hydroxyethyl | 3-[(isopropylamino)carbonyl]phenyl |
| 2,3-dihydroxypropyl | 2-hydroxyethyl | 3-[(propylamino)carbonyl]phenyl |

-continued

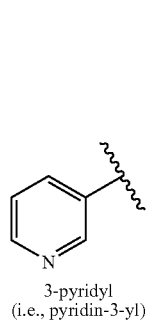
3-pyridyl
(i.e., pyridin-3-yl)

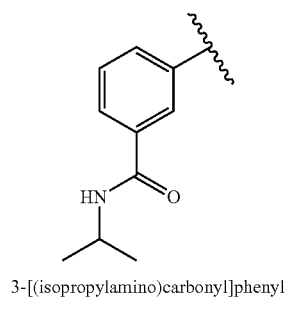
3-[(isopropylamino)carbonyl]phenyl

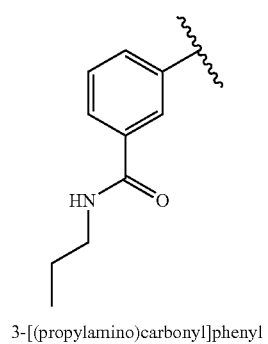
3-[(propylamino)carbonyl]phenyl

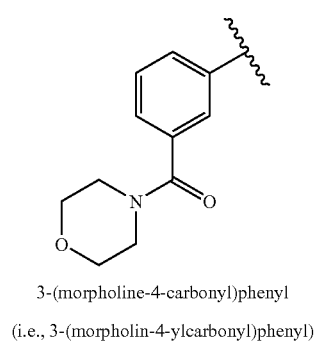
3-(morpholine-4-carbonyl)phenyl
(i.e., 3-(morpholin-4-ylcarbonyl)phenyl)

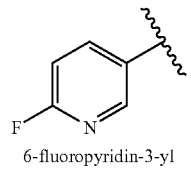
6-fluoropyridin-3-yl

5-(hydroxymethyl)pyridin-3-yl

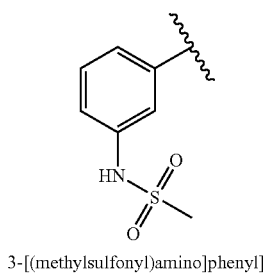
3-[(methylsulfonyl)amino]phenyl]

| R₁ | R₂ | R₃ |
|---|---|---|
| 2,3-dihydroxypropyl | 2-hydroxyethyl | 3-(morpholin-4-ylcarbonyl)phenyl |
| 2,3-dihydroxypropyl | 2-hydroxyethyl | 6-fluoropyridin-3-yl |
| 2,3-dihydroxypropyl | 2-hydroxyethyl | 5-(hydroxymethyl)pyridin-3-yl |
| 2,3-dihydroxypropyl | 2-hydroxyethyl | 3-[(methylsulfonyl)amino]phenyl |
| 2-methyl-2-[(methylsulfonyl)amino]propyl | methyl | pyridin-3-yl |
| 2-methyl-2-[(methylsulfonyl)amino]propyl | methyl | 3-[(isopropylamino)carbonyl]phenyl |
| 2-methyl-2-[(methylsulfonyl)amino]propyl | methyl | 3-[(propylamino)carbonyl]phenyl |
| 2-methyl-2-[(methylsulfonyl)amino]propyl | methyl | 3-(morphohn-4-ylcarbonyl)phenyl) |
| 2-methyl-2-[(methylsulfonyl)amino]propyl | methyl | 6-fluoropyridin-3-yl |
| 2-methyl-2-[(methylsulfonyl)amino]propyl | methyl | 5-(hydroxymethyl)pyridin-3-yl |
| 2-methyl-2-[(methylsulfonyl)amino]propyl | methyl | 3-[(methylsulfonyl)amino]phenyl |
| 2-methyl-2-[(methylsulfonyl)amino]propyl | ethyl | pyridin-3-yl |
| 2-methyl-2-[(methylsulfonyl)amino]propyl | ethyl | 3-[(isopropylamino)carbonyl]phenyl |

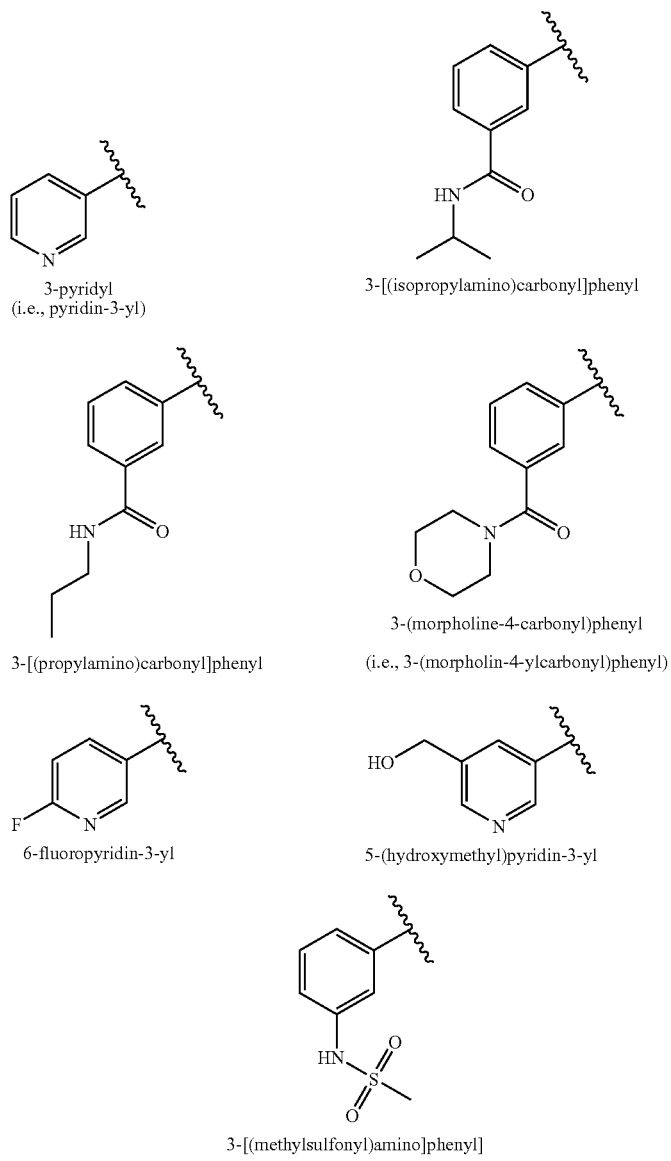

| R₁ | R₂ | R₃ |
| --- | --- | --- |
| 2-methyl-2-[(methylsulfonyl)amino]propyl | ethyl | 3-[(propylamino)carbonyl]phenyl |
| 2-methyl-2-[(methylsulfonyl)amino]propyl | ethyl | 3-(morpholin-4-ylcarbonyl)phenyl) |
| 2-methyl-2-[(methylsulfonyl)amino]propyl | ethyl | 6-fluoropyridin-3-yl |
| 2-methyl-2-[(methylsulfonyl)amino]propyl | ethyl | 5-(hydroxymethyl)pyridin-3-yl |
| 2-methyl-2-[(methylsulfonyl)amino]propyl | ethyl | 3-[(methylsulfonyl)amino]phenyl |
| 2-methyl-2-[(methylsulfonyl)amino]propyl | propyl | pyridin-3-.yl |
| 2-methyl-2-[(methylsulfonyl)amino]propyl | propyl | 3-[(isopropylamino)carbonyl]phenyl |
| 2-methyl-2-[(methylsulfonyl)amino]propyl | propyl | 3-[(propylamino)carbonyl]phenyl |
| 2-methyl-2-[(methylsulfonyl)amino]propyl | propyl | 3-(morpholin-4-ylcarbonyl)phenyl) |
| 2-methyl-2-[(methylsulfonyl)amino]propyl | propyl | 6-fluoropyridin-3-yl |
| 2-methyl-2-[(methylsulfonyl)amino]propyl | propyl | 5-(hydroxymethyl)pyridin-3-yl |

-continued

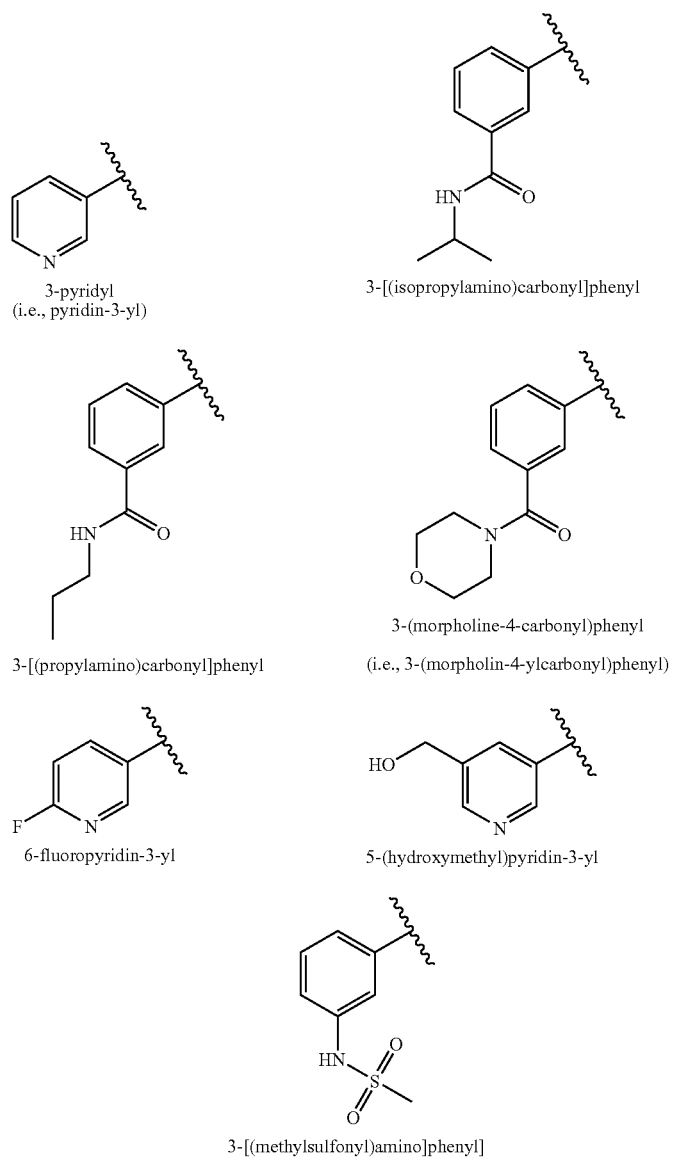

| R₁ | R₂ | R₃ |
|---|---|---|
| 2-methyl-2-[(methylsulfonyl)amino]propyl | propyl | 3-[(methylsulfonyl)amino]phenyl |
| 2-methyl-2-[(methylsulfonyl)amino]propyl | methoxymethyl | pyridin-3-yl |
| 2-methyl-2-[(methylsulfonyl)amino]propyl | methoxymethyl | 3-[(isopropylamino)carbonyl]phenyl |
| 2-methyl-2-[(methylsulfonyl)amino]propyl | methoxymethyl | 3-[(propylamino)carbonyl]phenyl |
| 2-methyl-2-[(methylsulfonyl)amino]propyl | methoxymethyl | 3-(morpholin-4-ylcarbonyl)phenyl) |
| 2-methyl-2-[(methylsulfonyl)amino]propyl | methoxymethyl | 6-fluoropyridin-3-yl |
| 2-methyl-2-[(methylsulfonyl)amino]propyl | methoxymethyl | 5-(hydroxymethyl)pyridin-3-yl |
| 2-methyl-2-[(methylsulfonyl)amino]propyl | methoxymethyl | 3-[(methylsulfonyl)amino]phenyl |
| 2-methyl-2-[(methylsulfonyl)amino]propyl | ethoxymethyl | pyridin-3-yl |
| 2-methyl-2-[(methylsulfonyl)amino]propyl | ethoxymethyl | 3-[(isopropylamino)carbonyl]phenyl |
| 2-methyl-2-[(methylsulfonyl)amino]propyl | ethoxymethyl | 3-[(propylamino)carbonyl]phenyl |

-continued

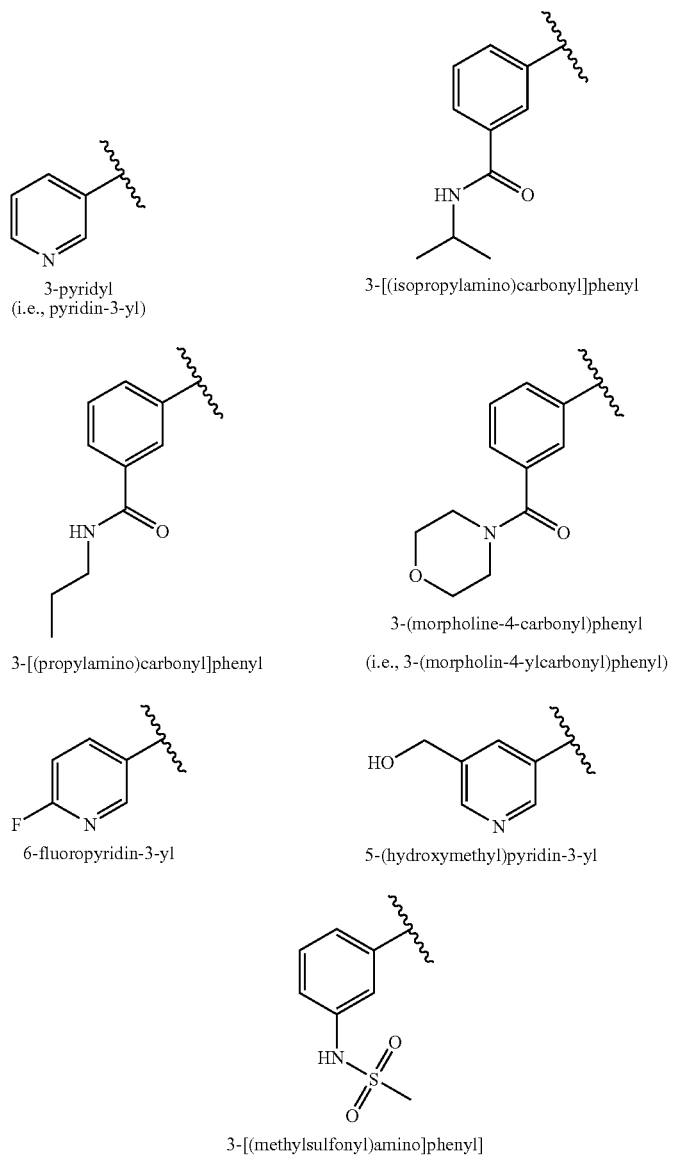

| R₁ | R₂ | R₃ |
|---|---|---|
| 2-methyl-2-[(methylsulfonyl)amino]propyl | ethoxymethyl | 3-(morpholin-4-ylcarbonyl)phenyl |
| 2-methyl-2-[(methylsulfonyl)amino]propyl | ethoxymethyl | 6-fluoropyridin-3-yl |
| 2-methyl-2-[(methylsulfonyl)amino]propyl | ethoxymethyl | 5-(hydroxymethyl)pyridin-3-yl |
| 2-methyl-2-[(methylsulfonyl)amino]propyl | ethoxymethyl | 3-[(methylsulfonyl)amino]phenyl |
| 2-methyl-2-[(methylsulfonyl)amino]propyl | 2-methoxyethyl | pyridin-3-yl |
| 2-methyl-2-[(methylsulfonyl)amino]propyl | 2-methoxyethyl | 3-[(isopropylamino)carbonyl]phenyl |
| 2-methyl-2-[(methylsulfonyl)amino]propyl | 2-methoxyethyl | 3-[(propylamino)carbonyl]phenyl |
| 2-methyl-2-[(methylsulfonyl)amino]propyl | 2-methoxyethyl | 3-(morphohn-4-ylcarbonyl)phenyl |
| 2-methyl-2-[(methylsulfonyl)amino]propyl | 2-methoxyethyl | 6-fluoropyridin-3-yl |
| 2-methyl-2-[(methylsulfonyl)amino]propyl | 2-methoxyethyl | 5-(hydroxymethyl)pyridin-3-yl |
| 2-methyl-2-[(methylsulfonyl)amino]propyl | 2-methoxyethyl | 3-[(methylsulfonyl)amino]phenyl |

-continued

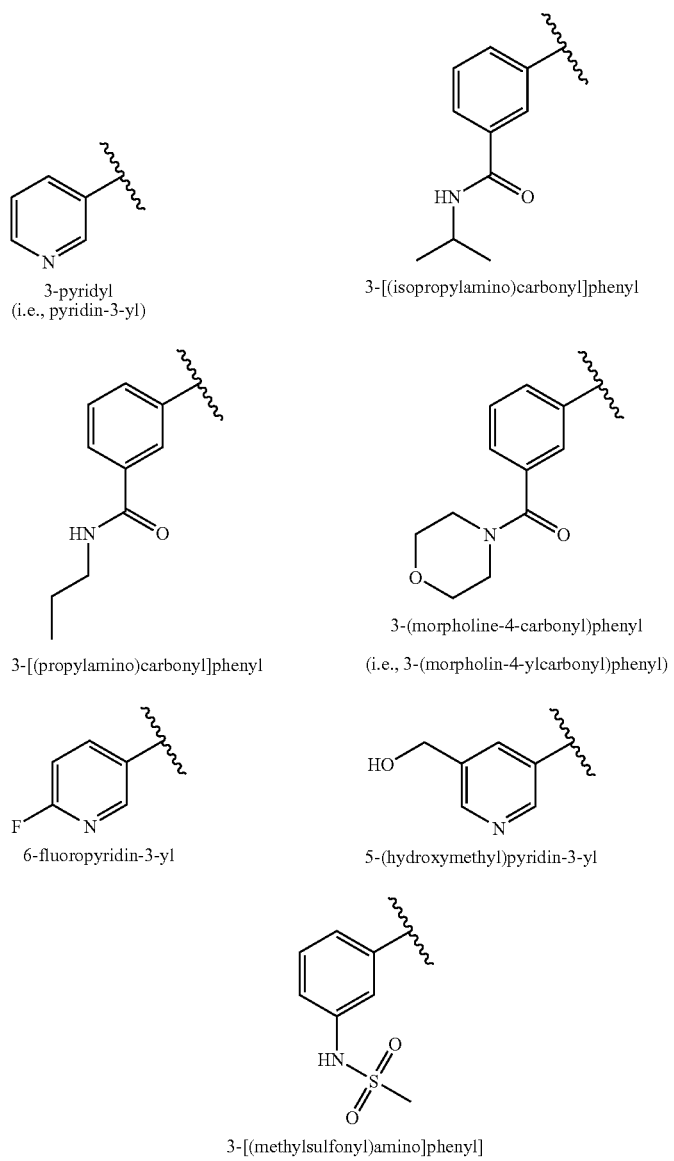

| R₁ | R₂ | R₃ |
| --- | --- | --- |
| 2-methyl-2-[(methylsulfonyl)amino]propyl | hydroxymethyl | pyridin-3-yl |
| 2-methyl-2-[(methylsulfonyl)amino]propyl | hydroxymethyl | 3-[(isopropylamino)carbonyl]phenyl |
| 2-methyl-2-[(methylsulfonyl)amino]propyl | hydroxymethyl | 3-[(propylamino)carbonyl]phenyl |
| 2-methyl-2-[(methylsulfonyl)amino]propyl | hydroxymethyl | 3-(morpholin-4-ylcarbonyl)phenyl) |
| 2-methyl-2-[(methylsulfonyl)amino]propyl | hydroxymethyl | 6-fluoropyridin-3-yl |
| 2-methyl-2-[(methylsulfonyl)amino]propyl | hydroxymethyl | 5-(hydroxymethyl)pyridin-3-yl |
| 2-methyl-2-[(methylsulfonyl)amino]propyl | hydroxymethyl | 3-[(methylsulfonyl)amino]phenyl |
| 2-methyl-2-[(methylsulfonyl)amino]propyl | 2-hydroxyethyl | pyridin-3-yl |
| 2-methyl-2-[(methylsulfonyl)amino]propyl | 2-hydroxyethyl | 3-[(isopropylamino)carbonyl]phenyl |
| 2-methyl-2-[(methylsulfonyl)amino]propyl | 2-hydroxyethyl | 3-[(propylamino)carbonyl]phenyl |
| 2-methyl-2-[(methylsulfonyl)amino]propyl | 2-hydroxyethyl | 3-(morphohn-4-ylcarbonyl)phenyl) |

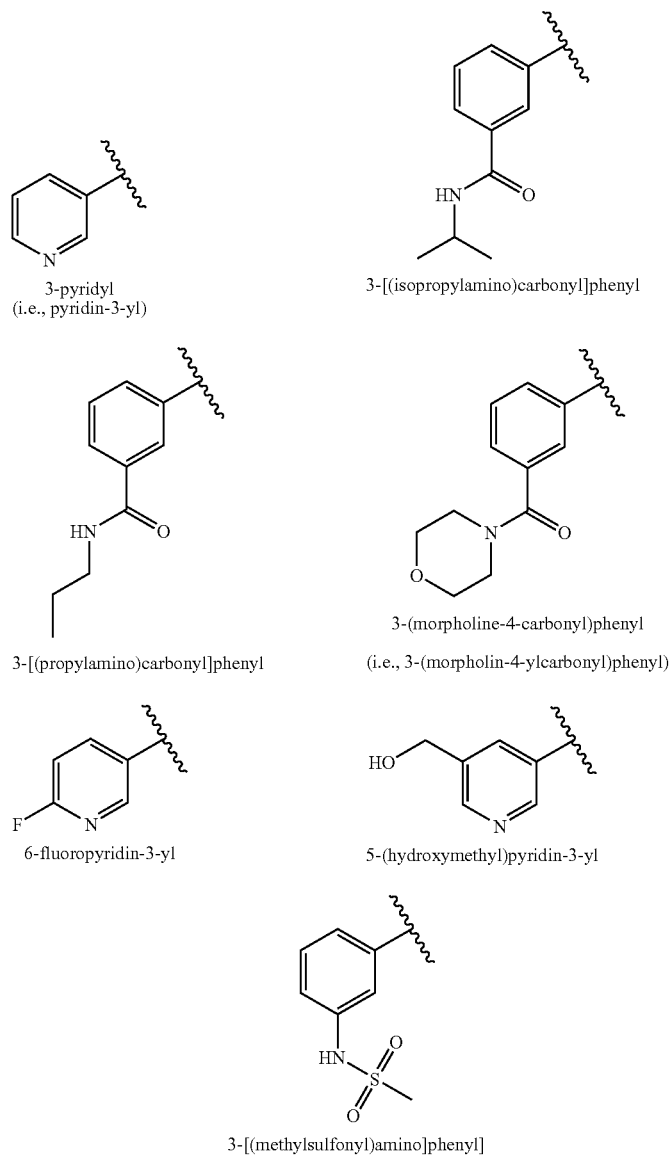

3-pyridyl
(i.e., pyridin-3-yl)

3-[(isopropylamino)carbonyl]phenyl

3-[(propylamino)carbonyl]phenyl 3-(morpholine-4-carbonyl)phenyl
(i.e., 3-(morpholin-4-ylcarbonyl)phenyl)

6-fluoropyridin-3-yl 5-(hydroxymethyl)pyridin-3-yl

3-[(methylsulfonyl)amino]phenyl]

| R$_1$ | R$_2$ | R$_3$ |
| --- | --- | --- |
| 2-methyl-2-[(methylsulfonyl)amino]propyl | 2-hydroxyethyl | 6-fluoropyridin-3-yl |
| 2-methyl-2-[(methylsulfonyl)amino]propyl | 2-hydroxyethyl | 5-(hydroxymethyl)pyridin-3-yl |
| 2-methyl-2-[(methylsulfonyl)amino]propyl | 2-hydroxyothyl | 3-[(methylsulfonyl)amino]phenyl |
| 4-[(methylsulfonyl)amino]butyl | methyl | pyridin-3-yl |
| 4-[(methylsulfonyl)amino]butyl | methyl | 3-[(isopropylamino)carbonyl]phenyl |
| 4-[(methylsulfonyl)amino]butyl | methyl | 3-[(propylamino)carbonyl]phenyl |
| 4-[(methylsulfonyl)amino]butyl | methyl | 3-(morpholin-4-ylcarbonyl)phenyl) |
| 4-[(methylsulfonyl)amino]butyl | methyl | 6-fluoropyridin-3-yl |
| 4-[(methylsulfonyl)amino]butyl | methyl | 5-(hydroxymethyl)pyridin-3-yl |
| 4-[(methylsulfonyl)amino]butyl | methyl | 3-[(methylsulfonyl)amino]phenyl |
| 4-[(methylsulfonyl)amino]butyl | ethyl | pyridin-3-yl |
| 4-[(methylsulfonyl)amino]butyl | ethyl | 3-[(isopropylamino)carbonyl]phenyl |
| 4-[(methylsulfonyl)amino]butyl | ethyl | 3-[(propylamino)carbonyl]phenyl |
| 4-[(methylsulfonyl)amino]butyl | ethyl | 3-(morpholin-4-ylcarbonyl)phenyl) |
| 4-[(methylsulfonyl)amino]butyl | ethyl | 6-fluoropyridin-3-yl |
| 4-[(methylsulfonyl)amino]butyl | ethyl | 5-(hydroxymethyl)pyridin-3-yl |
| 4-[(methylsulfonyl)amino]butyl | ethyl | 3-[(methylsulfonyl)amino]phenyl |
| 4-[(methylsulfonyl)amino]butyl | propyl | pyridin-3-yl |
| 4-[(methylsulfonyl)amino]butyl | propyl | 3-[(isopropylamino)carbonyl]phenyl |

-continued

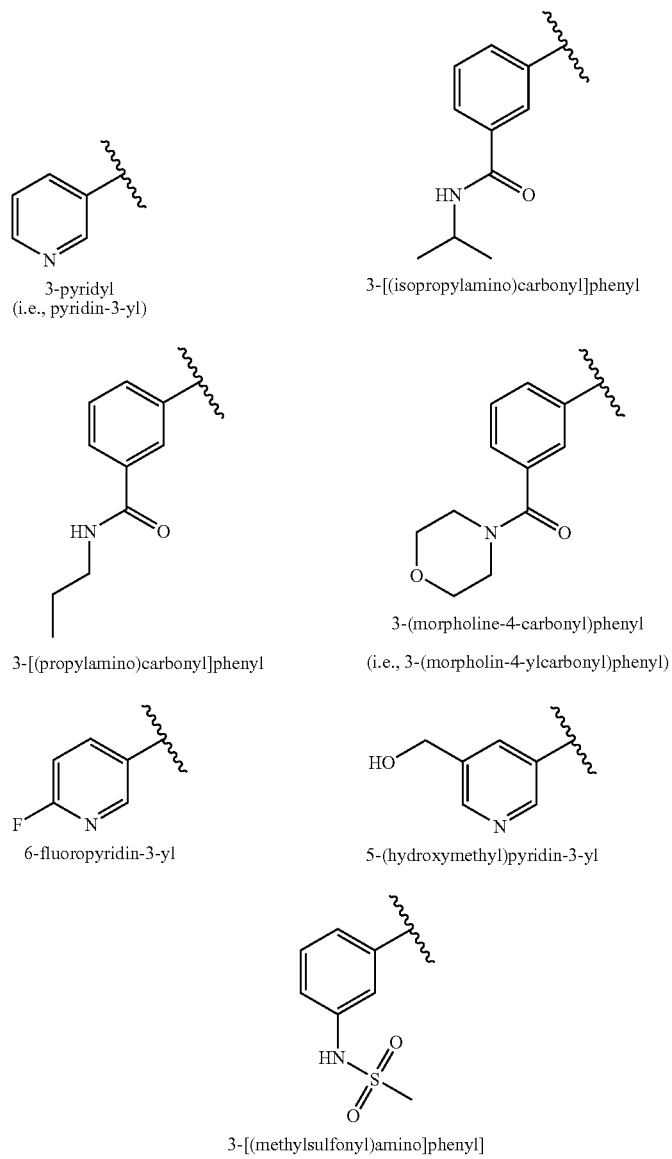

| R₁ | R₂ | R₃ |
|---|---|---|
| 4-[(methylsulfonyl)amino]butyl | propyl | 3-[(propylamino)carbonyl]phenyl |
| 4-[(methylsulfonyl)amino]butyl | propyl | 3-(morpholin-4-ylcarbonyl)phenyl |
| 4-[(methylsulfonyl)amino]butyl | propyl | 6-fluoropyridin-3-yl |
| 4-[(methylsulfonyl)amino]butyl | propyl | 5-(hydroxymethyl)pyridin-3-yl |
| 4-[(methylsulfonyl)amino]butyl | propyl | 3-[(methylsulfonyl)amino]phenyl |
| 4-[(methylsulfonyl)amino]butyl | methoxymethyl | pyridin-3-yl |
| 4-[(methylsulfonyl)amino]butyl | methoxymethyl | 3-[(isopropylamino)carbonyl]phenyl |
| 4-[(methylsulfonyl)amino]butyl | methoxymethyl | 3-[(propylamino)carbonyl]phenyl |
| 4-[(methylsulfonyl)amino]butyl | methoxymethyl | 3-(morpholin-4-ylcarbonyl)phenyl |
| 4-[(methylsulfonyl)amino]butyl | methoxymethyl | 6-fluoropyridin-3-yl |
| 4-[(methylsulfonyl)amino]butyl | methoxymethyl | 5-(hydroxymethyl)pyridin-3-yl |
| 4-[(methylsulfonyl)amino]butyl | methoxymethyl | 3-[(methylsulfonyl)amino]phenyl |
| 4-[(methylsulfonyl)amino]butyl | ethoxymethyl | pyridin-3-yl |
| 4-[(methylsulfonyl)amino]butyl | ethoxymethyl | 3-[(isopropylamino)carbonyl]phenyl |
| 4-[(methylsulfonyl)amino]butyl | ethoxymethyl | 3-[(propylamino)carbonyl]phenyl |
| 4-[(methylsulfonyl)amino]butyl | ethoxymethyl | 3-(morpholin-4-ylcarbonyl)phenyl |
| 4-[(methylsulfonyl)amino]butyl | ethoxymethyl | 6-fluoropyridin-3-yl |
| 4-[(methylsulfonyl)amino]butyl | ethoxymethyl | 5-(hydroxymethyl)pyridin-3-yl |
| 4-[(methylsulfonyl)amino]butyl | ethoxymethyl | 3-[(methylsulfonyl)amino]phenyl |
| 4-[(methylsulfonyl)amino]butyl | 2-methoxyethyl | pyridin-3-yl |
| 4-[(methylsulfonyl)amino]butyl | 2-methoxyethyl | 3-[(isopropylamino)carbonyl]phenyl |
| 4-[(methylsulfonyl)amino]butyl | 2-methoxyethyl | 3-[(propylamino)carbonyl]phenyl |

-continued

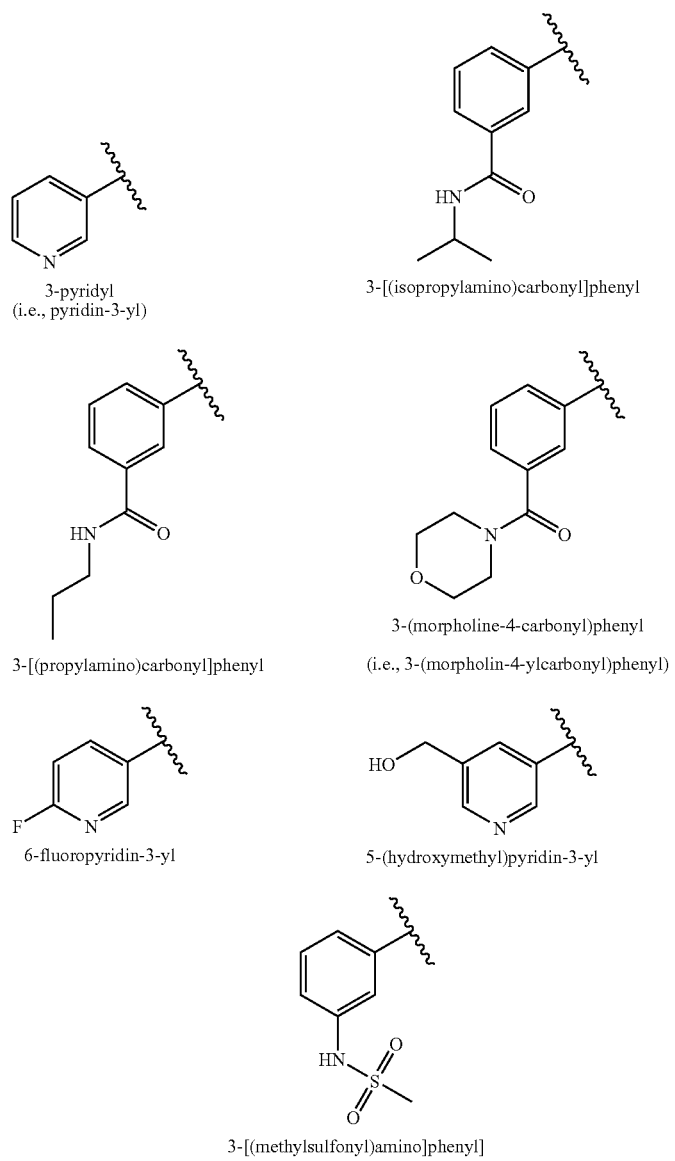

| R₁ | R₂ | R₃ |
|---|---|---|
| 4-[(methylsulfonyl)amino]butyl | 2-methoxyethyl | 3-(morpholin-4-ylcarbonyl)phenyl |
| 4-[(methylsulfonyl)amino]butyl | 2-methoxyethyl | 6-fluoropyridin-3-yl |
| 4-[(methylsulfonyl)amino]butyl | 2-methoxyethyl | 5-(hydroxymethyl)pyridin-3-yl |
| 4-[(methylsulfonyl)amino]butyl | 2-methoxyethyl | 3-[(methylsulfonyl)amino]phenyl |
| 4-[(methylsulfonyl)amino]butyl | hydroxymethyl | pyridin-3-yl |
| 4-[(methylsulfonyl)amino]butyl | hydroxymethyl | 3-[(isopropylamino)carbonyl]phenyl |
| 4-[(methylsulfonyl)amino]butyl | hydroxymethyl | 3-[(propylamino)carbonyl]phenyl |
| 4-[(methylsulfonyl)amino]butyl | hydroxymethyl | 3-(morpholin-4-ylcarbonyl)phenyl |
| 4-[(methylsulfonyl)amino]butyl | hydroxymethyl | 6-fluoropyridin-3-yl |
| 4-[(methylsulfonyl)amino]butyl | hydroxymethyl | 5-(hydroxymethyl)pyridin-3-yl |
| 4-[(methylsulfonyl)amino]butyl | hydroxymethyl | 3-[(methylsulfonyl)amino]phenyl |
| 4-[(methylsulfonyl)amino]butyl | 2-hydroxyethyl | pyridin-3-yl |
| 4-[(methylsulfonyl)amino]butyl | 2-hydroxyethyl | 3-[(isopropylamino)carbonyl]phenyl |
| 4-[(methylsulfonyl)amino]butyl | 2-hydroxyethyl | 3-[(propylamino)carbonyl]phenyl |
| 4-[(methylsulfonyl)amino]butyl | 2-hydroxyethyl | 3-(morpholin-4-ylcarbonyl)phenyl |
| 4-[(methylsulfonyl)amino]butyl | 2-hydroxyethyl | 6-fluoropyridin-3-yl |
| 4-[(methylsulfonyl)amino]butyl | 2-hydroxyethyl | 5-(hydroxymethyl)pyridin-3-yl |
| 4-[(methylsulfonyl)amino]butyl | 2-hydroxyethyl | 3-[(methylsulfonyl)amino]phenyl |
| 2-fluoro-2-methylpropyl | methyl | pyridin-3-yl |
| 2-fluoro-2-methylpropyl | methyl | 3-[(isopropylamino)carbonyl]phenyl |
| 2-fluoro-2-methylpropyl | methyl | 3-[(propylamino)carbonyl]phenyl |
| 2-fluoro-2-methylpropyl | methyl | 3-(morpholin-4-ylcarbonyl)phenyl |

-continued

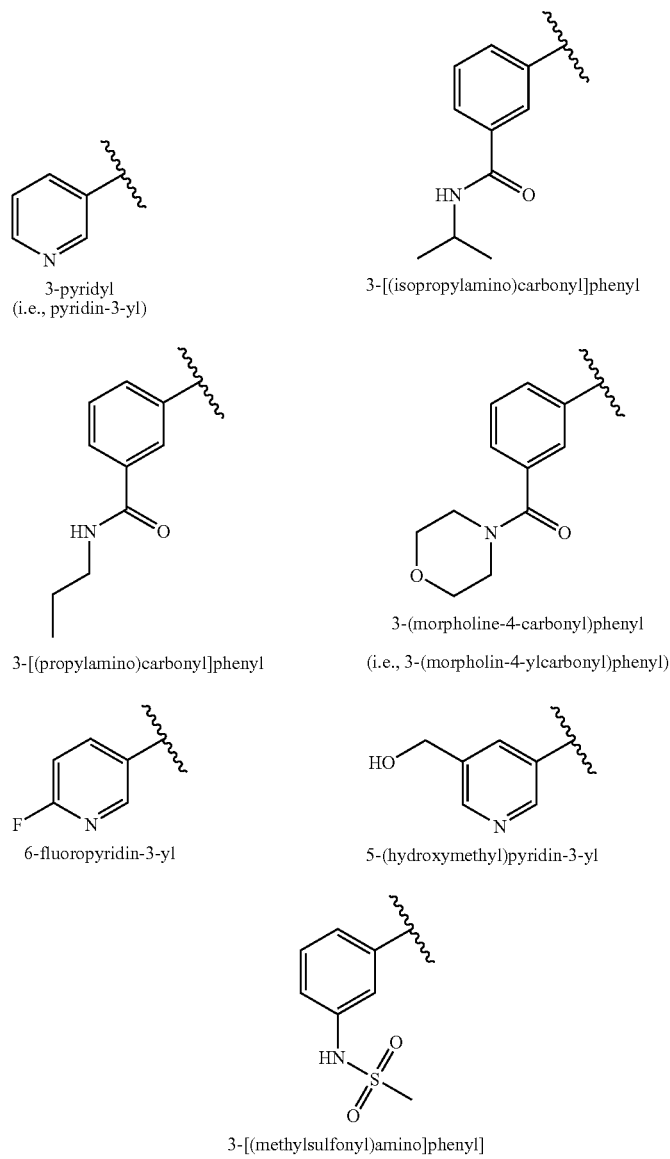

| R₁ | R₂ | R₃ |
|---|---|---|
| 2-fluoro-2-methylpropyl | methyl | 6-fluoropyridin-3-yl |
| 2-fluoro-2-methylpropyl | methyl | 5-(hydroxymethyl)pyridin-3-yl |
| 2-fluoro-2-methylpropyl | methyl | 3-[(methylsulfonyl)amino]phenyl |
| 2-fluoro-2-methylpropyl | ethyl | pyridin-3-yl |
| 2-fluoro-2-methylpropyl | ethyl | 3-[(isopropylamino)carbonyl]phenyl |
| 2-fluoro-2-methylpropyl | ethyl | 3-[(propylamino)carbonyl]phenyl |
| 2-fluoro-2-methylpropyl | ethyl | 3-(morpholin-4-ylcarbonyl)phenyl |
| 2-fluoro-2-methylpropyl | ethyl | 6-fluoropyridin-3-yl |
| 2-fluoro-2-methylpropyl | ethyl | 5-(hydroxymethyl)pyridin-3-yl |
| 2-fluoro-2-methylpropyl | ethyl | 3-[(methylsulfonyl)amino]phenyl |
| 2-fluoro-2-methylpropyl | propyl | pyridin-3-yl |
| 2-fluoro-2-methylpropyl | propyl | 3-[(isopropylamino)carbonyl]phenyl |
| 2-fluoro-2-methylpropyl | propyl | 3-[propylamino)carbonyl]phenyl |
| 2-fluoro-2-methylpropyl | propyl | 3-(morphohn-4-ylcarbonyl)phenyl |
| 2-fluoro-2-methylpropyl | propyl | 6-fluoropyridin-3-yl |
| 2-fluoro-2-methylpropyl | propyl | 5-(hydroxymethyl)pyridin-3-yl |
| 2-fluoro-2-methylpropyl | propyl | 3-[(methylsulfonyl)amino]phenyl |
| 2-fluoro-2-methylpropyl | methoxymethyl | pyridin-3-yl |
| 2-fluoro-2-methylpropyl | methoxymethyl | 3-[(isopropylamino)carbonyl]phenyl |
| 2-fluoro-2-methylpropyl | methoxymethyl | 3-[(propylamino)carbonyl]phenyl |
| 2-fluoro-2-methylpropyl | methoxymethyl | 3-(morpholin-4-ylcarbonyl)phenyl |
| 2-fluoro-2-methylpropyl | methoxymethyl | 6-fluoropyridin-3-yl |

-continued

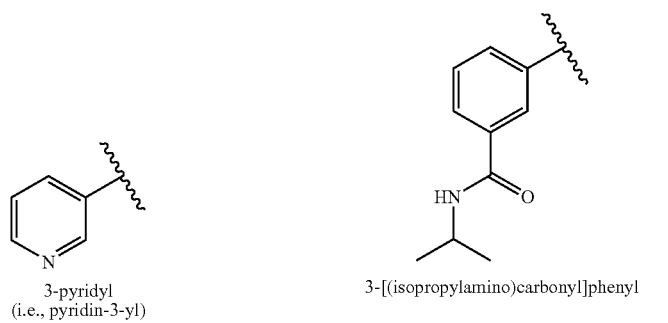

3-pyridyl
(i.e., pyridin-3-yl)

3-[(isopropylamino)carbonyl]phenyl

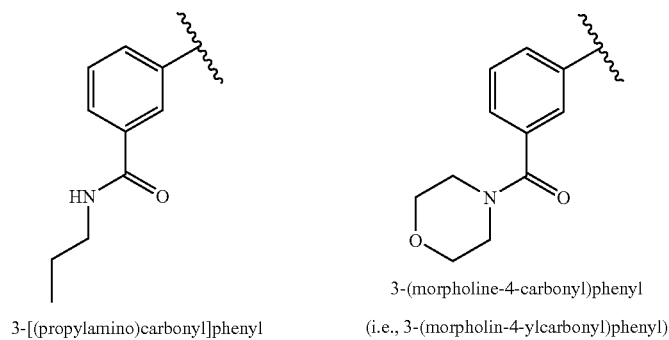

3-[(propylamino)carbonyl]phenyl 3-(morpholine-4-carbonyl)phenyl
(i.e., 3-(morpholin-4-ylcarbonyl)phenyl)

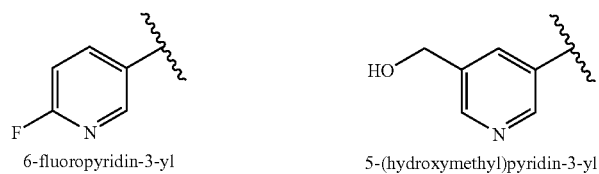

6-fluoropyridin-3-yl 5-(hydroxymethyl)pyridin-3-yl

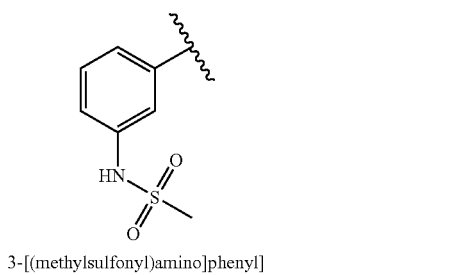

3-[(methylsulfonyl)amino]phenyl]

| $R_1$ | $R_2$ | $R_3$ |
|---|---|---|
| 2-fluoro-2-methylpropyl | methoxyinethyl | 5-(hydroxymethyl)pyridin-3-yl |
| 2-fluoro-2-methylpropyl | methoxyinethyl | 3-[(methylsulfonyl)amino]phenyl |
| 2-fluoro-2-methylpropyl | ethoxymethyl | pyridin-3-yl |
| 2-fluoro-2-methylpropyl | ethoxymethyl | 3-[(isopropylamino)carbonyl]phenyl |
| 2-fluoro-2-methylpropyl | ethoxymethyl | 3-[(propylamino)carbonyl]phenyl |
| 2-fluoro-2-methylpropyl | ethoxymethyl | 3-(morpholin-4-ylcarbonyl)phenyl |
| 2-fluoro-2-methylpropyl | ethoxymethyl | 6-fluoropyridin-3-yl |
| 2-fluoro-2-methylpropyl | ethoxymethyl | 5-(hydroxymethyl)pyridin-3-yl |
| 2-fluoro-2-methylpropyl | ethoxymethyl | 3-[(methylsulfonyl)amino]phenyl |
| 2-fluoro-2-methylpropyl | 2-methoxyethyl | pyridin-3-yl |
| 2-fluoro-2-methylpropyl | 2-methoxyethyl | 3-[(isopropylamino)carbonyl]phenyl |
| 2-fluoro-2-methylpropyl | 2-methoxetbyl | 3-[(propylamino)carbonyl]phenyl |
| 2-fluoro-2-methylpropyl | 2-methoxyethyl | 3-(morpholin-4-ylcarbonyl)phenyl |
| 2-fluoro-2-methylpropyl | 2-methoxyethyl | 6-fluoropyridin-3-yl |
| 2-fluoro-2-methylpropyl | 2-methoxyethyl | 5-(hydroxymethyl)pyridin-3-yl |
| 2-fluoro-2-methylpropyl | 2-methoxyethyl | 3-[(methylsulfonyl)amino]phenyl |
| 2-fluoro-2-methylpropyl | hydroxymethyl | pyridin-3-yl |
| 2-fluoro-2-methylpropyl | hydroxymethyl | 3-[(isopropylamino)carbonyl]phenyl |
| 2-fluoro-2-methylpropyl | hydroxymethyl | 3-[(propylamino)carbonyl]phenyl |
| 2-fluoro-2-methylpropyl | hydroxymethyl | 3-(morpholin-4-ylcarbonyl)phenyl |
| 2-fluoro-2-methylpropyl | hydroxymethyl | 6-fluoropyridin-3-yl |
| 2-fluoro-2-methylpropyl | hydroxymethyl | 5-(hydroxymethyl)pyridin-3-yl |

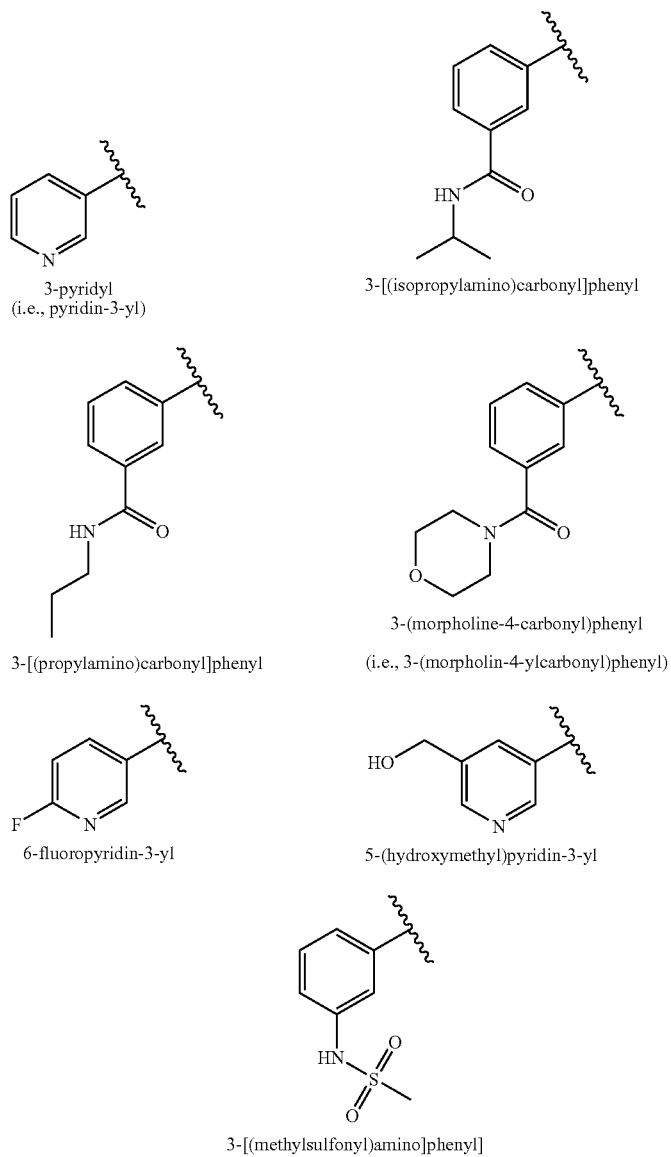

| R₁ | R₂ | R₃ |
|---|---|---|
| 2-fluoro-2-methylpropyl | hydroxymethyl | 3-[(methylsulfonyl)amino]phenyl |
| 2-fluoro-2-methylpropyl | 2-hydroxyethyl | pyridin-3-yl |
| 2-fluoro-2-methylpropyl | 2-hydroxyethyl | 3-[(isopropylamino)carbonyl]phenyl |
| 2-fluoro-2-methylpropyl | 2-hydroxyethyl | 3-[(propylamino)carbonyl]phenyl |
| 2-fluoro-2-methylpropyl | 2-hydroxyethyl | 3-(morpholin-4-ylcarbonyl)phenyl) |
| 2-fluoro-2-methylpropyl | 2-hydroxyethyl | 6-fluoropyridin-3-yl |
| 2-fluoro-2-methylpropyl | 2-hydroxyethyl | 5-(hydroxymethyl)pyridin-3-yl |

Cytokine Induction in Human Cells

Compounds of the invention have been found to modulate cytokine biosynthesis by inducing the production of interferon α and/or tumor necrosis factor α in human cells when tested using the method described below.

An in vitro human blood cell system is used to assess cytokine induction. Activity is based on the measurement of interferon (α) and tumor necrosis factor (α)(IFN-α and TNF-α, respectively) secreted into culture media as described by Testerman et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS).

Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4\times10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 µM. Controls include cell samples with media only, cell samples with DMSO only (no compound), and cell samples with reference compound.

Incubation

The solution of test compound is added at 60 µM to the first well containing RPMI complete and serial 3 fold dilutions are made in the wells. The PBMC suspension is then added to the wells in an equal volume, bringing the test compound concentrations to the desired range (usually 30-0.014 µM). The final concentration of PBMC suspension is $2\times10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype colorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (µmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

Cytokine Induction in Human Cells

High Throughput Screen

The CYTOKINE INDUCTION IN HUMAN CELLS test method described above was modified as follows for high throughput screening.

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4\times10^6$ cells/mL in RPMI complete (2-fold the final cell density). The PBMC suspension is added to 96-well flat bottom sterile tissue culture plates.

Compound Preparation

The compounds are solubilized in dimethyl sulfoxide (DMSO). The compounds are generally tested at concentrations ranging from 30-0.014 µM. Controls include cell samples with media only, cell samples with DMSO only (no compound), and cell samples with a reference compound 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) on each plate. The solution of test compound is added at 7.5 mM to the first well of a dosing plate and serial 3 fold dilutions are made for the 7 subsequent concentrations in DMSO. RPMI Complete media is then added to the test compound dilutions in order to reach a final compound concentration of 2-fold higher (60-0.028 µM) than the final tested concentration range.

Incubation

Compound solution is then added to the wells containing the PBMC suspension bringing the test compound concentrations to the desired range (usually 30-0.014 µM) and the DMSO concentration to 0.4%. The final concentration of PBMC suspension is $2\times10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200 g) at 4° C. 4-plex Human Panel MSD MULTI-SPOT 96-well plates are precoated with the appropriate capture antibodies by MesoScale Discovery, Inc. (MSD, Gaithersburg, Md.). The cell-free culture supernatants are removed and transferred to the MSD plates. Fresh samples are typically tested, although they may be maintained at −30 to −70° C. until analysis.

Interferon-α and Tumor Necrosis Factor-α Analysis

MSD MULTI-SPOT plates contain within each well capture antibodies for human TNF-α and human IFN-α that have been pre-coated on specific spots. Each well contains four spots: one human TNF-α capture antibody (MSD) spot, one human IFN-α capture antibody (PBL Biomedical Laboratories, Piscataway, N.J.) spot, and two inactive bovine serum albumin spots. The human TNF-α capture and detection antibody pair is from MesoScale Discovery. The human IFN-α multi-subtype antibody (PBL Biomedical Laboratories) captures all IFN-α subtypes except IFN-α F (IFNA21). Standards consist of recombinant human TNF-α (R&D Systems, Minneapolis, Minn.) and IFN-α (PBL Biomedical Laboratories). Samples and separate standards are added at the time of analysis to each MSD plate. Two human IFN-α detection antibodies (Cat. Nos. 21112 & 21100, PBL) are used in a two to one ratio (weight:weight) to each other to determine the IFN-α concentrations. The cytokine-specific detection antibodies are labeled with the SULFO-TAG reagent (MSD). After adding the SULFO-TAG labeled detection antibodies to the wells, each well's electrochemoluminescent levels are read using MSD's SECTOR HTS READER. Results are expressed in pg/mL upon calculation with known cytokine standards.

Assay Data and Analysis

In total, the data output of the assay consists of concentration values of TNF-α or IFN-α (y-axis) as a function of compound concentration (x-axis).

A plate-wise scaling is performed within a given experiment aimed at reducing plate-to-plate variability associated within the same experiment. First, the greater of the median DMSO (DMSO control wells) or the experimental background (usually 20 pg/mL for IFN-α and 40 pg/mL for TNF-α) is subtracted from each reading. Negative values that may result from background subtraction are set to zero. Each plate within a given experiment has a reference compound that serves as a control. This control is used to calculate a median expected area under the curve across all plates in the assay. A plate-wise scaling factor is calculated for each plate as a ratio of the area of the reference compound on the particular plate to the median expected area for the entire experiment. The data from each plate are then multiplied by the plate-wise scaling factor for all plates. Only data from plates bearing a scaling factor of between 0.5 and 2.0 (for both cytokines IFN-α, TNF-α) are reported. Data from plates with scaling factors outside the above mentioned interval are retested until they bear scaling factors inside the above mentioned interval. The above method produces a scaling of the y-values without altering the shape of the curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91). The median expected area is the median area across all plates that are part of a given experiment.

A second scaling may also be performed to reduce inter-experiment variability (across multiple experiments). All background-subtracted values are multiplied by a single adjustment ratio to decrease experiment-to-experiment variability. The adjustment ratio is the area of the reference compound in the new experiment divided by the expected area of the reference compound based on an average of previous experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from an average of previous experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

TNF-α Inhibition in Mouse Cells

Certain compounds of the invention may modulate cytokine biosynthesis by inhibiting production of tumor necrosis factor α (TNF-α) when tested using the method described below.

The mouse macrophage cell line Raw 264.7 is used to assess the ability of compounds to inhibit tumor necrosis factor-α (TNF-α) production upon stimulation by lipopolysaccharide (LPS).

Single Concentration Assay:
Blood Cell Preparation for Culture

Raw cells (ATCC) are harvested by gentle scraping and then counted. The cell suspension is brought to $3\times10^5$ cells/mL in RPMI with 10% fetal bovine serum (FBS). Cell suspension (100 μL) is added to 96-well flat bottom sterile tissues culture plates (Becton Dickinson Labware, Lincoln Park, N.J.). The final concentration of cells is $3\times10^4$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 5 μM. LPS (Lipopolysaccharide from *Salmonella typhimurium*, Sigma-Aldrich) is diluted with colorless RPMI to the $EC_{70}$ concentration as measured by a dose response assay.

Incubation

A solution of test compound (1 μl) is added to each well. The plates are mixed on a microtiter plate shaker for 1 minute and then placed in an incubator. Twenty minutes later the solution of LPS (1 μL, $EC_{70}$ concentration~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipette. TNF-α concentration is determined by ELISA using a mouse TNF-α kit (from Biosource International, Camarillo, Calif.). Results are expressed in pg/mL. TNF-α expression upon LPS stimulation alone is considered a 100% response.

Dose Response Assay:
Blood Cell Preparation for Culture

Raw cells (ATCC) are harvested by gentle scraping and then counted. The cell suspension is brought to $4\times10^5$ cells/mL in RPMI with 10% FBS. Cell suspension (250 μL) is added to 48-well flat bottom sterile tissues culture plates (Costar, Cambridge, Mass.). The final concentration of cells is $1\times10^5$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 0.03, 0.1, 0.3, 1, 3, 5 and 10 μM. LPS (Lipopolysaccharide from *Salmonella typhimurium*, Sigma-Aldrich) is diluted with colorless RPMI to the $EC_{70}$ concentration as measured by dose response assay.

Incubation

A solution of test compound (200 μl) is added to each well. The plates are mixed on a microtiter plate shaker for 1 minute and then placed in an incubator. Twenty minutes later the solution of LPS (200 μL, $EC_{70}$ concentration~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipette. TNF-α concentration is determined by ELISA using a mouse TNF-α kit (from Biosource International, Camarillo, Calif.). Results are expressed in pg/mL. TNF-α expression upon LPS stimulation alone is considered a 100% response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What claimed is:

1. A compound of the Formula II:

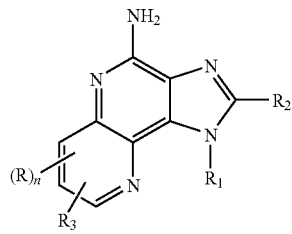

II wherein:
n is 0 or 1;
$R_1$ is selected from the group consisting of:
—$R_4$,
—X—$R_4$,
—X—Y—$R_4$,
—X—Y—X—Y—$R_4$, and
—X—$R_5$;
$R_2$ is selected from the group consisting of:
—$R_4$,
—X—$R_4$,
—X—Y—$R_4$, and
—X—$R_5$;
$R_3$ is selected from the group consisting of:
—Z—Ar,
—Z—Ar'—Y—$R_4$,
—Z—Ar'—X—Y—$R_4$,
—Z—Ar'—$R_5$, and
—Z—Ar'—X—$R_5$;

R is selected from the group consisting of alkyl, alkoxy, chloro, fluoro, hydroxy, and trifluoromethyl;

Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, aminoalkyl, alkylamino, and dialkylamino;

Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

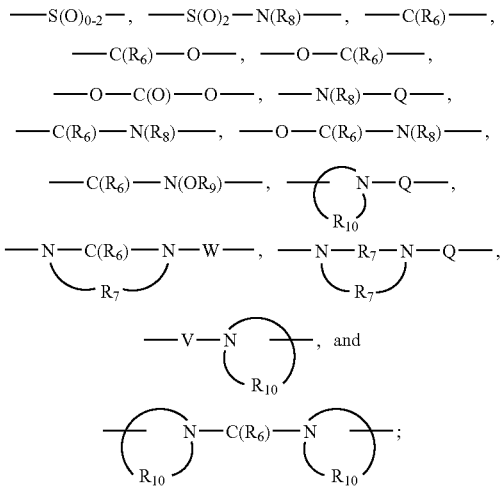

Z is selected from the group consisting of a bond, alkylene, alkenylene, and alkynylene, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of allyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

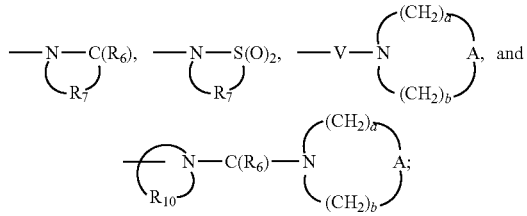

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7;
or a pharmaceutically acceptable salt thereof.

2. A compound of the Formula (III):

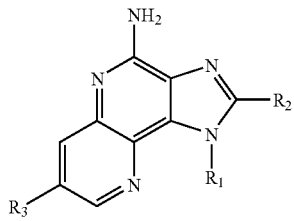

wherein:
$R_1$ is selected from the group consisting of:
—$R_4$,
—X—$R_4$,
—X—Y—$R_4$,
—X—Y—X—Y—$R_4$, and
—X—$R_5$;
$R_2$ is selected from the group consisting of:
—$R_4$,
—X—$R_4$,
—X—Y—$R_4$, and
—X—$R_5$;
$R_3$ is selected from the group consisting of:
—Z—Ar,
—Z—Ar'—Y—$R_4$,
—Z—Ar'—X—Y—$R_4$,
—Z—Ar'—$R_5$, and
—Z—Ar'—X—$R_5$;

Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, aminoalkyl, alkylamino, and dialkylamino;

Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

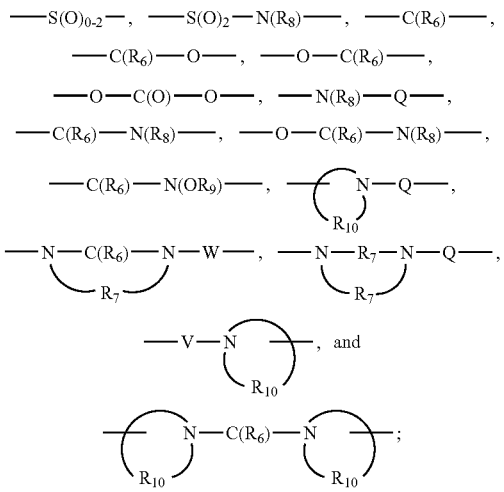

Z is selected from the group consisting of a bond, alkylene, alkenylene, and alkynylene;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

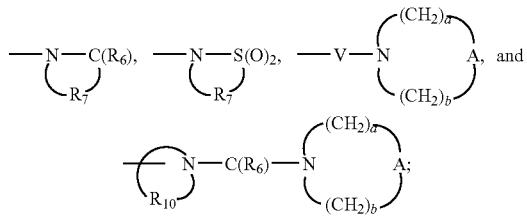

$R_6$ is selected from the group consisting of =O and =SS;

$R_7$ is $C_{2-7}$ alkylene;

$R_8$ is selected from the group consisting of hydrogen, alkyl, alkoxyalkylenyl, and arylalkylenyl;

$R_9$ is selected from the group consisting of hydrogen and alkyl;

$R_{10}$ is $C_{3-8}$ alkylene;

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R), —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7;

or a pharmaceutically acceptable salt thereof.

3. A compound of the Formula VII:

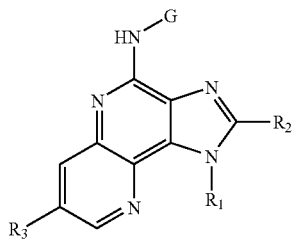

VII wherein:

G is selected from the group consisting of:
—C(O)—R',
α-aminoacyl,
α-aminoacyl-α-aminoacyl,
—C(O)—O—R',
—C(O)—N(R")R',
—C(=NY')—R',
—CH(OH)—C(O)—OY',
—CH(OC$_{1-4}$ alkyl)Y$_0$,
—CH$_2$Y$_1$, and
—CH(CH$_3$)Y$_1$;

R' and R" are independently selected from the group consisting of $C_{1-10}$ alkyl, $C_{3-7}$ cycloalkyl, and benzyl, each of which may be unsubstituted or substituted by one or more substitutents selected from the group consisting of halogen, hydroxy, nitro, cyano, carboxy, $C_{1-6}$ alkyl, $C_{1-4}$ alkoxy, aryl, heteroaryl, aryl$C_{1-4}$ alkylenyl, heteroaryl$C_{1-4}$ alkylenyl, halo$C_{1-4}$ alkylenyl, halo$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen;

α-aminoacyl is an acyl group derived from an amino acid selected from the group consisting of racemic, D-, and L-amino acids;

Y' is selected from the group consisting of hydrogen, $C_{1-6}$ alkyl, and benzyl;

Y$_0$ is selected from the group consisting of $C_{1-6}$ alkyl, carboxyC$_{1-6}$ alkylenyl, aminoC$_{1-4}$ alkylenyl, mono-N—C$_{1-6}$ alkylaminoC$_{1-4}$ alkylenyl, and di-N,N—C$_{1-6}$ alkylaminoC$_{1-4}$ alkylenyl;

Y$_1$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl;

$R_1$ is selected from the group consisting of:
—R$_4$,
—X—R$_4$,
—X—Y—R$_4$,
—X—Y—X—Y—R$_4$, and
—X—R$_5$;

$R_2$ is selected from the group consisting of:
—R$_4$,
—X—R$_4$,
—X—Y—R$_4$, and
—X—R$_5$;

$R_3$ is selected from the group consisting of:
—Z—Ar,
—Z—Ar'—Y—R$_4$,
—Z—Ar'—X—Y—R$_4$,
—Z—Ar'—R$_5$, and
—Z—Ar'—X—R$_5$;

Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, aminoalkyl, alkylamino, and dialkylamino;

Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

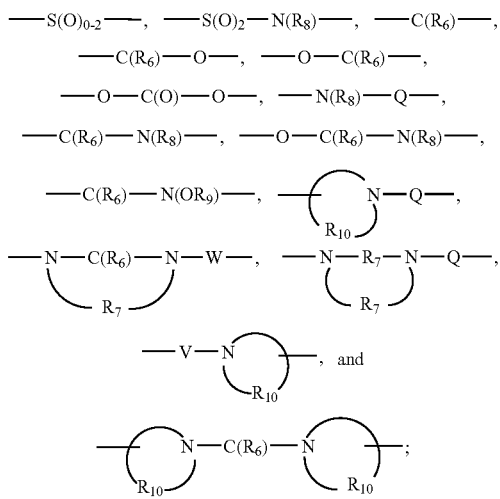

Z is selected from the group consisting of a bond, alkylene, alkenylene, and; alkynylene;

R₄ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R₅ is selected from the group consisting of:

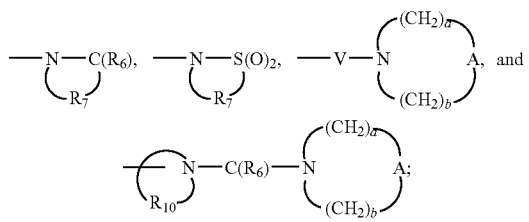

R₆ is selected from the group consisting of =O and =S;
R₇ is C₂₋₇ alkylene;
R₈ is selected from the group consisting of hydrogen, alkyl, alkoxyalkylenyl, and arylalkylenyl;
R₉ is selected from the group consisting of hydrogen and alkyl;
R₁₀ is C₃₋₈ alkylene;
A is selected from the group consisting of —O—, —C(O)—, —S(O)₀₋₂—, —CH₂—, and —N(R₄)—;
Q is selected from the group consisting of a bond, —C(R₆)—, —C(R₆)—C(R₆)—, —S(O)₂—, —C(R₆)—N(R₈)—W—, —S(O)₂—N(R₈)—, —C(R₆)—O—, and —C(R₆)—N(OR₉)—;

V is selected from the group consisting of —C(R₆)—, —O—C(R₆)—, —N(R₈)—C(R₆)—, and —S(O)₂—;
W is selected from the group consisting of a bond, —C(O)—, and —S(O)₂—; and
a and b are independently integers from 1 to 6 with the proviso that a+b is ≦7;
or a pharmaceutically acceptable salt thereof.

4. The compound or salt of claim 1 wherein n is 0.

5. The compound or salt of claim 1 wherein:
R₁ is selected from the group consisting of alkyl, arylalkylenyl, aryloxyalkylenyl, hydroxyalkyl, fluoroalkyl, heterocyclylalkylenyl which is unsubstituted or substituted by hydroxy, —X—Y—R₄, and —X—R₅, wherein:
X is alkylene;
Y is selected from the group consisting of —N(R₈)—C(O)—, —N(R₈)—S(O)₂—, —N(R₈)—C(O)—N(R₈)—, —S(O)₂—, and

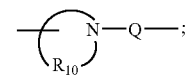

R₄ is selected from the group consisting of alkyl, aryl, and heteroaryl; and
R₅ is selected from the group consisting of:

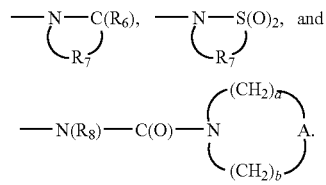

6. The compound or salt of claim 5 wherein R₁ is selected from the group consisting of alkyl and hydroxyalkyl.

7. The compound or salt of claim 5 wherein R₁ is selected from the group consisting of propyl, 2-methylpropyl, 2-hydroxy-2-methylpropyl, 2,3-dihydroxypropyl, 2-methyl-2-[(methylsulfonyl)amino]propyl, 4-[(methylsulfonyl)amino]butyl, 4-[(morpholin-4-ylcarbonyl)amino]butyl, (1-hydroxycyclopentyl)methyl, (1-hydroxycyclobutyl)methyl, 2-fluoro-2-methylpropyl, tetrahydro-2H-pyran-4-ylmethyl, and 4-hydroxytetrahydro-2H-pyran-4-ylmethyl.

8. The compound or salt of claim 1 wherein R₂ is selected from the group consisting of hydrogen, alkyl, alkoxyalklenyl, and hydroxyalkylenyl.

9. The compound or salt of claim 8 wherein R₂ is selected from the group consisting of hydrogen, methyl, ethyl, propyl, butyl, methoxymethyl, ethoxymethyl, 2-methoxyethyl, hydroxymethyl, and 2-hydroxyethyl.

10. The compound or salt of claim 1 wherein Z is selected from the group consisting of a bond, methylene, and ethylene.

11. The compound or salt of claim 10 wherein Z is a bond.

12. The compound or salt of claim 1 wherein R₃ is —Z—Ar.

13. The compound or salt of claim 1 wherein R₃ is selected from the group consisting of phenyl, pyridyl, pyrrolyl, pyrazolyl, imidazolyl, thienyl, pyrimidinyl, and furyl, each of which can be unsubstituted or can be substituted by one or more substituents selected from the group consisting of halogen, alkyl, alkenyl, hydroxy, hydroxyalkyl, alkoxy, amino, aminoalkyl, and cyano.

14. The compound or salt of claim 1 wherein $R_3$ is selected from the group consisting of pyridin-3-yl, pyridin-4-yl, 5-(hydroxymethyl)pyridin-3-yl, 2-ethoxyphenyl, 3-(morpholin-4-ylcarbonyl)phenyl, 3-[(isopropylamino)carbonyl]phenyl, 3-[(propylamino)carbonyl]phenyl, phenyl, 3-(hydroxymethyl)phenyl, 6-fluoropyridin-3-yl, 4-chlorophenyl, 2-hydroxyphenyl, 2-isopropoxyphenyl, 3,4-difluorophenyl, 3-[(methylsulfonyl)amino]phenyl, 4-[(methylsulfonyl)amino]phenyl, and 3-(aminocarbonyl)phenyl.

15. The compound or salt of claim 1 wherein $R_3$ is —Z—Ar'—Y—$R_4$, —Z—Ar'—X—Y—$R_4$, —Z—Ar'—$R_5$, or —Z—Ar'—X—$R_5$.

16. The compound or salt of claim 15 wherein:
Ar' is phenylene or pyridylene;
Y in —Z—'—Y—$R_4$ or —Z—'—X—Y—$R_4$ is selected from the group consisting of:
—S(O)$_{0-2}$—,
—S(O)$_2$—N($R_8$)—,
—C(O)—,
—N($R_8$)-Q-,
—C($R_6$)—N($R_8$)—,
—C(O)—O—, and
—C(O)—N(OCH$_3$)—;
wherein:
Q is selected from the group consisting of a bond, —C(O)—, —C(O)—O—, —C(O)—N(H)—, and —S(O)$_2$—; and
$R_8$ is selected from the group consisting of hydrogen, $C_{1-4}$ alkyl, and alkoxyalkylenyl;
X in —Z—'—X—Y—$R_4$ or —Z—'—X—$R_5$ is $C_{1-4}$ alkylene;

$R_4$ in —Z—'—Y—$R_4$ or —Z—'—X—Y—$R_4$ is selected from the group consisting of alkyl, haloalkyl, aryl, arylalkylenyl, heteroarylalkylenyl, heteroaryl, alkylheteroarylenyl, and heterocyclyl, with the proviso that $R_4$ may also be hydrogen when Y is —C(O)—O—, —C(O)—N(OCH$_3$)—, or —N($R_8$)—; and
$R_5$ in —Z—'—$R_5$ or —Z—'—X—$R_5$ is

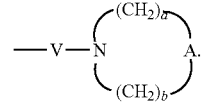

17. A pharmaceutical composition comprising a therapeutically effective amount of a compound or salt of claim 1 in combination with a pharmaceutically acceptable carrier.

18. A method of inducing cytokine biosynthesis in an animal comprising administering an effective amount of a compound or salt of claim 1 to the animal.

19. A method of treating a viral disease in an animal in need thereof comprising administering a therapeutically effective amount of a compound or salt of claim 1 to the animal.

20. A method of treating a neoplastic disease in an animal in need thereof comprising administering a therapeutically effective amount of a compound or salt of claim 1 to the animal.

* * * * *